(12) United States Patent
Danishefsky et al.

(10) Patent No.: US 7,645,454 B2
(45) Date of Patent: Jan. 12, 2010

(54) PROSTATE SPECIFIC ANTIGENS AND USES THEREOF

(75) Inventors: Samuel J. Danishefsky, Englewood, NJ (US); Vadim Dudkin, Lansdale, PA (US); Justin Miller, New York, NY (US); David A. Scheinberg, New York, NY (US); Christophe Antczak, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 169 days.

(21) Appl. No.: 11/145,002

(22) Filed: Jun. 3, 2005

(65) Prior Publication Data
US 2006/0223744 A1 Oct. 5, 2006

Related U.S. Application Data

(63) Continuation-in-part of application No. PCT/US03/38453, filed on Dec. 3, 2003.

(60) Provisional application No. 60/500,161, filed on Sep. 4, 2003, provisional application No. 60/430,822, filed on Dec. 3, 2002.

(51) Int. Cl.
*A61K 38/04* (2006.01)
(52) U.S. Cl. .................... 424/185.1; 530/330
(58) Field of Classification Search ............ 560/322; 424/185.1
See application file for complete search history.

(56) References Cited

U.S. PATENT DOCUMENTS

| 5,977,081 A | 11/1999 | Marciani |
| 6,080,725 A | 6/2000 | Marciani |

FOREIGN PATENT DOCUMENTS

| WO | WO 98/00711 | 1/1998 |
| WO | WO 2004/060915 | 7/2004 |

OTHER PUBLICATIONS

Ratner et al. (Eur. J. Org. Chem. 2002; 826-833).*
Wang et al. (Angew. Chem. Int. Ed. 2001; 40: 1728-1732).*
Belanger et al. (The Prostate 1995; 27: 187-197).*
Abrahamsson et al., *Urol. Clin. N. Am.* 1997, 24, 353.
Adluri et al., "Immunogenicity of Synthetic TF-KLH (Keyhole Limpet Hemocyanin) and STn-KLH Conjugates in Colorectal Carcinoma Patients." *Cancer Immunol. Immun.* 1995, 41, 185-192.
Ajisaka et al., I. "Efficient synthesis of O-linked glycopeptide by a transglycosylation using endo alpha-N-acetylgalactosaminidase from *Streptomyces* sp." Biosci. Biotechnol. Biochem. 2001, 65, 1240-1243.
Anisfeld et al., "A Convergent Approach to the Chemical Synthesis of Asparagine-Linked Glycopeptides." *J. Org. Chem.* 1990, 55, 5560-5562.
Armbruster, D. A. (1993) Clin Chem 39:181-195.

Arsequell, G.; Haurum, J. S.; Elliott, T.; Dwek, R. A.; Lellouch, A. C. "Synthesis of Major Histocompatibility Complex Class-I Binding Glycopeptides." *J. Chem. Soc.—Perkin Trans. 1* 1995, 1739-1745.
B. Imperiali, S. E. O'Connor, *Curr. Opin. Chem. Biol.* 1999, 3, 643-649.
B. Imperiali, S. E. O'Connor, T. Hendrickson, C. Kellenberger, *Pure Appl. Chem.* 1999, 71, 777-787.
B. L. Nilsson, L. L. Kiessling, R. T. Raines, *Org. Lett.* 2000, 2, 1939-1941.
Beduschi, M.; Oesterling, J. E. "Percent free prostate-specific antigen: The next frontier in prostatespecific antigen testing." *Urology* 1998, 51, 98-109.
Belanger, A.; Vanhalbeek, H.; Graves, H. C. B.; Grandbois, K.; Stamey, T. A.; Huang, L. H.; Poppe, I.; Labrie, F. *Prostate* 1995, 27, 187-197.
Bertozzi, C. R.; Kiessling, L. L. *Science* 2001, 291, 2357-2364.
Bu, X. Z.; Xie, G. Y.; Law, C. W.; Guo, Z. H. "An improved deblocking agent for direct Fmoc solidphase synthesis of peptide thioesters." *Tetrahedron Lett.* 2002, 43, 2419-2422.
C. F. Liu, J. P. Tam, *Proc. Natl. Acad. Sci. U. S. A.* 1994, 91, 6584-6588.
C. Unverzagt, *Tetrahedron Lett.* 1997, 38, 5627-5630.
Calarese, D. A.; Scanlan, C. N.; Zwick, M. B.; Deechongkit, S.; Mimura, Y.; Kunert, R.; Zhu, P.; Wormald, M. R.; Stanfield, R. L.; Roux, K. H.; Kelly, J. W.; Rudd, P. M.; Dwek, R. A.; Katinger, H.; Burton, D. R.; Wilson, I. A. *Science* 2003, 300, 2065-2071.
Canne, L. E.; Walker, S. M.; Kent, S. B. H. "A General Method for the Synthesis of Thioester Resin Linkers for Use in the Solid-Phase Synthesis of Peptide Alpha-Thioacids." *Tetrahedron Lett.* 1995, 36, 1217-1220.

(Continued)

*Primary Examiner*—Brandon J Fetterolf
(74) *Attorney, Agent, or Firm*—Choate, Hall & Stewart LLP; Brenda Herschbach Jarrell; John P. Rearick

(57) ABSTRACT

The present invention provides compounds having formula (I):

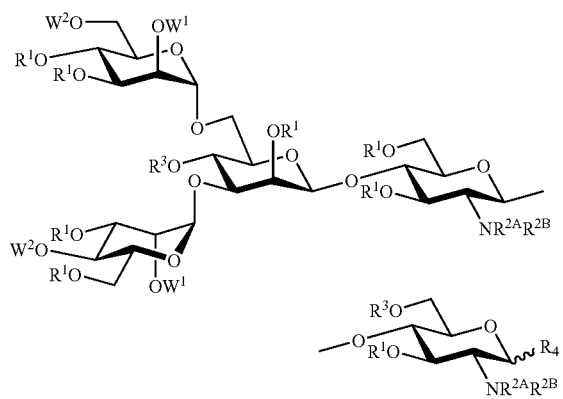

(I)

wherein $W^1$, $W^2$, $R^1$, $R^3$, $R^4$, $R^{2A}$ and $R^{2B}$ are as defined herein. In another aspect, the invention provides an antibody or antibody fragment which binds specifically to a normal or transformed PSA glycan or glycopeptide of the invention.

23 Claims, 14 Drawing Sheets

OTHER PUBLICATIONS

Carter, H. B.; Morrell, C. H.; Pearson, J. D.; Brant, L. J.; Plato, C. C.; Metter, E. J.; Chan, D. W.; Fozard, J. L.; Walsh, P. C. "Estimation of Prostatic Growth Using Serial Prostate-Specific Antigen Measurements in Men with and without Prostate Disease." *Cancer Res.* 1992, 52, 3323-3328.

Carter, H. B.; Pearson, J. D. "PSA Velocity for the Diagnosis of Early Prostate Cancer—a New Concept." *Urol. Clin. N. Am.* 1993, 20, 665-670.

Chen, X. T.; Sames, D.; Danishefsky, S. J. "Exploration of modalities in building alpha-O-linked systems through glycal assembly: A total synthesis of the mucin-related F1 alpha antigen." *J. Am. Chem. Soc.* 1998, 120, 7760-7769.

Chhabra, S. R.; Hothi, B.; Evans, D. J.; White, P. D.; Bycroft, B. W.; Chan, W. C. "An appraisal of new variants of Dde amine protecting group for solid phase peptide synthesis." *Tetrahedron Lett.* 1998, 39, 1603-1606.

Clippingdale, A. B.; Barrow, C. J.; Wade, J. D. "Peptide thioester preparation by Fmoc solid phase peptide synthesis for use in native chemical ligation." *J. Pept. Sci.* 2000, 6, 225-234.

Cohen-Anisfeld, S. T.; Lansbury, P. T. *J. Am. Chem. Soc.* 1993, 115, 10531-10537.

Crich, D.; Dudkin, V. "Why are the hydroxy groups of partially protected N-acetylglucosamine derivatives such poor glycosyl acceptors, and what can be done about it? A comparative study of the reactivity of N-acetyl-, N-phthalimido-, and 2-azido-2-deoxyglucosamine derivatives in glycosylation. 2-Picolinyl ethers as reactivity-enhancing replacements for benzyl ethers." *J. Am. Chem. Soc.* 2001, 123, 6819-6825.

Crich, D.; Smith, M. "1-Benzenesulfinyl piperidine/trifluoromethanesulfonic anhydride: A potent combination of shelf-stable reagents for the low-temperature conversion of thioglycosides to glycosyl triflates and for the formation of diverse glycosidic linkages." *J. Am. Chem. Soc.* 2001, 123, 9015-9020.

Crich, D.; Sun, S. *Tetrahedron* 1998, 54, 8321-8348.

Crich, D.; Sun, S. X. *J. Am. Chem. Soc.* 1998, 120, 435-436.

D. Swinnen, D. Hilvert, *Org. Lett.* 2000, 2, 2439-2442.

D. Vetter, M. A. Gallop, *Bioconjugate Chem.* 1995, 6, 316-318.

Danishefsky, S. J.; Gervay, J.; Peterson, J. M.; Mcdonald, F. E.; Koseki, K.; Oriyama, T.; Griffith, D. A.; Wong, C. H.; Dumas, D. P. "Remarkable Regioselectivity in the Chemical Glycosylation of Glycal Acceptors—a Concise Solution to the Synthesis of Sialyl-Lewis-X Glycal." *J. Am. Chem. Soc.* 1992, 114, 8329-8331.

Danishefsky, S.J.; Allen, J.R., *Angew. Chem. Int. Ed. Engl.* 2000, 39, 837-863.

Davis, B.G.; *Chem. Rev.* 2002, 102, 579-602.

Dawson, P. E.; Churchill, M. J.; Ghadiri, M. R.; Kent, S. B. H. "Modulation of reactivity in native chemical ligation through the use of thiol additives." *J. Am. Chem. Soc.* 1997, 119, 4325-4329.

Dawson, P. E.; Kent, S. B. H. *Annu. Rev. Biochem.* 2000, 69, 923-960.

Dawson, P. E.; Muir, T. W.; Clark-Lewis, I.; Kent, S. B. H. *Science* 1994, 266, 776-779.

Dennis, J. W.; Laferte, S. "Oncodevelopmental Expression of GlcNAc-Beta-1-6Man-Alpha-1-6Man- Beta-1-Branched Asparagine-Linked Oligosaccharides in Murine Tissues and Human-Breast Carcinomas." *Cancer Res.* 1989, 49, 945-950.

Dennis, J. W.; Laferte, S.; Waghorne, C.; Breitman, M. L.; Kerbel, R. S. "Beta-1-6 Branching of Asn-Linked Oligosaccharides Is Directly Associated with Metastasis." *Science* 1987, 236, 582-585.

Dranoff et al., *Proc. Natl. Acad. Sci*, USA 1993, 90, 3539.

Dudkin, V. Y.; Crich, D. *Tetrahedron Lett.* 2003, 44, 1787-1789.

Dudkin, V. Y.; Miller, J. S.; Danishefsky, S. J. *Tetrahedron Lett.* 2003, 44, 1791-1793.

E. Meinjohanns, M. Meldal, K. Bock, *Tetrahedron Lett.* 1995, 36, 9205-9208.

E. Saxon, J. I. Armstrong, C. R. Bertozzi, *Org. Lett.* 2000, 2, 2141-2143.

Egawa, S. *Biomed. Pharmacother.* 2001, 55, 130-134.

Egawa, S.; Soh, S.; Ohori, M.; Uchida, T.; Gohji, K.; Fujii, A.; Kuwao, S.; Koshiba, K. "The ratio of free to total serum prostate specific antigen and its use in differential diagnosis of prostate carcinoma in Japan." *Cancer* 1997, 79, 90-98.

Fernandes, B.; Sagman, U.; Auger, M.; Demetrio, M.; Dennis, J. W. "Beta-1-6 Branched Oligosaccharides as a Marker of Tumor Progression in Human Breast and Colon Neoplasia." *Cancer Res.* 1991, 51, 718-723.

G. Arsequell, G. Valencia, *Tetrahedron: Asymmetry* 1999, 10, 3045-3094.

G. M. Watt, L. Revers, M. C. Webberley, I. B. H. Wilson, S. L. Flitsch, *Angew. Chem.—Int. Ed. Engl.* 1997, 36, 2354-2356.

Glunz, P. W.; Hintermann, S.; Williams, L. J.; Schwarz, J. B.; Kuduk, S. D.; Kudryashov, V.; Lloyd, K. O.; Danishefsky, S. J. "Design and synthesis of Le(y)-bearing glycopeptides that mimic cell surface Le(y) mucin glycoprotein architecture." *J. Am. Chem. Soc.* 2000, 122, 7273-7279.

Griffith, D. A.; Danishefsky, S. J. "Sulfonamidoglycosylation of Glycals—a Route to Oligosaccharides with 2-Aminohexose Subunits." *J. Am. Chem. Soc.* 1990, 112, 5811-5819.

Grogan, M. J.; Pratt, M. R.; Marcaurelle, L. A.; Bertozzi, C. R. *Annu. Rev. Biochem.* 2002, 71, 593.

Hackeng, T. M.; Griffin, J. H.; Dawson, P. E. "Protein synthesis by native chemical ligation: Expanded scope by using straightforward methodology." *Proc. Natl. Acad. Sci. U. S. A.* 1999, 96, 10068-10073.

Hang, H. C.; Bertozzi, C. R. "Chemoselective approaches to glycoprotein assembly." *Acc. Chem. Res.* 2001, 34, 727-736.

Harris, J. R.; Markl, J. "Keyhole limpet hemocyanin (KLH): A biomedical review." *Micron* 1999, 30, 597-623.

Helling, F.; Shang, A.; Calves, M.; Zhang, S. L.; Ren, S. L.; Yu, R. K.; Oettgen, H. F.; Livingston, P. O. "G(D3) Vaccines for Melanoma—Superior Immunogenicity of Keyhole Limpet Hemocyanin Conjugate Vaccines." *Cancer Res.* 1994, 54, 197-203.

Hilz, H.; Noldus, J.; Hammerer, P.; Buck, F.; Luck, M.; Huland, H. *Eur. Urol.* 1999, 36, 286-292.

Hojo, H.; Aimoto, S. "Polypeptide Synthesis Using the 5-Alkyl Thioester of a Partially Protected Peptide Segment—Synthesis of the DNA- Binding Domain of C-Myb Protein (142-193)-NH2." *Bull. Chem. Soc. Jpn.* 1991, 64, 111-117.

Huber, P. R.; Schmid, H. P.; Mattarelli, G.; Strittmatter, B.; Vansteenbrugge, G. J.; Maurer, A. "Serum-Free Prostate-Specific Antigen—Isoenzymes in Benign Hyperplasia and Cancer of the Prostate." *Prostate* 1995, 27, 212-219.

Hudson, M. A.; Bahnson, R. R.; Catalona, W. J. "Clinical Use of Prostate Specific Antigen in Patients with Prostate Cancer." *J. Urol.* 1989, 142, 1011-1017.

Inazu, T.; Haneda, K.; Mizuno, M. "Synthetic study on N-glycopeptides." *J. Syn. Org. Chem. Jpn.* 1998, 56, 210-220.

Ingenito, R.; Bianchi, E.; Fattori, D.; Pessi, A. "Solid phase synthesis of peptide C-terminal thioesters by Fmoc/t-Bu chemistry." *J. Am. Chem. Soc.* 1999, 121, 11369-11374.

International Search Report, PCT/US03/38453, mailed on Feb. 12, 2004.

Iserloh, U.; Dudkin, V.; Wang, Z. G.; Danishefsky, S. J. *Tetrahedron Lett.* 2002, 43, 7027-7030.

J. A. Burns, J. C. Butler, J. Moran, G. M. Whitesides, *J. Org. Chem.* 1991, 56, 2648-2650.

J. P. Tam, J. X. Xu, K. D. Eom, *Biopolymers* 2001, 60, 194-205.

J. R. Allen, C. R. Harris, S. J. Danishefsky, *J. Am. Chem. Soc.* 2001, 123, 1890-1897.

J. van Ameijde, H. B. Albada, R. M. J. Liskamp, *J. Chem. Soc. —Perkin Trans. 1* 2002, 1042-1049.

J. W. Dennis, M. Granovsky, C. E. Warren, *Biochim. Biophys. Acta—Gen. Subj.* 1999, 1473, 21-34.

Jain, R. K.; Piskorz, C. F.; Huang, B. G.; Locke, R. D.; Han, H. L.; Koenig, A.; Varki, A.; Matta, K. L. "Inhibition of L- and P-selectin by a rationally synthesized novel core 2-like branched structure containing GalNAc-Lewis(X) and Neu5Ac alpha 2-3Gal beta 1-3GalNAc sequences." *Glycobiology* 1998, 8, 707-717.

Jiang, L.; Chan, T. H. "Borane/Bu2BOTf: A mild reagent for the regioselective reductive ring opening of benzylidene acetals in carbohydrates." *Tetrahedron Lett.* 1998, 39, 355-358.

Junker, R.; Brandt, B.; Zechel, C.; Assmann, G. "Comparison of prostate-specific antigen (PSA) measured by four combinations of free PSA and total PSA assays." *Clin. Chem.* 1997, 43, 1588-1594.

K. M. Koeller, M. E. B. Smith, R. F. Huang, C. H. Wong, *J. Am. Chem. Soc.* 2000, 122, 4241-4242.

K. Witte, P. Sears, R. Martin, C. H. Wong, *J. Am. Chem. Soc.* 1997, 119, 2114-2118.

Kellner, J.; Erhard, M.; Schranner, I.; Losch, U. "The Influence of Various Adjuvants on Antibody Synthesis Following Immunization with an Hapten." *Biol. Chem. Hoppe-Seyler* 1992, 373, 51-55.

Kensil, C. R.; Patel, U.; Lennick, M.; Marciani, D. "Separation and Characterization of Saponins with Adjuvant Activity from Quillaja-Saponaria Molina Cortex." *J. Immunol.* 1991, 146, 431-437.

Kent, S. B. H. "Chemical Synthesis of Peptides and Proteins." *Annu. Rev. Biochem.* 1988, 57, 957-989.

Kochanska-Dziurowicz, A. A.; Mielniczuk, M. R.; Stojko, A.; Kaletka, J. "The clinical utility of measuring free-to-total prostate-specific antigen (PSA) ratio and PSA density in differentiating between benign prostatic hyperplasia and prostate cancer." *Br. J. Urol.* 1998, 81, 834-838.

Kudryashov, V.; Glunz, P. W.; Williams, L. J.; Hintermann, S.; Danishefsky, S. J.; Lloyd, K. O. "Toward optimized carbohydrate-based anticancer vaccines: Epitope clustering, carrier structure, and adjuvant all influence antibody responses to Lewis(y) conjugates in mice." *Proc. Natl. Acad. Sci. U. S. A.* 2001, 98, 3264-3269.

Kuster et al., "Sequencing of N-linked oligosaccharides directly from protein gels: in-gel deglycosylation followed by matrix-assisted laser desorption/ionization mass spectrometry and normal-phase high-performance liquid chromatography", *Analytical Biochemistry*, 250:82-101, 1997.

L. X. Wang, M. Tang, T. Suzuki, K. Kitajima, Y. Inoue, S. Inoue, J. Q. Fan, Y. C. Lee, *J. Am. Chem. Soc.* 1997, 119, 11137-11146.

Lanzavecchia, *Science*, 260, 937-944, 1993.

Leinonen, J.; Stenman, U. H. "Significance of free and bound prostate-specific antigen." *Endocr.—Relat. Cancer* 1996, 3, 191-197.

Li, X. Q.; Kawakami, T.; Aimoto, S. "Direct preparation of peptide thioesters using an Fmoc solidphase method." *Tetrahedron Lett.* 1998, 39, 8669-8672.

Likhosherstov, L. M.; Novikova, O. S.; Derevitskaja, V. A.; Kochetkov, N. K. *Carbohydr. Res.* 1986, 146, C1-C5.

Livingston et al., *Curr. Opin. Immunol.* 1992, 4, 624-629.

Livingston, et al., *J. Clin. Oncol.*, 1994, 12, 1036.

Livingston, P. O.; Adluri, S.; Helling, F.; Yao, T. J.; Kensil, C. R.; Newman, M. J.; Marciani, D. "Phase-1 Trial of Immunological Adjuvant QS-21 with a GM2 Ganglioside-Keyhole Limpet Hemocyanin Conjugate Vaccine in Patients with Malignant-Melanoma." *Vaccine* 1994, 12, 1275-1280.

Lönn, H.; Lönngren, J. *Carbohydr. Res.* 1983, 120, 17-24.

M. Bodanszky, S. Natarajan, *J. Org. Chem.* 1975, 40, 2495-2499.

M. Ciommer, H. Kunz, *Synlett* 1991, 593-595.

M. Mizuno, K. Haneda, R. Iguchi, I. Muramoto, T. Kawakami, S. Aimoto, K. Yamamoto, T. Inazu, *J. Am. Chem. Soc.* 1999, 121, 284-290.

M. V. Chiesa, R. R. Schmidt, *Eur. J. Org. Chem.* 2000, 3541-3554.

M.A. Bernstein; L.D. Hall, *Carbohydr. Res.* 1980, 78, C1.

M.H. Taoet et al., *Nature*, 1993, 362, 755.

Macmillan, D.; Bertozzi, C. R. "New directions in glycoprotein engineering." *Tetrahedron* 2000, 56, 9515-9525.

Marcaurelle, L. A.; Mizoue, L. S.; Wilken, J.; Oldham, L.; Kent, S. B. H.; Handel, T. M.; Bertozzi, C. R. "Chemical synthesis of lymphotactin: A glycosylated chemokine with a C-terminal mucin-like domain." *Chem. Eur. J.* 2001, 7, 1129-1132.

Marciani et al., *Vaccine*, 2000, 18, 3141.

Masters, J. G.; Keegan, P. E.; Hildreth, A. J.; Greene, D. R. J. *Br. J. Urol.* 1998, 81, 419-423.

Matsumoto, H.; Muramatsu, H.; Muramatsu, T.; Shimazu, H. "Carbohydrate Profiles Shown by a Lectin and a Monoclonal Antibody Correlate with Metastatic Potential and Prognosis of Human Lung Carcinomas." *Cancer* 1992, 69, 2084-2090.

Matsuzaki, Y.; Ito, Y.; Nakahara, Y.; Ogawa, T. *Tetrahedron Lett.* 1993, 34, 1061-1064.

Meinjohanns, E.; Meldal, M.; Paulsen, H.; Dwek, R. A.; Bock, K. *J. Chem. Soc.—Perkin Trans. 1* 1998, 549-560.

Metzger, J.; Wiesmuller, K. H.; Schaude, R.; Bessler, W. G.; Jung, G. "Synthesis of Novel Immunologically Active Tripalmitoyl-S-Glycerylcysteinyl Lipopeptides as Useful Intermediates for Immunogen Preparations." *Int. J. Pept. Protein Res.* 1991, 37, 46-57.

Mikolajczyk, S. D.; Grauer, L. S.; Millar, L. S.; Hill, T. M.; Kumar, A.; Rittenhouse, H. G.; Wolfert, R. L.; Saedi, M. S. "A precursor form of PSA (pPSA) is a component of the free PSA in prostate cancer serum." *Urology* 1997, 50, 710-714.

Miller, J. S. et al., *Angew. Chemie Int. Ed.*, 2003, 42, 431.

Musselli, C.; Livingston, P. O.; Ragupathi, G. "Keyhole limpet hemocyanin conjugate vaccines against cancer: the Memorial Sloan Kettering experience." *J. Cancer Res. Clin. Oncol.* 2001, 127, R20-R26.

N. Bezay, G. Dudziak, A. Liese, H. Kunz, *Angew. Chem.—Int. Ed.* 2001, 40, 2292-2295.

Nurmikko, P.; Pettersson, K.; Piironen, T.; Hugosson, J.; Lilja, H. "Discrimination of prostate cancer from benign disease by plasma measurement of intact, free prostate-specific antigen lacking an internal cleavage site at Lys(145)-Lys(146)." *Clin. Chem.* 2001, 47, 1415-1423.

O. Blixt, K. Allin, L. Pereira, A. Datta, J. C. Paulson, *J. Am. Chem. Soc.* 2002, 124, 5739-5746.

O'Connor, S. E.; Imperiali, B. "A molecular basis for glycosylation-induced conformational switching." *Chem. Biol.* 1998, 5, 427-437.

Okada, T.; Sato, Y.; Kobayashi, N.; Sumida, K.; Satomura, S.; Matsuura, S.; Takasaki, M.; Endo, T. *Biochim. Biophys. Acta—Gen. Subj.* 2001, 1525, 149-160.

P. J. Sabbatini, V. Kudryashov, G. Ragupathi, S. J. Danishefsky, P. O. Livingston, W. Bornmann, M. Spassova, A. Zatorski, D. Spriggs, C. Aghajanian, S. Soignet, M. Peyton, C. O'Flaherty, J. Curtin, K. O. Lloyd, *Int. J. Cancer* 2000, 87, 79-85.

P. M. Rudd, T. Elliott, P. Cresswell, I. A. Wilson, R. A. Dwek, *Science* 2001, 291, 2370-2376.

Pardoll et al., *Curr. Opin. Immunol.* 1993, 5, 719-725.

Prahl, I.; Unverzagt, C. *Angew. Chem. Int. Ed.* 2002, 41, 4259-4262.

Prakash, S.; Robbins, P. W. *Glycobiology* 2000, 10, 173-176.

R.U. Lemieux *Chem. Soc. Rev.* 1978, 7, 423.

Ragupathi, G. "Carbohydrate antigens as targets for active specific immunotherapy." *Cancer Immunol. Immun.* 1996, 43, 152-157.

Ragupathi, G.; Howard, L.; Cappello, S.; Koganty, R. R.; Qiu, D. X.; Longenecker, B. M.; Reddish, M. A.; Lloyd, K. O.; Livingston, P. O. "Vaccines prepared with sialyl-Tn and sialyl-Tn trimers using the 4-(4-maleimidomethyl)cyclohexane-1-carboxyl hydrazide linker group result in optimal antibody titers against ovine submaxillary mucin and sialyl-Tn-positive tumor cells." *Cancer Immunol. Immun.* 1999, 48, 1-8.

Ravery, V.; Boccon-Gibod, L. "Free/total prostate-specific antigen ratio—hope and controversies." *Eur. Urol.* 1997, 31, 385-388.

Reiter, W.; Stieber, P.; Schmeller, N.; Nagel, D.; Jansen, H. M.; Schambeck, C.; Fabricius, P. G.; Pahl, H.; Mattes, M.; Constabel, H.; FatehMoghadam, A. "The ratio of free to total prostate specific antigen: An advantageous addition in the differential diagnosis of benign hyperplasia and cancer of the prostate?" *Anticancer Res.* 1997, 17, 2987-2991.

S. F. Slovin, G. Ragupathi, S. Adluri, G. Ungers, K. Terry, S. Kim, M. Spassova, W. G. Bornmann, M. Fazzari, L. Dantis, K. Olkiewicz, K. O. Lloyd, P. O. Livingston, S. J. Danishefsky, H. I. Scher, *Proc. Natl. Acad. Sci. U. S. A.* 1999, 96, 5710-5715.

S. J. Danishefsky, S. Hu, P. F. Cirillo, M. Eckhardt, P. H. Seeberger, *Chem.—Eur. J.* 1997, 3, 1617-1628.

Schwarz, J. B.; Kuduk, S. D.; Chen, X. T.; Sames, D.; Glunz, P. W.; Danishefsky, S. J. "A broadly applicable method for the efficient synthesis of alpha-O-linked glycopeptides and clustered sialic acid residues." *J. Am. Chem. Soc.* 1999, 121, 2662-2673.

Seifert, J.; Lergenmuller, M.; Ito, Y. *Angew. Chem. Int. Ed.* 2000, 39, 531-534.

Semjonow, A.; Brandt, B.; Oberpenning, F.; Roth, S.; Hertle, L. *Prostate* 1996, 3-16.

Semjonow, A.; Hertle, L. *Urol.—Ausg. A* 1995, 34, 290-296.

Sewing et al., *Angew. Chem.—Int. Ed.* 2001, 40, 3395-3396.

Shin, Y.; Winans, K. A.; Backes, B. J.; Kent, S. B. H.; Ellman, J. A.; Bertozzi, C. R. "Fmoc-based synthesis of peptide-(alpha)thioesters: Application to the total chemical synthesis of a glycoprotein by native chemical ligation." *J. Am. Chem. Soc.* 1999, 121, 11684-11689.

Stamey, T. A.; Yang, N.; Hay, A. R.; McNeal, J. E.; Freiha, F. S.; Redwine, E. "Prostate-Specific Antigen as a Serum Marker for Adenocarcinoma of the Prostate." *N. Engl. J. Med.* 1987, 317, 909-916.

T. Boon, *Int. J. Cancer* 1993, 54, 177.

T. Gilewski, G. Ragupathi, S. Bhuta, L. J. Williams, C. Musselli, X. F. Zhang, K. P. Bencsath, K. S. Panageas, J. Chin, C. A. Hudis, L. Norton, A. N. Houghton, P. O. Livingston, S. J. Danishefsky, *Proc. Natl. Acad. Sci. U. S. A.* 2001, 98, 3270-3275.

T. J. Tolbert, C. H. Wong, *J. Am. Chem. Soc.* 2000, 122, 5421-5428.

T. W. Muir, D. Sondhi, P. A. Cole, *Proc. Natl. Acad. Sci. U. S. A.* 1998, 95, 6705-6710.

Tam, J. P.; Lu, Y. A. "Coupling Difficulty Associated with Interchain Clustering and Phase-Transition in Solid-Phase Peptide-Synthesis." *J. Am. Chem. Soc.* 1995, 117, 12058-12063.

Thaler, A.; Seebach, D.; Cardinaux, F. "Lithium Salt Effects in Peptide Synthesis. 2. Improvement of Degree of Resin Swelling and of Efficiency of Coupling in Solid-Phase Synthesis." *Helv. Chim. Acta* 1991, 74, 628-643.

Unverzagt, C. *Carbohydr. Res.* 1997, 305, 423-431.

Unverzagt, C.; Andre, S.; Seifert, J.; Kojima, S.; Fink, C.; Srikrishna, G.; Freeze, H.; Kayser, K.; Gabius, H. J. *J. Med. Chem.* 2002, 45, 478-491.

Wang, T. J.; Linton, H. J.; Sokoloff, R. L.; Grauer, L. S.; Rittenhouse, H. G.; Wolfert, R. L. "Western blotting analysis of antibodies to prostate-specific antigen: Specificities for prostate-specific antigen and prostate-specific antigen fragments." *Tumor Biol.* 1999, 20, 79-85.

Wang, Z. G.; Zhang, X. F.; Live, D.; Danishefsky, S. J. "From glycals to glycopeptides: A convergent and stereoselective total synthesis of a high mannose N-linked glycopeptide." *Angew. Chem. Int. Ed.* 2000, 39, 3652-3656.

Wang, Z. G.; Zhang, X. F.; Visser, M.; Live, D.; Zatorski, A.; Iserloh, U.; Lloyd, K. O.; Danishefsky, S. J. *Angew. Chem. Int. Ed.* 2001, 40, 1728-1732.

Ward, A. M.; Catto, J. W. F.; Hamdy, F. C. *Ann. Clin. Biochem.* 2001, 38, 633-651.

Weiss, H.; Unverzagt, C. *Angew. Chem. Int. Ed.* 2003, 42, 4261-4263.

Yamashita, K; et al. *J. Biol. Chem.* 1984, 259, 10834-10840.

Zhang, S. L.; Graeber, L. A.; Helling, F.; Ragupathi, G.; Adluri, S.; Lloyd, K. O.; Livingston, P. O. "Augmenting the immunogenicity of synthetic MUC1 peptide vaccines in mice." *Cancer Res.* 1996, 56, 3315-3319.

Zhang, W. M.; Finne, P.; Leinonen, J.; Salo, J.; Stenman, U. H. "Determination of prostate-specific antigen complexed to alpha(2)-macroglobulin in serum increases the specificity of free to total PSA for prostate cancer." *Urology* 2000, 56, 267-272.

Zhang, Y. M.; Mallet, J. M.; Sinay, P. *Carbohydr. Res.* 1992, 236, 73-88.

Zietman, A. L., Shipley, W. L., and Willett, C. G. (1993) Cancer 71:959-969.

Dudkin et al. J. Am. Chem. Soc. 2008, 130, 13598-13607.

* cited by examiner

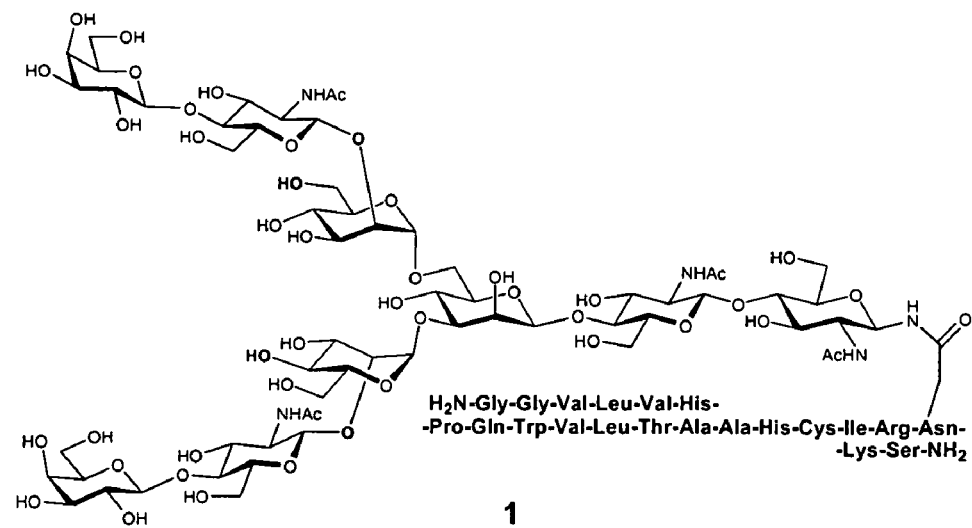
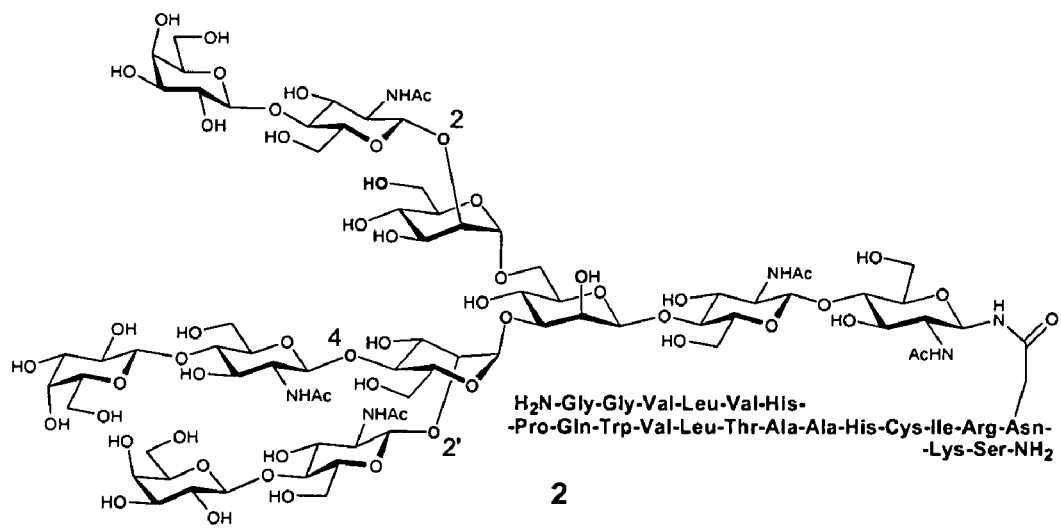
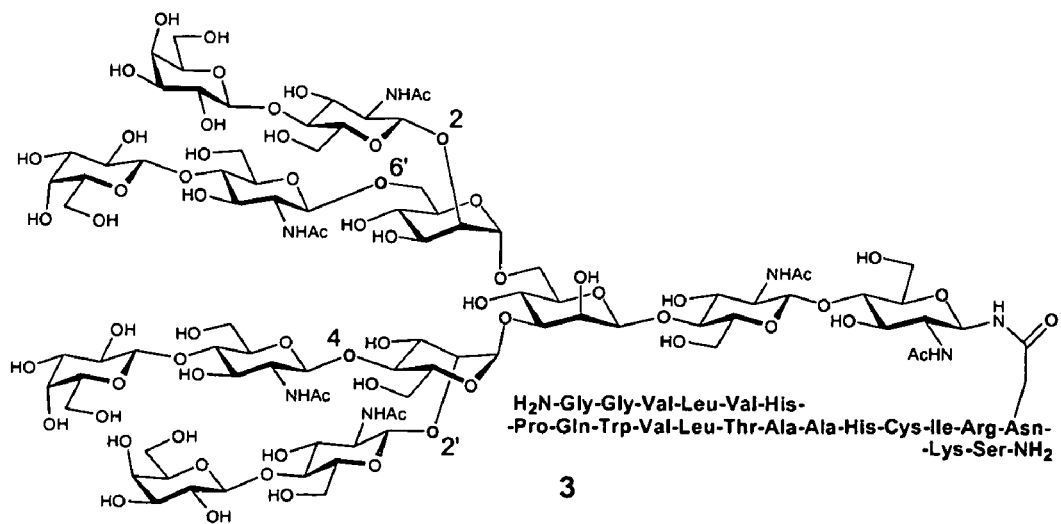
FIG. 1

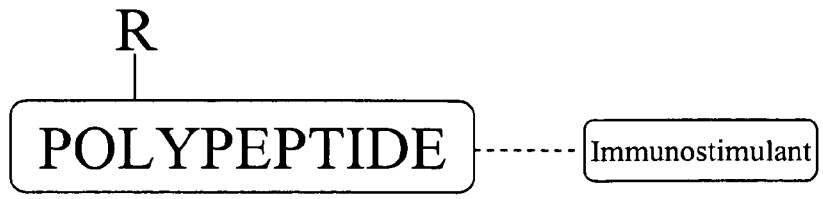

R is a complex-type N-linked glycan (see below for examples), which may be sialylated to varying degrees.

The "POLYPEPTIDE" is a peptide whose structure is either identical to or closely related to that of PSA near the N-glycosylation site.

Immunostimulant designates, for example, an immunogenic carrier and/or an adjuvant -------  Designates covalent conjugation or co-administration

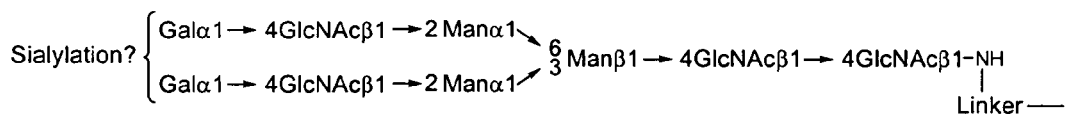

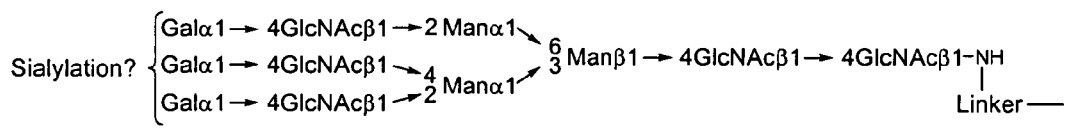

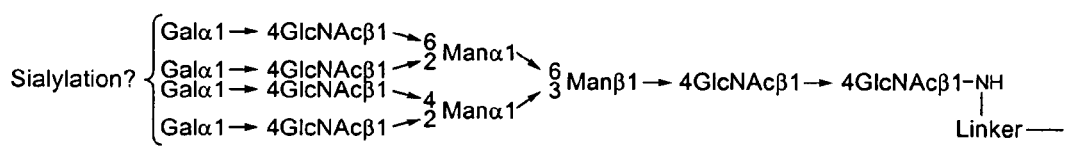

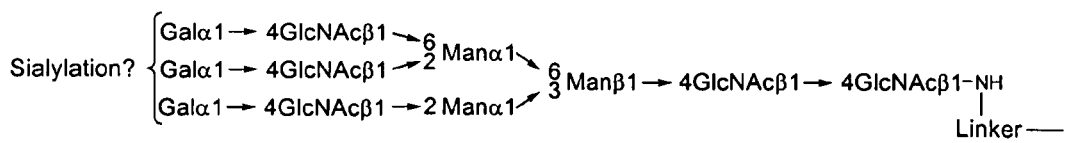

FIG. 5

- Primary screening for clones that recognize the tribranched PSA glycopeptide.

Result: about 10% of hybridomas are positive of the 1,500 screened.

- Secondary screening of hybridomas from the previous selection for hybridomas that recognize the dibranched PSA glycopeptide to a much lower extent.

Result: about 1% from the 1,500 screened are positive.

PROSTATE SPECIFIC ANTIGENS AND USES THEREOF

PRIORITY CLAIM

This application is a Continuation-In-Part and claims the benefit under 35 U.S.C. §120 of co-pending International Application PCT/US03/38453, filed Dec. 3, 2003, and published in English under PCT Article 21(2), which claims priority to U.S. Provisional Application Nos.: U.S. Ser. No. 60/500,161, filed Sep. 4, 2003, and U.S. Ser. No. 60/430,822, filed Dec. 3, 2002; each of the above applications is hereby incorporated by reference in its entirety.

GOVERNMENT SUPPORT

The invention was supported in part by Grant Nos.: AI16943 and CA 10382 from the National Institutes of Health and Grant No.: PC020147 from the US Army Prostate Cancer Research Program. The U.S. government has certain rights in this invention.

BACKGROUND OF THE INVENTION

Cancer of the prostate is the most commonly diagnosed cancer in man and is the second most common cause of cancer death ((1) American Cancer Society, *Cancer Facts & Figures*, 2003; (2) Carter, H. B. and Coffey, D. S. (1990) Prostate 16:39-48; (3) Armbruster, D. A. (1993) Clin Chem 39:181-195). If detected at an early stage, prostate cancer is potentially curable. However, a majority of cases are diagnosed at later stages when metastasis of the primary tumor has already occurred (Wang, M. C., Kuriyama, M., Papsidero, L. D., Loor, R. M., Valenzuela, L. A., Murphy, G. P., and Chu, T. M. (1982) Methods in Cancer Research 19:179-197). Present treatments for prostate cancer include radical prostatectomy, radiation therapy, or hormonal therapy. No systemic therapy has clearly improved survival in cases of hormone refractory disease. With surgical intervention, complete eradication of the tumor is not always achieved and the observed reoccurrence of the cancer (12-68%) is dependent upon the initial clinical tumor stage (Zietman, A. L., Shipley, W. L., and Willett, C. G. (1993) Cancer 71:959-969). Thus, alternative methods of treatment including prophylaxis or prevention are desirable.

Over the last decade, diagnostic tools for prostate cancer (PCa) have improved tremendously with the use of prostate specific antigen (PSA) as a marker for the disease. PSA is a 28 kDa glycoprotein secreted by the prostatic epithelium. It consists of 237 amino acids and approximately 8% carbohydrate N-linked to the peptide backbone through an asparagine (Asn, N) residue[1], and exists in several natural isoforms[2,3]. Serum levels of PSA in its various bound (e.g., PSA-α1-antichymotrypsin, or PSA-ACT) and free (f-PSA and pro-PSA[3]) states are currently used as markers for the diagnosis of prostate cancer,[4-13] but immunoassays based on PSA concentration alone do not clearly distinguish between benign prostatic hyperplasia (BPH) and prostate cancer. PSA-based assays originally measured gross serum levels[14,15] of total PSA (t-PSA) and yielded an ambiguous diagnosis for PCa or BPH at concentrations ranging from 4 to 10 µg/L. Improved accuracy in this range is reportedly achieved using serum level comparisons of f-PSA and t-PSA known as the PSA index, but the utility of such immunoassays is debatable.[16-19] Another method for diagnosis based on serum PSA content, called PSA velocity, involves monitoring increased PSA levels over time for a particular patient.[20,21] Though free from the dependence upon average values for expected PSA concentrations in healthy, BPH, and PCa patients, such diagnostics place considerable demands on assay stability and consistency over time.[16]

Thus prostate cancer diagnosis would benefit from a new, more accurate immunoassay. To this end, we note that differentially expressed N-linked carbohydrates have been associated with the onset or metastasis of several cancers,[22] including breast,[23,24] colon,[23] and lung[25] cancers. Carbohydrates from normal PSA are reportedly biantennary N-linked glycans (see structure below) terminated in variable numbers of sialic acid residues.[26,27]

(SEQ ID NO: 1)

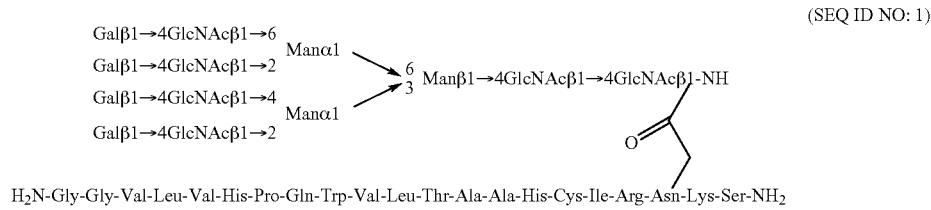

However, a recent study indicates that PSA from a metastatic prostate cell line (LnCaP) also exhibits larger, more highly branched carbohydrates of the type illustrated in the boxed structure of Scheme 1, though the altered glycans were not isolated and their precise structures are yet to be determined.[28] It has been suggested that the differentially glycosylated region of transformed PSA could be used as a molecular marker specific for PCa over BPH.[27,28] To study this issue in detail requires pure, homogeneous PSA glycopeptides; however, useful samples of homogeneous glycosylated PSA from natural sources are prohibitively difficult to obtain. Furthermore, purified PSA displays several glycoforms upon hydrazinolytic cleavage.[27] Obtaining homogeneous samples of PSA glycopeptides thus requires a source of homogeneous carbohydrates and a chemoselective method for construction of the glycosylated peptide.

Accordingly, there remains a need for novel synthetic methods leading to the preparation of normal and transformed PSA glycans and conjugates thereof, and their evaluation in immunologic and therapeutic studies.

SUMMARY OF THE INVENTION

In recognition of the need to provide access to synthetically unavailable PSA glycans and glycopeptides, the present invention, in one aspect, provides novel normal (e.g., dibranched) and transformed (e.g., multibranched) PSA glycans and N-linked peptide conjugates thereof, and methods for the synthesis and use thereof.

In one aspect, the present invention provides compounds having formula (I^A):

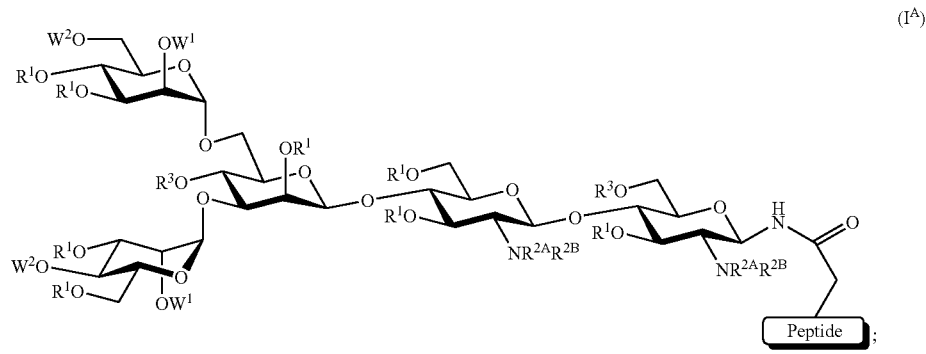

(I^A)

wherein each occurrence of $R^1$ is independently hydrogen or an oxygen protecting group;
each occurrence of $R^{2A}$ and $R^{2B}$ is independently hydrogen or a nitrogen protecting group;
each occurrence of $R^3$ is independently hydrogen, a protecting group or a carbohydrate domain comprising a saccharide moiety having the structure:

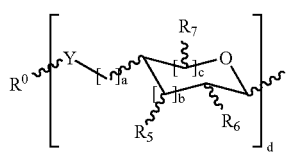

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;
each occurrence of $W^1$ and $W^2$ is independently $R^1$, $R^3$ or a moiety having the structure:

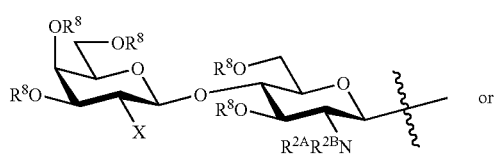 or 

-continued wherein X is $-OR^1$ or $-NR^{2A}R^{2B}$; and each occurrence of $R^8$ is independently $R^1$ or a sialic acid moiety;

and wherein the peptide which is either identical to or closely related to that of PSA near the N-glycosylation site, said peptide having the structure:

(SEQ ID NO: 1)

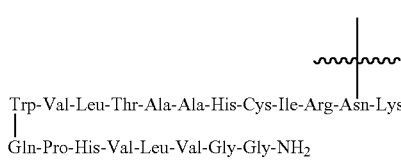

Trp-Val-Leu-Thr-Ala-Ala-His-Cys-Ile-Arg-Asn-Lys-Ser-NH₂;
|
Gln-Pro-His-Val-Leu-Val-Gly-Gly-NH₂ or truncated, elongated or derivatized version thereof; wherein any one or more of the amino acid residues may bear one or more protecting groups;
with the proviso that the compound is not a naturally occurring PSA glycoprotein.

In certain embodiments, the present invention provides compounds having formula (II^A):

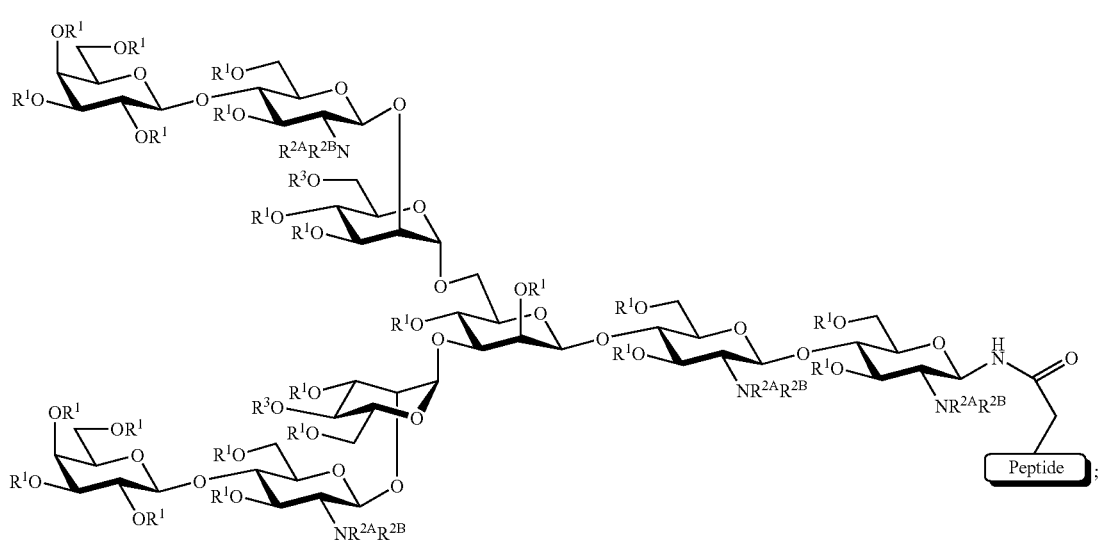

(II^A)

wherein $R^1$, $R^{2A}$, $R^{2B}$, $R^3$ and the peptide moiety are as defined generally above and in classes and subclasses herein.

In certain embodiments, for the constructs depicted above, each occurrence of $R^1$ is independently hydrogen, alkyl, alkenyl, alkynyl, heteroalkyl, heteroalkenyl, heteroalkynyl, aryl, heteroaryl, alkylaryl, alkylheteroaryl, —Si($R^{1A}$)$_3$, —C(=O)$R^{1A}$, —C(=S)$R^{1A}$, —C(=N$R^{1A}$)$R^{1B}$, —SO$_2R^{1A}$, wherein $R^{1A}$ and $R^{1B}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{1C}$ or —Z$R^{1C}$, wherein Z is —O—, —S—, —N$R^{1D}$, wherein each occurrence of $R^{1C}$ and $R^{1D}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety.

In certain embodiments, for the constructs depicted above, each occurrence of $R^{2A}$ and $R^{2B}$ is independently hydrogen, alkyl, alkenyl, —C(=O)$R^{2C}$, —C(=O)O$R^{2C}$, —S$R^{2C}$, SO$_2R^{2C}$, or $R^{2A}$ and $R^{2B}$, taken together with the nitrogen atom to which they are attached, form a substituted or unsubstituted heterocyclic or heteroaryl moiety; wherein each occurrence of $R^{2C}$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{2D}$ or —Z$R^{2D}$, wherein Z is —O—, —S—, —N$R^{2E}$, wherein each occurrence of $R^{2D}$ and $R^{2E}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety.

In certain embodiments, compounds of formula (II$^A$) comprise a normal PSA glycan and each occurrence of $R^3$ is hydrogen or a protecting group.

In certain other embodiments, compounds of formula (II$^A$) comprise a transformed PSA glycan and either or both occurrences of $R^3$ comprise a saccharide moiety having the structure:

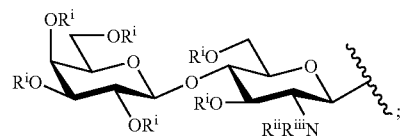

wherein each occurrence of $R^1$ is independently hydrogen, alkyl, alkenyl, alkynyl, heteroalkyl, heteroalkenyl, heteroalkynyl, aryl, heteroaryl, alkylaryl, alkylheteroaryl, —Si($R^{1A}$)$_3$, —C(=O)$R^{iA}$, —C(=S)$R^{iA}$, —C(=N$R^{iA}$)$R^{iB}$, —SO$_2R^{iA}$, wherein $R^{iA}$ and $R^{iB}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{iC}$ or —Z$R^{iC}$, wherein Z is —O—, —S—, —N$R^{iD}$, wherein each occurrence of $R^{iC}$ and $R^{iD}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety; and each occurrence of $R^{ii}$ and $R^{iii}$ is independently hydrogen, alkyl, alkenyl, —C(=O)$R^{iiA}$, —C(=O)O$R^{iiA}$, —S$R^{iiA}$, SO$_2R^{iiA}$, or $R^{ii}$ and $R^{iii}$, taken together with the nitrogen atom to which they are attached, form a substituted or unsubstituted heterocyclic or heteroaryl moiety; wherein each occurrence of $R^{iiA}$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{iiB}$ or —Z$R^{iiB}$, wherein Z is —O—, —S—, —N$R^{iiC}$, wherein each occurrence of $R^{iiB}$ and $R^{iiC}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety.

In certain embodiments, compounds of formula (II$^A$) have the structure:

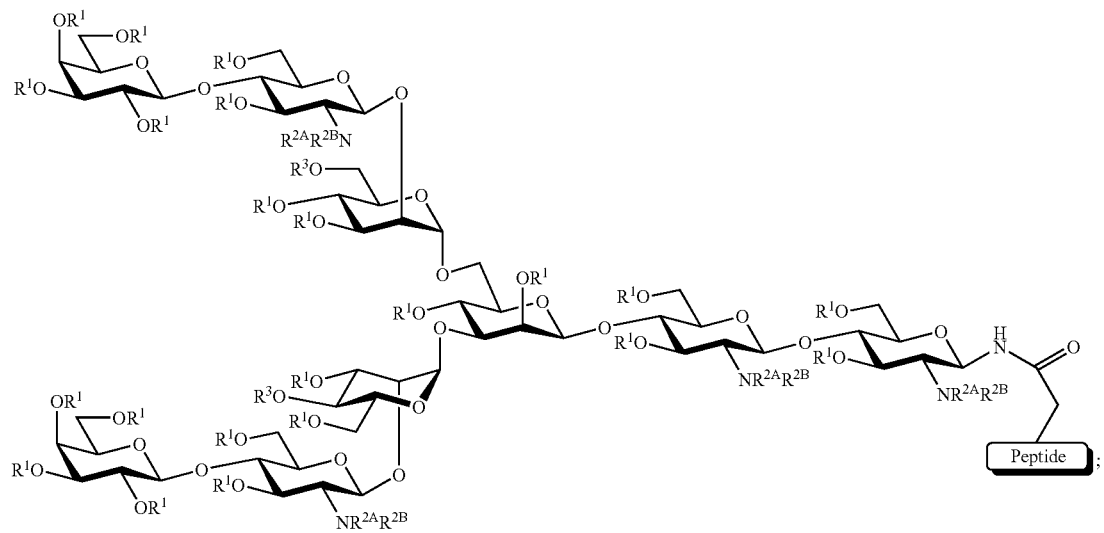

wherein the peptide and each occurrence of $R^1$, $R^{2A}$ and $R^{2B}$ are as defined generally above and in classes and subclasses herein; and each occurrence of $R^3$ is independently hydrogen, alkyl, alkenyl, alkynyl, heteroalkyl, heteroalkenyl, heteroalkynyl, aryl, heteroaryl, alkylaryl, alkylheteroaryl, $-Si(R^{3A})_3$, $-C(=O)R^{3A}$, $-C(=S)R^{3A}$, $C(=NR^{3A})R^{3B}$, $SO_2R^{3A}$, wherein $R^{3A}$ and $R^{3B}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, $-C(=O)R^{3C}$ or $-ZR^{3C}$, wherein Z is $-O-$, $-S-$, $-NR^{3D}$, wherein each occurrence of $R^{3C}$ and $R^{3D}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety.

In certain embodiments, compounds of formula $(II^A)$ have the structure:

wherein the peptide and each occurrence of $R^1$, $R^{2A}$ and $R^{2B}$ are as defined generally above and in classes and subclasses herein; and each occurrence of $R^3$ is independently hydrogen, alkyl, alkenyl, alkynyl, heteroalkyl, heteroalkenyl, heteroalkynyl, aryl, heteroaryl, alkylaryl, alkylheteroaryl, $-S(R^{3A})_3$, $-C(=O)R^{3A}$, $-C(=S)R^{3A}$, $-C(=NR^{3A})R^{3B}$, $-SO_2R^{3A}$, wherein $R^{3A}$ and $R^{3B}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, $-C(=O)R^{3C}$ or $-ZR^{3C}$, wherein Z is $-O-$, $-S-$, $-NR^{3D}$, wherein each occurrence of $R^{3C}$ and $R^{3D}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety.

In certain embodiments, compounds of formula $(II^A)$ have the structure:

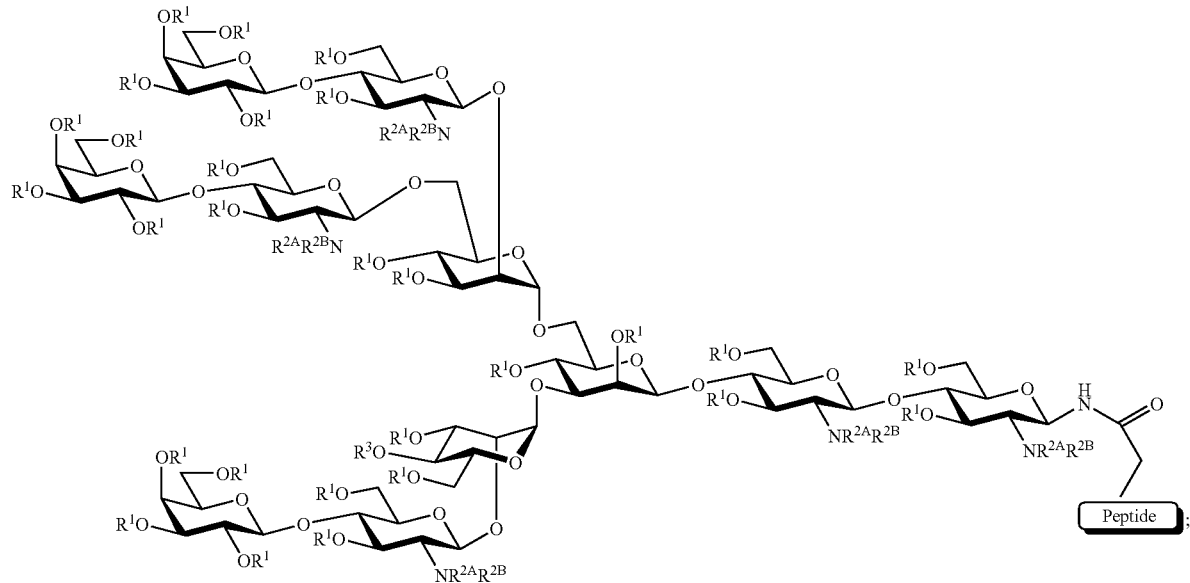

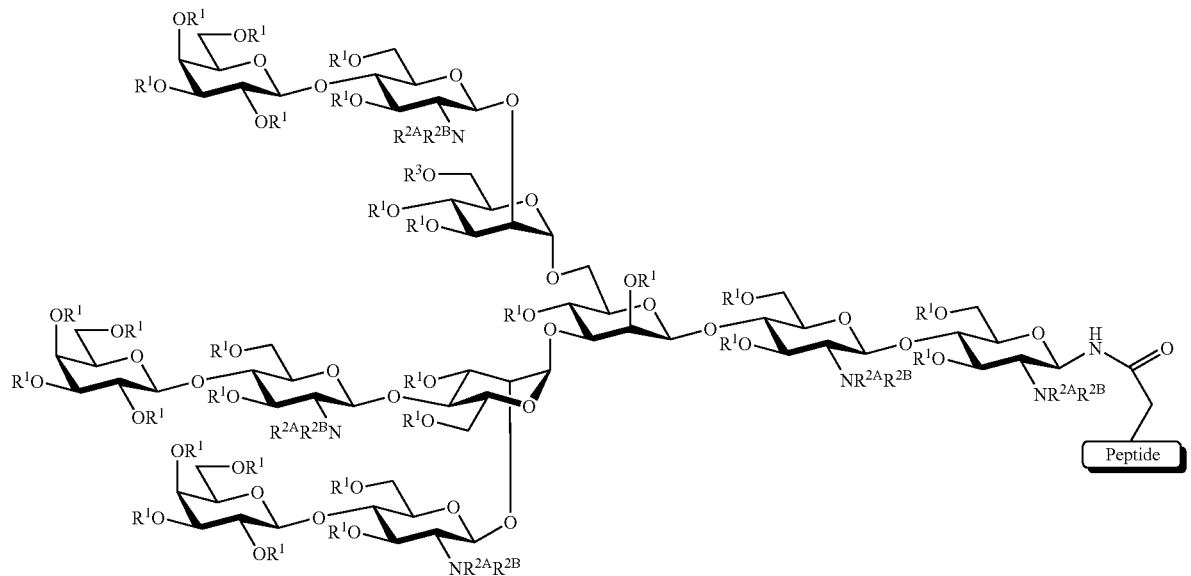

wherein the peptide and each occurrence of $R^1$, $R^{2A}$ and $R^{2B}$ are as defined generally above and in classes and subclasses herein; and each occurrence of $R^3$ is independently hydrogen, alkyl, alkenyl, alkynyl, heteroalkyl, heteroalkenyl, heteroalkynyl, aryl, heteroaryl, alkylaryl, alkylheteroaryl, —Si$(R^{3A})_3$, —C(=O)$R^{3A}$, C(=S)$R^{3A}$, —C(=N$R^{3A}$)$R^{3B}$, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety.

In certain embodiments, compounds of formula (II$^4$) have the structure:

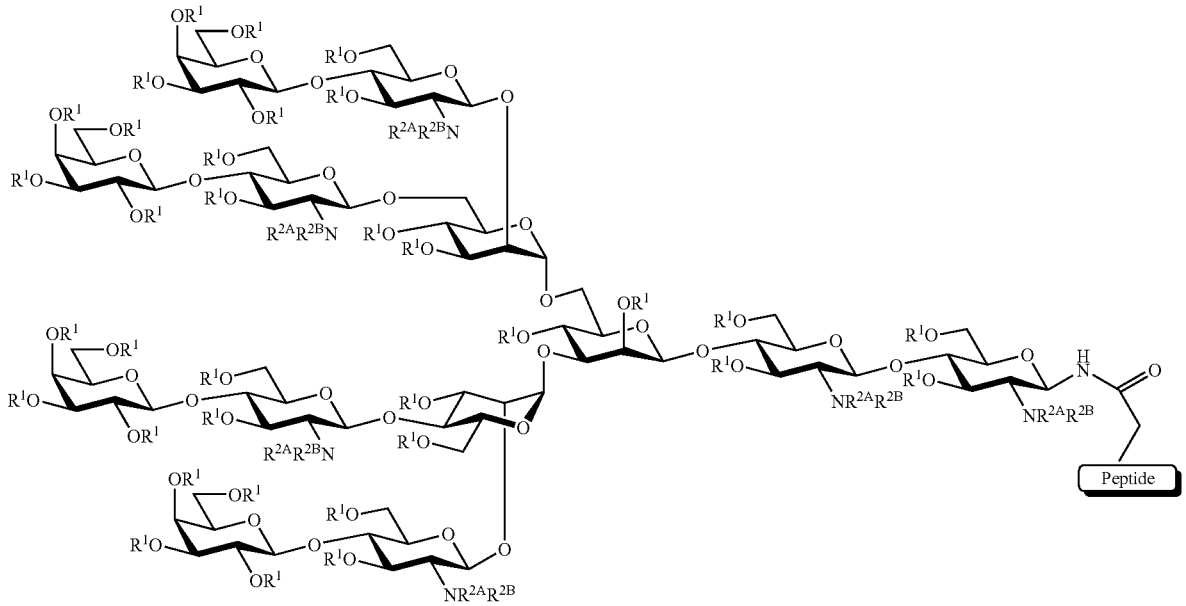

SO$_2R^{3A}$, wherein $R^{3A}$ and $R^{3B}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{3C}$ or —Z$R^{3C}$, wherein Z is —O—, —S—, —N$R^{3D}$, wherein each occurrence of $R^{3C}$ and $R^{3D}$ is independently hydrogen, wherein the peptide and each occurrene of $R^1$, $R^{2A}$ and $R^{2B}$ are as defined generally above and in classes and subclasses herein.

In certain embodiments, for the glycopeptide compounds described above, the peptide is attached to the glycan portion of the compound through an Asparagine residue (Asn). In certain exemplary embodiments, the peptide has the following structure:

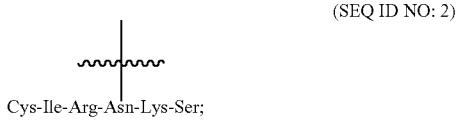

Cys-Ile-Arg-Asn-Lys-Ser; (SEQ ID NO: 2)

wherein any of the amino acid residues may bear one or more protecting groups. In certain other exemplary embodiments, the peptide has the following structure:

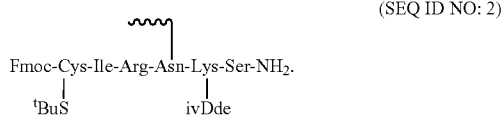

Fmoc-Cys-Ile-Arg-Asn-Lys-Ser-NH$_2$. (SEQ ID NO: 2)
$^t$BuS         ivDde

In yet other exemplary embodiments, the peptide has the following structure:

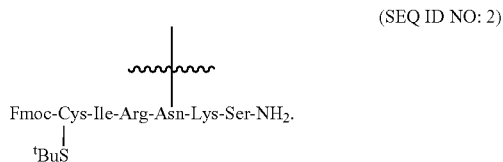

Fmoc-Cys-Ile-Arg-Asn-Lys-Ser-NH$_2$. (SEQ ID NO: 2)
$^t$BuS

In further exemplary embodiments, the peptide has the following structure:

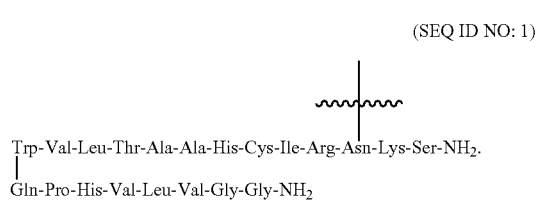

Trp-Val-Leu-Thr-Ala-Ala-His-Cys-Ile-Arg-Asn-Lys-Ser-NH$_2$. (SEQ ID NO: 1)
Gln-Pro-His-Val-Leu-Val-Gly-Gly-NH$_2$

In another aspect, the invention provides an antibody or antibody fragment which is specific to any one of the inventive carbohydrate antigens (independently of the others) comprising a carbohydrate domain having the structure:

wherein each occurrence of $R^1$ is independently hydrogen or an oxygen protecting group;

each occurrence of $R^{2A}$ and $R^{2B}$ is independently hydrogen or a nitrogen protecting group;

each occurrence of $R^3$ is independently hydrogen, a protecting group or a carbohydrate domain comprising a saccharide moiety having the structure:

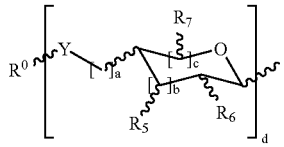

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;

each occurrence of $W_1$ and $W_2$ is independently $R^1$, $R^3$ or a moiety having the structure:

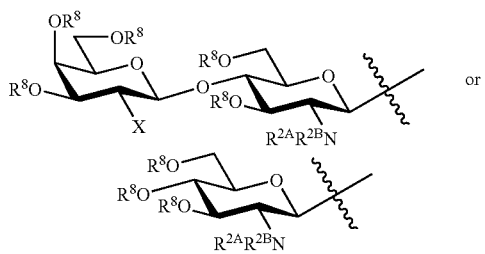

or wherein X is $-OR^1$ or $-NR^{2A}R^{2B}$; and each occurrence of $R^8$ is independently $R^1$ or a sialic acid moiety;

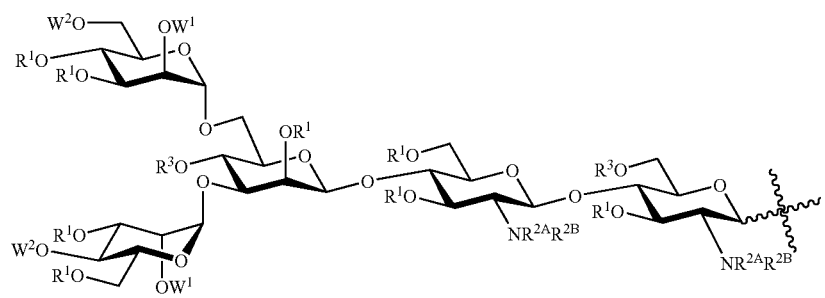

and wherein said antibody is a purified polyclonal antibody or a monoclonal antibody. In certain embodiments, the antibody is a monoclonal antibody. In certain other embodiments, the carbohydrate domain has the structure:

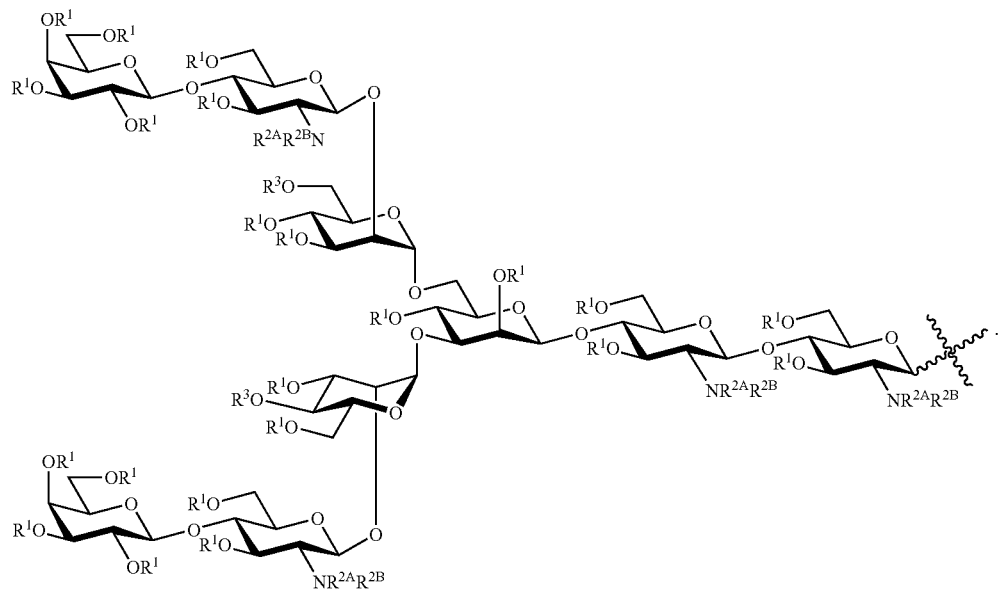

In yet other embodiments, the carbohydrate antigen has the structure:

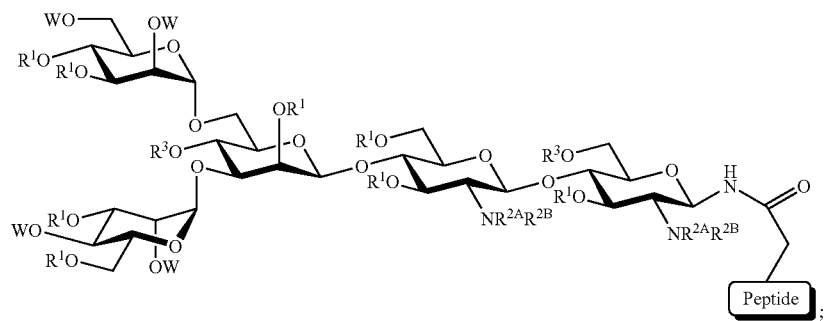

wherein the peptide has a structure either identical to or closely related to that of PSA near the N-glycosylation site. In yet other embodiments, the carbohydrate antigen has the structure:

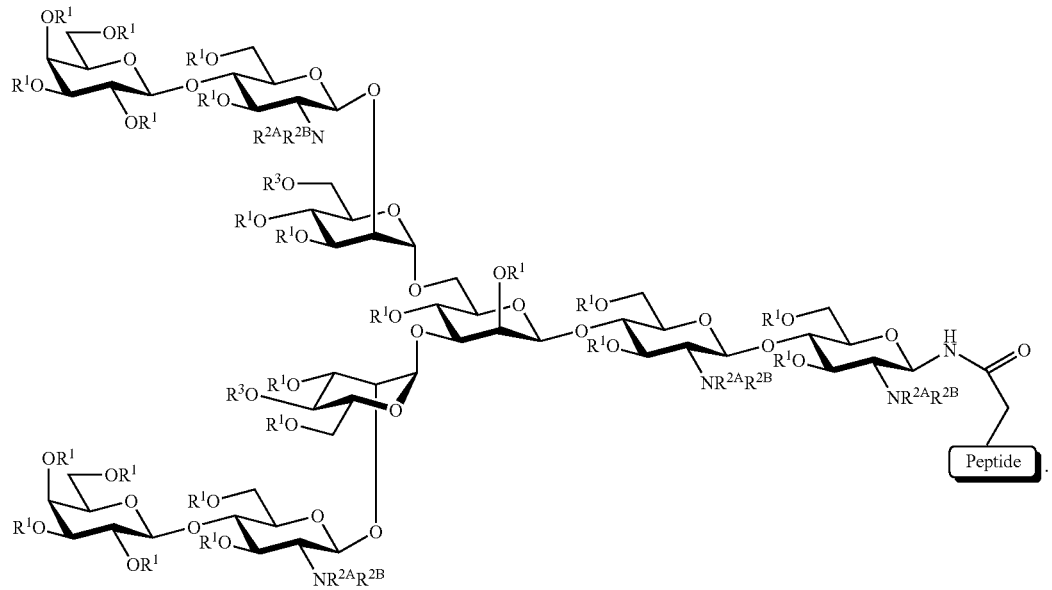

DEFINITIONS

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75th Ed., inside cover, and specific functional groups are defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position unless otherwise indicated. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment of cancer, or in the inducement of antibodies, as described herein. The term "stable", as used herein, preferably refers to compounds which possess stability sufficient to allow manufacture and which maintain the integrity of the compound for a sufficient period of time to be useful for the purposes detailed herein.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substituents.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure NH$_2$R'—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. It will also be appreciated that aryl and heteroaryl moieties, as defined herein may be attached via an aliphatic, alicyclic, heteroaliphatic, heteroalicyclic, alkyl or heteroalkyl moiety and thus also include -(aliphatic)aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and -heteroalkyl)heteroaryl moieties. Thus, as used herein, the phrases "aryl or heteroaryl" and "aryl, heteroaryl, -(aliphatic)aryl, -(heteroaliphatic)aryl, -(aliphatic)heteroaryl, -(heteroaliphatic)heteroaryl, -alkyl)aryl, -(heteroalkyl)aryl, -(heteroalkyl)aryl, and -heteroalkyl)heteroaryl" are interchangeable. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted with substituents including, but not limited to aliphatic; heteroaliphatic; aryl; heteroaryl; alkylaryl; alkylheteroaryl; alkoxy; aryloxy; heteroalkoxy; heteroaryloxy;

alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroalicyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein.

Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substitutents described above and herein may be substituted or unsubstituted. Additional examples or generally applicable substituents are illustrated by the specific embodiments shown in the Examples, which are described herein.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heteroalicyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aryl", "heteroaryl" and the like encompass both substituted and unsubstituted groups.

It will be appreciated that additional examples of generally applicable substitutents are illustrated by the specific embodiments shown in the Examples which are described herein, but are not limited to these Examples.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the prodrugs, are known and may be adapted to the present invention. Certain exemplary pharmaceutical compositions and pharmaceutically acceptable derivatives will be discussed in more detail herein below.

By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably non-toxic reagents that do not attack the other functional groups; the protecting group forms a readily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM(methoxymethyl ether), MTM(m-ethylthiomethyl ether), BOM(benzyloxymethyl ether), PMBM or MPM(p-methoxybenzyloxymethyl ether), to name a few), substituted ethyl ethers, substituted benzyl ethers, silyl ethers (e.g., TMS(trimethylsilyl ether), TES(tri-ethylsilylether), TIPS(triisopropylsilyl ether), TBDMS(t-butyldimethylsilyl ether), tribenzyl silyl ether, TBDPS(t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

As used herein, the term "adjuvant" or "immunogenic stimulant" refers to a moiety, which, when co-administered with an immunogen, enhances the immunogenicity of the immunogen. Specifically, in certain embodiments, immunogenicity of the inventive PSA compounds can be significantly improved if the immunizing agent(s) (e.g., PSA glycan and/or glycopeptide(s)) and/or composition thereof is, regardless of administration format, co-immunized with an adjuvant. Commonly, adjuvants are used as an 0.05 to 1.0 percent solution in phosphate-buffered saline. Adjuvants enhance the immunogenicity of an immunogen but are not necessarily immunogenic themselves. Adjuvants may act by retaining the immunogen locally near the site of administration to produce a depot effect facilitating a slow, sustained release of immunogen to cells of the immune system. Adjuvants can also attract cells of the immune system to an immunogen depot and stimulate such cells to elicit immune responses. As such, embodiments of this invention encompass compositions further comprising adjuvants.

Adjuvants have been used for many years to improve the host immune responses to, for example, vaccines. Intrinsic adjuvants (such as lipopolysaccharides) normally are the components of killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects making them unsuitable for use in humans and many animals. Indeed, aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established. Notwithstanding, it does have limitations. For example, alum is ineffective for influenza vaccination and inconsistently elicits a cell mediated immune response with other immunogens. The antibodies elicited by alum-adjuvanted antigens are mainly of the IgG1 isotype in the mouse, which may not be optimal for protection by some vaccinal agents. In addition to adjuvants used for therapeutic purposes (e.g., vaccines), other adjuvants may be used for raising antibodies in animals, which antibodies may be used, for example, in diagnostic and immunoassays. Examples of such adjuvants include, but are not limited to, bacteria or liposomes. For example, suitable adjuvants include but are not limited to, saponin adjuvants (e.g., GPI-0100), *Salmonella minnesota* cells, bacille Calmette-Guerin or QS21.

A wide range of extrinsic adjuvants can provoke potent immune responses to immunogens. These include saponins complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

The term "natural amino acid" as used herein refers to any one of the common, naturally occurring L-amino acids found in naturally occurring proteins: glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

The term "unnatural amino acid" as used herein refers to all amino acids which are not natural amino acids. This includes, for example, α-, β-, D-, L-amino acid residues, and compounds of the general formula

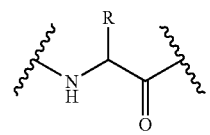

wherein the side chain R is other than the amino acid side chains occurring in nature.

More generally, the term "amino acid", as used herein, encompasses natural amino acids and unnatural amino acids.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof; or purified versions thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. In certain embodiments, the biological sample is obtained from the prostate epithelium. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques. In certain embodiments, the biological sample is taken from a male human subject. In certain exemplary embodiments, the biological samle has been processed so that the PSA glycan concentration out of the total glycan concentration in the original sample is increased. In certain exemplary embodiments, the sample may be purified serum PSA, purified PSA glycoprotein, purified PSA glycoprotein that has undergone sialidase digestion, purified PSA glycans obtained from deglycosylated PSA glycoprotein. It will be appreciated that the term "biological sample", as used herein, encompasses any combination of PSA materials obtained from any biological sources (e.g., as detailed above) or by any processes that may be used to obtain PSA glycan from the original sample (e.g., extraction, purification, glycoprotein deglycosylation, sialidase digestion, etc.).

As used herein, the term "isolated", when applied to the compounds of the present invention, refers to such compounds that are (i) separated from at least some components with which they are associated in nature or when they are made and/or (ii) produced, prepared or manufactured by the hand of man. In certain embodiments, isolated compounds of the invention are not substantially contaminated with, or otherwise in contact with any other compound. Accordingly, the present invention provides compounds of formula (I) and/or (II) in substantially pure form, i.e., in a purity of greater than about 95% by weight (not including $H_2O$ or salt content, which is to be expected, for example, from lyophilized peptides and glycopeptides), preferably greater than about 98%, and more preferably greater than about 99% by weight. In one aspect, the impurity in contact with a compound of formula (I) and/or (II) of the invention is an organic chemical, e.g., an organic solvent. In another aspect, the impurity in contact with a compound of formula (I) and/or (II) is another compound of formula (I) and/or (II). Thus, in one aspect, the present invention provides a compound of formula (I) and/or (II) that is pure in that it is not in contact with another compound of formula (I) and/or (II).

As used herein, the term "PSA glycan" refers to the carbohydrate domain of PSA. More specifically, PSA glycan designates the carbohydrate portion of compounds of formula (I) and/or (II) described herein. In certain embodiments, the term refers to compounds of formula (I) where $R^4$ is a moiety other than a peptide, protein or other polymeric construct.

As used herein, the term "PSA glycopeptide" refers to compounds of formula (I) and/or (II) where $R^4$ comprises a peptide moiety covalently linked to the rest of the construct either directly (e.g., through N or O) or through a crosslinker.

As used herein, the term "normal PSA" refers to PSA glycoform(s) expressed in non-malignant prostate epithelial cells (e.g., PSA glycoform(s) that is/are present in subjects suffering from benign pathology of the prostate or in non-malignant cultured prostate epithelial cells). In certain embodiments, normal PSA refers to compounds of formula (I) and/or (II) of the dibranched type (e.g., compounds of formula (I) where each occurrence of $R^3$ and $W^2$ is independently hydrogen or a protecting group; or compounds of formula (II) where each occurrence of $R^3$ is hydrogen or a protecting group). Similarly, "normal PSA glycan" refers to the carbohydrate domain of normal PSA (e.g., compounds of formula (I) where each occurrence of $R^3$ and $W^2$ is independently hydrogen or a protecting group; or compounds of formula (II) where each occurrence of $R^3$ is hydrogen or a protecting group and $R^4$ is a moiety other than a peptide, protein or other polymeric construct). In addition, "normal PSA glycopeptide" refers to normal PSA, as defined above, covalently attached to a peptide moiety (e.g., compounds of formula ($I^4$) where each occurrence of $R^3$ and $W^2$ is independently hydrogen or a protecting group; or compounds of formula ($II^4$) where each occurrence of $R^3$ is hydrogen or a protecting group; or compounds of formula (I) or (II) (where each occurrence of $R^3$ and $W^2$ are as defined for ($I^4$) and ($II^4$) directly above) where $R^4$ comprises a peptide moiety covalently linked to the rest of the construct either directly (e.g., through N or O) or through a crosslinker).

As used herein, the term "transformed PSA" refers to PSA glycoform(s) expressed in malignant prostate epithelial cells (e.g., PSA glycoform(s) that is/are present in subjects suffering from an adenocarcinoma of the prostate or in cultured prostate cancer cells (e.g., LnCaP cell line)). In certain embodiments, transformed PSA refers to compounds of formula (I) and/or (II) of the multi-branched type (e.g., compounds of formula (I) where at least three occurrences of $W^1$ and $W^2$ independently comprise a moiety having the structure:

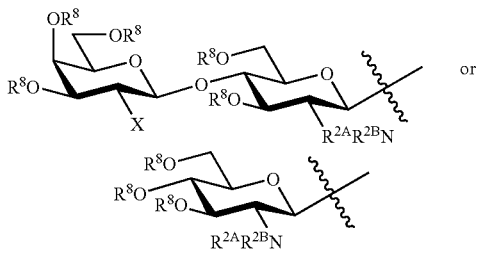

wherein X is —OR$^1$ or —NR$^{2A}$R$^{2B}$; and each occurrence of R$^8$ is independently R$^1$ or a sialic acid moiety; or compounds of formula (II) where at least one occurrence of R$^3$ comprises a carbohydrate domain comprising a saccharide moiety having the structure:

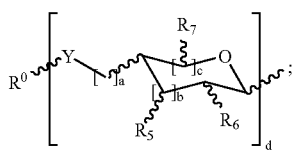

wherein R$^0$, R$^5$-R$^7$, a, b, c and d are as defined in classes and subclasses herein). Similarly, "transformed PSA glycan" refers to the carbohydrate domain of transformed PSA where R$^4$ is a moiety other than a peptide, protein or other polymeric construct. In addition, "transformed PSA glycopeptide" refers to transformed PSA, as defined above, covalently attached to a peptide moiety (e.g., compounds of formula (I$^4$) where at least three occurrences of W$^1$ and W$^2$ independently comprise a moiety having the structure:

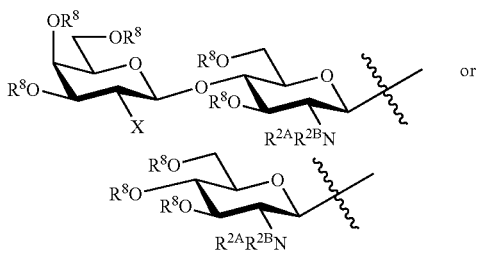

wherein X is —OR$^1$ or —NR$^{2A}$R$^{2B}$; and each occurrence of R$^8$ is independently R$^1$ or a sialic acid moiety; compounds of formula (II$^4$) where at least one occurrence of R$^3$ comprises a carbohydrate domain comprising a saccharide moiety having the structure:

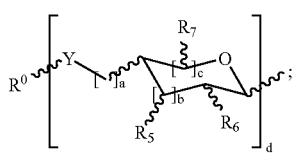

wherein R$^0$, R$^5$-R$^7$, a, b, c and d are as defined in classes and subclasses herein; or compounds of formula (I) or (II) (where each occurrence of R$^3$ and W$^2$ are as defined for (I$^4$) and (II$^4$) directly above) where R$^4$ comprises a peptide moiety covalently linked to the rest of the construct either directly (e.g., through N or O) or through a crosslinker).

As used herein, the term "eliciting an immune response" is defined as initiating, triggering, causing, enhancing, improving or augmenting any response of the immune system, for example, of either a humoral nature. The initiation or enhancement of an immune response can be assessed using assays known to those skilled in the art including, but not limited to, antibody assays (for example ELISA assays). In certain exemplary embodiments, the PSA glycans and glycopeptides of the present invention, and the method of the present invention essentially trigger or enhance a humoral immune response.

BRIEF DESCRIPTION OF THE DRAWING

FIG. 1 depicts structures of PSA glycopeptides 1-3. 1: "Normal" dibranched PSA fragment with N-acetyllactosamines at 2,2'. 2: tribranched at 2,4,2' positions. 3: tetrabranched at 2,4,2',6'.
FIG. 5 depicts potential PSA diagnostic constructs.

DETAILED DESCRIPTION OF CERTAIN PREFERRED EMBODIMENTS OF THE INVENTION

Figure 2:
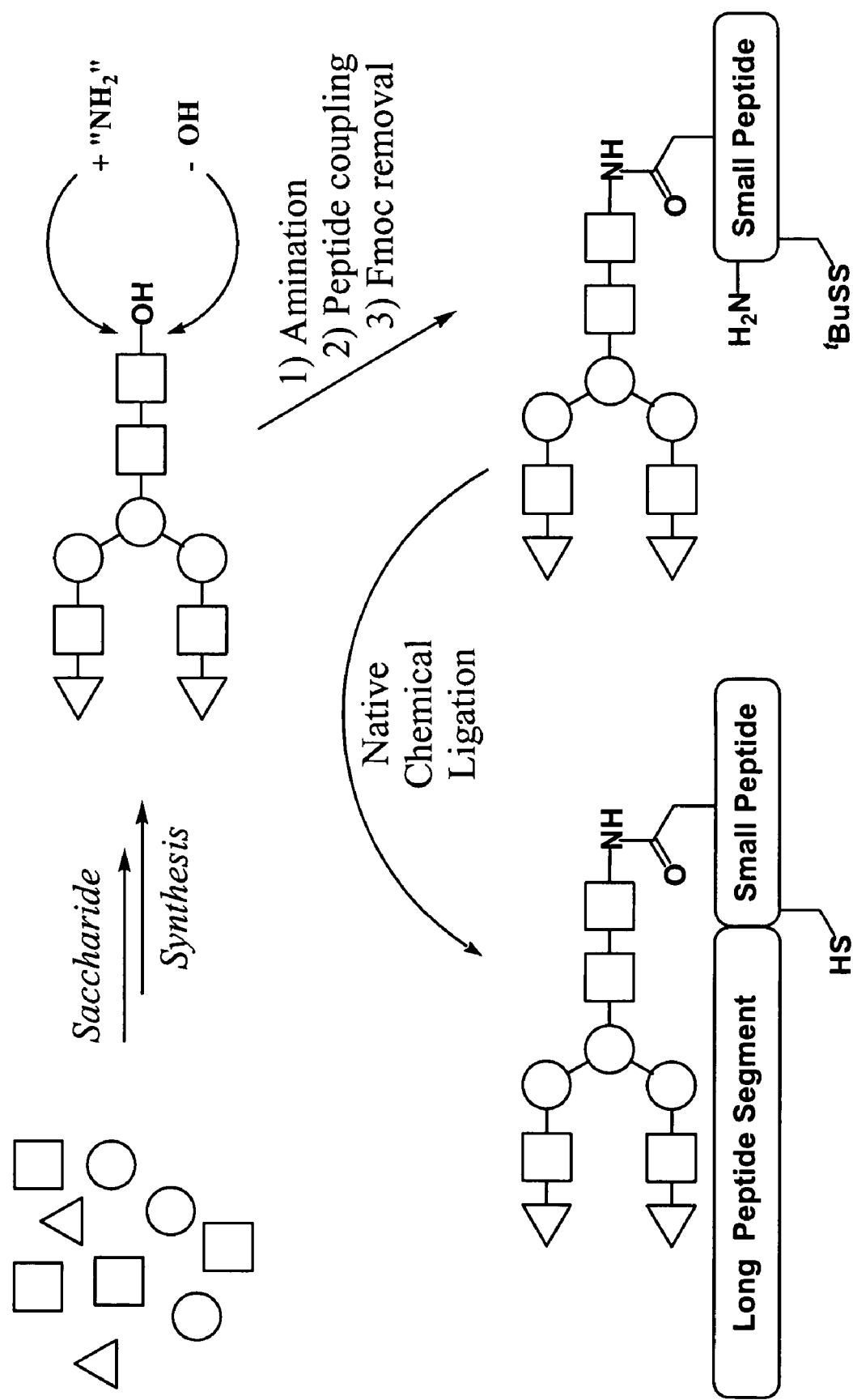
FIG. 2 depicts a synthetic approach for the chemical synthesis of homogeneous N-linked glycopeptides.
Figure 3:
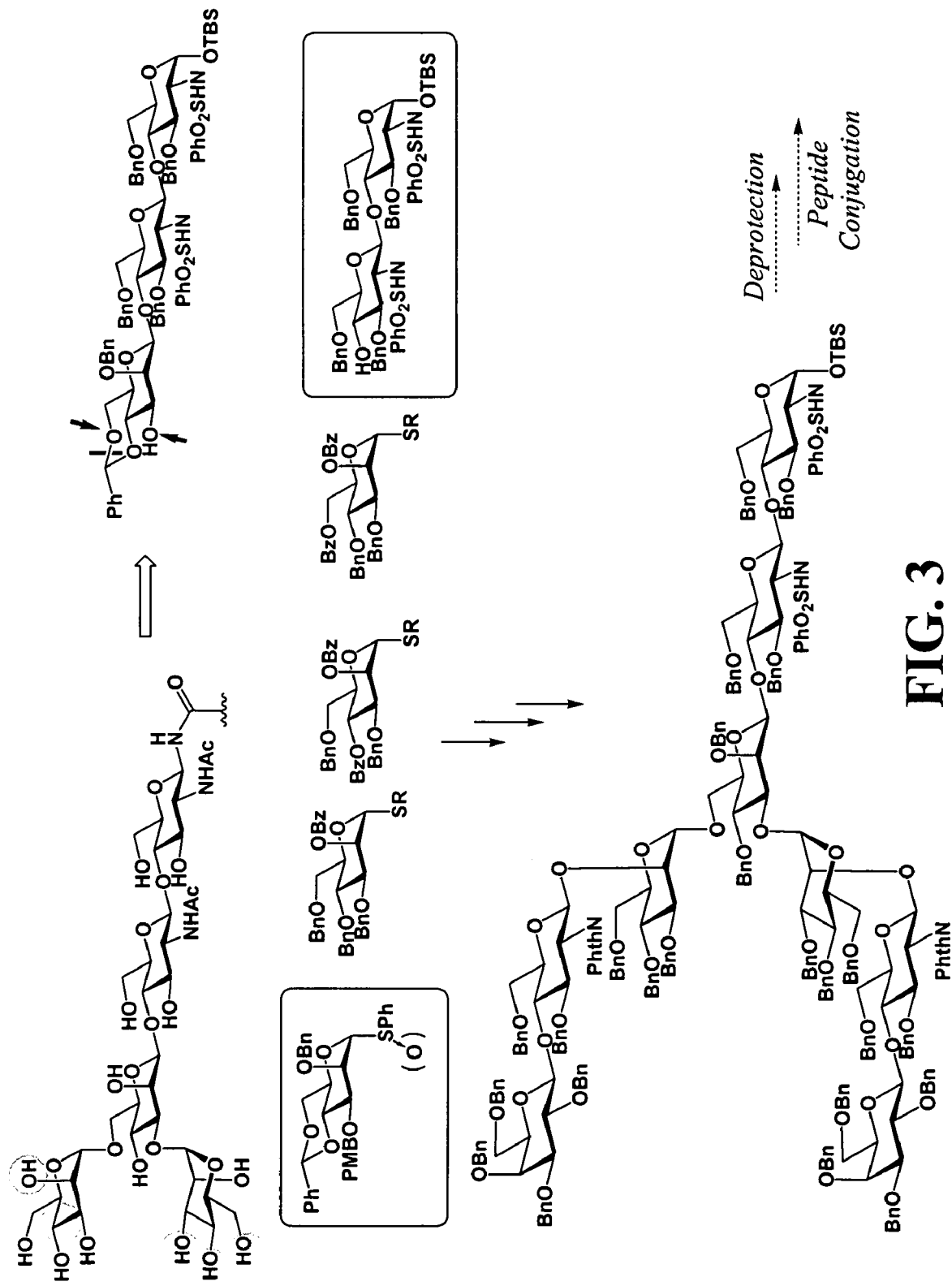
FIG. 3 depicts a synthetic approach for the chemical synthesis of "asymmetrically" substituted oligosaccharides.
Figure 4:
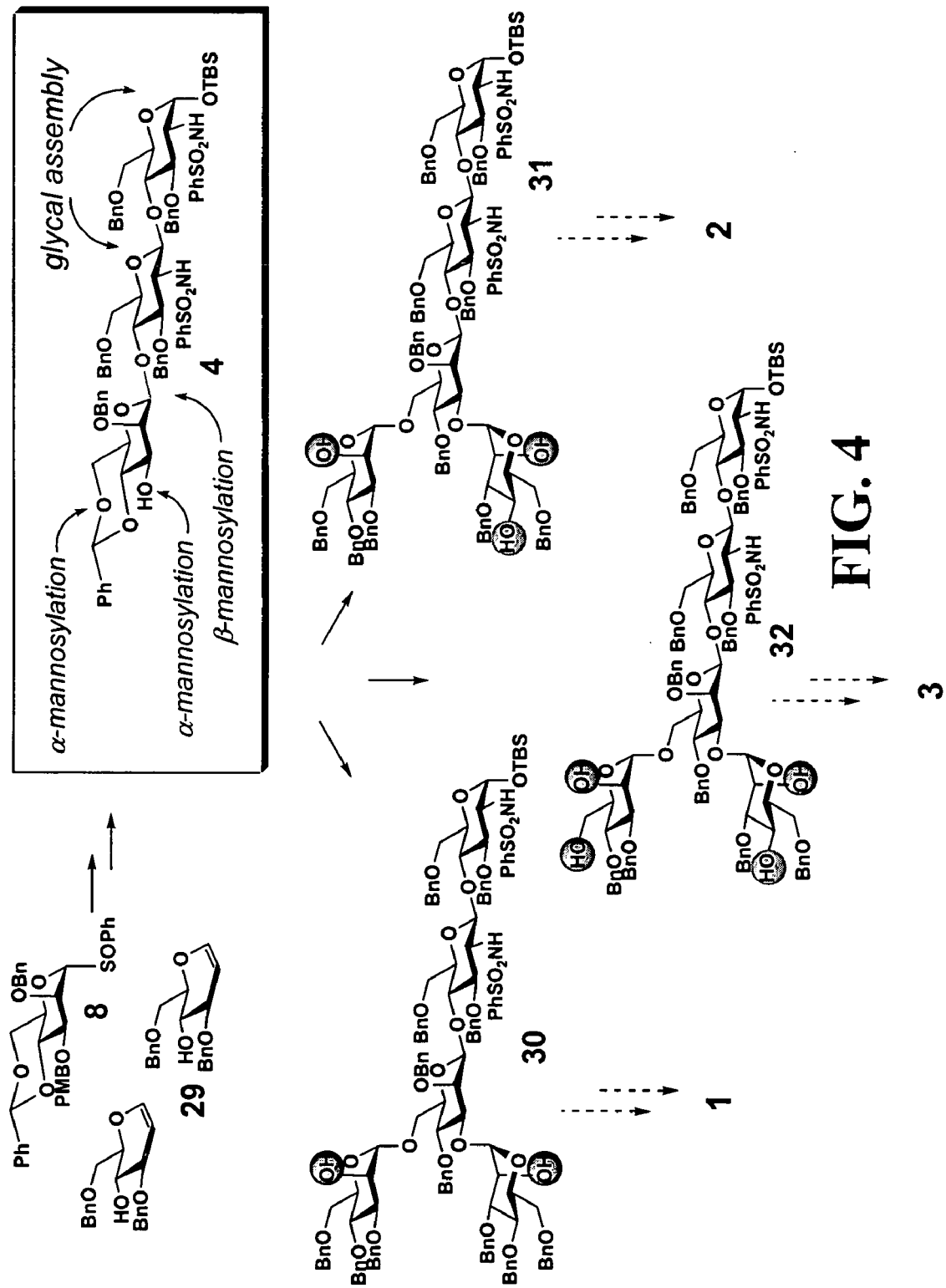
FIG. 4 depicts a retrosynthetic approach for the preparation of normal and transformed PSA glycopeptides 1-3.

As discussed above, the desire to develop improved methods for the preparation of synthetic vaccines has led to increased research efforts directed toward the synthesis of naturally occurring complex carbohydrate antigens, as well as novel complex structures (e.g., glycopeptides) incorporating these antigenic structures. As is often the case during the course of any such large synthetic undertaking, improved synthetic methods are often developed that can be applied universally. In particular, synthetic studies of naturally occurring antigenic structures has led to the development of novel methodologies enabling the development of heretofore unavailable synthetic carbohydrate-based vaccines. For a review, see Danishefsky, S. J.; Allen, J. R., Angew. Chem. Int. Ed. Engl. 2000, 39, 836-863, and references cited therein.

Significantly, the present invention provides novel methodologies for the synthesis of complex carbohydrates and related therapeutic compounds (e.g., glycoconjugates and/or glycopeptides). In particular, in the context of synthetic studies developed for the total synthesis of normal and transformed Prostate Specific Antigen (PSA), generalized methodologies were developed for the improved synthesis of complex carbohydrate structures. This general synthetic method encompasses the realization that the incorporation of an amino group at the reducing end of a carbohydrate acceptor allows for accessibility to complex N-linked carbohydrate conjugates. In yet another aspect, the present invention also provides the recognition that for certain protected carbohydrates, the amino carbohydrate moieties can serve as useful precursors that can be utilized ultimately for the synthesis of complex N-linked glycopeptides.

Specific examples, particularly with respect to the total synthesis of N-acetyllactosamine-type glycans and their incorporation into PSA glycopeptide fragments are described in more detail below, along with certain general methodologies developed during the course of these syntheses. It will be appreciated by one of ordinary skill in the art that these examples are not intended to be limiting; rather all equivalents are intended to be incorporated into the scope of the present invention.

1) Inventive Compounds

As mentioned above, the total synthesis of complex antigenic structures has led to significant development in methodologies for complex carbohydrate synthesis. Of particular recent interest is the naturally occurring antigenic structure PSA (See construct 1 in FIG. 1), as well as transformed (e.g., multi-branched) glycoforms thereof (See constructs 2-3 in FIG. 1) which heretofore had not yet been synthesized. As discussed above, it has been suggested that the differentially glycosylated region of transformed PSA could be used as a molecular marker specific for PCa over BPH[27,28].

Thus, in one aspect of the present invention, the synthesis of the complex normal and transformed PSA carbohydrate domains has been achieved and an isolated compound of formula (I) having the structure as shown below is provided:

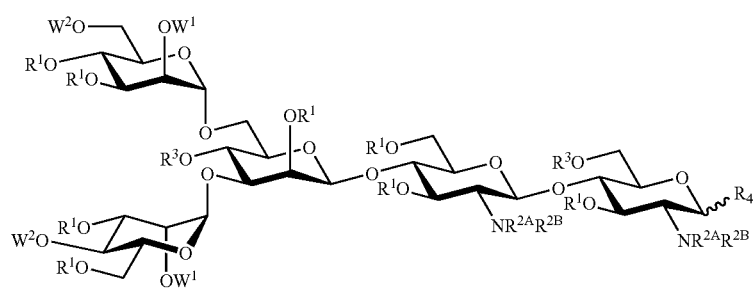

(I)

hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;

each occurrence of $W_1$ and $W_2$ is independently $R^1$, $R^3$ or a moiety having the structure:

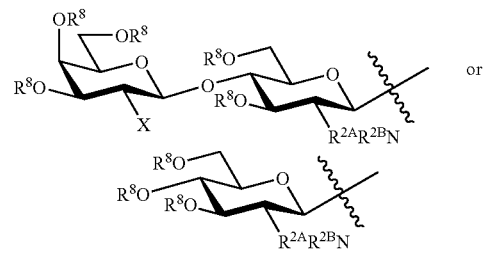

wherein each occurrence of $R^1$ is independently hydrogen or an oxygen protecting group;

each occurrence of $R^{2A}$ and $R^{2B}$ is independently hydrogen or a nitrogen protecting group;

each occurrence of $R^3$ is independently hydrogen, a protecting group or a carbohydrate domain comprising a saccharide moiety having the structure:

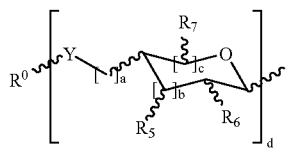

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is wherein X is $-OR^1$ or $-NR^{2A}R^{2B}$; and each occurrence of $R^8$ is independently $R^1$ or a sialic acid moiety;

and wherein $R^4$ is $-OR^{4A}$ or $-NHR^{4A}$; wherein $R^{4A}$ is hydrogen, aliphatic, heteroaliphatic, aryl, heteroaryl, an amino acyl moiety, an amino acyl residue of a peptide, an amino acyl residue of a protein, or $R^{4A}$ comprises a protein, peptide or lipid moiety covalently linked to the rest of the construct, or to the N or O atom to which it is attached, either directly or through a crosslinker.

In certain embodiments, compounds of formula (I) have at least three occurrences of $W^1$ and $W^2$ independently comprising a moiety having the structure:

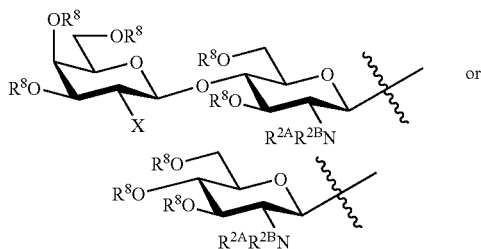

wherein X is —OR$^1$ or —NR$^{2A}$R$^{2B}$; and each occurrence of R$^8$ is independently R$^1$ or a sialic acid moiety.

In certain embodiments, in compounds of formula (I), each occurrence of R$^3$ and W$^2$ is independently hydrogen or a protecting group.

In certain embodiments, a compound of formula (II) having the structure as shown below is provided:

aryl group; wherein each occurrence of R$^5$, R$^6$ and R$^7$ is independently hydrogen, OH, OR$^i$, NR$^{ii}$R$^{iii}$, NHCOR$^i$, F, CH$_2$OH, CH$_2$OR$^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of R$^i$, R$^{ii}$ and R$^{iii}$ is independently hydrogen, a protecting group, CHO, COOR$^{iv}$, or a substituted or unsubstituted linear or branched chain alkyl, acyl, arylalkyl or aryl group, or R$^{ii}$ and R$^{iii}$, taken together with the nitrogen atom to which they are attached, form a substituted or unsubstituted heterocyclic or heteroaryl moiety; and wherein each occurrence of R$^{iv}$ is independently H, or a substituted or unsubstituted linear or branched chain alkyl, arylalkyl or aryl group;

and wherein R$^4$ is —OR$^{4A}$ or —NHR$^{4A}$; wherein R$^{4A}$ is hydrogen, aliphatic, heteroaliphatic, aryl, heteroaryl, an amino acyl moiety, an amino acyl residue of a peptide, an amino acyl residue of a protein, or R$^{4A}$ comprises a protein, peptide or lipid moiety covalently linked to the rest of the (II)

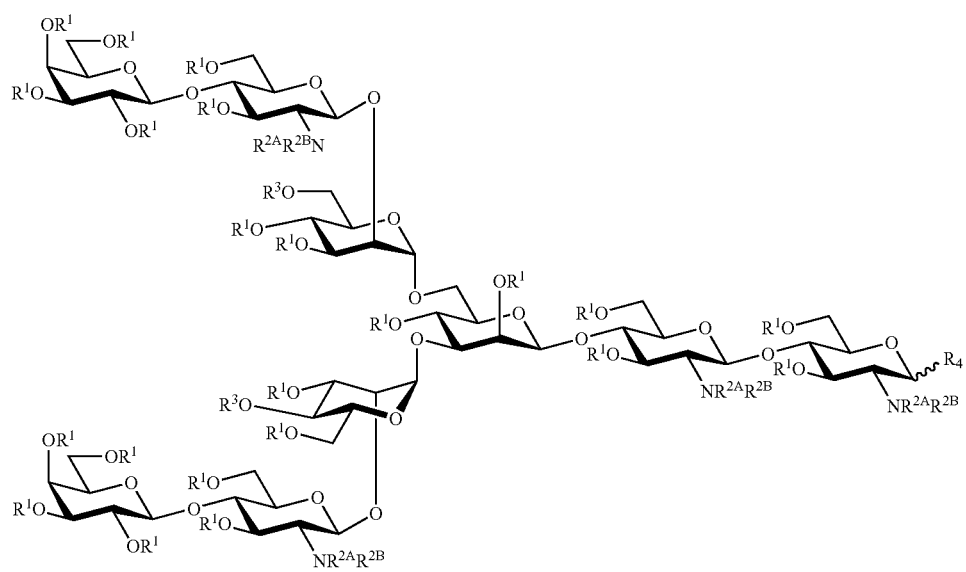

wherein each occurrence of R$^1$ is independently hydrogen or an oxygen protecting group; each occurrence of R$^{2A}$ and R$^{2B}$ is independently hydrogen or a nitrogen protecting group; each occurrence of R$^3$ is independently hydrogen, a protecting group or a carbohydrate domain comprising a saccharide moiety having the structure:

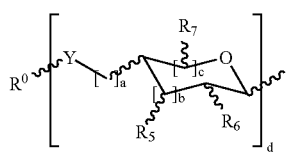

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein R$^0$ is hydrogen, a linear or branched chain alkyl, acyl, arylalkyl or construct, or to the N or O atom to which it is attached, either directly or through a crosslinker.

In certain embodiments, compounds of formula (I) or (II) exclude naturally occurring PSA (e.g., a glycan fragment of naturally occurring PSA glycoprotein).

In certain embodiments, when R4 comprises a peptide, the peptide is either identical to or closely related to that of PSA near the N-glycosylation site. In certain exemplary embodiments, the peptide has the structure:

(SEQ ID NO: 1)

Trp-Val-Leu-Thr-Ala-Ala-His-Cys-Ile-Arg-Asn-Lys-Ser-NH$_2$;

Gln-Pro-His-Val-Leu-Val-Gly-Gly-NH$_2$ or truncated, elongated or derivatized version thereof; wherein any one or more of the amino acid residues may bear one or more protecting groups. For the purpose of the invention, "truncated", refers to a peptide fragment comprising no fewer than about 6 amino acid residues; "elongated", refers to a peptide comprising no more than about 60 amino acid residues; and "derivatized" refers to a peptide in which at least one, but not more than about 2 out of every 10, amino acid residues have been added and/or deleted; and/or in which at least one amino acid residue has been substituted with a natural or non-natural amino acid residue so that the resulting peptide has a sequence identity equal or greater to about 70% with the original peptide.

In certain exemplary embodiments, for compounds of formula (I) or (II) above, each occurrence of $R^1$ is independently an oxygen protecting group. In certain other exemplary embodiments, each occurrence of $R^1$ is independently alkyl, alkenyl, alkynyl, heteroalkyl, heteroalkenyl, heteroalkynyl, aryl, heteroaryl, alkylaryl, alkylheteroaryl, $-Si(R^{1A})_3$, $-C(=O)R^{1A}$, $-C(=S)R^{1A}$, $-C(=NR^{1A})R^{1B}$, $-SO_2R^{1A}$, wherein $R^{1A}$ and $R^{1B}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, $-C(=O)R^{1C}$ or $-ZR^{1C}$, wherein Z is $-O-$, $-S-$, $-NR^{1D}$, wherein each occurrence of $R^{1C}$ and $R^{1D}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In yet other exemplary embodiments, each occurrence of $R^1$ is independently hydrogen, alkylaryl, $-Si(R^{1A})_3$ or $-C(=O)R^{1A}$, wherein $R^{1A}$ is as defined above. In yet other exemplary embodiments, each occurrence of $R^1$ is independently hydrogen, Bn or Bz. In certain other exemplary embodiments, each occurrence of $R^1$ is independently hydrogen.

In certain other exemplary embodiments, for compounds of formula (I) or (II) above, for each occurrence of $-NR^{2A}R^{2B}$, at least one occurrence of $R^{2A}$ or $R^{2B}$ is independently a nitrogen protecting group. In certain other exemplary embodiments, each occurrence of $R^{2A}$ and $R^{2B}$ is independently hydrogen, alkyl, alkenyl, $-C(=O)R^{2C}$, $-C(=O)OR^{2C}$, $-SR^{2C}$, $SO_2R^{2C}$, or $R^{2A}$ and $R^{2B}$, taken together with the nitrogen atom to which they are attached, form a substituted or unsubstituted heterocyclic or heteroaryl moiety; wherein each occurrence of $R^{2C}$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, $-C(=O)R^{2D}$ or $-ZR^{2D}$, wherein Z is $-O-$, $-S-$, $-NR^{2E}$, wherein each occurrence of $R^{2D}$ and $R^{2E}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, for each occurrence of $-NR^{2A}R^{2B}$, at least one occurrence of $R^{2A}$ or $R^{2B}$ is independently $-C(=O)R^{2A}$ or $SO_2R^{2A}$; or $R^{2A}$ and $R^{2B}$, taken together with the nitrogen atom to which they are attached, form a substituted or unsubstituted heterocyclic or heteroaryl moiety. In yet other exemplary embodiments, for each occurrence of $-NR^{2A}R^{2B}$, at least one occurrence of $R^{2A}$ or $R^{2B}$ is independently $-C(=O)R^{2C}$ or $SO_2R^{2C}$ wherein $R^{2C}$ is as defined above, or $R^{2A}$ and $R^{2B}$, taken together with the nitrogen atom to which they are attached, form an azide or a substituted or unsubstituted phthalimide moiety. In yet other exemplary embodiments, for each occurrence of $-NR^{2A}R^{2B}$, at least one occurrence of $R^{2A}$ or $R^{2B}$ is independently acyl, $-SO_2Ph$ or $R^{2A}$ and $R^{2B}$, taken together with the nitrogen atom to which they are attached, form an azide or a substituted or unsubstituted phthalimide moiety. In certain other exemplary embodiments, each occurrence of $-NR^{2A}R^{2B}$ is $-NHAc$.

In certain other embodiments, for compounds of formula (II) above, at least one occurrence of $R^3$ is a saccharide moiety having the structure:

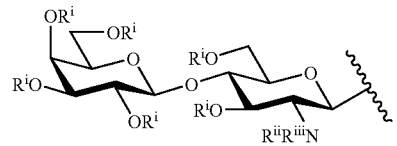

wherein each occurrence of $R^i$ is independently hydrogen, alkyl, alkenyl, alkynyl, heteroalkyl, heteroalkenyl, heteroalkynyl, aryl, heteroaryl, alkylaryl, alkylheteroaryl, $-Si(R^{1A})_3$, $-C(=O)R^{iA}$, $-C(=S)R^{iA}$, $-C(=NR^{iA})R^{iB}$, $-SO_2R^{iA}$, wherein $R^{iA}$ and $R^{iB}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, $-C(=O)R^{iC}$ or $-ZR^{iC}$, wherein Z is $-O-$, $-S-$, $-NR^{iD}$, wherein each occurrence of $R^{iC}$ and $R^{iD}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety; and each occurrence of $R^{ii}$ and $R^{iii}$ is independently hydrogen, alkyl, alkenyl, $-C(=O)R^{iiA}$, $-C(=O)OR^{iiA}$, $SR^{iiA}$, $SO_2R^{iiA}$, or $R^{ii}$ and $R^{iii}$, taken together with the nitrogen atom to which they are attached, form a substituted or unsubstituted heterocyclic or heteroaryl moiety; wherein each occurrence of $R^{iiA}$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, $-C(=O)R^{iiB}$ or $-ZR^{iiB}$, wherein Z is $-O-$, $-S-$, $-NR^{iiC}$, wherein each occurrence of $R^{iiB}$ and $R^{iiC}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety.

In certain other embodiments, for compounds of formula (II) above, both occurrences of $R^3$ is independently a saccharide moiety having the structure:

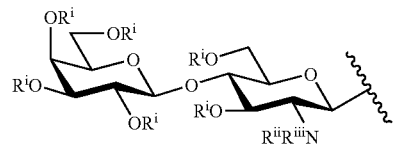

wherein $R^i$, $R^{ii}$ and $R^{iii}$ are as defined above.

In yet other exemplary embodiments, for compounds of formula (II) above, when either or both occurrences of $R^3$ is the disaccharide moiety depicted directly above, each occurrence of $R^i$ is independently hydrogen, alkylaryl, —Si($R^{iA}$)$_3$ or —C(=O)$R^{iA}$, wherein $R^{iA}$ is as defined above. In yet other exemplary embodiments, each occurrence of $R^i$ is independently hydrogen, Bn or Bz. In certain other exemplary embodiments, each occurrence of $R^i$ is independently hydrogen.

In certain other embodiments, for compounds of formula (II) above, when either or both occurrences of $R^3$ is the disaccharide moiety depicted above, at least one occurrence of $R^{ii}$ or $R^{iii}$ is independently —C(=O)$R^{iiA}$ or SO$_2$$R^{iiA}$; or $R^{ii}$ and $R^{iii}$, taken together with the nitrogen atom to which they are attached, form a substituted or unsubstituted heterocyclic or heteroaryl moiety; wherein $R^{iiA}$ is as defined above. In yet other exemplary embodiments, at least one occurrence of $R^{ii}$ or $R^{iii}$ is independently —C(=O)$R^{iiA}$ or SO$_2$$R^{iiA}$ wherein $R^{iiA}$ is as defined above, or $R^{ii}$ and $R^{iii}$, taken together with the nitrogen atom to which they are attached, form an azide or a substituted or unsubstituted phthalimide moiety. In yet other exemplary embodiments, at least one occurrence of $R^{ii}$ or $R^{iii}$ is independently acyl, —SO$_2$Ph or $R^{ii}$ and $R^{iii}$, taken together with the nitrogen atom to which they are attached, form an azide or a substituted or unsubstituted phthalimide moiety. In certain other exemplary embodiments, —NR$^{ii}$R$^{iii}$ is —NHAc.

In certain other embodiments, the invention provides an isolated compound having the structure:

eroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{3C}$ or —Z$R^{3C}$, wherein Z is —O—, —S—, —NR$^{3D}$, wherein each occurrence of $R^{3C}$ and $R^{3D}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, each occurrence of $R^1$ and $R^3$ is independently hydrogen, alkylaryl, —Si($R^{3A}$)$_3$ or —C(=O)$R^{3A}$, wherein $R^{3A}$ is as defined above. In yet other exemplary embodiments, each occurrence of $R^1$ and $R^3$ is independently hydrogen, Bn or Bz. In certain other exemplary embodiments, each occurrence of $R^1$ is Bn and each occurrence of $R^3$ is Bz. In certain other exemplary embodiments, each occurrence of $R^1$ and $R^3$ is independently hydrogen. In certain other embodiments, for each occurrence of —NR$^{2A}$R$^{2B}$, at least one occurrence of $R^{2A}$ or $R^{2B}$ is independently —C(=O)$R^{2A}$ or SO$_2$$R^{2A}$; or $R^{2A}$ and $R^{2B}$, taken together with the nitrogen atom to which they are attached, form a substituted or unsubstituted heterocyclic or heteroaryl moiety. In certain other embodiments, for each occurrence of —NR$^{2A}$R$^{2B}$, at least one occurrence of $R^{2A}$ or $R^{2B}$ is independently acyl, —SO$_2$Ph or $R^{2A}$ and $R^{2B}$, taken

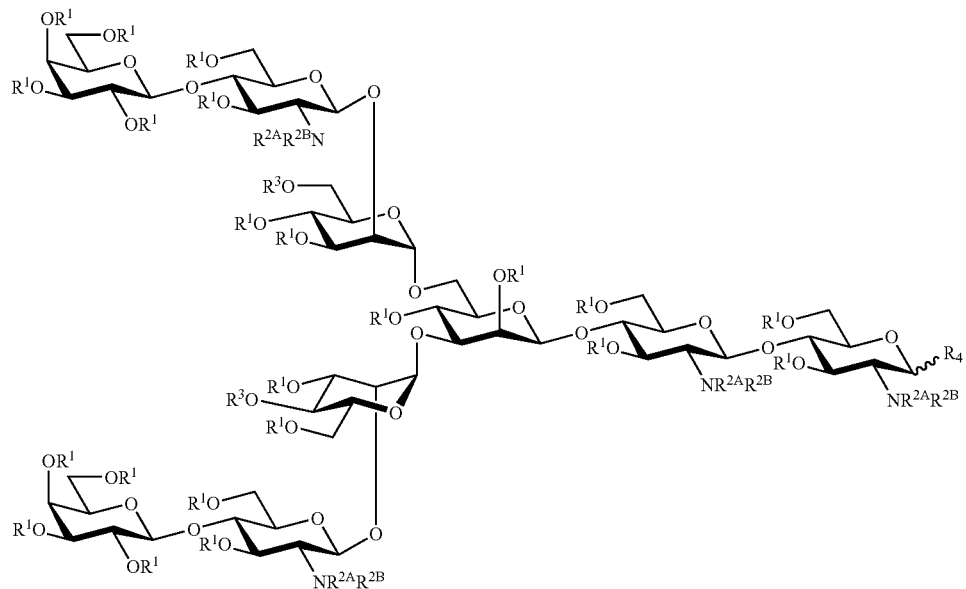

wherein $R^4$ and each occurrence of $R^1$, $R^{2A}$ and $R^{2B}$ are as defined generally above and in classes and subclasses herein; and each occurrence of $R^3$ is independently hydrogen, alkyl, alkenyl, alkynyl, heteroalkyl, heteroalkenyl, heteroalkynyl, aryl, heteroaryl, alkylaryl, alkylheteroaryl, —Si($R^{3A}$)$_3$, —C(=O)$R^{3A}$, —C(=S)$R^{3A}$, —C(=NR$^{3A}$)$R^{3B}$, —SO$_2$$R^{3A}$, wherein $R^{3A}$ and $R^{3B}$ are each independently hydrogen, alkyl, alkenyl, alkynyl, cycloalkyl, cycloalkenyl, cycloalkynyl, hettogether with the nitrogen atom to which they are attached, form an azide or a substituted or unsubstituted phthalimide moiety. In certain other exemplary embodiments, each occurrence of —NR$^{2A}$R$^{2B}$ is —NHAc. In certain other exemplary embodiments, each occurrence of $R^1$ is independently hydrogen and each occurrence of —NR$^{2A}$R$^{2B}$ is —NHAc.

In certain other embodiments, the invention provides an isolated compound having the structure:

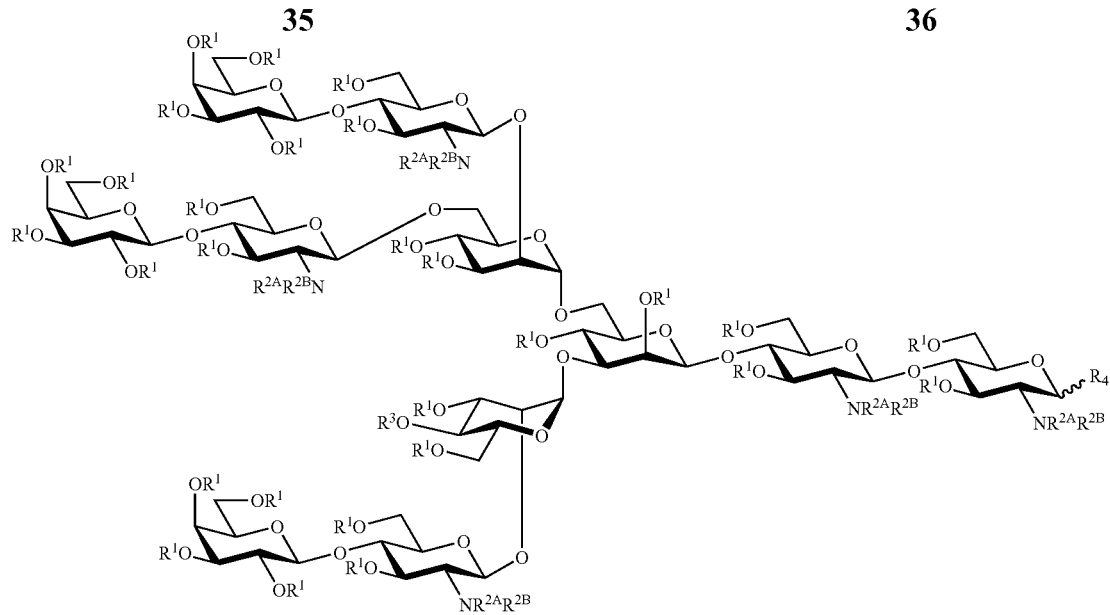

wherein $R^4$ and each occurrence of $R^1$, $R^{2A}$ and $R^{2B}$ are as defined generally above and in classes and subclasses herein; and $R^3$ is independently hydrogen, alkyl, alkenyl, alkynyl, heteroalkyl, heteroalkenyl, heteroalkynyl, aryl, heteroaryl, alkylaryl, alkylheteroaryl, —Si($R^{3A}$)$_3$, —C(=O)$R^{3A}$, —C(=S)$R^{3A}$, —C(=N$R^{3A}$)$R^{3B}$, —SO$_2R^{3A}$, wherein $R^{3A}$ and $R^{3B}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{3C}$ or —Z$R^{3C}$, wherein Z is —O—, —S—, —N$R^{3D}$, wherein each occurrence of $R^{3C}$ and $R^{3D}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $R^3$ and each occurrence of $R^1$ is independently hydrogen, alkylaryl, —Si($R^{3A}$)$_3$ or —C(=O)$R^{3A}$, wherein $R^{3A}$ is as defined above. In yet other exemplary embodiments, $R^3$ and each occurrence of $R^1$ is independently hydrogen, Bn or Bz.

In certain other exemplary embodiments, each occurrence of $R^1$ is Bn and $R^3$ is Bz. In certain other exemplary embodiments, $R^3$ and each occurrence of $R^1$ is independently hydrogen. In certain other embodiments, for each occurrence of —N$R^{2A}R^{2B}$, at least one occurrence of $R^{2A}$ or $R^{2B}$ is independently —C(=O)$R^{2A}$ or SO$_2R^{2A}$; or $R^{2A}$ and $R^{2B}$, taken together with the nitrogen atom to which they are attached, form a substituted or unsubstituted heterocyclic or heteroaryl moiety. In certain other embodiments, for each occurrence of —N$R^{2A}R^{2B}$, at least one occurrence of $R^{2A}$ or $R^{2B}$ is independently acyl, —SO$_2$Ph or $R^{2A}$ and $R^{2B}$, taken together with the nitrogen atom to which they are attached, form an azide or a substituted or unsubstituted phthalimide moiety. In certain other exemplary embodiments, each occurrence of —N$R^{2A}R^{2B}$ is —NHAc. In certain other exemplary embodiments, each occurrence of $R^1$ is independently hydrogen and each occurrence of —N$R^{2A}R^{2B}$ is —NHAc.

In certain other embodiments, the invention provides an isolated compound having the structure:

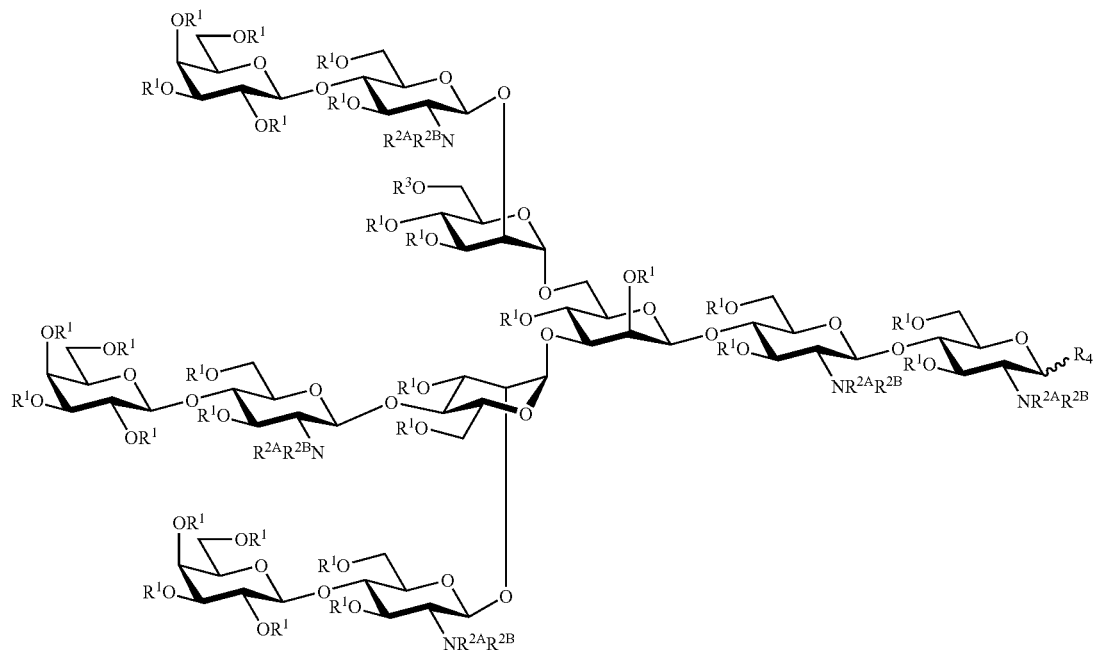

wherein $R^4$ and each occurrence of $R^1$, $R^{2A}$ and $R^{2B}$ are as defined generally above and in classes and subclasses herein; and $R^3$ is independently hydrogen, alkyl, alkenyl, alkynyl, heteroalkyl, heteroalkenyl, heteroalkynyl, aryl, heteroaryl, alkylaryl, alkylheteroaryl, —Si($R^{3A}$)$_3$, —C(=O)$R^{3A}$, —C(=S)$R^{3A}$, —C(=N$R^{3A}$)$R^{3B}$, —SO$_2R^{3A}$, wherein $R^{3A}$ and $R^{3B}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{3C}$ or —Z$R^{3C}$, wherein Z is —O—, —S—, —N$R^{3D}$, wherein each occurrence of $R^{3C}$ and $R^{3D}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $R^3$ and each occurrence of $R^1$ is independently hydrogen, alkylaryl, —Si($R^{3A}$)$_3$ or —C(=O)$R^{3A}$, wherein $R^{3A}$ is as defined above. In yet other exemplary embodiments, $R^3$ and each occurrence of $R^1$ is independently hydrogen, Bn or Bz. In certain other exemplary embodiments, each occurrence of $R^1$ is Bn and $R^3$ is Bz. In certain other exemplary embodiments, $R^3$ and each occurrence of $R^1$ is independently hydrogen. In certain other embodiments, for each occurrence of —N$R^{2A}R^{2B}$, at least one occurrence of $R^{2A}$ or $R^{2B}$ is independently —C(=O)$R^{2A}$ or SO$_2R^{2A}$; or $R^{2A}$ and $R^{2B}$, taken together with the nitrogen atom to which they are attached, form a substituted or unsubstituted heterocyclic or heteroaryl moiety. In certain other embodiments, for each occurrence of —N$R^{2A}R^{2B}$, at least one occurrence of $R^{2A}$ or $R^{2B}$ is independently acyl, —SO$_2$Ph or $R^{2A}$ and $R^{2B}$, taken together with the nitrogen atom to which they are attached, form an azide or a substituted or unsubstituted phthalimide moiety. In certain other exemplary embodiments, each occurrence of —N$R^{2A}R^{2B}$ is —NHAc. In certain other exemplary embodiments, each occurrence of $R^1$ is independently hydrogen and each occurrence of —N$R^{2A}R^{2B}$ is —NHAc.

In certain other embodiments, the invention provides an isolated compound having the structure:

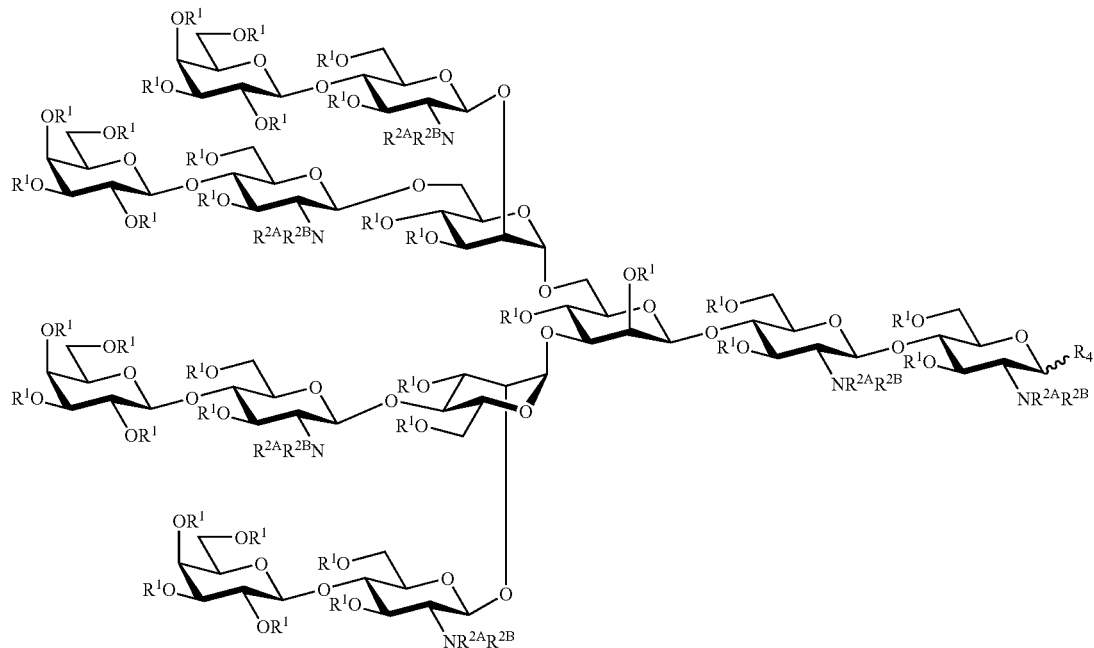

wherein $R^4$ and each occurrence of $R^1$, $R^{2A}$ and $R^{2B}$ are as defined generally above and in classes and subclasses herein. In certain exemplary embodiments, each occurrence of $R^1$ is independently hydrogen, alkylaryl, —Si($R^{1A}$)$_3$ or —C(=O)$R^{1A}$, wherein $R^{1A}$ is as defined above. In yet other exemplary embodiments, each occurrence of $R^1$ is independently hydrogen, Bn or Bz. In certain other exemplary embodiments, each occurrence of $R^1$ is Bn. In certain other exemplary embodiments, each occurrence of $R^1$ is independently hydrogen. In certain other embodiments, for each occurrence of —N$R^{2A}R^{2B}$, at least one occurrence of $R^{2A}$ or $R^{2B}$ is independently —C(=O)$R^{2A}$ or SO$_2R^{2A}$; or $R^{2A}$ and $R^{2B}$, taken together with the nitrogen atom to which they are attached, form a substituted or unsubstituted heterocyclic or heteroaryl moiety. In certain other embodiments, for each occurrence of —N$R^{2A}R^{2B}$, at least one occurrence of $R^{2A}$ or $R^{2B}$ is independently acyl, —SO$_2$Ph or $R^{2A}$ and $R^{2B}$, taken together with the nitrogen atom to which they are attached, form an azide or a substituted or unsubstituted phthalimide moiety. In certain other exemplary embodiments, each occurrence of —N$R^{2A}R^{2B}$ is —NHAc. In certain other exemplary embodiments, each occurrence of $R^1$ is independently hydrogen and each occurrence of —N$R^{2A}R^{2B}$ is —NHAc.

In certain embodiments, for each of the isolated compounds described herein, $R^4$ is —O$R^{4A}$ and the saccharide unit bearing $R^4$ has the structure:

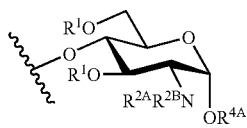

wherein $R^1$, $R^{2A}$ and $R^{2B}$ are as defined generally above and in classes and subclasses herein; $R^{4A}$ is hydrogen, alkyl, alkenyl, alkynyl, heteroalkyl, heteroalkenyl, heteroalkynyl, aryl, heteroaryl, alkylaryl, alkylheteroaryl, an amino acyl moiety, an amino acyl residue of a peptide, an amino acyl residue of a protein, —Si($R^{4B}$)$_3$, —C(=O)$R^{4B}$, —C(=S)$R^{4B}$, —C(=N$R^{4B}$)$R^{4C}$, —SO$_2R^{4B}$, wherein $R^{4B}$ and $R^{4C}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{4D}$ or —Z$R^{4D}$, wherein Z is —O—, —S—, —N$R^{4E}$, wherein each occurrence of $R^{4D}$ and $R^{4E}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety; or $R^{4A}$ comprises a protein, peptide or lipid moiety covalently linked to the O atom to which it is attached, either directly or through a crosslinker. In yet other exemplary embodiments, $R^{4A}$ is —Si($R^{4B}$)$_3$, wherein $R^{4B}$ is as defined above. In yet other exemplary embodiments, $R^{4A}$ is TBS. In yet other exemplary embodiments, $R^{4A}$ is hydrogen. In yet other exemplary embodiments $R^{4A}$ comprises a serine (ser) amino acyl residue. In yet other exemplary embodiments $R^{4A}$ comprises a threonine (Thr) amino acyl residue. In yet other exemplary embodiments $R^{4A}$ comprises a peptide attached to O through a serine (Ser) residue. In yet other exemplary embodiments $R^{4A}$ comprises a peptide attached to O through a Threonine (Thr) residue.

In certain embodiments, for each of the isolated compounds described herein, $R^4$ is —NH$R^{4A}$ and the saccharide unit bearing $R^4$ has the structure:

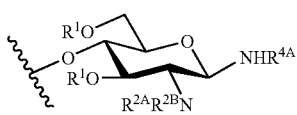

wherein $R^1$, $R^{2A}$ and $R^{2B}$ are as defined generally above and in classes and subclasses herein; and $R^{4A}$ is hydrogen, aliphatic, heteroaliphatic, aryl, heteroaryl, an amino acyl moiety, an amino acyl residue of a peptide, an amino acyl residue of a protein, or $R^{4A}$ comprises a protein, peptide or lipid moiety covalently linked to the rest of the construct, or to the N atom to which it is attached, either directly or through a crosslinker.

In certain exemplary embodiments, $R^{4A}$ is hydrogen.

In certain other exemplary embodiments, $R^{4A}$ is an amino acyl residue of a peptide whose structure is either identical or closely related to that of PSA near the N-glycosylation site.

In certain other exemplary embodiments, $R^{4A}$ comprises an Asparagine residue (Asn) of a peptide whose structure is either identical or closely related to that of PSA near the N-glycosylation site.

For the purpose of the invention, a peptide whose structure is "closely related to that of PSA near the N-glycosylation site" designates a PSA peptide fragment, or truncated, elongated or derivatized version thereof, comprising ≦about 60 amino acid residues, wherein one amino acid residue bears the N-glycosylation site, at least one amino acid residue has been added, deleted and/or substituted with a natural or non-natural amino acid residue, so that the resulting peptide has a sequence identity greater or equal to about 70% with the original PSA peptide fragment. In certain embodiments, the peptide comprises ≦about 55 amino acid residues. In certain embodiments, the peptide comprises ≦about 50 amino acid residues. In certain embodiments, the peptide comprises ≦about 45 amino acid residues. In certain embodiments, the peptide comprises ≦about 40 amino acid residues. In certain embodiments, the peptide comprises ≦about 35 amino acid residues. In certain embodiments, the peptide comprises ≦about 30 amino acid residues. In certain embodiments, the peptide comprises ≦about 25 amino acid residues. In certain embodiments, the peptide comprises ≦about 20 amino acid residues. In certain embodiments, the peptide has a sequence identity greater or equal to about 75% with the original PSA peptide fragment. In certain other embodiments, the peptide has a sequence identity greater or equal to about 80% with the original PSA peptide fragment. In certain other embodiments, the peptide has a sequence identity greater or equal to about 85% with the original PSA peptide fragment. In certain other embodiments, the peptide has a sequence identity greater or equal to about 90% with the original PSA peptide fragment. In certain other embodiments, the peptide has a sequence identity greater or equal to about 95% with the original PSA peptide fragment.

A peptide whose structure is "identical to that of PSA near the N-glycosylation site" designates a PSA peptide fragment of a naturally occurring PSA glycoprotein, comprising ≦about 60 amino acid residues, wherein one amino acid residue bears the N-glycosylation site. In certain embodiments, the peptide comprises ≦about 55 amino acid residues. In certain embodiments, the peptide comprises ≦about 50 amino acid residues. In certain embodiments, the peptide comprises ≦about 45 amino acid residues. In certain embodiments, the peptide comprises ≦about 40 amino acid residues. In certain embodiments, the peptide comprises ≦about 35 amino acid residues. In certain embodiments, the peptide comprises ≦about 30 amino acid residues. In certain embodiments, the peptide comprises ≦about 25 amino acid residues. In certain embodiments, the peptide comprises ≦about 20 amino acid residues.

In certain embodiments, for each of the isolated compounds described herein, $R^4$ is —$NHR^{4A}$ wherein $R^{4A}$ comprises an Asparagine residue (Asn) of a peptide whose structure is either identical or closely related to that of PSA near the N-glycosylation site and the saccharide unit bearing $R^4$ has the structure:

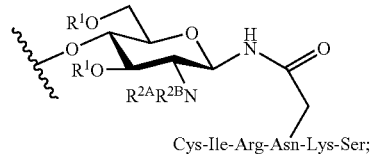

(SEQ ID NO: 2)

Cys-Ile-Arg-Asn-Lys-Ser;

wherein $R^1$, $R^{2A}$ and $R^{2B}$ are as defined generally above and in classes and subclasses herein and wherein any of the amino acid residues may bear one or more protecting groups.

In certain exemplary embodiments, the saccharide unit bearing $R^4$ has the structure:

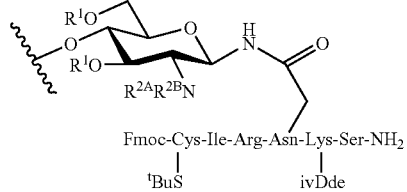

(SEQ ID NO: 2)

Fmoc-Cys-Ile-Arg-Asn-Lys-Ser-NH$_2$
             |                    |
           tBuS                 ivDde wherein $R^1$, $R^{2A}$ and $R^{2B}$ are as defined generally above and in classes and subclasses herein.

In certain other exemplary embodiments, the saccharide unit bearing $R^4$ has the structure:

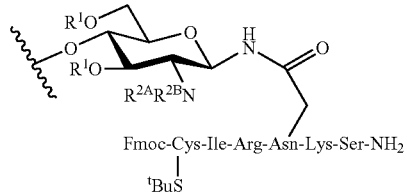

(SEQ ID NO: 2)

Fmoc-Cys-Ile-Arg-Asn-Lys-Ser-NH$_2$
             |
           tBuS wherein $R^1$, $R^{2A}$ and $R^{2B}$ are as defined generally above and in classes and subclasses herein.

In certain exemplary embodiments, the saccharide unit bearing $R^4$ has the structure:

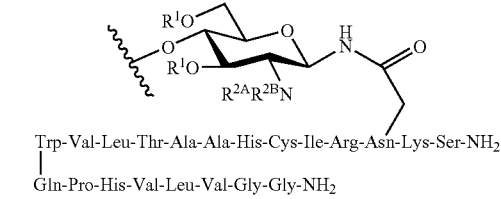

(SEQ ID NO: 1)

Trp-Val-Leu-Thr-Ala-Ala-His-Cys-Ile-Arg-Asn-Lys-Ser-NH$_2$
|
Gln-Pro-His-Val-Leu-Val-Gly-Gly-NH$_2$ wherein $R^1$, $R^{2A}$ and $R^{2B}$ are as defined generally above and in classes and subclasses herein.

In certain embodiments, any of the isolated compounds and/or glycopeptides described herein may be further conjugated to an immunogenic carrier. In certain exemplary embodiments, the carrier is a protein, a peptide or a lipid. In certain other exemplary embodiments, the carrier is Bovine Serum Albumin (BSA), Keyhole Limpet Hemocyanin (KLH) or polylysine. In certain other embodiments, the carrier is is a lipid carrier having the structure:

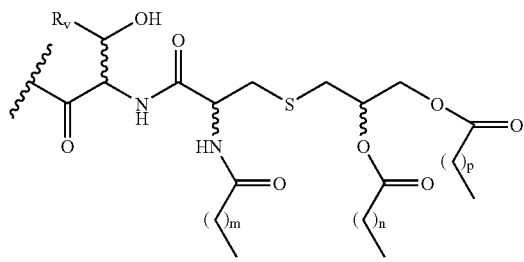

wherein m, n and p are each independently integers between about 8 and 20; and $R_V$ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (e.g., PamCys).

In certain embodiments, $R^4$ is not —NHC(=O)—(CH$_2$)$_5$—NH—$R^x$; wherein $R^x$ is H, =C=S, —C(=O)OBzl or —C(=S)NH—BSA; where Bzl designates a benzyl radical.

In certain other embodiments, $R^4$ is not protected or unprotected Asparagine or one of the following structures:

(SEQ ID NO: 3)

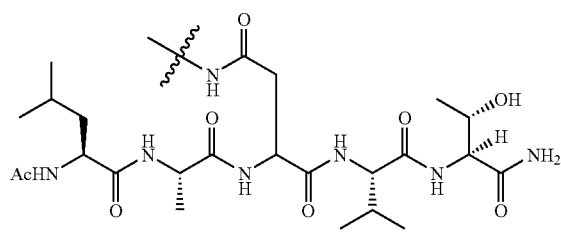

(SEQ ID NO: 4)

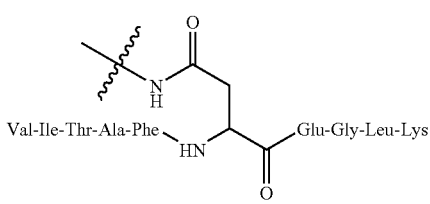

-continued (SEQ ID NO: 5)

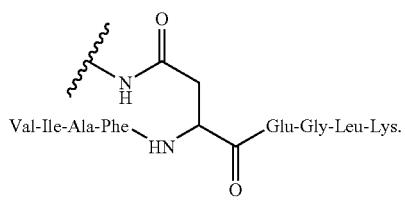

It will be appreciated that the carrier can be linked to the rest of the construct either directly or through a crosslinker, and thus $R^4$ encompasses proteins, peptides, and lipids, as well as (crosslinker-protein), (crosslinker-peptide) and (crosslinker-lipid) moieties.

Crosslinkers suited to the invention are widely known in the art (see, for example, 1994 Pierce Technical Handbook: cross-linking (See Appendix A in WO 04/60915), which is also available at http://www.piercenet.com/resources/browse.cfm?fldID=184), including bromoacetic NHS ester, 6-(iodoacetamido)caproic acid NHS ester, maleimidoacetic acid NHS ester, maleimidobenzoic acide NHS ester, etc. In certain preferred embodiments, the crosslinker is MMCCH (4-(maleimidomethyl)cyclohexane-1-carboxyl hydrazide). In certain other preferred embodiments, the crosslinker is MBS(m-maleimidobenzoyl acid N-Hydroxysuccinimidyl ester). In certain embodiments, the crosslinker is a fragment having the structure:

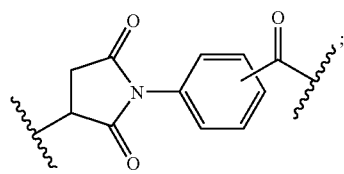

whereby said structure is generated upon conjugation of a maleimidobenzoic acid N-hydroxy succinimide ester with a suitable functionality on $R^4$.

2) Synthetic Methodology

The practitioner has a a well-established literature of carbohydrate chemistry to draw upon, in combination with the information contained herein, for guidance on synthetic strategies, protecting groups, and other materials and methods useful for the synthesis of the compounds of this invention, and conjugates thereof.

The various patent documents and other references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

In one aspect of the invention, there is provided a method for preparing isolated an compound of formula (II):

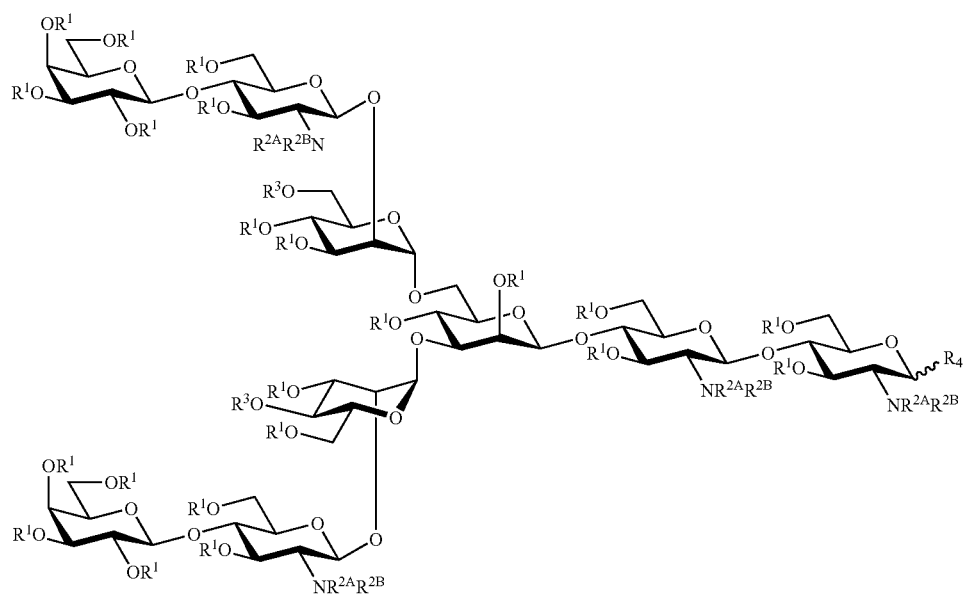

(II)

wherein $R^1$, $R^{2A}$, $R^{2B}$, $R^3$ and $R^4$ are as defined generally above and in classes and subclasses herein.

In certain exemplary embodiments, $R^4$ is —$NHR^{4A}$; wherein $R^{4A}$ is an amino acyl residue of a peptide and the invention provides a method for preparing homogeneous N-linked PSA-derived glycopeptides.

Glycan Synthesis

Glycan synthesis generally suffers from the stereochemical diversity of its targets and therefore of its building blocks, as well. The advent of a new target often requires a reworked, if not entirely different synthetic plan, based on varying protecting groups, coupling strategies, and starting materials. The present invention provides a method allowing access to a number of PSA-derived saccharides using only a small set of building blocks and the same general procedure for each glycan.

In certain embodiments, trisaccharide 4 in Scheme 1 embodies the protected core structure reported for the glycoforms expressed in normal PSA (See, for example, Okada, T.; Sato, Y.; Kobayashi, N.; Sumida, K.; Satomura, S.; Matsuura, S.; Takasaki, M.; Endo, T. "Structural characteristics of the N-glycans of two isoforms of prostate-specific antigens purified from human seminal fluid." Biochim. Biophys. Acta-Gen. Subj. 2001, 1525, 149-160).

In certain exemplary embodiments, trisaccharide 4 may be elaborated to give a pentasaccharide either by deprotection of the 6-position followed by simultaneous α-mannosylation at the free 3- and 6-positions or by sequential mannosylation at the 3- and 6-positions with an intermediate deprotection step. Simultaneous mannosylation with equivalently protected mannosyl donors would yield a "symmetrically" substituted pentasaccharide; further deprotections and glycosylations could be achieved in a synchronous fashion at both nonreducing termini. Sequential mannosylation would allow the inclusion of differentially protected mannose building blocks, permitting independent elaboration of the 3- and 6-substituted antennae. Thus the high-mannose pentasaccharide core (which is conserved in most natural N-linked glycans) may be synthesized in large quantities and used as a starting point for all of the normal PSA targets. Moreover, because transformed PSA is expected to differ from normal PSA in its degree of branching beyond the core pentasaccharide (See, for example, Dennis, J. W.; Laferte, S.; Waghorne, C.; Breitman, M. L.; Kerbel, R. S. "Beta-1-6 Branching of Asn-Linked Oligosaccharides Is Directly Associated with Metastasis." Science 1987, 236, 582-585), this synthetic scheme would provide easy access to the tri- or tetraantennary glycoforms expressed in transformed PSA (See, for example, Prakash, S.; Robbins, P. W. "Glycotyping of prostate specific antigen." Glycobiology 2000, 10, 173-176).

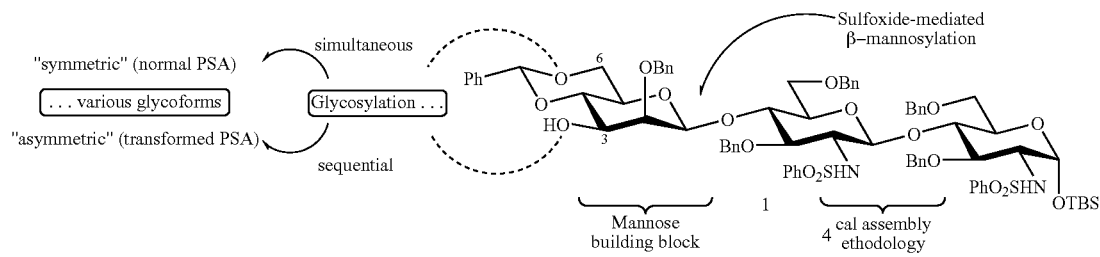

Scheme 1.
Proposed methodology for glycan synthesis.

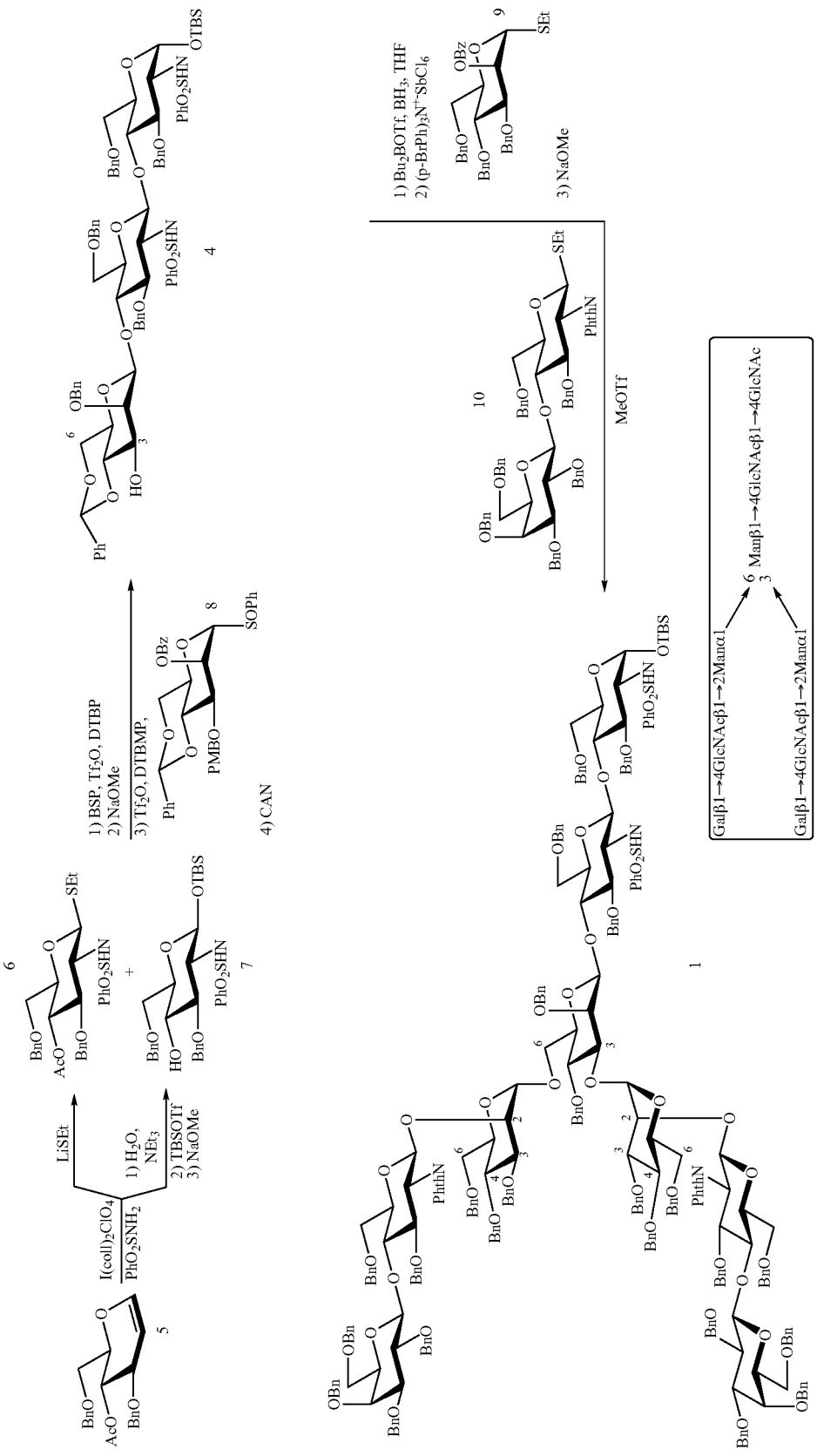

An embodiment of a synthetic approach is depicted in Scheme 2 above. In certain embodiments, glucal 5 is iodosulfonamidated (See, for example, (1) Griffith, D. A.; Danishefsky, S. J. "Sulfonamidoglycosylation of Glycals—a Route to Oligosaccharides with 2-Aminohexose Subunits." *J. Am. Chem. Soc.* 1990, 112, 5811-5819; and (2) Danishefsky, S. J.; Gervay, J.; Peterson, J. M.; Mcdonald, F. E.; Koseki, K.; Oriyama, T.; Griffith, D. A.; Wong, C. H.; Dumas, D. P. "Remarkable Regioselectivity in the Chemical Glycosylation of Glycal Acceptors—a Concise Solution to the Synthesis of Sialyl-Lewis-X Glycal." *J. Am. Chem. Soc.* 1992, 114, 8329-8331) to give either thiodonor 6 or eventually silyl-protected acceptor 7, depending on the rollover conditions. Benzenesulfinyl piperidine (BSP) and trifluoromethanesulfonic anhydride (Tf2O) promoted coupling (See, for example, Crich, D.; Smith, M. "1-Benzenesulfinyl piperidine/trifluoromethanesulfonic anhydride: A potent combination of shelf-stable reagents for the low-temperature conversion of thioglycosides to glycosyl triflates and for the formation of diverse glycosidic linkages." *J. Am. Chem. Soc.* 2001, 123, 9015-9020) of 6 and 7 followed by deacetylation, β-mannosylation with sulfoxide 8 (See, for example, (1) Crich, D.; Dudkin, V. "Why are the hydroxy groups of partially protected N-acetylglucosamine derivatives such poor glycosyl accepters, and what can be done about it? A comparative study of the reactivity of N-acetyl-, N-phthalimido-, and 2-azido-2-deoxyglucosamine derivatives in glycosylation. 2-Picolinyl ethers as reactivity-enhancing replacements for benzyl ethers." *J. Am. Chem. Soc.* 2001, 123, 6819-6825; and (2) Crich, D.; Sun, S. X. "Direct chemical synthesis of beta-mannopyranosides and other glycosides via glycosyl triflates." *Tetrahedron* 1998, 54, 8321-8348) and oxidative removal of the p-methoxybenzyl (PMB) group with ceric ammonium nitrate (CAN) gives trisaccharide 4. Selective deprotection of the 6-hydroxyl (Jiang, L.; Chan, T. H. "Borane/Bu2BOTf: A mild reagent for the regioselective reductive ring opening of benzylidene acetals in carbohydrates." *Tetrahedron Lett.* 1998, 39, 355-358) and subsequent radical cation activated double glycosylation (Zhang, Y. M.; Mallet, J. M.; Sinay, P. "Glycosylation Using a One-Electron-Transfer, Homogeneous Reagent—Application to an Efficient Synthesis of the Trimannosyl Core of N-Glycosylproteins." *Carbohydr. Res.* 1992, 236, 73-88) with thiodonor 9 affords a "symmetrically" substituted pentasaccharide; after deprotection at both terminal mannose 2-hydroxyls, further elaboration via methyl triflate (MeOTf) activated double coupling with lactosamine thioglycoside 10 (See, for example, (1) Wang, Z. G.; Zhang, X. F.; Visser, M.; Live, D.; Zatorski, A.; Iserloh, U.; Lloyd, K. O.; Danishefsky, S. J. "Toward fully synthetic homogeneous glycoproteins: A high mannose core containing glycopeptide carrying full H-type2 human flood group specificity." *Angew. Chem. Int. Ed.* 2001, 40, 1728-1732; and (2) Wang, Z. G.; Zhang, X. F.; Live, D.; Danishefsky, S. J. "From glycals to glycopeptides: A convergent and stereoselective total synthesis of a high mannose N-linked glycopeptide." *Angew. Chem. Int. Ed.* 2000, 39, 3652-3656) provides fully protected nonasaccharide 11. In certain embodiments, normal PSA glycan (boxed, Scheme 2) may be obtained by global deprotection and N-acetylation.

In certain other embodiments, and as detailed in Example 2 herein, extension of the synthesis along the "asymmetric" route of Scheme 1 to include more highly branched saccharides (at the 2-, 4-, and/or 6-positions; see e.g. boxed structure, Scheme 3) allows access to transformed PSA glycans.

It will be appreciated that natural PSA glycosides are both sialylated and fucosylated to varying degrees; these saccharide residues can pose significant synthetic challenges, though they can of course be included in a glycoside synthesis (See, for example, (1) Schwarz, J. B.; Kuduk, S. D.; Chen, X. T.; Sames, D.; Glunz, P. W.; Danishefsky, S. J. "A broadly applicable method for the efficient synthesis of alpha-O-linked glycopeptides and clustered sialic acid residues." *J. Am. Chem. Soc.* 1999, 121, 2662-2673; and (2) Jain, R. K.; Piskorz, C. F.; Huang, B. G.; Locke, R. D.; Han, H. L.; Koenig, A.; Varki, A.; Matta, K. L. "Inhibition of L- and P-selectin by a rationally synthesized novel core 2-like branched structure containing GalNAc-Lewis(X) and Neu5Ac alpha 2-3Gal beta 1-3GalNAc sequences." *Glycobiology* 1998, 8, 707-717]. In certain embodiments, to circumvent this issue, rather than providing methods to synthesize (and raise antibodies against) a number of sialylated and fucosylated variants, the present invention provides a method to synthesize the most abundant transformed glycan (and to generate antibodies using it). Without wishing to be bound to any particular theory, it is proposed that predigestion of a biological sample (e.g., serum) with sialidase and fucosidase would provide a much more homogeneous sample (with respect to PSA glycans) for immunoassay, thus making detection of errant glycoforms more likely.

Glycopeptides

Automated peptide synthesis is reliable for sequences up to about 60 amino acid residues in length, but saccharide moieties contained in glycopeptides render their solid phase synthesis less practical. Unlike peptide synthesis, complex glycan and glycoconjugate synthesis remains readily accessible only to a few select laboratories (See, for example, Hang, H. C.; Bertozzi, C. R. "Chemoselective approaches to glycoprotein assembly." *Acc. Chem. Res.* 2001, 34, 727-736). Syntheses of several natural O-linked glycopeptides containing simple glycans have been reported (See, for example, (1) Arsequell, G.; Haurum, J. S.; Elliott, T.; Dwek, R. A.; Lellouch, A. C. "Synthesis of Major Histocompatibility Complex Class-I Binding Glycopeptides." *J. Chem. Soc.-Perkin Trans. 1* 1995, 1739-1745, (2) Chen, X. T.; Sames, D.; Danishefsky, S. J. "Exploration of modalities in building alpha-O-linked systems through glycal assembly: A total synthesis of the mucin-related F1 alpha antigen." *J. Am. Chem. Soc.* 1998, 120, 7760-7769; (3) Macmillan, D.; Bertozzi, C. R. "New directions in glycoprotein engineering." *Tetrahedron* 2000, 56, 9515-9525; (4) Koeller, K. M.; Smith, M. E. B.; Huang, R. F.; Wong, C. H. "Chemoenzymatic synthesis of a PSGL-1 N-terminal glycopeptide containing tyrosine sulfate and alpha-O-linked sialyl Lewis X." *J. Am. Chem. Soc.* 2000, 122, 4241-4242; (5) Ajisaka, K.; Miyasato, M.; Ishii-Karakasa, I. "Efficient synthesis of O-linked glycopeptide by a transglycosylation using endo alpha-N-acetylgalactosaminidase from *Streptomyces* sp." *Biosci. Biotechnol. Biochem.* 2001, 65, 1240-1243; and (6) Marcaurelle, L. A.; Mizoue, L. S.; Wilken, J.; Oldham, L.; Kent, S. B. H.; Handel, T. M.; Bertozzi, C. R. "Chemical synthesis of lymphotactin: A glycosylated chemokine with a C-terminal mucin-like domain." *Chem. Eur. J.* 2001, 7, 1129-1132), as have examples of mimetics for N-linked glycopeptides (See, for example, Hang, H. C.; Bertozzi, C. R. "Chemoselective approaches to glycoprotein assembly." *Acc. Chem. Res.* 2001, 34, 727-736), and a chemoenzymatic synthesis of an N-linked glycopeptide (See, for example, Inazu, T.; Haneda, K.; Mizuno, M. "Synthetic study on N-glycopeptides." *J. Syn. Org. Chem. Jpn.* 1998, 56, 210-220), but no chemical synthesis has been reported for a natural N-linked glycopeptide with complex glycan and peptide structure. The state of the art for chemically synthesized N-linked glycopeptides is exemplified by the pentadecasaccharide N-linked to a pentapeptide reported by Wang and coworkers, which was recognized by appropriate antibodies to the H-type blood group antigens present at the glycan nonreducing termini (See, for example, Wang, Z. G.; Zhang, X. F.; Visser, M.; Live, D.; Zatorski, A.; Iserloh, U.; Lloyd, K. O.; Danishefsky, S. J. "Toward fully synthetic homogeneous glycoproteins: A high mannose core containing glycopeptide carrying full H-type2 human flood group specificity." *Angew. Chem. Int. Ed.* 2001, 40, 1728-1732).

923-960). The glycan is fashioned here in a more convergent manner than previously realized, allowing the strategy to be adjusted in its late stage to accommodate the synthesis of various glycoforms, as illustrated in the next section.

Glycopeptide Assembly

In certain embodiments, the glycopeptide assembly strategy outlined in Scheme 3, which involves peptide glycosyla-

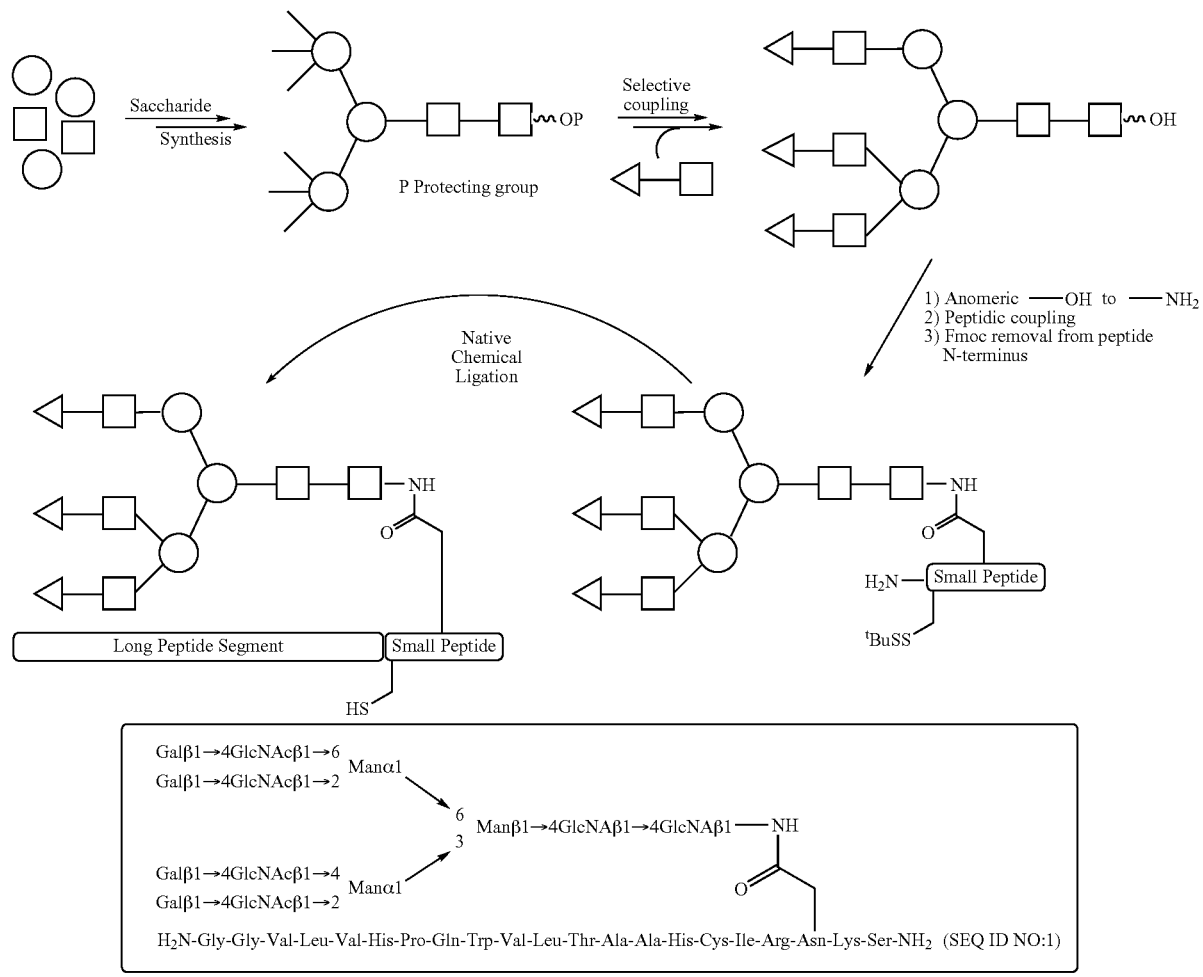

In certain embodiments, as shown in Scheme 3, the chemical synthesis of inventive homogeneous glycopeptides may be divided logically into two sections: glycan synthesis (top) and glycopeptide assembly (bottom). At its core, the inventive method would extend the method of Wang, et al. (Wang, Z. G.; Zhang, X. F.; Visser, M.; Live, D.; Zatorski, A.; Iserloh, U.; Lloyd, K. O.; Danishefsky, S. J. "Toward fully synthetic homogeneous glycoproteins: A high mannose core containing glycopeptide carrying full H-type2 human flood group specificity." *Angew. Chem. Int. Ed.* 2001, 40, 1728-1732) to include one or more peptide elongation steps after synthesis of a short glycopeptide, allowing entry into the realm of fully elaborated, naturally derived glycoproteins (See, for example, Dawson, P. E.; Kent, S. B. H. "Synthesis of native proteins by chemical ligation." *Annu. Rev. Biochem.* 2000, 69, tion followed by elongation of the peptide backbone, was examined, as illustrated in Scheme 4, using a model peptide and glycan (Miller, J. S. et al., *Angew. Chemie Int. Ed.*, 2003, 42, 431). To prepare free glycan 12 for coupling, its anomeric hydroxyl was first aminated to give β-aminoglycoside 13 as described by Kochetkov (See, for example, Likhosherstov, L. M.; Novikova, O. S.; Derevitskaja, V. A.; Kochetkov, N. K. "A New Simple Synthesis of Amino Sugar Beta-D-Glycosylamines." *Carbohydr. Res.* 1986, 146, C1-C5). Glycosylamine 13 and the aspartate free acid of peptide 14 were coupled in peptidic fashion according to the procedure of Lansbury and coworkers ((1) Cohen-Anisfeld, S. T.; Lansbury, P. T. "A Practical, Convergent Method for Glycopeptide Synthesis." *J. Am. Chem. Soc.* 1993, 115, 10531-10537; and (2) Anisfeld, S. T.; Lansbury, P. T. "A Convergent Approach to the Chemical Synthesis of Asparagine-Linked Glycopeptides." *J. Org. Chem.* 1990, 55, 5560-5562) with certain modifications: the reported peptide glycosylations involved excess or equimolar amounts of glycosylamine relative to peptide, and their isolated yields (50-60%) are reported based on peptide starting material (Cohen-Anisfeld, S. T.; Lansbury, P. T. "A Practical, Convergent Method for Glycopeptide Synthesis." *J. Am. Chem. Soc.* 1993, 115, 10531-10537). As is often the case, however, the saccharide here is the more precious material entering glycosylation because its preparation involves multistep, solution phase synthesis in relatively low overall yield compared to that of the peptide. A trial glycosylation of model pentapeptide 14 with pentasaccharide 13 indicates that under the appropriate reaction conditions, an excess of peptide produces a significantly greater yield of coupled product (over 70% based on valuable glycosylamine) [Miller, J. S. et al., *Angew. Chemie Int. Ed.,* 2003, 42, 431. Subsequent Fmoc (Fmoc=9-fluorenylmethyloxy-carbonyl) removal with piperidine afforded glycopeptide 15.

rearrangement to give fully unprotected glycopeptide 18. PSA-derived glycopeptides obtained using the tactics detailed in Scheme 4 will require no additional manipulation other than purification before they can be examined for the generation of antibodies. The synthetic strategy thus requires only four assembly steps starting from free glycans to obtain homogeneous glycopeptides.

Model peptide 14 (see Scheme 4) contains two alanine (Ala, A) residues flanking the Asp residue, whereas the appropriate peptide for PSA contains an arginine (Arg, R) and a lysine (Lys, K) in the comparable positions (see Scheme 3, boxed structure). In certain embodiments, the lysine residue is differentially protected with respect to Fmoc removal during peptide synthesis, and remains protected through the peptide glycosylation step (due to its free amine side chain). Suitably protected Lys derivatives have been designed (See, for example, Chhabra, S. R.; Hothi, B.; Evans, D. J.; White, P. D.; Bycroft, B. W.; Chan, W. C. "An appraisal of new variants of Dde amine protecting group for solid phase peptide syn-

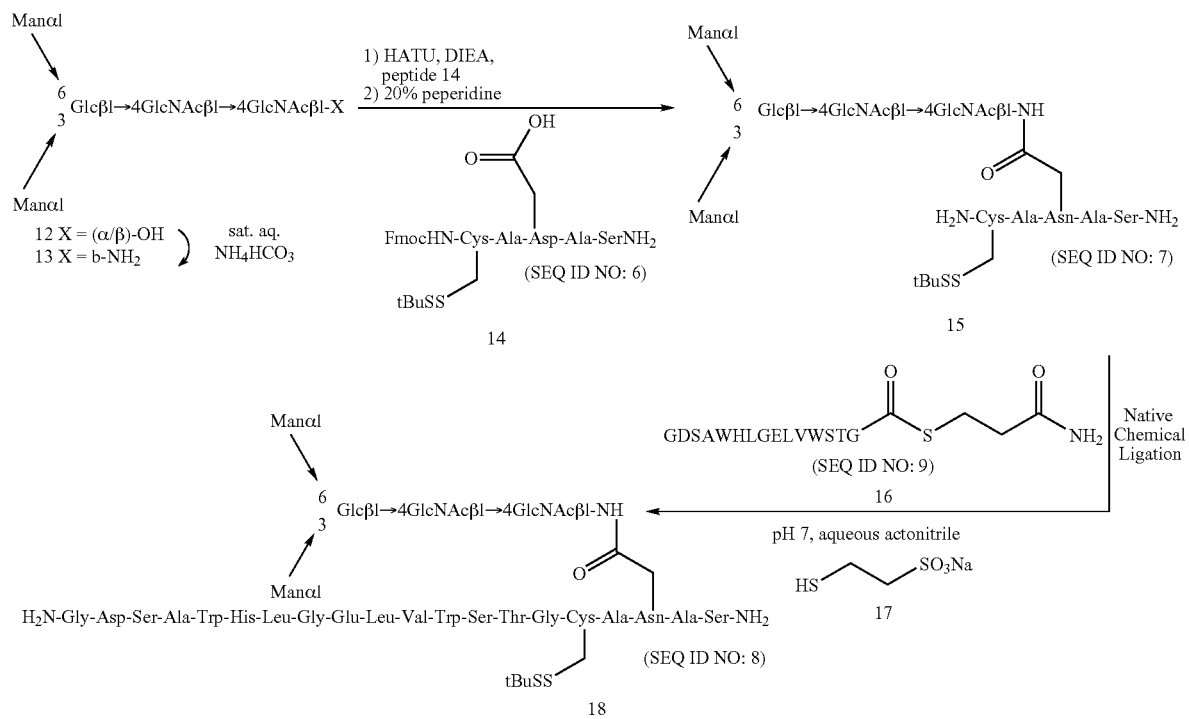

Scheme 4.
Exemplary glycopeptide assembly route with a model peptide and glycan.

The final step toward completion of a model glycopeptide involved native chemical ligation (NCL) [See, for example, Dawson, P. E.; Muir, T. W.; Clark-Lewis, I.; Kent, S. B. H. "Synthesis of Proteins by Native Chemical Ligation." *Science* 1994, 266, 776-779], as indicated in Scheme 4. In situ deprotection of cysteine disulfide 15 and transthioesterification (See, for example, Dawson, P. E.; Churchill, M. J.; Ghadiri, M. R.; Kent, S. B. H. "Modulation of reactivity in native chemical ligation through the use of thiol additives." *J. Am. Chem. Soc.* 1997, 119, 4325-4329) of peptide thioester 16 with sodium 2-mercaptoethanesulfonate (17) in phosphate-buffered saline (PBS) at neutral pH led to a second thioester exchange with the (now free) cysteine thiol and subsequent thesis." *Tetrahedron Lett.* 1998, 39, 1603-1606), and can be deprotected in the presence of N-linked saccharides along with the N-terminal Fmoc amine in minutes using hydrazine at room temperature.

Native Chemical Ligation

One of the more widely used methods for the synthesis of glycopeptides is native chemical ligation (NCL)—See, for example, a) Dawson, P. E.; Muir, T. W.; Clark-Lewis, I.; Kent, S. B. H. *Science* 1994, 266, 776. b) Dawson, P. E.; Kent, S. B. H. *Annu. Rev. Biochem.* 2000, 69, 923. c) Grogan, M. J.; Pratt, M. R.; Marcaurelle, L. A.; Bertozzi, C. R. *Annu. Rev. Biochem.* 2002, 71, 593. First reported by Kent in 1994, NCL allows for the assembly of large proteins with native amide bonds from unprotected peptide building blocks (see below). Furthermore, the reaction is mild, selective, and compatible with the presence of glycans. When glycans are present in the reaction, they are typically found on the C-terminal side. In the event, a glycopeptide containing a C-terminal cysteine undergoes a chemoselective reaction with a peptide thioester. The resulting peptide thioester then rearranges spontaneously to furnish a native peptide bond, effectively lengthening the peptide backbone of the glycopeptide.

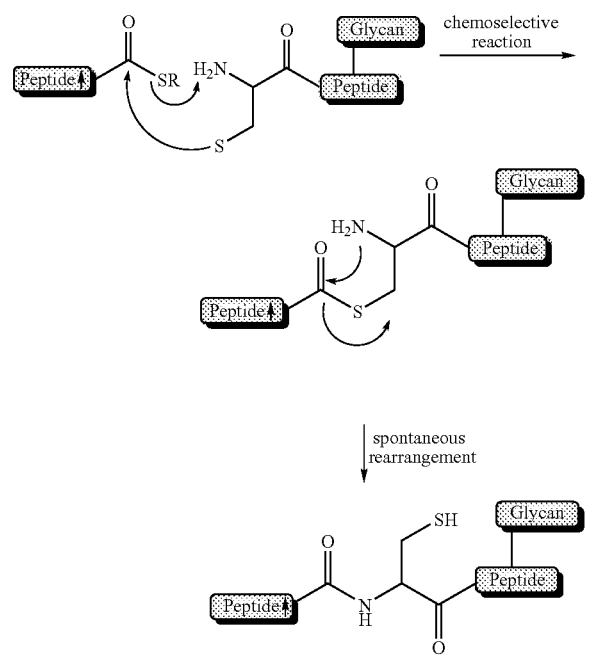

One example of R group suitable to achieve this process includes —$(CH_2)_2C(=O)NH_2$. Other R groups may be used.

Peptide Thioester Synthesis

Several methods have been developed for peptide thioester synthesis, including the original "Boc chemistry" (Boc=tert-butyloxycarbonyl) method (See, for example, (1) Canne, L. E.; Walker, S. M.; Kent, S. B. H. "A General Method for the Synthesis of Thioester Resin Linkers for Use in the Solid-Phase Synthesis of Peptide Alpha-Thioacids." *Tetrahedron Lett.* 1995, 36, 1217-1220; and (2) Hojo, H.; Aimoto, S. "Polypeptide Synthesis Using the S-Alkyl Thioester of a Partially Protected Peptide Segment—Synthesis of the DNA-Binding Domain of C-Myb Protein (142-193)-NH2." *Bull. Chem. Soc. Jpn.* 1991, 64, 111-117) and several Fmoc-compatible systems (See, for example, (1) Shin, Y.; Winans, K. A.; Backes, B. J.; Kent, S. B. H.; Ellman, J. A.; Bertozzi, C. R. "Fmoc-based synthesis of peptide-(alpha)thioesters: Application to the total chemical synthesis of a glycoprotein by native chemical ligation." *J. Am. Chem. Soc.* 1999, 121, 11684-11689; (2) Ingenito, R.; Bianchi, E.; Fattori, D.; Pessi, A. "Solid phase synthesis of peptide C-terminal thioesters by Fmoc/t-Bu chemistry." *J. Am. Chem. Soc.* 1999, 121, 11369-11374; (3) Li, X. Q.; Kawakami, T.; Aimoto, S. "Direct preparation of peptide thioesters using an Fmoc solidphase method." *Tetrahedron Lett.* 1998, 39, 8669-8672; (4) Clippingdale, A. B.; Barrow, C. J.; Wade, J. D. "Peptide thioester preparation by Fmoc solid phase peptide synthesis for use in native chemical ligation." *J. Pept. Sci.* 2000, 6, 225-234; and (5) Bu, X. Z.; Xie, G. Y.; Law, C. W.; Guo, Z. H. "An improved deblocking agent for direct Fmoc solidphase synthesis of peptide thioesters." *Tetrahedron Lett.* 2002, 43, 2419-2422). Model thioester 13 is a C-terminal glycine thioester, which is locally achiral and cannot be epimerized, and is therefore easy to synthesize. Though the desired PSA thioester contains an epimerization-prone C-terminal histidine (His) residue, such thioesters have been synthesized previously and have in fact been shown to modulate favorably the rate of NCL (See, for example, Hackeng, T. M.; Griffin, J. H.; Dawson, P. E. "Protein synthesis by native chemical ligation: Expanded scope by using straightforward methodology." *Proc. Natl. Acad Sci. U.S.A.* 1999, 96, 10068-10073).

In another aspect of the present invention, a method of preparing an isolated compound having the structure:

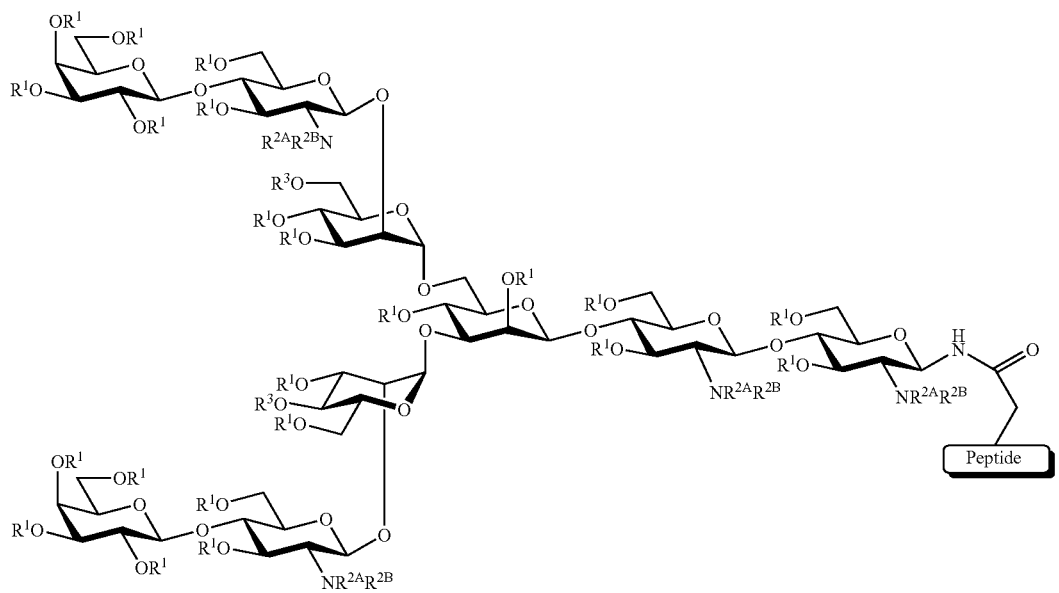

wherein each occurrence of $R^1$ is independently hydrogen or an oxygen protecting group; each occurrence of $R^{2A}$ and $R^{2B}$ is independently hydrogen or a nitrogen protecting group; and each occurrence of $R^3$ is independently hydrogen, a protecting group or a carbohydrate domain comprising a saccharide moiety having the structure:

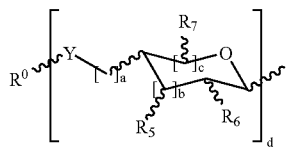

wherein Y is NH or O; wherein a, b and c are each independently 0, 1 or 2; d is an integer from 1-3; with the proviso that the d bracketed structure represents a faranose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;

said method comprising steps of:

(a) providing an α-O-protected carbohydrate construct having the structure:

wherein each occurrence of $R^1$ is independently hydrogen or an oxygen protecting group; each occurrence of $R^{2A}$ and $R^{2B}$ is independently hydrogen or a nitrogen protecting group; each occurrence of $R^3$ is independently hydrogen, a protecting group or a carbohydrate domain comprising a saccharide moiety having the structure:

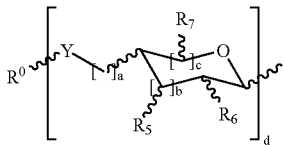

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;

and $R^{4A}$ is hydrogen or a suitable oxygen protecting group;

(b) reacting the construct of step (a) under suitable conditions to form a β-amino carbohydrate construct having the structure:

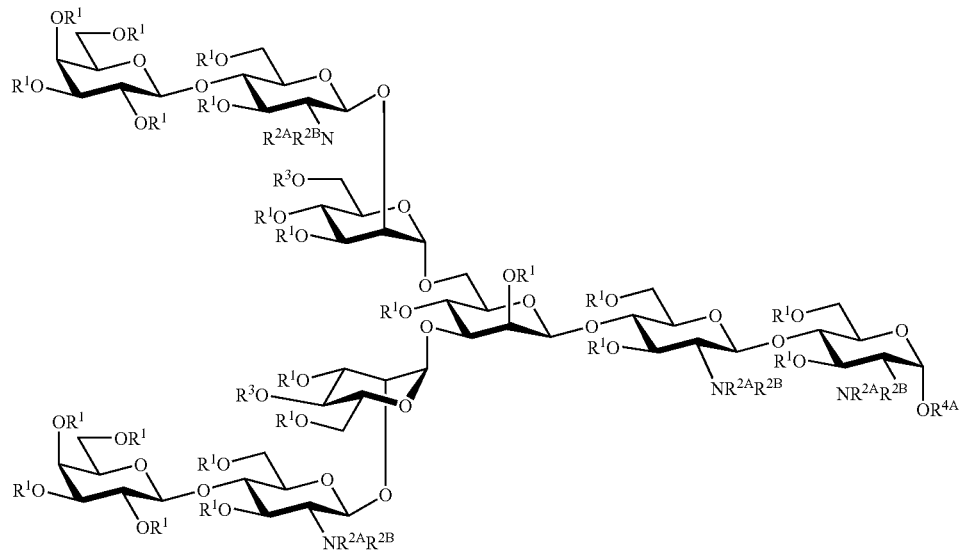

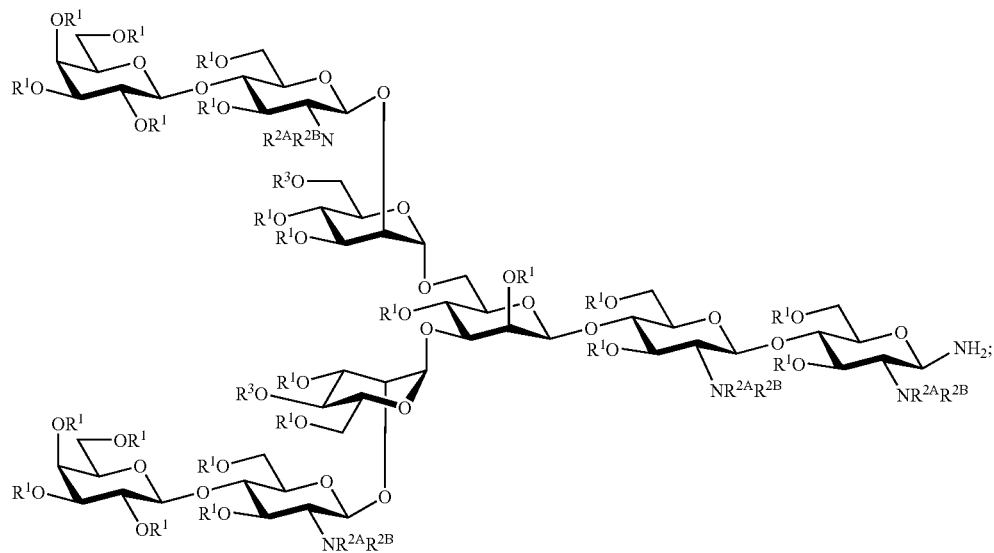

(c) reacting said β-amino carbohydrate construct under suitable conditions with a peptide whose structure is either identical or closely related to that of PSA near the N-glycosylation site and which comprises a —CH$_2$CO$_2$H moiety, to form a glycopeptide having the structure:

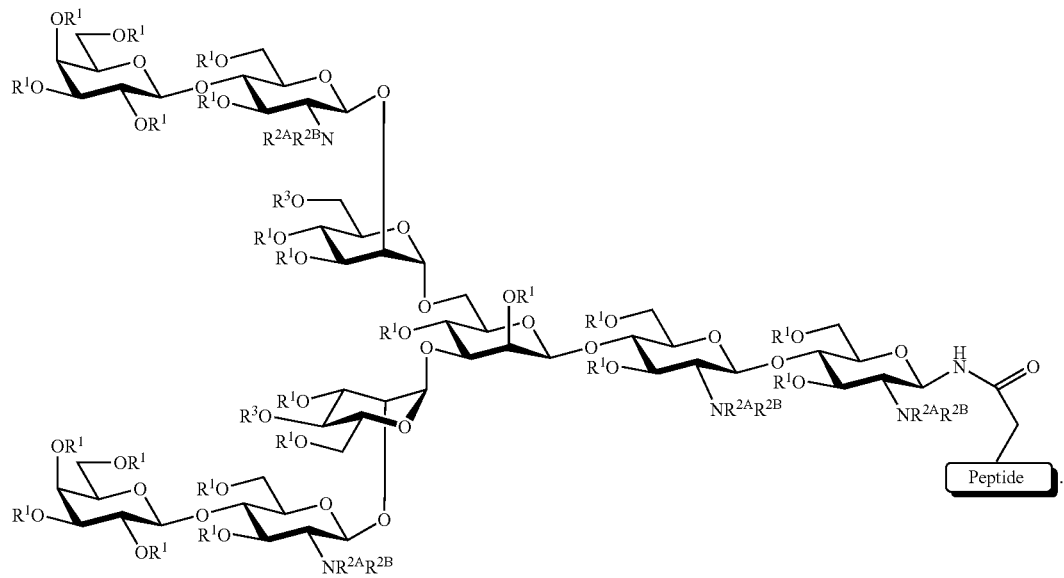

In certain exemplary embodiments, in the step of reacting the carbohydrate construct of step (a) under suitable conditions to form the β-amino carbohydrate construct, Kochetkov amination conditions are used. In certain exemplary embodiments, in the step of reacting the carbohydrate construct of step (a) under suitable conditions to form the β-amino carbohydrate construct, NH$_4$HCO$_3$/H$_2$O is used. In certain exemplary embodiments, in the β-amino carbohydrate construct of step (b), each occurrence of R$^1$ is hydrogen and each occurrence of —NR$^{2A}$R$^{2B}$ is —NHAc.

In certain other exemplary embodiments, in the step of reacting the β-amino carbohydrate construct under suitable conditions with a peptide whose structure is either identical or closely related to that of PSA near the N-glycosylation site, the reaction conditions comprise HATU and Hünig's base is a suitable solvent. In certain embodiments, the solvent is DMSO. In certain embodiments, the peptide has the following structure:

(SEQ ID NO:10)

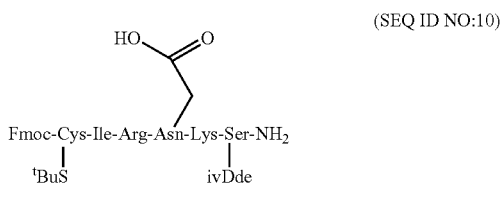

and the glycopeptide of step (c) has the structure:

(SEQ ID NO: 2)

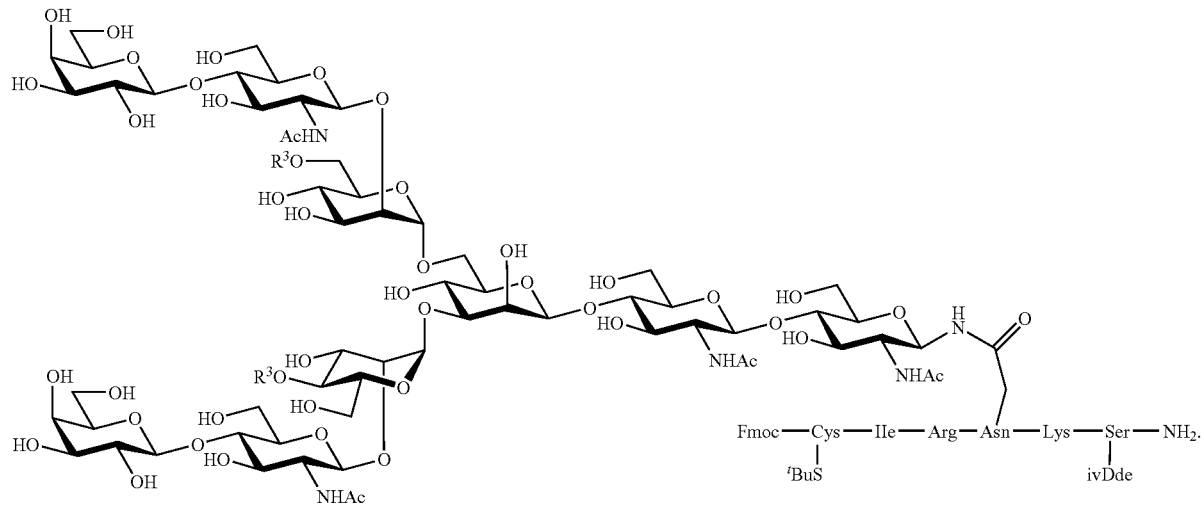

In certain exemplary embodiments, in the β-amino carbohydrate construct formed in step (b), each occurrence of $R^1$ is hydrogen, each occurrence of $-NR^{2A}R^{2B}$ is $-NHAc$, and each occurrence of $R^3$ is independently hydrogen or a carbohydrate domain comprising a saccharide moiety having the structure:

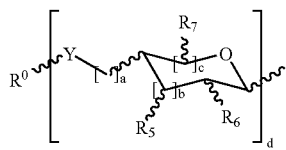

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group.

In certain other exemplary embodiments, the α-O-protected carbohydrate construct of step (a) has the structure:

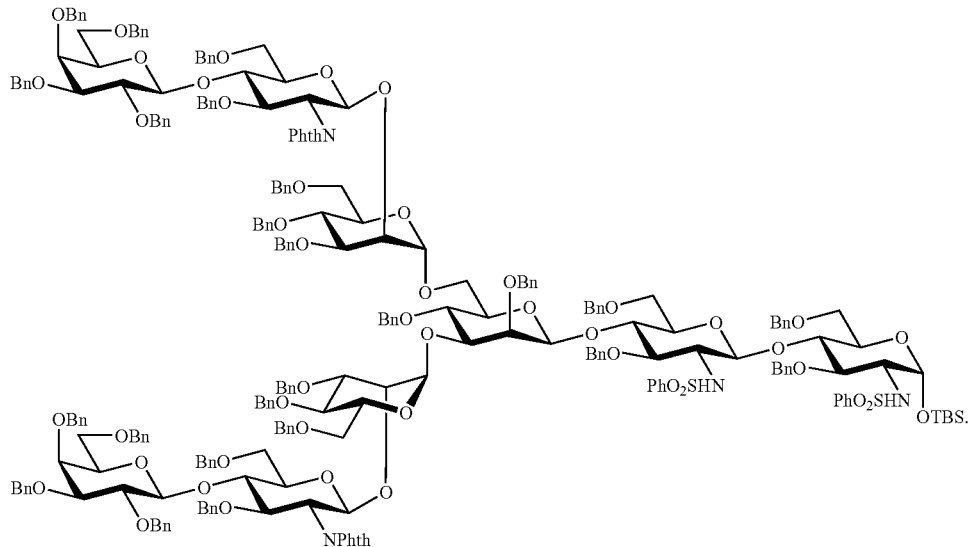

In certain other exemplary embodiments, the glycopeptide formed in step (c) has the structure:
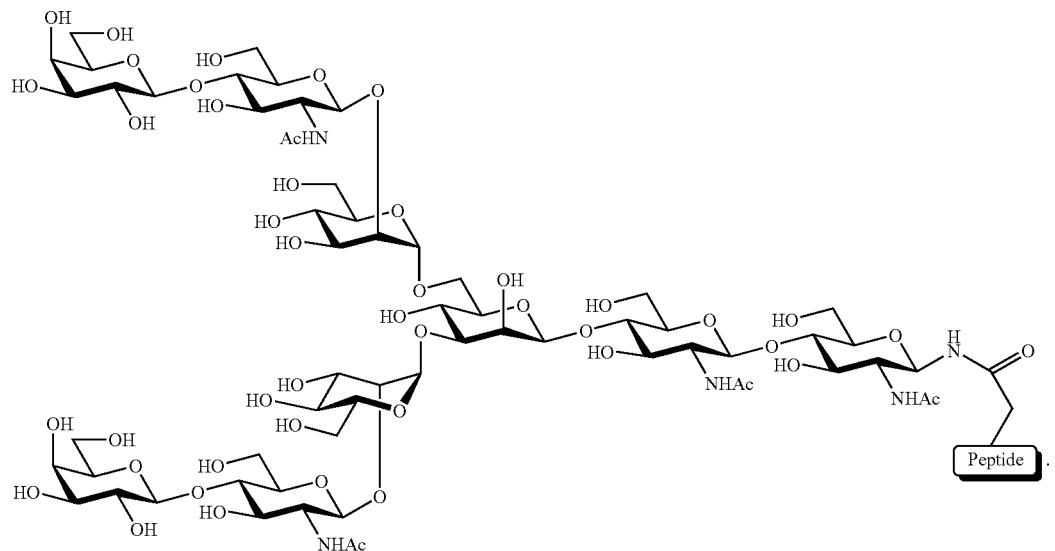
In certain other exemplary embodiments, the α-O-protected carbohydrate construct of step (a) has the structure:
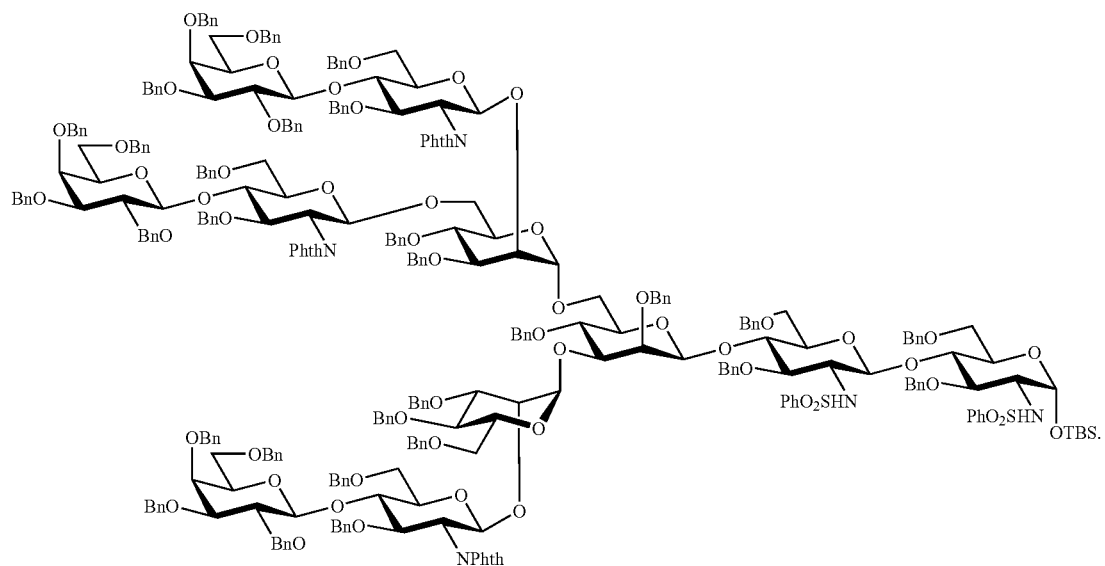

In certain other exemplary embodiments, the glycopeptide formed in step (c) has the structure:
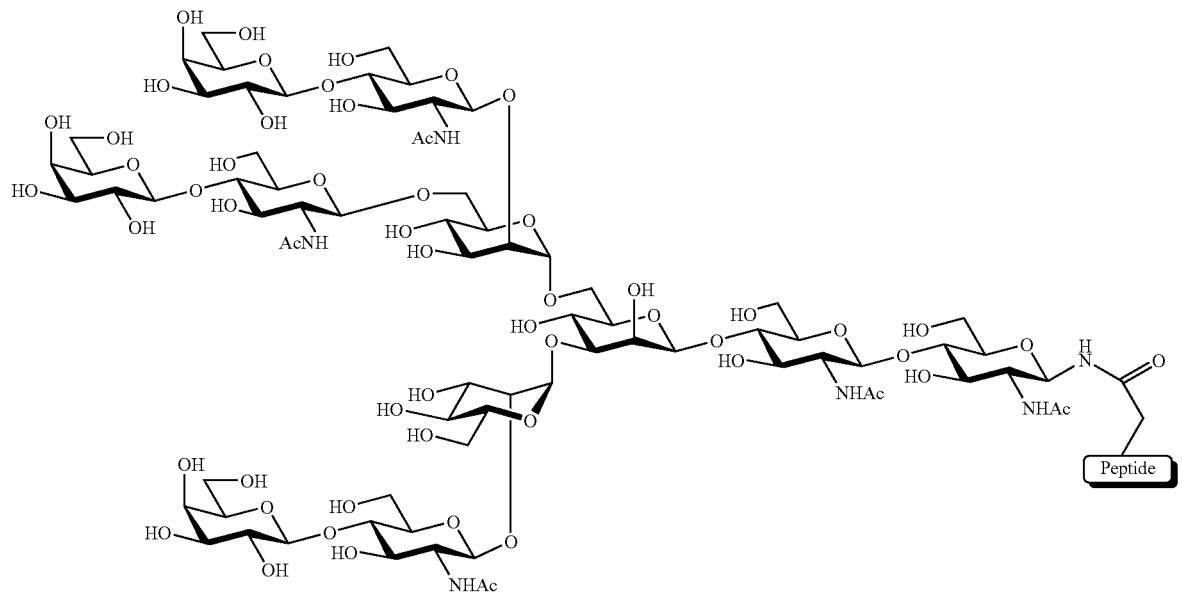
In certain other exemplary embodiments, the α-O-protected carbohydrate construct of step (a) has the structure:
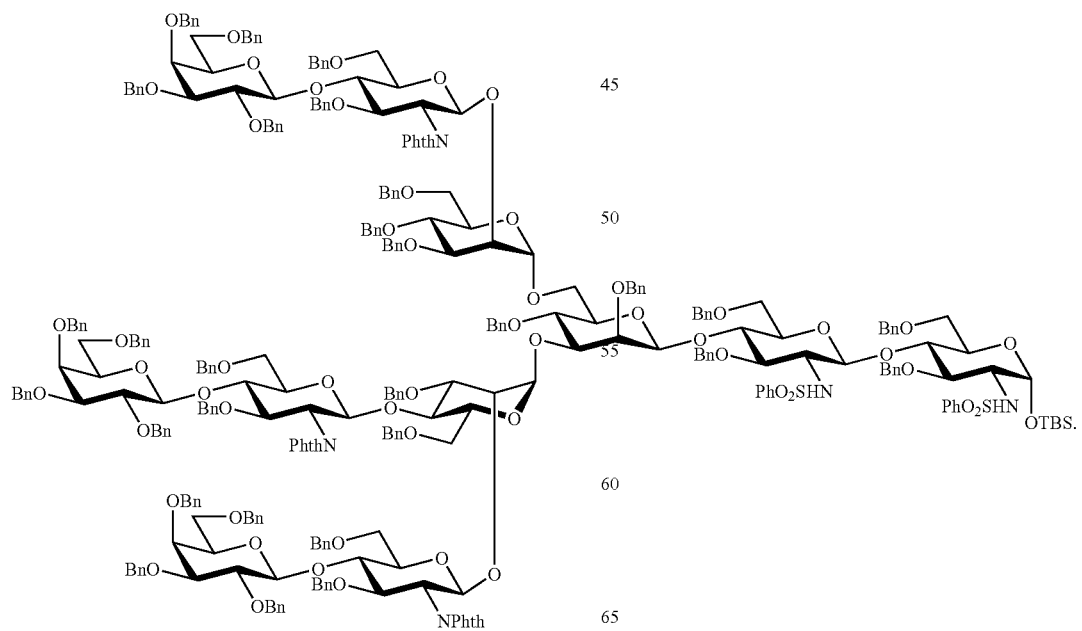

In certain other exemplary embodiments, the glycopeptide formed in step (c) has the structure:
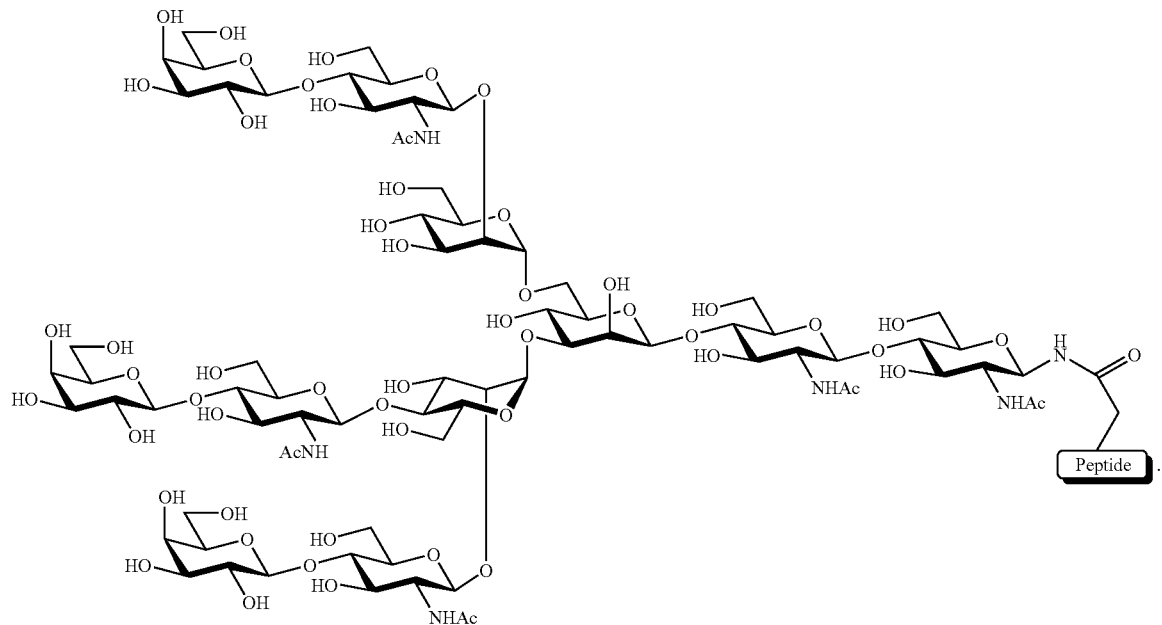
In certain other exemplary embodiments, the α-O-protected carbohydrate construct of step (a) has the structure:
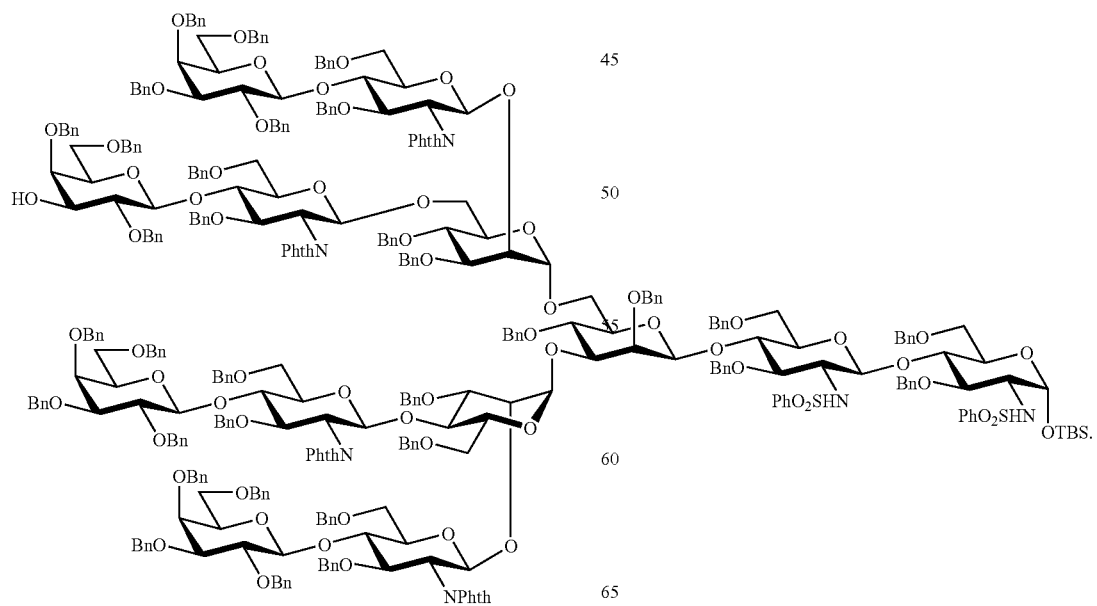

In certain other exemplary embodiments, the glycopeptide formed in step (c) has the structure:

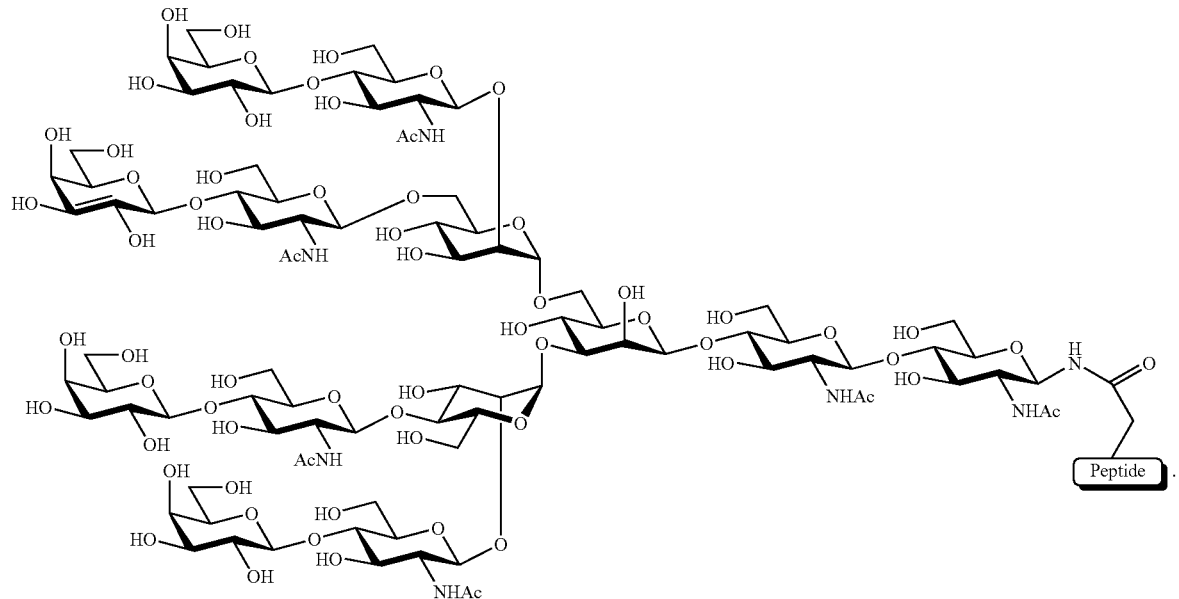

In certain other embodiments, the method further comprises a step of subjecting the glycopeptide formed in step (c) to Native Chemical Ligation conditions in the presence of a suitable polypeptide to form a glycopolypeptide having the structure:

In certain embodiments, the peptide whose structure is either identical to or closely related to that of PSA near the N-glycosylation site comprises the amino acid sequence: Cys-Ile-Arg-Asn-Lys-Ser wherein any one or more of the amino acid residues may bear one or more protecting groups. In certain exemplary embodiments, the carbohydrate construct is attached to an Asparagine residue (Asn) on the pep-

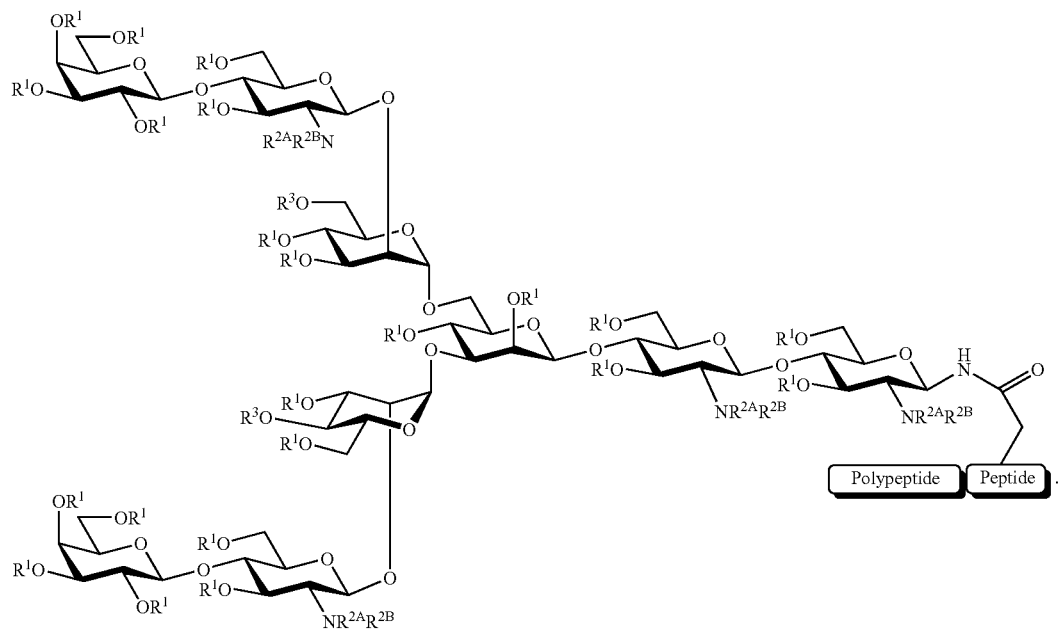

tide via an amide linkage. In certain other exemplary embodiments, the peptide whose structure is either identical to or closely related to that of PSA near the N-glycosylation site comprises the amino acid sequence:

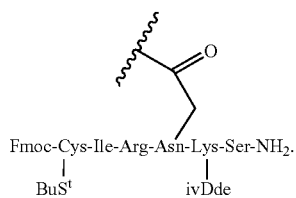

(SEQ ID NO: 2)

In certain other exemplary embodiments, the peptide whose structure is either identical to or closely related to that of PSA near the N-glycosylation site comprises the amino acid sequence:

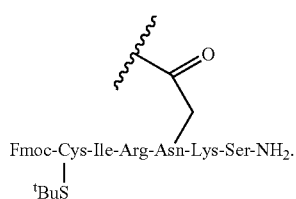

(SEQ ID NO: 2)

In certain other embodiments, when the glycopeptide formed in step (c) is further subjected to Native Chemical Ligation, the polypeptide comprises the amino acid sequence: Gly-Gly-Val-Leu-Val-His-Pro-Gln-Trp-Val-Leu-Thr-Ala-Ala-His (SEQ ID NO: 11), wherein any one or more of the amino acid residues may bear one or more protecting groups or a moiety suitable for Native Chemical Ligation. In certain embodiments, the polypeptide comprises a moiety suitable for Native Chemical Ligation, wherein the NCL moiety comprises a thioester.

The synthetic methodology is readily applicable to the generation of significantly longer (or shorter) segments of PSA. Both the peptide to be glycosylated and the thioester utilized for NCL can more closely approach the ~50 residue limit for linear synthesis; the resulting peptide can thus extend entirely to the N-terminus of PSA. If the peptide to be glycosylated (cf. 11) is extended significantly towards the C-terminus of PSA the glycosylation yield might suffer due to secondary structure formation of the longer peptide (See, for example, (1) Kent, S. B. H. "Chemical Synthesis of Peptides and Proteins." *Annu. Rev. Biochem.* 1988, 57, 957-989; and (2) Tam, J. P.; Lu, Y. A. "Coupling Difficulty Associated with Interchain Clustering and Phase-Transition in Solid-Phase Peptide-Synthesis." *J. Am. Chem. Soc.* 1995, 117, 12058-12063), but reaction conditions involving chaotropic salts have been devised to overcome issues of aggregation (See, for example, Thaler, A.; Seebach, D.; Cardinaux, F. "Lithium Salt Effects in Peptide Synthesis. 2. Improvement of Degree of Resin Swelling and of Efficiency of Coupling in Solid-Phase Synthesis." *Helv. Chim. Acta* 1991, 74, 628-643).

In certain exemplary embodiments, the polypeptide has the structure: Gly-Gly-Val-Leu-Val-His-Pro-Gln-Trp-Val-Leu-Thr-Ala-Ala-His SR (SEQ ID NO: 11); where R is a functional group suitable for effecting chemical ligation; and the resulting glycopeptide has the structure:

(SEQ ID NO: 1)

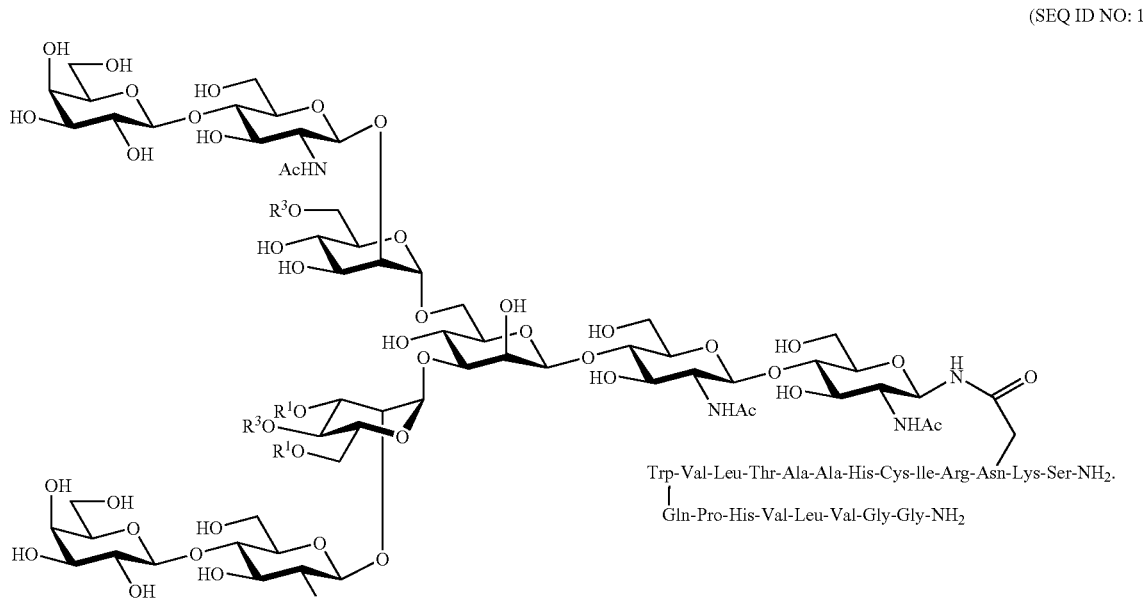

In certain embodiments, R is —(CH$_2$)$_2$C(=O)NH$_2$.

In another aspect, the invention provides a method of preparing an α-O-protected carbohydrate construct having the structure:

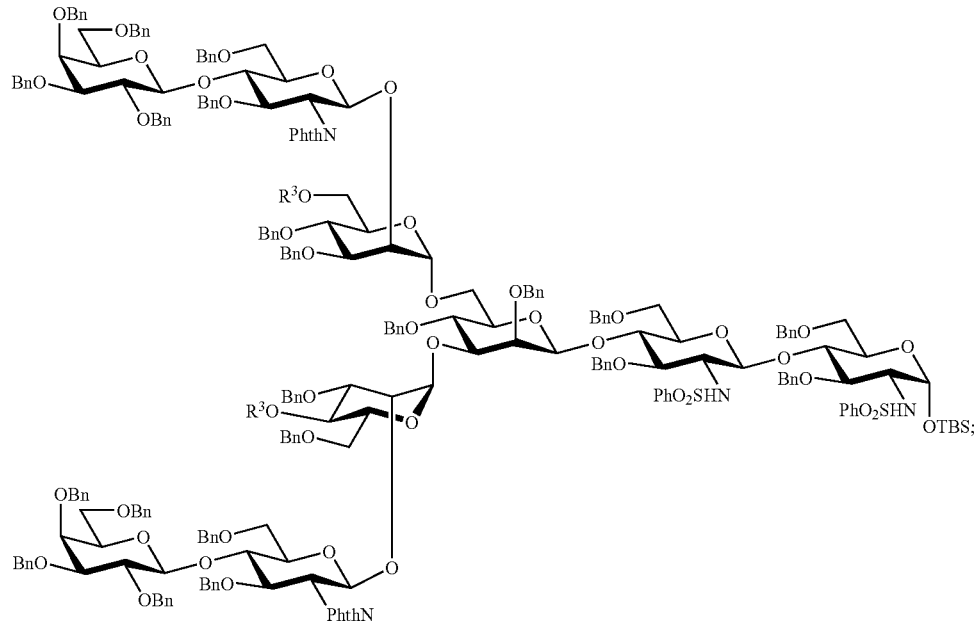

wherein each occurrence of R$^3$ is independently Bn or a disaccharide having the structure:

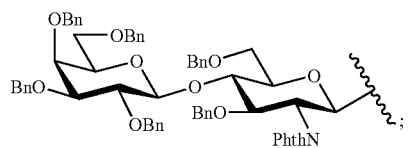

said method comprising steps of:
(a) coupling a trisaccharide having the structure:

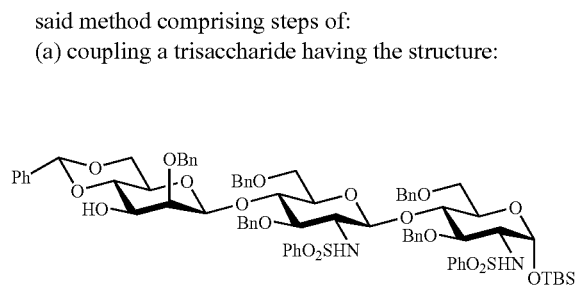

with a monosaccharide having the structure:

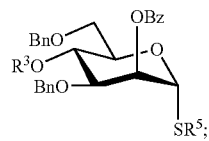

wherein R$^3$ is Bn or Bz; and R$^5$ is lower alkyl or aryl;

in the presence of an activating agent under suitable conditions to form a protected tetrasaccharide ester having the structure:

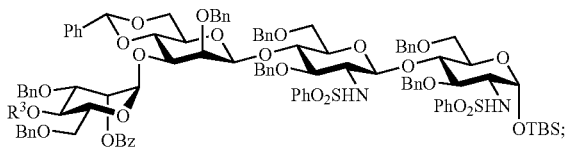

wherein R$^3$ is Bn or Bz;

(b) partially deprotecting the protected tetrasaccharide ester formed in step (a) under suitable conditions to form a partially deprotected tetrasaccharide having the structure:

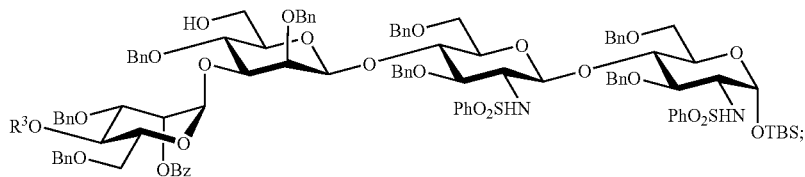

wherein $R^3$ is Bn or Bz;

(c) coupling the partially deprotected tetrasaccharide formed in step (b) with a monosaccharide having the structure:

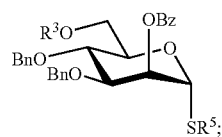

wherein $R^3$ is Bn or Bz; and $R^5$ is lower alkyl or aryl;
in the presence of an activating agent under suitable conditions to form a protected pentasaccharide having the structure:

wherein each occurrence of $R^3$ is independently Bn or H; and (e) coupling the partially deprotected pentasaccharide formed in step (d) with a disaccharide having the structure:

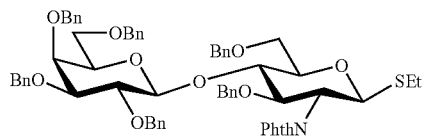

in the presence of activating agent under suitable conditions to form the α-O-protected carbohydrate construct.

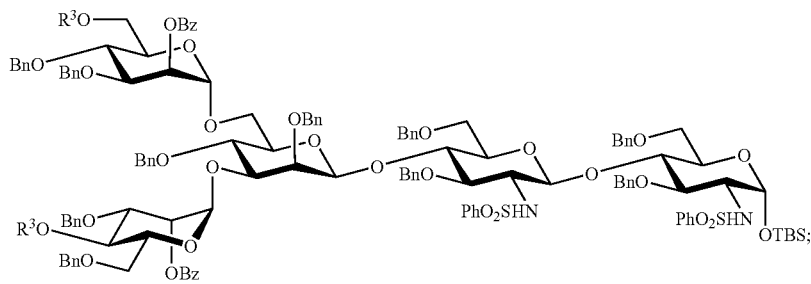

wherein each occurrence of $R^3$ is independently Bn or Bz;

(d) partially deprotecting the pentasaccharide formed in step (c) under suitable conditions to form a partially deprotected pentasaccharide having the structure:

In certain exemplary embodiments, the activating agent used in steps (a) and (c) comprises $(BrC_6H_4)_3NSbCl_6$. In certain other exemplary embodiments, in the step of partially deprotecting the protected tetrasaccharide ester (step (b)), the protected tetrasaccharide ester formed in step (a) is subjected

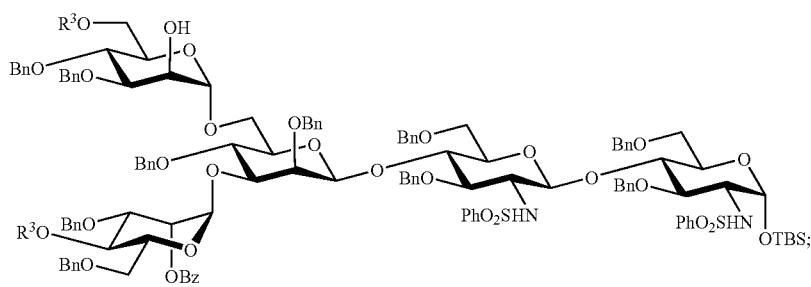

to reductive reaction conditions comprising Bu$_2$BOTf, BH$_3$. In certain other exemplary embodiments, in the step of partially deprotecting the protected pentasaccharide (step (d)), the protected pentasaccharide formed in step (c) is subjected to reaction conditions comprising NaOMe. In certain exemplary embodiments, the activating agent used in step (e) comprises (BrC$_6$H$_4$)$_3$NSbCl$_6$.

In certain exemplary embodiments, in the α-O-protected carbohydrate construct, each occurrence of R$^3$ is Bn. In certain other exemplary embodiments, in the α-O-protected carbohydrate construct, either one or both occurrences of R$^3$ is a disaccharide moiety having the structure:

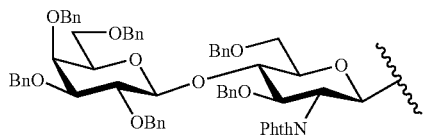

In certain exemplary embodiments, when the α-O-protected carbohydrate construct is symmetrical (i.e., each occurrence of R$^3$ is Bn), the protected pentasaccharide obtained in step (c) has the structure:

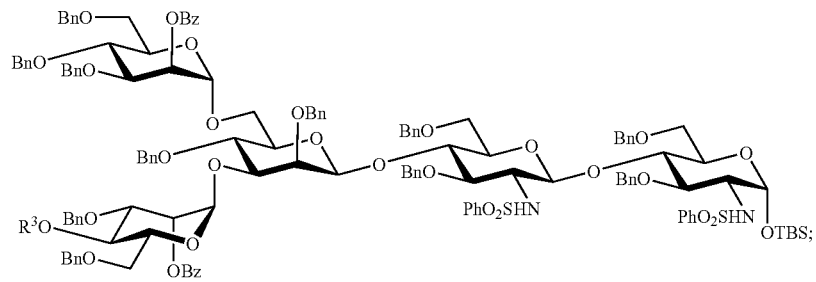

and is obtained by a process comprising coupling a trisaccharide having the structure:

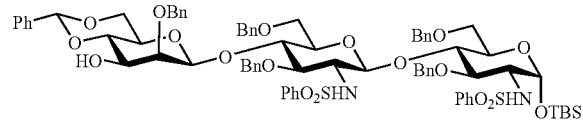

with two monosaccharides each having the structure:

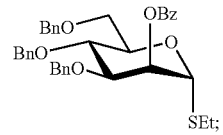

under suitable conditions.

In certain embodiments, the coupling conditions comprise reductive ring opening of the trisaccharide benzilidene acetal (e.g., BH$_3$.THF, Bu$_2$BOTf, THF), followed by reaction with the two monosaccharides (e.g., (BrC$_6$H$_4$)$_3$NSbCl$_6$, MeCN).

In another aspect, the invention provides a method of preparing a trisaccharide having the structure:

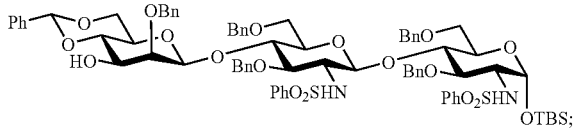

said method comprising steps of:

(a) Providing an ethylthioglycoside having the structure:

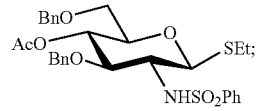

(b) Subjecting a glucal having the structure:

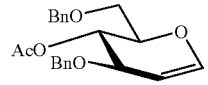

to suitable conditions to form a monosaccharide having the structure:

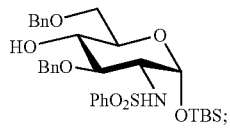

(c) Coupling the ethylglycoside of step (a) and the monosaccharide formed in step (b) under suitable conditions to form a protected disaccharide having the structure:

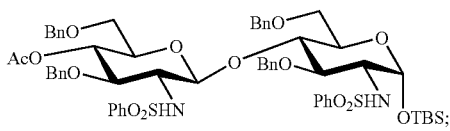

(d) partially deprotecting the protected disaccharide formed in step (c) under suitable conditions to form a partially deprotected disaccharide having the structure:

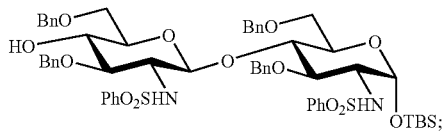

(e) coupling the partially deprotected disaccharide formed in step (d) with a monosaccharide having the structure:

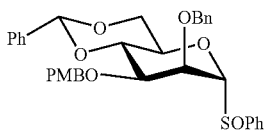

in the presence of an activating agent under suitable conditions to form a protected trisaccharide having the structure:

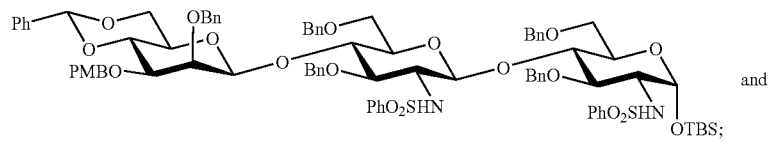

and (f) partially deprotecting the trisaccharide formed in step (e) under suitable conditions to form a partially deprotected trisaccharide having the structure:

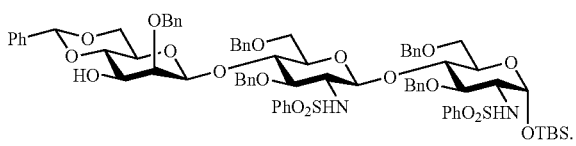

In certain other exemplary embodiments, the conditions used in step (b) include treating the glucal with an iodosulfonamidating agent (e.g., I(Coll)$_2$ClO$_4$ in the presence of PhSO$_2$NH$_2$), followed by treatment with LiSEt to yield the corresponding ethylthioglycoside. In certain other exemplary embodiments, the coupling conditions in step (c) comprise BSP, Tf$_2$O and DTBP. In certain other exemplary embodiments, in the step of partially deprotecting the protected disaccharide formed in step (d), the reaction conditions comprise NaOMe. In certain other exemplary embodiments, the coupling conditions in step (e) comprise Tf$_2$O and DTBMP. In certain other exemplary embodiments, in the step of partially deprotecting the protected disaccharide formed in step (e), the reaction conditions comprise NaOMe.

It will be appreciated that for each of the methods as detailed herein, the full arsenal of protecting groups known in the art of organic synthesis can be utilized, for example, as set forth in "Activating Agents and Protecting Groups: Handbook of Reagents for Organic Synthesis" Roush, W. R. and Pearson, A. J., Eds., John Wiley & Sons: 1999; and "Protective Groups in Organic Synthesis" Greene, T. W. and Wuts, P. G., John Wiley & Sons, New York: 1999, the entire contents of which are hereby incorporated by reference. In but a few examples, suitable protecting groups utilized herein include, but are not limited to, Bn (benzyl), TIPS (triisopropylsilyl), and Ac (acetate). In a certain exemplary embodiments of the present invention, coupling of glycoside moieties are effected under MeOTf promotion, as described herein. It will be appreciated by one of ordinary skill in the art however, that a variety of conditions known in the art of organic synthesis can be utilized to effect coupling of glycoside moieties.

The skilled practitioner will know how to adapt the synthetic methods detailed in the present invention to access a variety of other multi-branched PSA glycans and glycopeptides thereof.

In certain other exemplary embodiments, the construct should be so functionalized as to anticipate the need for its conjugation to an immunogenic carrier (e.g., protein or lipid) in anticipation of the need to stimulate an immune response. As discussed above, such constructs may be used to generate antibodies for use in a PCa immunoassay. The present invention provides improvements in total synthesis and cancer diagnostics. For example, as discussed exetensively herein, the present invention provides novel glycopeptide synthetic methodology that allows access to complex glycans N-linked to peptide backbones. In addition, the present invention sets the stage a new model for cancer diagnosis based on the errant glycan expression of transformed cells. In certain embodiments, there is provided a new immunoassay that could, in conjunction with existing diagnostic technology, differentiate more accurately between BPH and PCa.

As discussed above, in one embodiment of the present invention, the inventive compounds can be conjugated either directly or through a crosslinker to an appropriate carrier (e.g., KLH) to generate a synthetic tumor antigen. Methods of conjugation are well known in the art. For example, a conjugation strategy may be employed that involves a reductive coupling of an aldehyde (CHO) functionality on the antigenic compound, with the intended protein carrier, or lipid, presumably at the ε-amino acid residues of exposed lysines. (M. A. Bernstein; L. D. Hall, Carbohydr. Res. 1980, 78, C1; R. V. Lemieux Chem. Soc. Rev. 1978, 7, 423). Thus, in another aspect, the present invention provides synthetic constructs, whereby novel antigenic structures, as described herein, are conjugated to immunogenic carriers (e.g., proteins, peptides or lipids).

In summary, there is provided a method for PSA glycan synthesis that is readily modified to incorporate higher degrees of carbohydrate branching. In addition, the inventive synthetic method allows the incorporation of synthetic glycans into relatively long PSA peptides using a fast, high-yielding strategy that remains synthetically flexible. Accordingly, the glycopeptide structures may be optimized based on their abilities to generate antibodies for use in an immunoassay while retaining the glycan features that distinguish cancerous PSA from normal PSA.

3) Compositions

In another aspect, the present invention provides compositions comprising any one or more of the inventive normal and/or transformed PSA glycans and/or glycopeptides.

In certain embodiments, the inventive compositions may comprise an adjuvant. In certain embodiments, the adjuvant is a saponin adjuvant (see, e.g., Marciani et al., *Vaccine,* 2000, 18, 3141, U.S. Pat. Nos. 6,080,725 and 5,977,081, the entire contents of which are hereby incorporated by reference). One example of a preferred saponin adjuvant includes, but is not limited to, GPI-0100, (Galenica Pharmaceuticals, Inc., Frederick, Md.) which is a semi-synthetic adjuvant derived by modifying selected natural saponins.

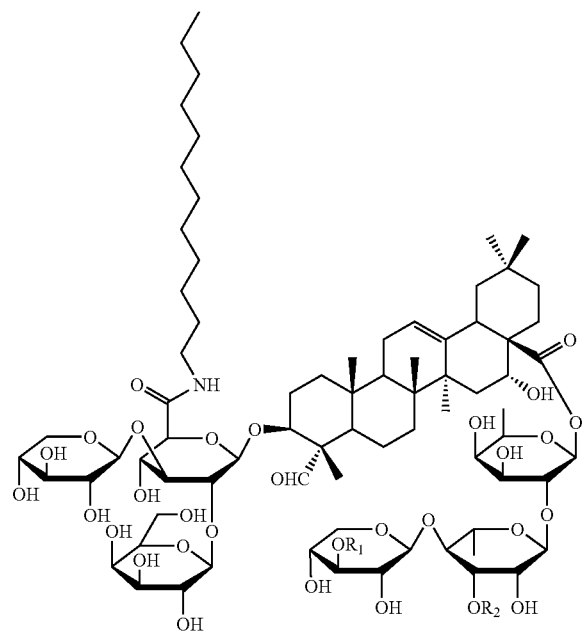

GPI-0100

Saponins isolated from *Quillaja soponaria* Molina contain two acyl moieties, a normonoterpene carboxylic acid and a normonoterpene carboxylic acid glycoside, which are linked linearly to a fucosyl residue attached at position C-28. It has been hypothesized that these lipophilic acyl groups may be responsible for these saponins' toxicity and their ability to stimulate cytotoxic T cells against exogenous antigens. The linkage between the fucosyl residue and the acyl group is unstable and hydrolyzes under mild conditions (pH≧6) with concomittant loss of saponins capability to stimulate cell-mediated immune response. Unlike their saponin precursors, GPI-0100 adjuvants comprise a stable non-toxic lipophilic moiety in the saponin's glucuronic residue. Methods for preparing these semi-synthetic adjuvants are well-known in the art. For example, GPI-0100 adjuvants may be prepared by hydrolizing quillaja saponins (which are commercially available) under basic conditions to yield the corresponding deacylated product. The deacylated intermediate may then be reacted with a suitable amine reagent using standard carboxylic acid moiety activation methodology to give the desired compounds. A wide variety of procedures are effective for extrating saponin compounds. They are generalized as follows: (i) defatting of the organic matter with a hydrophobic organic solvent such as petroleum ether; (ii) extraction with a suitable alcohol (e.g., methanol or ethanol) or alcohol-water mixture; (iii) evaporation of the carinol solvent; and (iv) partitioning of the dried alcohol extract between water and n-butanol saturated with water, followed by precipitation of the crude saponins from the n-butanol/water with a suitable organic solvent (e.g., diethyl ether). Purification of the saponin extract may require multiple separation steps. For example, preliminary fractionation may be carried out using conventional open column chromatography or flash chromatography on silica gel, in combination with a more sophisticated chromatographic technique such as High Pressure Liquid Chromatography (HPLC), droplet counter-current liquid chromatography (DCCC) or centrifugal Liquid Chromatography (RLCC). The integration of these techniques with preparative TLC typically affords separated and purified saponins.

In certain other preferred embodiments, the adjuvant is bacteria or liposomes. In certain examples, the adjuvant includes but is not limited to, *Salmonella minnesota* cells, bacille Calmette-Guerin or QS21.

As described above, the present invention provides compounds and synthetic methodologies useful in the development of novel therapeutic agents, particularly for fully synthetic cancer vaccines and/or therapeutics. In general, the compounds and glycopeptides prepared as disclosed herein can be conjugated to a protein carrier or a lipid to generate useful glycoconjugates for the treatment and/or prevention, (preferably the prevention of the recurrence), of cancer in a subject suffering therefrom. In addition, glycoconjugates prepared by processes disclosed herein are useful in adjuvant therapies as vaccines capable of inducing antibodies immunoreactive with various tumor cells. Such adjuvant therapies may reduce the rate of recurrence of certain cancers, and increase survival rates after surgery. Clinical trials on patients surgically treated for cancer who are then treated with vaccines prepared from a cell surface differentiation antigen found in patients lacking the antibody prior to immunization, a highly significant increase in disease-free interval may be observed. Cf. P. O. Livingston, et al., *J. Clin. Oncol.,* 1994, 12, 1036.

Thus, the present invention provides pharmaceutical compositions for treating cancer, preferably for preventing the recurrence of cancer, comprising any of the compounds of the present invention disclosed herein, as an active ingredient, optionally, though typically in combination with a pharmaceutically acceptable carrier. In certain embodiments, the cancer is prostate cancer. The pharmaceutical compositions of the present invention may further comprise other therapeutically active ingredients (e.g., chemotherapeutic and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

The inventive compositions include those suitable for oral, rectal, topical (including transdermal devices, aerosols, creams, ointments, lotions and dusting powders), parenteral (including subcutaneous, intramuscular, and intravenous), ocular (opthalmic), pulmonary (nasal or buccal inhalation) or nasal administration. Although the most suitable route in any given case will depend largely on the nature and severity of the condition being treated and on the nature of the active ingredient. They may be conveniently presented in unit dosage form and prepared by any of the methods well known in the art of pharmacy.

In preparing oral dosage forms, any of the unusual pharmaceutical media may be used, such as water, glycols, oils, alcohols, flavoring agents, preservatives, coloring agents, and the like in the case of oral liquid preparations (e.g., suspensions, elixers and solutions); or carriers such as starches, sugars, microcrystalline cellulose, diluents, granulating agents, lubricants, binders, disinterating agents, etc., in the case of oral solid preparations are preferred over liquid oral preparations such as powders, capsules and tablets. If desired, capsules may be coated by standard aqueous or non-aqueous techniques. In addition to the dosage forms described above, the compounds of the invention may be administered by controlled release means and devices.

Pharmaceutical compositions of the present invention suitable for oral administration may be prepared as discrete units such as capsules, cachets or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general, compositions are prepared by uniformly and intimately admixing the active ingredient with liquid carriers, finely divided solid carriers, or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as a powder or granule optionally mixed with a binder, lubricant, inert diluent or surface active or dispersing agent. Molded tablets may be made by molding in a suitable machine, a mixture of the powdered compound moistened with an inert liquid diluent.

4) Pharmaceutical Uses and Methods of Treatment
Pharmaceutical Uses

Total PSA (tPSA) is the most common PSA test used to detect prostate cancer. However, tPSA has low specificity leading to high levels of false positives (indicating PCa was present when, in fact it was not) and false negatives (indicating PCa was not present, when in fact, it was). In addition to expensive follow-up testing because of the high levels of false positives associated with PSA, and the corresponding anxiety, pain and inconvenience, research has focused on the development of enhanced serum tests.

Accordingly, diagnostic tools for prostate cancer (PCa) have improved tremendously over the last decade with the use of prostate specific antigen (PSA) as a marker for the disease. Gross serum levels of PSA were originally used as key diagnostics, but such assays cannot distinguish between patients with PCa and those with benign prostatic hyperplasia (BPH) at PSA serum levels between 4 and 10 µg/L. It was later found that patients with BPH displayed elevated levels of free PSA relative to their total amount of serum PSA; combinations of the original assay and the new, comparative assay of free to total PSA were reported to yield more accurate diagnoses, but the utility of such assays remains under debate.)

Another method for PCa diagnosis based on serum PSA content, called PSA velocity, involves monitoring increased PSA levels over time for a particular patient, but this method is prone to errors as it necessitates accurate concentration measurements over large time intervals. Thus prostate cancer diagnosis would benefit from a new, more accurate immunoassay. The structure of PSA consists of a polypeptide backbone comprising an N-linked carbohydrate moiety. It has been shown that metastatic prostate cancer cells express larger, more highly branched carbohydrates than do normal prostate cells. The differentially glycosylated region of transformed PSA could be used as a molecular marker specific for PCa over BPH. Study of this issue in detail to develop a new PCa immunoassay requires pure, homogeneous PSA glycopeptides, but useful samples of homogeneous glycosylated PSA from natural sources are prohibitively difficult to obtain. As described above, the present invention provides normal and transformed PSA glycans and N-linked glycopeptides thereof and methods of preparing them. Thus, in one aspect, the invention provides access, through chemical synthesis, to substantially all of the potential glycoforms of PSA, both normal and transformed. The inventive normal and transformed PSA glycans and N-linked glycopeptides thereof can be used to generate antibodies for use in a prostate cancer screening method.

Thus, in one aspect, the present invention provides normal and transformed PSA glycans and N-linked PSA glycopeptides thereof for use in developing an immunoassay based on the errant expression of highly branched N-linked PSA glycopeptides. Specifically, in certain embodiments, the present invention provides a novel diagnostic immunoassay that distinguishes between PCa and BPH. For example, the inventive transformed PSA glycans and N-linked glycopeptides thereof may be used to raise antibodies specific to PCa. These antibodies can in turn be used in ELISA-type screening assays for prostate cancer diagnostics.

Accordingly, in one aspect of the invention, there is provided an antibody or antibody fragment which binds specifically to normal or transformed PSA, said antibody being a purified polyclonal antibody or a monoclonal antibody. As used herein, the term "antibody fragment" is generally intended to mean any antibody fragment having conserved the specificity of the antibody of origin, and in particular fragments of the Fab and F(ab.sup.1) type. Unless otherwise indicated, the term "antibody" also subsequently denotes antibody fragments when appropriate. The expression "antibody which binds specifically to normal or transformed PSA" or "antibody which is specific to normal or transformed PSA" is intended to denote, an antibody which binds to normal and/or transformed PSA glycans and N-linked glycopeptides thereof with high specificity. For example, in certain embodiments, the product which is bound to the antibody consists of at least 80% and preferably of at least 90%, of said normal or transformed PSA.

Thus, in one aspect, the invention provides an antibody or antibody fragment which is specific to a carbohydrate antigen comprising a carbohydrate domain having the structure:

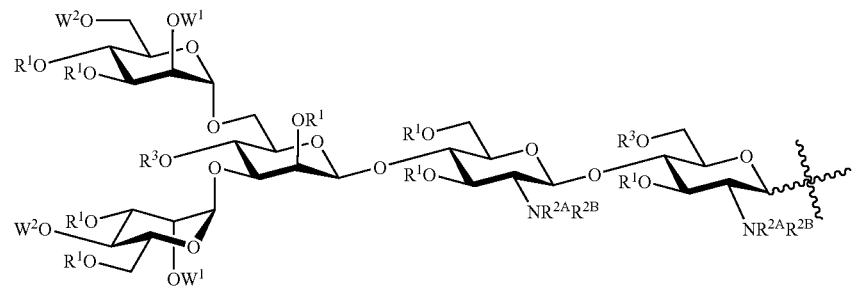

wherein each occurrence of $R^1$ is independently hydrogen or an oxygen protecting group;

each occurrence of $R^{2A}$ and $R^{2B}$ is independently hydrogen or a nitrogen protecting group;

each occurrence of $R^3$ is independently hydrogen, a protecting group or a carbohydrate domain comprising a saccharide moiety having the structure:

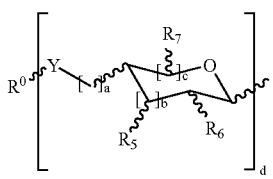

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;

each occurrence of $W_1$ and $W_2$ is independently $R^1$, $R^3$ or a moiety having the structure:

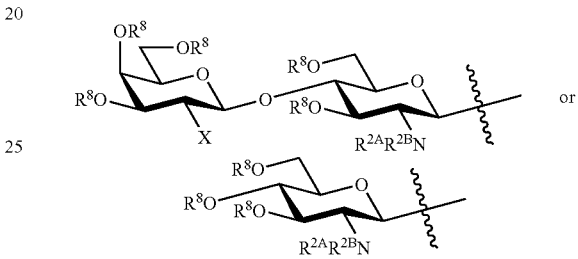

wherein X is $-OR^1$ or $-NR^{2A}R^{2B}$; and each occurrence of $R^8$ is independently $R^1$ or a sialic acid moiety;

and wherein said antibody is a purified polyclonal antibody or a monoclonal antibody. In certain embodiments, the antibody is a monoclonal antibody. In certain other embodiments, the carbohydrate domain has the structure:

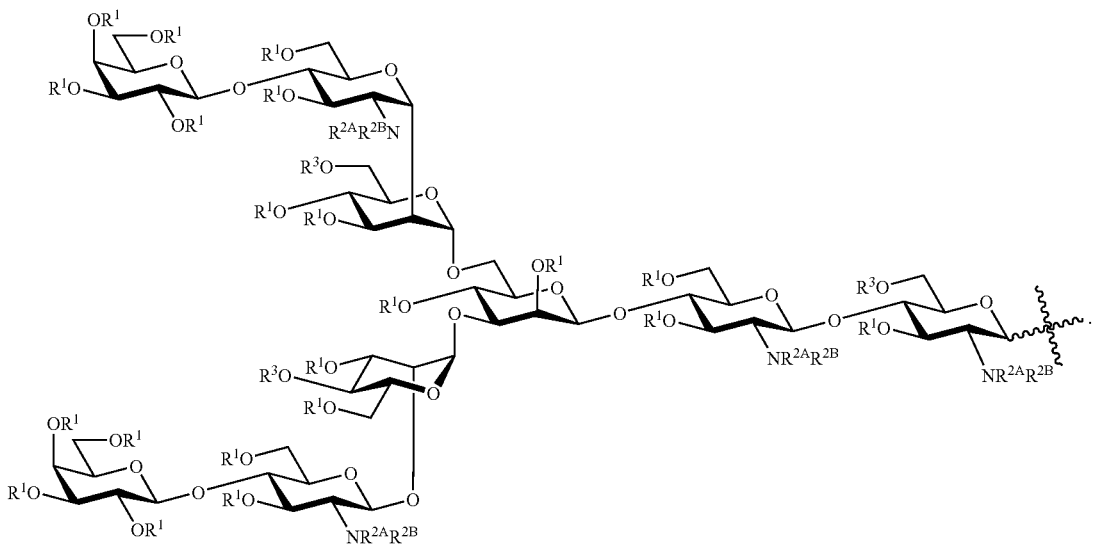

In yet other embodiments, the carbohydrate antigen has the structure:

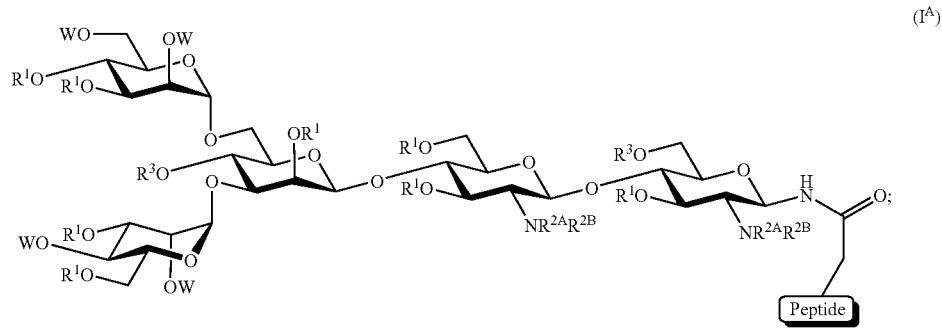

wherein the peptide has a structure either identical to or closely related to that of PSA near the N-glycosylation site.

In certain embodiments, the invention provides an antibody or antibody fragment which is specific to a compound of formula ($II^A$) having the structure:

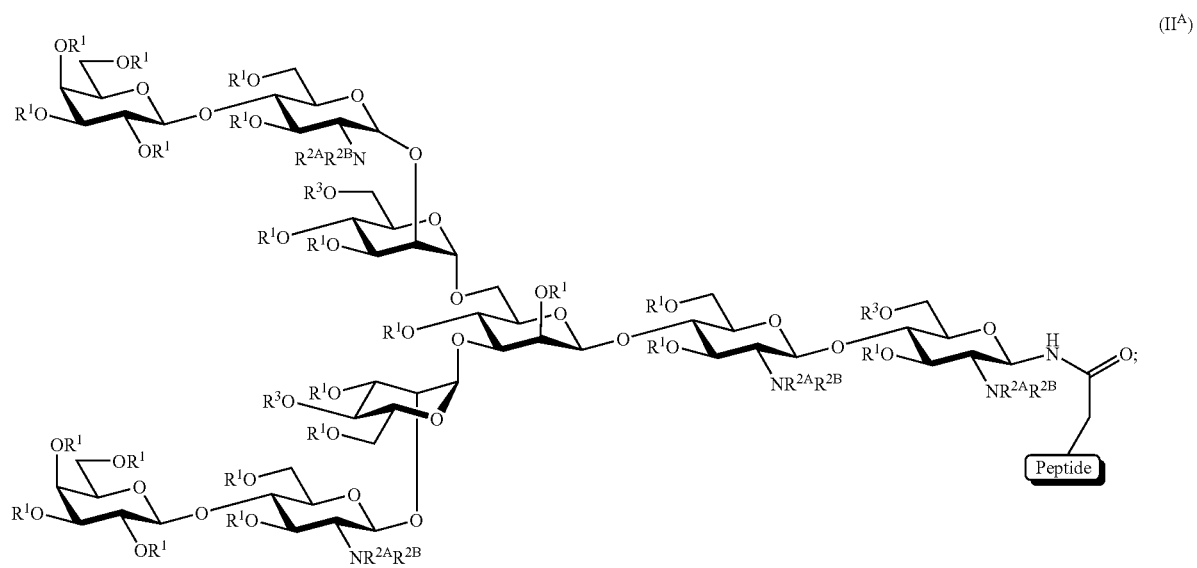

wherein each occurrence of $R^1$ is independently hydrogen or an oxygen protecting group; each occurrence of $R^{2A}$ and $R^{2B}$ is independently hydrogen or a nitrogen protecting group; and each occurrence of $R^3$ is independently hydrogen or a protecting group;

wherein the peptide has a structure either identical to or closely related to that of PSA near the N-glycosylation site;

and wherein said antibody is a purified polyclonal antibody or a monoclonal antibody.

In certain exemplary embodiments, the antibody is a monoclonal antibody.

In certain embodiments, the invention provides an antibody or antibody fragment which binds specifically to transformed PSA glycans and/or N-linked glycopeptides thereof. In certain embodiments, the antibody or antibody fragment which binds specifically to a compound of formula (I) wherein at least three occurrences of $W^1$ and $W^2$ independently comprise a moiety having the structure:

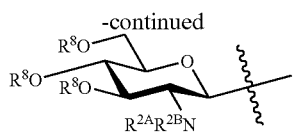

wherein X is —OR$^1$ or —NR$^{2A}$R$^{2B}$; and each occurrence of R$^8$ is independently R$^1$ or a sialic acid moiety. In certain embodiments, the antibody or antibody fragment which binds specifically to a compound of formula (I) wherein wherein each occurrence of R$^3$ and W$^2$ is independently hydrogen or a protecting group. In certain embodiments, the antibody or antibody fragment which binds specifically to a compound of formula (II) or (II$^A$) wherein each occurrence of R$^3$ is H or a protecting group. In certain embodiments, the antibody or antibody fragment which binds specifically to a compound of formula (II) or (II$^A$) wherein at least one occurrence of R$^3$ comprises a carbohydrate domain comprising a saccharide moiety having the structure:

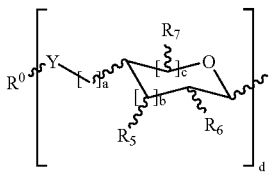

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein R$^0$ is hydrogen, a linear or branched chain alkyl, acyl, arylalkyl or aryl group; wherein each occurrence of R$^5$, R$^6$ and R$^7$ is independently hydrogen, OH, OR$^i$, NR$^{ii}$R$^{iii}$, NHCOR$^i$, F, CH$_2$OH, CH$_2$OR$^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of R$^i$, R$^{ii}$ and R$^{iii}$ is independently hydrogen, a protecting group, CHO, COOR$^{iv}$, or a substituted or unsubstituted linear or branched chain alkyl, acyl, arylalkyl or aryl group, or R$^{ii}$ and R$^{iii}$, taken together with the nitrogen atom to which they are attached, form a substituted or unsubstituted heterocyclic or heteroaryl moiety; and wherein each occurrence of R$^{iv}$ is independently H, or a substituted or unsubstituted linear or branched chain alkyl, arylalkyl or aryl group;

wherein said antibody is a purified polyclonal antibody or a monoclonal antibody;

and wherein, for compounds of formula (II$^A$), the peptide has a structure either identical to or closely related to that of PSA near the N-glycosylation site.

In certain exemplary embodiments, the antibody is a monoclonal antibody.

For an immunoassay based on differential PSA glycoform expression (e.g., normal vs. transformed PSA glycoforms) to be effective it is preferable that the desired antibodies be specific to PSA containing the "transformed" glycoform. However, antibodies specific to PSA containing the "normal" or "transformed" glycoform are considered part of the invention. A partial synthesis of PSA containing only its glycosylated region is therefore advantageous because it has been shown that antibodies recognize a number of different PSA epitopes.[29]

The glycopeptides of the invention may be used to prepare monoclonal or polyclonal antibodies. Conventional methods can be used to prepare the antibodies. As to the details relating to the preparation of monoclonal antibodies reference can be made to Goding, J. W., Monoclonal Antibodies: Principles and Practice, 2nd Ed., Academic Press, London, 1986.

The glycopeptides and antibodies specific for the PSA glycans and/or glycopeptides of the invention may be labelled using conventional methods with various enzymes, fluorescent materials, luminescent materials and radioactive material. Linking an antibody or an antibody fragment to a label, whether it is a radioactive, enzymatic or colored label or any other type of label commonly used in immunological techniques, is well known and described in the literature. Suitable enzymes, fluorescent materials, luminescent materials, and radioactive material are well known to the skilled artisan. Labelled antibodies specific for the peptides of the invention may be used in immunoassays to screen for prostate cancer.

It is presently unknown, however, how large a segment of PSA is required to generate appropriate antibodies. The secondary structure imparted from its N-linkage β-turn motif[30] may not provide the glycopeptide with enough native structure to develop appropriately specific antibodies. Also, though a short (~20 residue) segment of PSA is long enough to be recognized by the major histocompatibility complex (MHC), it might not itself be immunogenic, and could therefore require the use of an adjuvant to stimulate an immune response. Examples of suitable adjuvants include, but are not limited to, saponin adjuvants (e.g., GPI-0100), Salmonella minnesota cells, bacille Calmette-Guerin and/or QS21.

A lack of immune response with any length glycopeptide would call for the use of a carrier protein such as keyhole limpet hemocyanin (KLH),[34-36] an adjuvant[37] such as covalently bound Pam$_3$Cys,[38] or coadministered QS21.[39] Such immunostimulants have been used alone or in concert[40-42] to generate antibodies from small glycopeptide haptens,[43-45] and should prove effective here, as well. Though the first two systems require covalent conjugation, the synthetic design allows late-stage conjugation as demonstrated previously for other glycopeptides.[46]

In certain embodiments, the antibodies raised against the inventive normal and/or transformed PSA glycans and/or N-linked glycopeptides thereof can be used in diagnostic assays.

In another aspect, the invention encompasses an immunoassay method for the quantitative determination of normal PSA in a biological sample, which method comprises:

providing a biological sample;

contacting the sample with an immunoassay kit comprising an antibody or antibody fragment that binds specifically to a compound of formula (I) or (I$^A$) wherein each occurrence of R$^3$ and W$^2$ is independently hydrogen or a protecting group; wherein said antibody is a purified polyclonal antibody or a monoclonal antibody; and evaluating the amount of compound bound to the antibodies.

In another aspect, the invention encompasses an immunoassay method for the quantitative determination of normal PSA in a biological sample, which method comprises:

providing a biological sample;

contacting the sample with an immunoassay kit comprising an antibody or antibody fragment that binds specifically to a compound of formula (II) or (II$^A$) wherein each occurrence of R$^3$ is independently hydrogen or a protecting group; wherein said antibody is a purified polyclonal antibody or a monoclonal antibody; and evaluating the amount of compound bound to the antibodies.

In another aspect, the invention encompasses an immunoassay method for the quantitative determination of transformed PSA in a biological sample, which method comprises:
providing a biological sample;
contacting the sample with an immunoassay kit comprising an antibody or antibody fragment that binds specifically to a compound of formula (I) or (I$^4$) wherein at least three occurrences of W$^1$ and W$^2$ independently comprise a moiety having the structure:

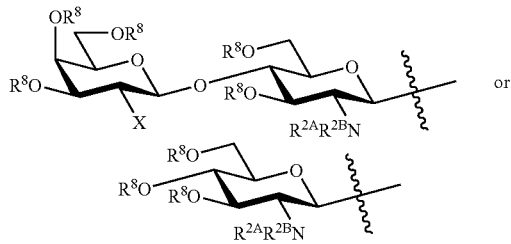

wherein X is —OR$^1$ or —NR$^{2A}$R$^{2B}$; and each occurrence of R$^8$ is independently R$^1$ or a sialic acid moiety; wherein said antibody is a purified polyclonal antibody or a monoclonal antibody; and
evaluating the amount of compound bound to the antibodies.

In another aspect, the invention encompasses an immunoassay method for the quantitative determination of transformed PSA glycoform in a biological sample, which method comprises:
providing a biological sample;
contacting the sample with the immunoassay kit comprising antibodies or antibody fragments that bind specifically to a compound of formula (II) or (II$^4$) wherein at least one occurrence of R$^3$ comprises a carbohydrate domain comprising a saccharide moiety having the structure:

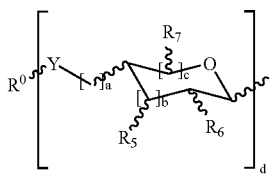

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein R$^0$ is hydrogen, a linear or branched chain alkyl, acyl, arylalkyl or aryl group; wherein each occurrence of R$^5$, R$^6$ and R$^7$ is independently hydrogen, OH, OR$^i$, NR$^{ii}$R$^{iii}$, NHCOR$^i$, F, CH$_2$OH, CH$_2$OR$^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of R$^i$, R$^{ii}$ and R$^{iii}$ is independently hydrogen, a protecting group, CHO, COOR$^{iv}$, or a substituted or unsubstituted linear or branched chain alkyl, acyl, arylalkyl or aryl group, or R$^{ii}$ and R$^{iii}$, taken together with the nitrogen atom to which they are attached, form a substituted or unsubstituted heterocyclic or heteroaryl moiety; and wherein each occurrence of R$^{iv}$ is independently H, or a substituted or unsubstituted linear or branched chain alkyl, arylalkyl or aryl group; wherein said antibody is a purified polyclonal antibody or a monoclonal antibody; and
evaluating the amount of compound bound to the antibodies.

In certain embodiments, the biological sample is a blood or serum sample. If desired, it may have undergone a concentration or dilution step prior to it being assayed. In certain other embodiment, the biological sample may be subjected to a chemical or enzymatic treatment prior to being assayed. For example, naturally occurring PSA glycosides exist as sialylated and/or fucosylated variants. Predigestion of the biological sample (or PSA isolated from said sample) with sialidase and/or fucosidase may be carried out prior to immunoassaying the sample. This would allow access to a much mire homogeneous sample (with respect to PSA glycans) for immunoassay (thus making detection of errant PSA glycoforms more likely).

The skilled practitioner will recognize that the quantification of the normal/transformed PSA with said antibodies or antibody fragments may be carried out in various well-known ways. For example, the amount of normal/transformed PSA may be evaluated using sandwich-type assays. Accordingly, in certain exemplary embodiments, an immunometric assay system is provided wherein the antibody or antibody fragment which binds specifically to normal/transformed PSA are attached to a support, is brought into contact with the biological sample for which it is desired to determine the normal/transformed PSA content, and then, after optional washing, said support is brought into contact with a second labeled antibody which binds to PSA. After further washing, the amount of label attached may be measured and the normal/transformed PSA content is deduced therefrom by comparison with a standard curve established beforehand. In certain embodiments, the antibodies or antibody fragments are covalently attached to the support. In other embodiments, the antibodies or antibody fragments are coated onto the surface of the support (i.e., the antibodies or antibody fragments are "attached" to the solid support by physical and electrical forces of attraction).

In certain embodiments, the antibodies are attached to a solid support. The attachment of antibodies or of antibody fragments to a solid support is well known in the art. The support may be made with any solid, biological or synthetic material with adsorbent properties or capable of attaching a coupling agent. Materials are known and described in the literature. Among the solid materials capable of attaching the antibodies by adsorption, mention should be made, for example, of polystyrene, polypropylene, latex, etc. Among the materials which make it possible to attach the antibodies covalently using a coupling agent, mention may in particular be made of dextran, cellulose, etc. The support may, for example, be in the form of disks, of tubes, of beads or plates, in particular of microtitration plates.

In certain embodiments, the antibodies are coated on a surface [e.g., 96- (or higher desity format) well plate] and are made to react with the antigen present in standards or samples (e.g., normal/transformed PSA). This reaction leads to the formation of a capture antibody-antigen complex, which is typically detected using a second (signal) antibody (e.g., antibody conjugated to horseradish peroxidase). After the addition of a suitable reagent for visualization purposes (e.g., tetramethyl-benzidine (TMB)/peroxide substrate), the signal may be measured in an ELISA photometer at 450 nm wavelength. In certain embodiments, the second (signal) antibody is an anti-PSA antibody and the concentration of antigen is directly proportional to the optical density measured in the wells. In certain other embodiments, the second (signal) antibody recognizes the PSA antibody and the concentration of antigen is inversely proportional to the optical density measured in the wells. The unknown concentration of normal/transformed PSA in biological samples may be read off a calibration curve constructed by plotting binding values against a series of calibrators containing known amounts of PSA.

In another aspect, the present invention provides a method for diagnosing an adenocarcinoma of the prostate in a subject suspected of suffering from said adenocarcinoma, without performing a biopsy, in which one or more immunoassays as defined above are carried out. As discussed previously, it has been reported that normal PSA is preferentially expressed in non-malignant prostate epithelial cells, whereas it has been found that transformed PSA is expressed in certain prostatic cancer cell lines. Therefore, the concentration (for example serum concentration) of transformed PSA is expected to be higher in subjects having an adenocarcinoma of the prostate than in subjects suffering from benign prostatic hyperplasia (BPH).

Accordingly, the invention also provides a method for diagnosing PCa or for differentiating between a cancer of the prostate or a BPH. In certain embodiments, the diagnostic method comprises providing a biological sample (e.g., from a subject) to be diagnosed, evaluating the amount of normal and/or transformed PSA in the sample, and assessing whether the normal and/or transformed PSA amount is consistent with PCa or BPH. In certain embodiments, the step of evaluating the amount of normal and/or transformed PSA in the sample is carried out according to the immunoassay method of the invention. In certain embodiments, the step of assessing comprises comparing the normal and/or transformed PSA amount to amounts observed in patients suffering from a recognized BPH and those observed in patients suffering from a recognized adenocarcinoma of the prostate. In certain embodiments, the diagnostic method utilizes an immunoassay kit of the invention.

In certain other embodiments, the step of evaluating the amount of normal and/or transformed PSA in the sample is carried out using a lectin binding assay. Lectins (selective binders of carbohydrates) could potentially be used to distinguish between the various glycans expressed in normal and transformed PSA. For example, if an "orthogonal" set of lectins exist for our carbohydrates, these would comprise a good basis for an immunoassay for PCa. In certain embodiments, the method involves an immunoassay for the independent quantitative determination of normal and of transformed PSA levels using different antibodies (lectins) that recognize only one or the other type of carbohydrate (i.e., normal or transformed). Comparison of the normal and transformed PSA levels to some base level of each (which can be determined experimentally) would then yield a diagnosis: high levels of transformed PSA would mean PCa, low levels of transformed, but high levels of normal would mean BPH. The lectins, if they are available, would operate independently of the peptide sequence, making this actually a very general method for the evaluation of PSA content. Note that the method described here is essentially the same as that to be used with poly- or monoclonal antibodies generated specifically for the PSA glycopeptides, except that the lectins would recognize only the carbohydrate portion of PSA.

One of ordinary skill in the art will appreciate that, in general, the results of immunoassays depend to a large extent on the specificity and affinity characteristics of the antibodies used, and that these characteristics influence the values measured with these antibodies. It is therefore understood that the "amounts observed in patients suffering from a recognized BPH and those observed in patients suffering from a recognized adenocarcinoma of the prostate" referred to above may be determined for the particular type of antibody used in the immunoassay.

In another aspect, the invention encompasses a diagnostic method for diagnosing an adenocarcinoma of the prostate in an individual suspected of suffering therefrom, or for differentiating between a benign pathology of the prostate and an adenocarcinoma of the prostate in an individual suspected of suffering therefrom by quantitative determination of levels of normal and transformed PSA glycan in a biological sample. In certain embodiment, mass spectrometry is used as a detection method. Carbohydrate moieties can be characterized by mass spectrometry after cleavage from the peptide or protein. Molecular weight measurements give information on the possible composition as well as the heterogeneity of the carbohydrate. Since carbohydrates tend to fragment at glycosidic bonds in the mass spectrometer, structural information can also be observed. For example, PSA glycans may be analyzed by mass spectrometry (MS) or tandem mass spectrometry (MS/MS), and used to screen databases for unique carbohydrate MS fragmentation patterns. With the ability to synthesize any free glycan likely to correspond to normal or transformed asialo-PSA glycans, we can generate a library of the MS fragmentation patterns for all appropriate structures. These reference MS fragmentation patterns may be used to detect the presence of PSA glycoforms in a sample, and quantify the relative levels of different PSA glycoforms (e.g., normal vs transformed PSA).

In certain embodiments, the sample to be analyzed is a crude biological sample or purified version thereof. In certain exemplary embodiments, the sample is a biological sample, as defined generally herein, that has been processed so that the PSA glycan concentration out of the total glycan concentration in the sample is increased. In certain exemplary embodiments, the sample may be purified serum PSA, purified PSA glycoprotein, purified PSA glycoprotein that has undergone sialidase digestion, purified PSA glycans obtained from deglycosylated PSA glycoprotein. In certain other embodiments, the sample encompasses any combination of PSA materials obtained from any biological sources (e.g., as detailed generally herein in the definition of the term "biological sample") or by any processes that may be used to obtain PSA glycan from the original sample (e.g., extraction, purification, glycoprotein deglycosylation, sialidase digestion, etc.).

For example, in certain embodiments, serum PSA from a known volume of serum could be purified through preferential binding to (already known) PSA backbone epitopes, which do not depend on glycan structure, then subjected to sialidase digestion. Following release of the asialosugars from the PSA peptide backbone, MS techniques could be used, along with the fragmentation pattern library, to determine quantitatively the content of both normal and transformed PSA.

Alternatively, the sample can be treated with a suitable enzyme that effects deglycosylation of PSA glycoprotein. For example, PNGase F may be used. Although PNGase F will remove glycans from many glycoproteins in their native conformation, denaturation is usually required to ensure complete hydrolysis of all susceptible bonds. Denaturation can be accomplished by running the sample on SDS-PAGE. Typically, proteins which have been run on SDS-PAGE are in a fully denatured state, which can be maintained by reduction and alkylation of all cysteine residues. Thus, the sample to be analyzed may be run on SDS-PAGE and be subjected to in-gel digestion with PNGase F [See, for example, Kuster et al., "Sequencing of N-linked oligosaccharides directly from protein gels: in-gel deglycosylation followed by matrix-assisted laser desorption/ionization mass spectrometry and normal-phase high-performance liquid chromatography", *Analytical Biochemistry*, 250:82-101, 1997; which is incorporated herein by reference in its entirety]. The isolated glycans may optionally be subjected to sialidase digestion to facilitate comparison of their MS fragmentation patterns with reference MS profiles of various PSA glycoforms.

Suitable mass spectrometry techniques include, but are not limited to, matrix-assisted laser desorption/ionization combined with time-of-flight mass analysis (MALDI-TOF MS) or electrospray ionization mass spectrometry (ESI MS). In certain embodiments, tandem MS is used. In this technique, selected oligosaccharide masses are isolated in the first stage of the spectrometer and subjected to collision-induced chemical dissociation, and the masses of the subfragments are then analyzed in the second stage to deduce the carbohydrate sequence.

In certain embodiments, sample PSA glycans can be analyzed by matrix assisted laser desorption ionization (MALDI)-mass spectrometry to determine their masses and obtain their fragmentation pattern. Matrix-assisted laser desorption ionization (MALDI) used in conjunction with a time-of-flight (TOF) mass analyzer holds great potential for identifying carbohydrates because of its relatively broad mass range, high resolution (10,000 at mass 5,000) and sampling rate (up to 1 sample/second). In one aspect MALDI offers a potential advantage over ESI and FAB in that biomolecules of large mass can be ionized and analyzed readily. Furthermore, in contrast to ESI, MALDI produces predominantly singly charged species. In one embodiment, the PSA glycans isolated from the biological sample to be diagnosed are analyzed by MALDI-TOF MS according to methods known in the art. Typically, this involves forming a matrix on the membrane with an agent which absorbs the incident light strongly at the particular wavelength employed. The sample is excited by UV, or IR laser light into the vapor phase in the MALDI mass spectrometer. Ions are generated by the vaporization and form an ion plume. The ions are accelerated in an electric field and separated according to their time of travel along a given distance, giving a mass/charge (m/z) reading which is very sensitive.

Neutral oligosaccharides with masses greater than about 1000 Da have been shown to exhibit similar signal strengths, irrespective of structure, when examined by MALDI TOF MS (see, for example, Naven et al., *Rapid Commun. Mass Spectrom.*, 10:1361-1366, 1996; which is hereby incorporated herein by reference in its entirety). Therefore, MALDI mass spectra allow the relative quantities of constituents of a mixture to be determined (See, for example, Harvey et al., *Rapid Commun. Mass Spectrom.*, 7:6140619, 1993). In addition, the molecular weight obtained allows an isobaric monosaccharide composition of the sample to be deduced, which can serve as a starting point for the design of further glycan characterization experiments. MALDI ion sources equipped with delayed extraction are particularly useful in this respect because ions can now be resolved routinely up to m/z 3000, making it possible to distinguish between glycan compositions differing by only one mass unit.

Preferably, but not necessarily, experimental conditions are selected so as to impart desirable characteristics to the analysis. Examples of such characteristics include decreasing the laser energy required to volatilize the glycan, facilitating ionization, creating predominantly singly charged ions, reducing the peak width, and increasing the sensitivity and/or selectivity of the desired analysis product.

In another embodiment, the mass spectrometer is directly or indirectly coupled with a liquid chromatography technique, such as HPLC, RP-HPLC CE or gel electrophoresis to further resolve the glycans (or glycoproteins) prior to MS analysis. This is particularly useful for resolving glycans of identical or similar molecular weight.

Once the MS fragmentation pattern of the sample glycans has been experimentally determined, a computer program can be used to search available MS databases for reference glycan MS spectra, which, added together (with proper coefficients applied to take into account the relative amount of each PSA glycoform present in the sample), would match the fragmentation pattern obtained experimentally. Various informatics tools are known in the art that can perform this task. For example, quantitative determination of PSA glycoforms in a sample may be performed with a computer-assisted technique in which the sample MS fragmentation pattern is obtained, followed by searching reference MS fragmentation patterns of known PSA-related glycans. A computer program is then used to determine all possible combinations of available reference carbohydrate MS fragmentation patterns that can sum to the measured pattern of the sample. The algorithm can then calculate various combinations of coefficients that need to be associated with relevant reference carbohydrate MS fragmentation patterns to sum to the measured pattern of the sample. The theoretical fragmentation spectrum most closely matching the experimental fragmentation pattern reveals the glycan composition of the sample. The coefficient associated with each glycan MS pattern indicates the relative level of each glycan in the original sample.

Thus, in one aspect, the invention provides a diagnostic method for diagnosing an adenocarcinoma of the prostate in an individual suspected of suffering therefrom, or for differentiating between a benign pathology of the prostate and an adenocarcinoma of the prostate in an individual suspected of suffering therefrom; the method comprising: providing a biological sample; experimentally obtaining an MS fragmentation pattern of the sample; generating a theoretical fragmentation spectrum from individual spectra in a library of known PSA-related glycan MS fragmentation patterns; and comparing the theoretical pattern with the experimental one to identify a combination of reference glycan MS fragmentation patterns that sums up to the experimental MS fragmentation pattern.

Methods of Treatment

The improvement of existing therapeutics and the development of novel therapeutics to treat and/or prolong survival of cancer patients has been the subject of continuing research in the scientific community. Although certain of these efforts have been directed to "traditional" chemotherapeutics (e.g., Paclitaxel and other small molecule and/or natural product based therapies) that act by killing malignant cancer cells, it has also been a long-standing goal (Lanzavechis, *Science*, 260, 937-944; Pardoll et al., *Curr. Opin. Immunol.* 1993, 5, 719-725; Livingston et al., *Curr. Opin. Immunol.* 1992, 4, 2; Dranoff et al., *Proc. Natl. Acad. Sci, USA* 1993, 90, 3539; M. H. Taoet et al., *Nature*, 1993, 362, 755; T. Boon, *Int. J. Cancer* 1993, 54, 177) to develop an anti-cancer vaccine that will induce an anticancer immune response. Although cancer vaccines have thus far been perceived as a mode of treatment subsequent to the detection of the disease (for example, by providing an enhanced immunological response), it would be most desirable to develop a selective vaccine that would be able to provide enhanced protection against tumor recurrence and metastasis, for example when the tumor burden has been addressed through surgery, radiation or other chemotherapeutic treatment.

In general, tumor immunotherapy is based on the theory that tumors possess specific antigens that can be recognized when presented to or processed by a properly trained immune system. One goal for the development of an effective anticancer vaccine is to break the tolerance which the immune system has for these antigens expressed mainly or exclusively by the tumor. One approach researchers have taken has been to present glycoconjugate versions of the antigens, to induce an effective immune response. As discussed above, prostate specific antigen (PSA) has been identified as a marker for prostate cancer. Other cancer carbohydrate antigens such as TF, Tn, sTN, KH-1, Le$^y$, Globo-H and PSA have been carefully characterized as being over-expressed at the surface of malignant cells in a variety of cancers (breast, colon, prostate, ovarian, liver, small cell lung and adenocarcinomas) and have been studied for use as therapeutic agents in immunotherapy of various cancers.

As detailed above, a major drawback in using carbohydrate epitopes, is that they are generally not readily available by isolation from natural sources. For example, the immense difficulties associated with their purification from natural sources render them virtually nonavailable as homogeneous starting materials for a clinical program. Thus, the incorporation of these naturally occurring epitopes into carrier proteins/peptides or any favorable molecular context via conjugation for eliciting a therapeutically useful immunological response is inefficient at best, and often virtually impossible. Therefore, to effectively study these vaccines as therapeutic agents, sufficient material can only be obtained by chemical synthesis. As discussed above, the present invention provides a variety of synthetic glycoforms of PSA (carbohydrate constructs and glycopeptide conjugates), and methods for preparing them.

Accordingly, in another aspect of the invention, a method of treatment is provided comprising administering to a subject in need thereof a therapeutically effective amount of any of the PSA glycans and/or glycoconjugates thereof disclosed herein (e.g., glycopeptides, which may additionally be conjugated to a protein, peptide or lipid carrier, either directly or through a crosslinker), optionally in combination with a pharmaceutically acceptable carrier. As discussed herein, the present invention provides various glycoforms (both normal and transformed) of PSA (e.g., di- and multi-branched forms). In certain embodiments, any one or more of the transformed PSA glycans and/or glycoconjugates thereof disclosed herein are used. The method may be applied wherein the cancer is prostate cancer. In certain embodiments, the cancer is a solid tumor or an epithelial tumor. In certain embodiments, methods for the treatment of prostate cancer (preferably for the prevention of recurrence of prostate cancer) are provided, as well as methods for inducing antibodies in a human subject, wherein the antibodies are capable of specifically binding with human prostate tumor cells, which comprises administering to the subject an amount of any of the glycoconjugates disclosed above effective to induce antibodies. In certain embodiments, the method utilized any one or more of the transformed PSA glycans and/or glycopeptides thereof disclosed herein, where the glycan(s) and/or glycopeptide(s) is/are linked to an immunogenic carrier either directly or through a crosslinker, which carrier is a protein, peptide or lipid. In certain embodiments, the carrier is Bovine Serum Albumin, polylysine or KLH. In certain other embodiments, the carrier is a lipid having the structure:

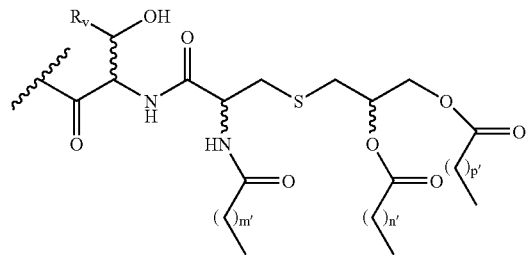

wherein m', n' and p' are each independently integers between about 8 and 20; and $R_V$ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (e.g., PamCys).

In certain other embodiments, the method comprises administering to a subject in need thereof a therapeutically effective amount of any of the compounds and/or glycopeptides disclosed herein, in combination with an immunogenic carrier, optionally in combination with a pharmaceutically acceptable carrier. Specifically, in certain exemplary embodiments, the method comprises administering a PSA glycan and/or glycopeptide additionally conjugated to an immunogenic carrier. In certain embodiments, the PSA glycan and/or glycopeptide is a transformed PSA glycan and/or glycopeptide. As discussed herein, the present invention provides various glycoforms of PSA (e.g., normal and transformed glycoforms). In certain embodiments, the method comprises administering to the subject a therapeutically effective amount of any one or more of the glycoconjugates disclosed herein (e.g., glycopeptides, which may additionally be conjugated to a protein, peptide or lipid carrier, either directly or through a crosslinker), in combination with an immunogenic carrier, optionally in combination with a pharmaceutically acceptable carrier. In certain embodiments, the method comprises administering one or more PSA glycopeptides and an immunogenic carrier that have not been conjugated. Rather, they are administered concurrently, or successively, as separate entities. In certain other exemplary embodiments, the method comprises administering one or more glycopeptide of the invention conjugated (i.e., covalently linked) to an immunogenic carrier. In certain embodiments, the method comprises administering any one or more inventive glycopeptides disclosed herein that have not been conjugated to an immunogenic carrier. Rather, the glycopeptide(s) and the immunogenic carrier are administered concurrently, or successively, as separate entities. In certain embodiments, the immunogenic carrier is a protein, peptide or lipid. In certain exemplary embodiments, the carrier is Bovine Serum Albumin, polylysine or KLH. In certain other embodiments, the carrier is PamCys. For the purpose of the invention, a compound/glycopeptide and a carrier are said to be administered concurrently when they are administered (i) as a single composition containing the compound/glycopeptide and the carrier, (ii) as two separate compositions or (iii) are delivered by separate routes within a short enough period of time that the effective result is equivalent to that obtained when both compound/glycopeptide and carrier are administered as a single composition.

In still other embodiments, the present invention provides the related method of inducing antibodies which further comprises co-administering an immunological adjuvant, or a combination of immunological adjuvants.

In certain exemplary embodiments, the inventive PSA glycans and glycopeptides thereof comprise carbohydrate domains, or truncated or elongated versions thereof, that are found on prostate tumor cells. In certain exemplary embodiments, the inventive glycopeptides comprise peptidic domains, or truncated or elongated versions thereof, that are found near the N-glycosylation site of naturally occurring PSA on prostate tumor cells.

Accordingly, embodiments of this invention encompass methods of eliciting immune responses in animals comprising administering effective amounts of inventive PSA glycans and/or glycopeptide(s) thereof and/or compositions of the invention. The present invention also includes methods of treating cancer comprising administering effective amounts of inventive PSA glycans and/or glycopeptide(s) thereof and/or compositions of the invention. In a preferred embodiment, the methods of the invention are utilized to treat prostate cancer.

A further embodiment of this invention encompasses a use of effective amounts of inventive PSA glycans and/or glycopeptide(s) thereof and/or a composition of the present invention to elicit an immune response in an animal preferably to treat cancer, more preferably prostate cancer. The present invention further includes a use of effective amounts of inventive PSA glycans and/or glycopeptide(s) thereof and/or a composition of the present invention to prepare a medicament to elicit an immune response in animal, preferably to treat cancer, more preferably prostate cancer.

It will be appreciated that the magnitude of the therapeutic dose of the compounds of the invention will vary with the nature and severity of the condition to be treated and with the particular compound and its route of administration. In general, the daily dose range for anticancer activity lies in the range of 0.0001 to 1.0 mg/kg of body weight in a mammal, although the present invention is not intended to be limited by this range.

Any suitable route of administration may be employed for providing a mammal, especially a human, with an effective dosage of a compound disclosed herein. For example, oral, rectal, topical, parenteral, ocular, pulmonary, nasal, etc. routes may be employed. Dosage forms include tablets, troches, dispersions, suspensions, solutions, capsules, creams, ointments, aerosols, etc. In preferred embodiments, the effective dosage is employed using a syringe injection.

It will be appreciated by one of ordinary skill in the art, however, that the most suitable route for administration will depend largely on the nature and severity of the condition being treated and on the nature of the active ingredient. As discussed above, the inventive therapeutics may be conveniently presented in unit dosage form and prepared by any of the methods well known in the art of pharmacy.

Additionally, once a synthetic vaccine has been derivatized and characterized, mouse immunological studies can be performed to assess the potency and/or specificity of the novel tumor vaccines.

Kits of the Invention

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

In another aspect, the invention provides an immunoassay kit for assessing the presence and/or amount of transformed PSA in a sample, wherein the kit comprises an antibody or antibody fragment that binds specifically to transformed PSA. In certain embodiments, the immunoassay kit according to the invention comprises antibodies or antibody fragments which bind specifically to a transformed PSA glycoform of the invention. In certain embodiments, the immunoassay kit according to the invention comprises antibodies or antibody fragments which bind specifically to an N-linked transformed PSA glycopeptide of the invention. In certain embodiments, the immunoassay kit according to the invention comprises antibodies or antibody fragments which bind specifically to a compound of formula (I) or (I$^A$), wherein at least three occurrences of $W^1$ and $W^2$ independently comprise a moiety having the structure:

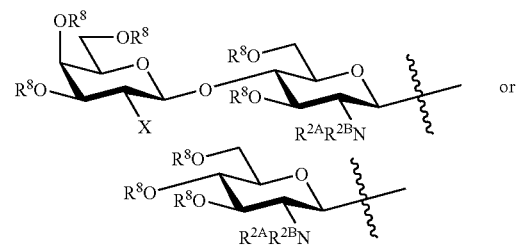

wherein X is —$OR^1$ or —$NR^{2A}R^{2B}$; and each occurrence of $R^8$ is independently $R^1$ or a sialic acid moiety. In certain embodiments, the immunoassay kit according to the invention comprises antibodies or antibody fragments which bind specifically to a compound of formula (II) or (II$^A$), wherein at least one occurrence of $R^3$ comprises a saccharide moiety having the structure:

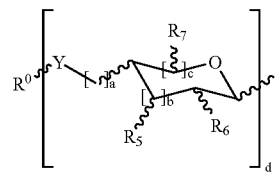

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, CHO, COOR$^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;

wherein said antibody is a purified polyclonal antibody or a monoclonal antibody.

In certain embodiments, the immunoassay kit according to the invention comprises antibodies or antibody fragments which bind specifically to a compound of formula ($II^A$) having the structure:

branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, CHO, COOR$^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group; wherein the peptide has a structure either identical to or closely related to that of PSA near the N-glycosylation site;

wherein said antibody is a purified polyclonal antibody or a monoclonal antibody.

In another aspect, the invention provides an immunoassay kit for assessing the presence and/or amount of normal PSA in a sample, wherein the kit comprises an antibody or antibody fragment that binds specifically to normal PSA. In certain embodiments, the immunoassay kit according to the invention comprises antibodies or antibody fragments which bind specifically to a normal PSA glycoform of the invention. In certain embodiments, the immunoassay kit according to the invention comprises antibodies or antibody fragments which bind specifically to an N-linked normal PSA glycopeptide of the invention. In certain embodiments, the immunoassay kit according to the invention comprises antibodies or antibody fragments which bind specifically to a compound of formula (I) or ($I^A$), wherein each occurrence of $R^3$ and $W^2$ is independently hydrogen or a protecting group. In certain embodiments, the immunoassay kit according to the invention comprises antibodies or antibody fragments which bind specifically to a compound of formula (II), wherein each occurrence of $R^3$ is independently hydrogen or a protecting group; wherein said antibody is a purified polyclonal antibody or a monoclonal antibody.

In certain embodiments, the immunoassay kit according to the invention comprises antibodies or antibody fragments which bind specifically to a compound of formula ($II^A$) having the structure:

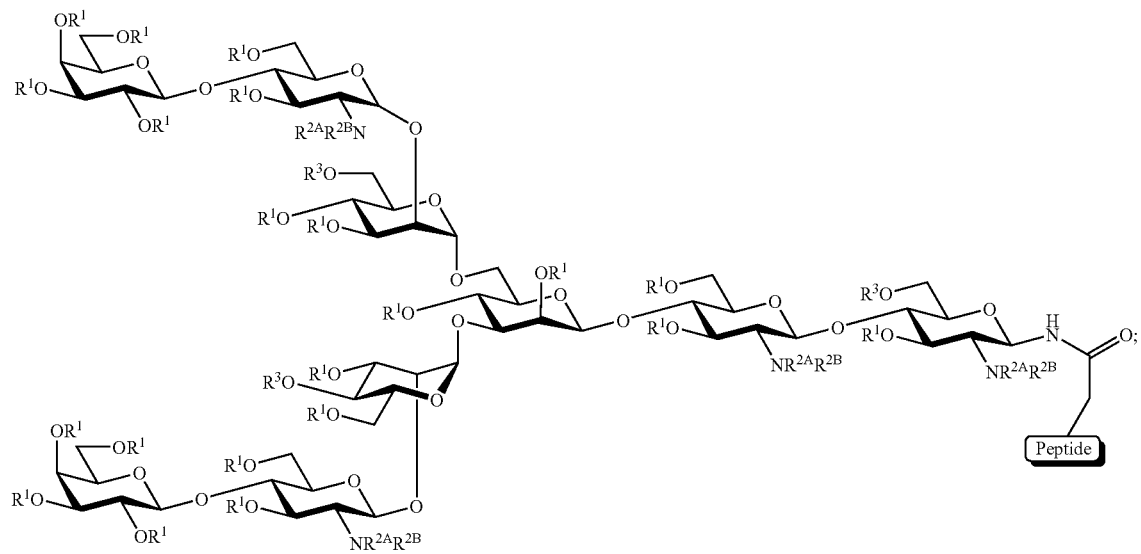

wherein each occurrence of $R^1$ is independently hydrogen or an oxygen protecting group; each occurrence of $R^{2A}$ and $R^{2B}$ is independently hydrogen or a nitrogen protecting group; and at least one occurrence of $R^3$ comprises a carbohydrate domain comprising a saccharide moiety having the structure:

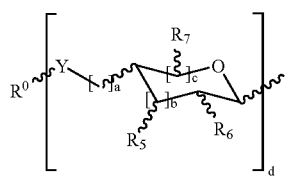

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, OR$^i$, NR$^{ii}$R$^{iii}$, NHCOR$^i$, F, CH$_2$OH, CH$_2$OR$^i$, or a substituted or unsubstituted linear or

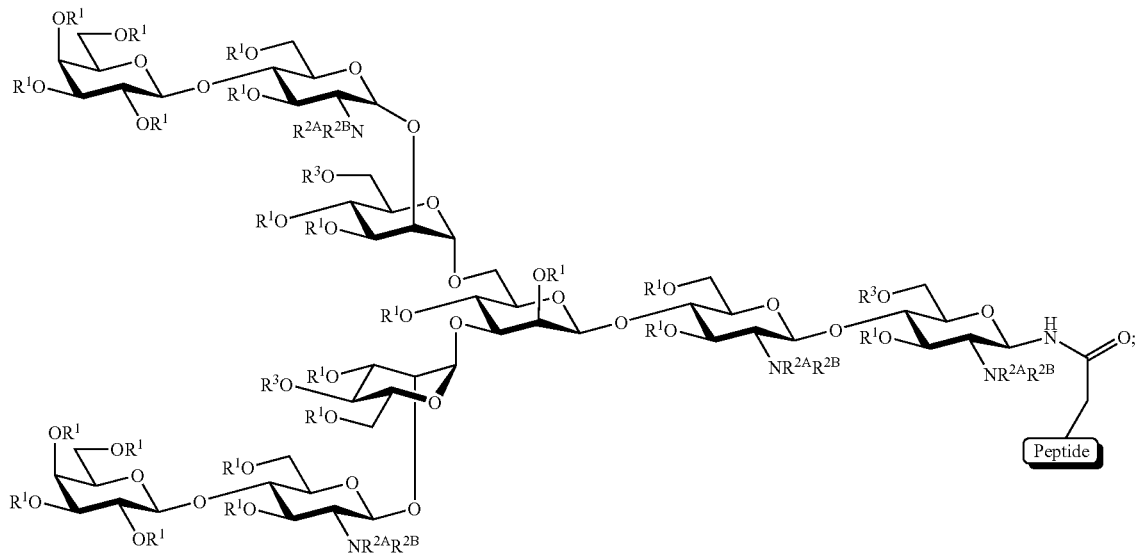

wherein each occurrence of $R^1$ is independently hydrogen or an oxygen protecting group; each occurrence of $R^{2A}$ and $R^{2B}$ is independently hydrogen or a nitrogen protecting group; and each occurrence of $R^3$ is hydrogen or a protecting group; wherein the peptide has a structure either identical to or closely related to that of PSA near the N-glycosylation site; and wherein said antibody is a purified polyclonal antibody or a monoclonal antibody.

In certain embodiments, the immunoassay kit according to the invention comprises antibodies or antibody fragments can be used as such or else in particular in a form attached to a solid support and/or linked to a label.

In another aspect, the invention provides a diagnostic kit for diagnosing an adenocarcinoma of the prostate in an individual suspected of suffering therefrom, or for differentiating between a benign pathology of the prostate and an adenocarcinoma of the prostate in an individual suspected of suffering therefrom, said kit comprising means for assaying transformed PSA in a biological sample obtained from said subject. In certain embodiments, the means for assaying transformed PSA in the biological sample comprises antibodies or antibody fragments which bind specifically to a transformed PSA. In certain embodiments, the means for assaying transformed PSA in the biological sample comprises an antibody or antibody fragment which binds specifically to a compound of formula (I) or ($I^A$) wherein at least three occurrences of $W^1$ and $W^2$ independently comprise a moiety having the structure:

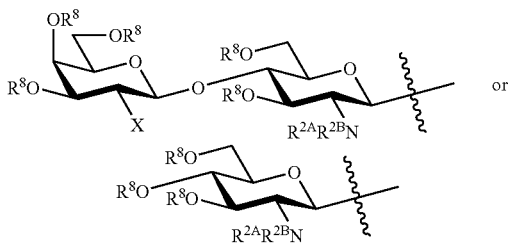

wherein X is —$OR^1$ or —$NR^{2A}R^{2B}$; and each occurrence of $R^8$ is independently $R^1$ or a sialic acid moiety. In certain embodiments, the means for assaying transformed PSA in the biological sample comprises an antibody or antibody fragment which binds specifically to a compound of formula (II) wherein at least one occurrence of $R^3$ comprises a carbohydrate domain comprising a saccharide moiety having the structure:

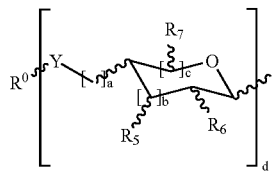

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group; wherein the peptide has a structure either identical to or closely related to that of PSA near the N-glycosylation site; wherein said antibody is a purified polyclonal antibody or a monoclonal antibody.

In certain embodiments, the means for assaying transformed PSA in the biological sample comprises antibodies or antibody fragments which bind specifically to a compound of formula (II^A) having the structure:

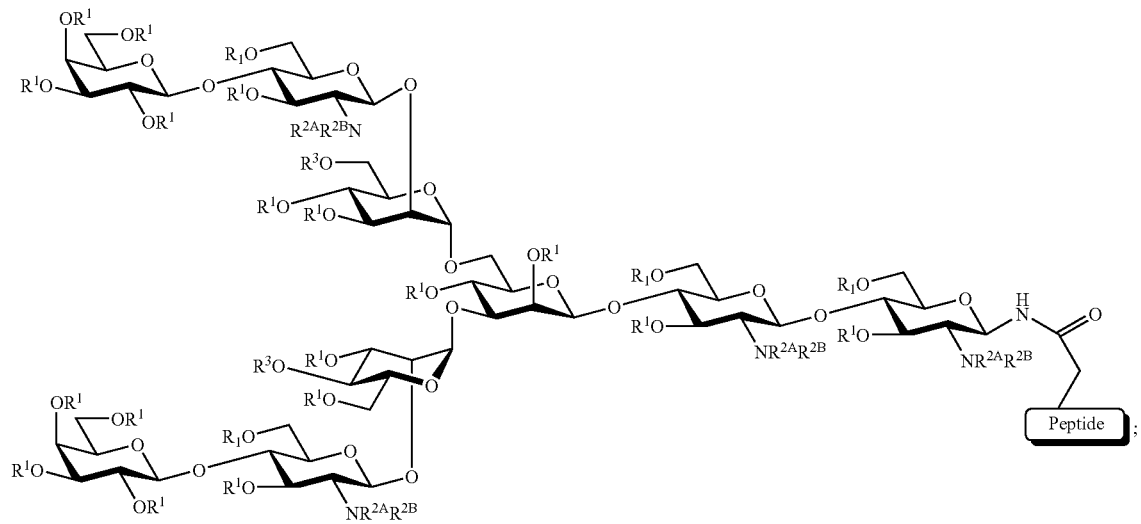

wherein each occurrence of $R^1$ is independently hydrogen or an oxygen protecting group; each occurrence of $R^{2A}$ and $R^{2B}$ is independently hydrogen or a nitrogen protecting group; and at least one occurrence of $R^3$ comprises a carbohydrate domain comprising a saccharide moiety having the structure:

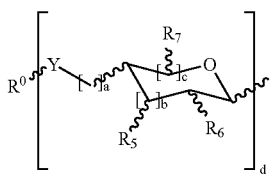

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group; wherein the peptide has a structure either identical to or closely related to that of PSA near the N-glycosylation site;

wherein said antibody is a purified polyclonal antibody or a monoclonal antibody.

Equivalents

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. In but one illustrative example, protecting groups play an important role in the synthesis of the carbohydrate domains and synthetic conjugates, as described herein; however it will be appreciated by one of ordinary skill in the art that the present invention encompasses the use of various alternate protecting groups known in the art. Those protecting groups used in the disclosure including the Examples below are merely illustrative.

It should further be appreciated that, unless otherwise indicated, the contents of those cited references are incorporated herein by reference to help illustrate the state of the art. The following examples contain important additional informa-

EXEMPLIFICATION

Example 1

N-linked pentasaccharide glycopeptide 18

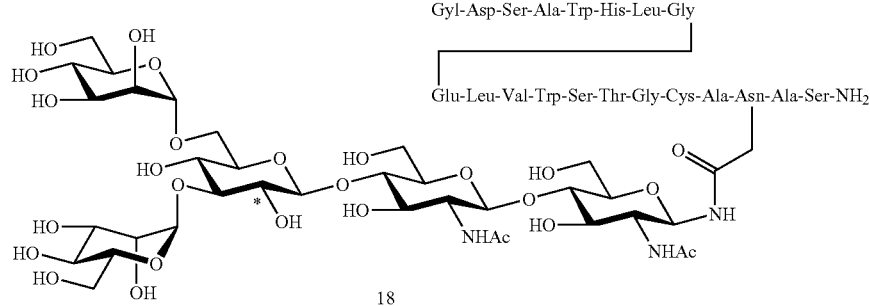

(SEQ ID NO: 8)

1) Discussion of Exemplary Synthesis:

The structural and biological consequences of cellular protein modification via posttranslational glycosylation are central issues in the rapidly growing field of glycobiology. Among the postulated consequences of glycosylation are effects on protein conformational stability and folding (See, for example, (1) B. Imperiali, S. E. O'Connor, Curr. Opin. Chem. Biol. 1999, 3, 643-649; and (2) B. Imperiali, S. E. O'Connor, T. Hendrickson, C. Kellenberger, Pure Appl. Chem. 1999, 71, 777-787). The added informational content of glycosylated cell surface proteins may also have implications in cell-cell signaling and adhesion (See, for example, P. M. Rudd, T. Elliott, P. Cresswell, I. A. Wilson, R. A. Dwek, Science 2001, 291, 2370-2376). Aberrant glycosylation can be a marker for the presence or progression of disease (See, for example, J. W. Dennis, M. Granovsky, C. E. Warren, Biochim. Biophys. Acta-Gen. Subj. 1999, 1473, 21-34). For nearly a decade we have been pursuing the total synthesis of complex oligosaccharides with a view to fashioning fully synthetic carbohydrate based antitumor vaccines (See, for example, J. R. Allen, C. R. Harris, S. J. Danishefsky, J. Am. Chem. Soc. 2001, 123, 1890-1897). Several early clinical trials based on these principles have been completed and expanded trials are currently being organized (See, for example, (1) S. F. Slovin, G. Ragupathi, S. Adluri, G. Ungers, K. Terry, S. Kim, M. Spassova, W. G. Bornmann, M. Fazzari, L. Dantis, K. Olkiewicz, K. O. Lloyd, P. O. Livingston, S. J. Danishefsky, H. I. Scher, Proc. Natl. Acad. Sci. U.S.A. 1999, 96, 5710-5715; (2) P. J. Sabbatini, V. Kudryashov, G. Ragupathi, S. J. Danishefsky, P. O. Livingston, W. Bornmann, M. Spassova, A. Zatorski, D. Spriggs, C. Aghajanian, S. Soignet, M. Peyton, C. O'Flaherty, J. Curtin, K. O. Lloyd, Int. J. Cancer 2000, 87, 79-85; and (3) T. Gilewski, G. Ragupathi, S. Bhuta, L. J. Williams, C. Musselli, X. F. Zhang, K. P. Bencsath, K. S. Panageas, J. Chin, C. A. Hudis, L. Norton, A. N. Houghton, P. O. Livingston, S. J. Danishefsky, Proc. Natl. Acad Sci. U.S.A. 2001, 98, 3270-3275).

Research studies have been conducted in an effort to sort out the structural implications of peptide glycosylation as a model for modular domains of larger glycopeptides and, eventually, even glycoproteins (See, for example, Z. G. Wang, X. F. Zhang, D. Live, S. J. Danishefsky, Angew. Chem.-Int. Ed. 2000, 39, 3652-3656). The availability of homogeneous glycopeptides, both O-linked (serine, threonine, or tyrosine α-glycosides) and N-linked (asparagine β-glycosides), could greatly enhance insights into glycobiology (See, for example, C. R. Bertozzi, L. L. Kiessling, Science 2001, 291, 2357-2364). The present invention may ultimately be applied to the total synthesis of homogeneous glycoproteins.

Numerous methods exist for glycopeptide synthesis; glycans have been introduced into peptides via amino acid "cassettes" with pendant protected saccharides (See, for example, (1) X. T. Chen, D. Sames, S. J. Danishefsky, J. Am. Chem. Soc. 1998, 120, 7760-7769; (2) N. Bezay, G. Dudziak, A. Liese, H. Kunz, Angew. Chem.-Int. Ed. 2001, 40, 2292-2295; (3) J. van Ameijde, H. B. Albada, R. M. J. Liskamp, J. Chem. Soc.-Perkin Trans. 1 2002, 1042-1049; (4) M. Ciommer, H. Kunz, Synlett 1991, 593-595; (5) M. V. Chiesa, R. R. Schmidt, Eur. J. Org. Chem. 2000, 3541-3554; and (6) E. Meinjohanns, M. Meldal, K. Bock, Tetrahedron Lett. 1995, 36, 9205-9208), through enzymatic manipulations of glycopeptides (See, for example, (1) C. Unverzagt, Tetrahedron Lett. 1997, 38, 5627-5630; (2) K. Witte, P. Sears, R. Martin, C. H. Wong, J. Am. Chem. Soc. 1997, 119, 2114-2118; (3) L. X. Wang, M. Tang, T. Suzuki, K. Kitajima, Y. Inoue, S. Inoue, J. Q. Fan, Y. C. Lee, J. Am. Chem. Soc. 1997, 119, 11137-11146; (4) G. Arsequell, G. Valencia, Tetrahedron: Asymmetry 1999, 10, 3045-3094; (5) M. Mizuno, K. Haneda, R. Iguchi, I. Muramoto, T. Kawakami, S. Aimoto, K. Yamamoto, T. Inazu, J. Am. Chem. Soc. 1999, 121, 284-290; (6) K. M. Koeller, M. E. B. Smith, R. F. Huang, C. H. Wong, J. Am. Chem. Soc. 2000, 122, 4241-4242; and (7) O. Blixt, K. Allin, L. Pereira, A. Datta, J. C. Paulson, J. Am. Chem. Soc. 2002, 124, 5739-5746), or by conjugation of fully elaborated, complex saccharides to short synthetic peptides (See, for example, (1) S. T. Anisfeld, P. T. Lansbury, J. Org. Chem. 1990, 55, 5560-5562; (2) S. T. Cohen-Anisfeld, P. T. Lansbury, J. Am. Chem. Soc. 1993, 115, 10531-10537; and (3) E. Meinjohanns, M. Meldal, H. Paulsen, R. A. Dwek, K. Bock, J. Chem. Soc.-Perkin Trans. 1 1998, 549-560). Larger O-linked glycopeptides have been synthesized using ligation techniques (See, for example, (1) P. E. Dawson, T. W. Muir, I. Clark-Lewis, S. B. H. Kent, Science 1994, 266, 776-779; and (2) C. F. Liu, J. P. Tam, Proc. Natl. Acad. Sci. U.S.A. 1994, 91, 6584-6588) such as expressed protein ligation (See, for example, (1) T. W. Muir, D. Sondhi, P. A. Cole, Proc. Natl. Acad. Sci. U.S.A. 1998, 95, 6705-6710; (2) D. Macmillan, C. R. Bertozzi, *Tetrahedron* 2000, 56, 9515-9525; and (3) T. J. Tolbert, C. H. Wong, *J. Am. Chem. Soc.* 2000, 122, 5421-5428). Bertozzi and coworkers extended the scope of the "cassette" approach by applying native chemical ligation to the synthesis of a biologically active glycoprotein with two single-residue O-linked glycans (See, for example, Y. Shin, K. A. Winans, B. J. Backes, S. B. H. Kent, J. A. Ellman, C. R. Bertozzi, *J. Am. Chem. Soc.* 1999, 121, 11684-11689). Tolbert and Wong describe the ligation of a 392-residue intein-generated peptide thioester and a dipeptide functionalized with a single N-acetylglucosamine residue.

the invention are assembled by total chemical synthesis (See, for example, S. J. Danishefsky, S. Hu, P. F. Cirillo, M. Eckhardt, P. H. Seeberger, *Chem.-Eur. J.* 1997, 3, 1617-1628). There is thus in principle no limit to the structural complexity of the carbohydrate sectors of the glycopeptide targets of the invention, even as homogeneity is maintained. Other advantages of the invention include maximal feasible convergence and the capacity to deliver final products in substantial quantities that can support precision level structural, mechanistic and immunological applications. In certain embodiments, the present invention provides fully synthetic, N-linked glycopolypeptides.

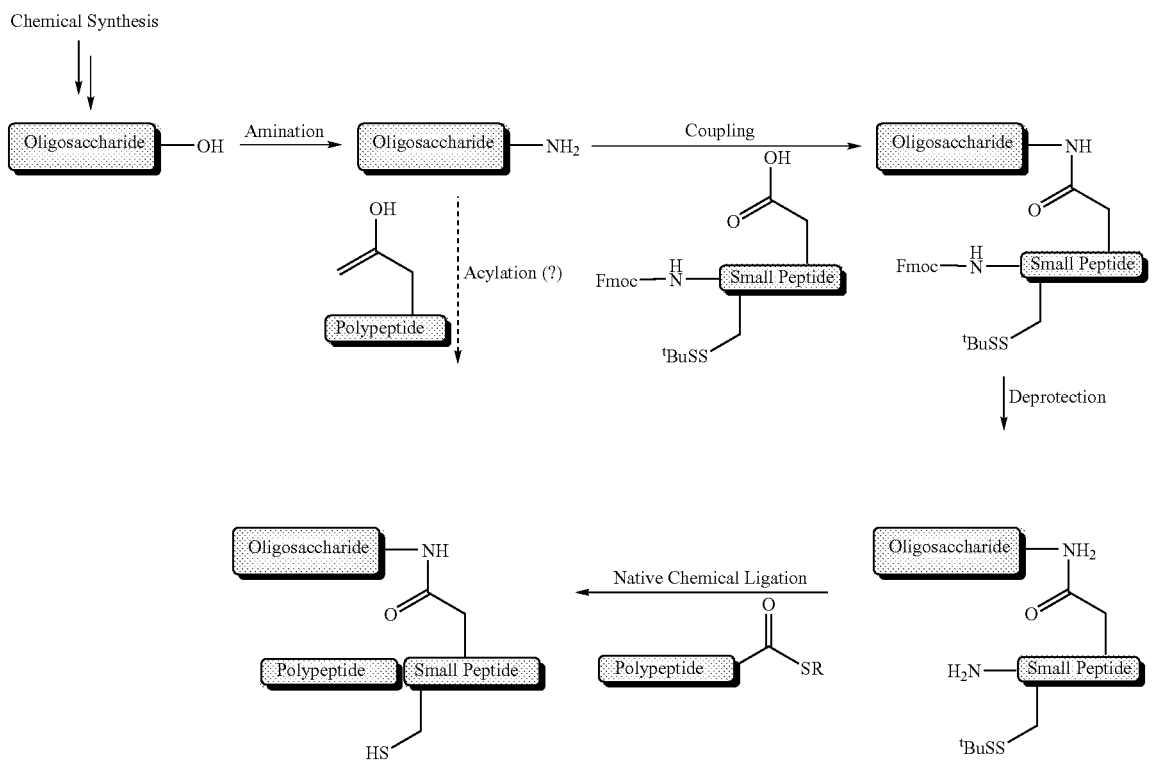

Scheme 5.
Convergent approach to N-linked glycopeptides

In certain embodiments, fully synthetic routes to complex glycopolypeptides are provided, which may, in due course, provide access to glycoproteins. The present invention encompasses building a complex glycodomain of interest and incorporating it into a polypeptide setting. The inventive method utilizes, in part, the work of Kochetkov (See, for example, L. M. Likhosherstov, O. S. Novikova, V. A. Derevitskaja, N. K. Kochetkov, *Carbohydr. Res.* 1986, 146, C1-C5), and Lansbury (See, for example, S. T. Cohen-Anisfeld, P. T. Lansbury, *J. Am. Chem. Soc.* 1993, 115, 10531-10537), involving direct anomeric β-amination of unprotected saccharides followed by acylation with a peptide carboxylic acid In certain embodiments, natural O- and N-linkages as opposed to non-natural arrangements asre provided. Furthermore, in certain other embodiments, the oligosaccharides of In certain embodiments, the glycopeptides of the invention are prepared by merging fully mature oligosaccharide and polypeptide domains in one grand acylation event (dashed arrow, Scheme 5). In certain other embodiments, the glycopeptides of the invention are prepared using a slightly less convergent, but in the end more practical and certainly more flexible, route illustrated in Scheme 5 (plain arrows). In the latter case, the anomeric amine of an oligosaccharide domain is acylated with a more manageable small peptide; native chemical ligation is then used to anneal this construct to a larger polypeptide segment. In certain embodiments, the fully synthetic glycan is the limiting reagent in the chemical mergers.

An exemplary approach is detailed in Scheme 6.

SCHEME 6

Glycan preparation and peptide conjugation.

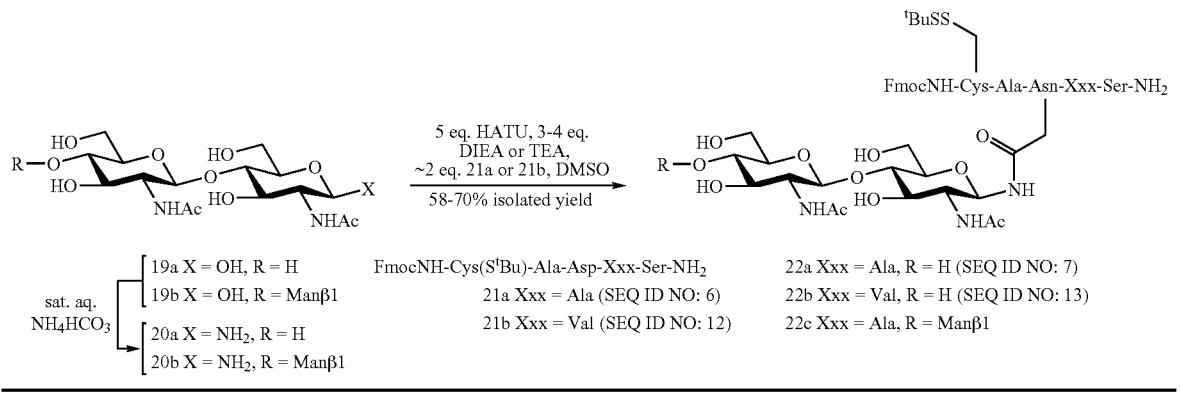

Treatment of known unprotected saccharides 19a-b (See, for example, (1) T. Usui, M. Suzuki, T. Sato, H. Kawagishi, K. Adachi, H. Sano, *Glycoconjugate J.* 1994, 11, 105-110; and (2) G. M. Watt, L. Revers, M. C. Webberley, I. B. H. Wilson, S. L. Flitsch, *Angew. Chem.-Int. Ed. Engl.* 1997, 36, 2354-2356) with saturated aqueous ammonium hydrogencarbonate followed by lyophilization to a constant mass afforded glycosylamines 20a-b. Due to the known instability of anomeric glycosylamines and our desire to maximize yields, the resulting white powders were used without further purification or analysis aside from mass spectroscopy. The results of Kochetkov amination are well documented (See, for example, D. Vetter, M. A. Gallop, *Bioconjugate Chem.* 1995, 6, 316-318), and could in any case be confirmed after peptide conjugation. Using optimized conditions developed for this purpose, acylation of glycosylamines 20a-b with pentapeptides 21a or 21b was accomplished by adding to the glycosylamine a two-fold excess of peptide preactivated with 5 equivalents of HATU and 3-4 equivalents of a tertiary amine in DMSO. Upon completion of the reactions after only 2-4 hours as monitored by analytical HPLC or LCMS, the reaction mixtures were purified by semipreparative HPLC. Two major side products were observed, showing molecular ions 1 and 18 daltons less than the starting aspartate-containing peptides. These are consistent with Asp to Asn conversion through acylation of spurious ammonia and aspartimide formation as shown in Scheme 7 (See, also, M. Bodanszky, S. Natarajan, *J. Org. Chem.* 1975, 40, 2495-2499), which several other authors also note and seek to avoid by various methods.

Though these processes are competitive rate-wise with glycopeptide formation, their products are solely peptide-derived. Thus an excess of peptide starting material sidesteps most losses due to these processes, even with an Ala residue C-terminal to the activated Asp (See Experimental Section 2) below for details). The isolated yields of the combined amination and acylation products 22a-c was in the range of 58 to 70% based on starting glycan, representing a significant improvement over the best yields previously reported.

Deprotection of Fmoc-glycopeptide 22c with 20% piperidine in DMF followed by HPLC purification afforded free glycopeptide 23 as a cysteine thiol tert-butyl disulfide in 68% yield. Additional products were observed with molecular ions identical to that of the desired material, perhaps due to epimerization of cysteine or the anomeric amide. The purified, isolated material at this stage was characterized by $^1$H NMR, ESMS, and LCMS as a single isomer with peptidic $^1$H NMR shifts and coupling patterns indicating the presence of a β-linked anomeric glycosylamide, thus validating the results of Kochetkov-Lansbury amination.

Glycopeptide 23 was then extended via native chemical ligation on a sizable (~15 mg) scale as shown in Scheme 8. As an independent test of the methodology, tetradecapeptide thioester 24 was synthesized employing the Fmoc/$^t$Bu solid phase peptide synthesis method recently reported by Hilvert and coworkers (See, for example, (1) D. Swinnen, D. Hilvert, *Org. Lett.* 2000, 2, 2439-2442; and (2) A. Sewing, D. Hilvert, *Angew. Chem.-Int. Ed.* 2001, 40, 3395-3396). After automated peptide synthesis on a PEG-type Wang resin (Solid phase synthesis of this peptide met with difficulties that were overcome using a pseudoproline dipeptide monomer; see Section 2 below for details), cleavage with trimethylaluminum and ethanethiol in dichloromethane afforded the desired thioester along with several (presumably Glu side chain) thioester derivatives. Significant improvement in peptide purity was observed when the cleavage was quenched by filtration of the cleavage mixture (to remove resin) into a stirred mixture of trifluoroacetic acid, water, and phenol over an ice bath rather than pouring the entire cleavage reaction mixture into the TFA mixture at room temperature; in fact, no side chain thioesters at all were observed when the cleavage was quenched as described.

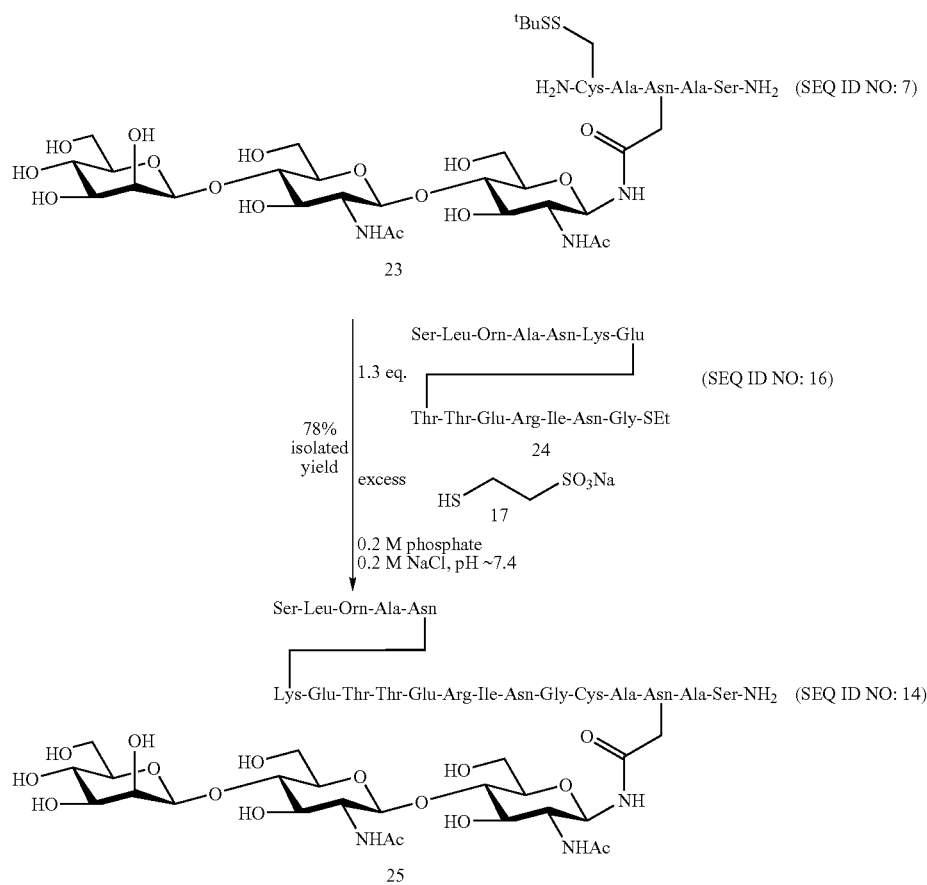

Ligation of 23 and 24 was achieved in aqueous PBS, 0.2 M in both saline and phosphate, pH ~7.4, in the presence of excess mercaptoethane-2-sulfonate 17 as illustrated in Scheme 8. Global disulfide reduction with TCEP (See, for example, J. A. Burns, J. C. Butler, J. Moran, G. M. Whitesides, *J. Org. Chem.* 1991, 56, 2648-2650) followed by semi-preparative HPLC afforded the desired, fully unprotected glycopeptide 25 in 78% yield based on starting glycopeptide. Characterization of glycopeptide 25 by ESMS, LCMS, and $^1$H and $^{13}$C NMR in D$_2$O was consistent with a single compound containing a β-linked glycosylamide.

As an example of the power of this method for complex glycopeptide synthesis pentasaccharide 26 was employed (Scheme 9), and prepared by chemical synthesis (See, for example, S. J. Danishefsky, S. Hu, P. F. Cirillo, M. Eckhardt, P. H. Seeberger, *Chem.-Eur. J.* 1997, 3, 1617-1628). Note that the compound differs from a characteristic high mannose pentasaccharide at one of its 25 stereogenic centers (asterisk, Scheme 9; The implications of such a point mutation on binding to high mannose lectins is but one example of an interesting question that can now be answered). Amination followed by suitable peptide acylation conditions with pentapeptide 21a and Fmoc removal yielded pentasaccharide glycopeptide 27 as a single isomer by HPLC and $^1$H NMR. Native chemical ligation with 27 and excess pentadecapeptide thioester 28 synthesized by Boc chemistry (See Experimental Section 2 below) afforded glycopeptide 18 as evidenced by HPLC and ESMS, again demonstrating proof of principle.

In summary, a highly convergent route capable of producing substantial quantities of homogeneous glycopolypeptides was provided. The method allows to retain the full flexibility accruing from total chemical synthesis of the oligosaccharide (cf. compound 26). Of course the same flexibility is also retained in the polypeptide. Given the exciting methods for accomplishing peptide extension, the flexibility is magnified still further (See, for example, (1) B. L. Nilsson, L. L. Kiessling, R. T. Raines, *Org. Lett.* 2000, 2, 1939-1941; (2) E. Saxon, J. I. Armstrong, C. R. Bertozzi, *Org. Lett.* 2000, 2, 2141-2143; and (3) J. P. Tam, J. X. Xu, K. D. Eom, *Biopolymers* 2001, 60, 194-205). Notwithstanding various difficulties that may be encountered along the way, the present invention sets the stage to progression towards fully synthetic, homogeneous, complex glycoproteins.

Scheme 9.
Exemplary native chemical ligation of a pentasaccharide glycopeptide and a pentadecapeptide.

Glycal Assembly Method

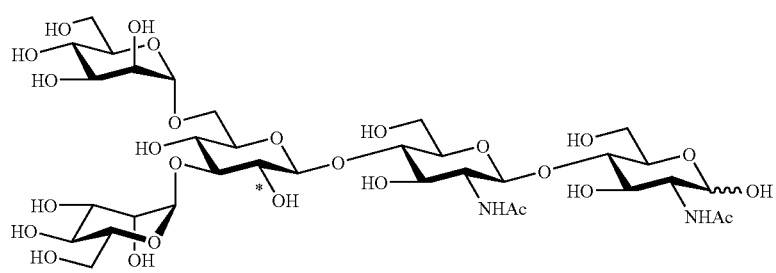

26

1.) NH$_4$HCO$_3$
2.) Peptide 20a, HATU, DIEA
71% (2 steps)
3.) Piperidine, DMF, 63%

-continued

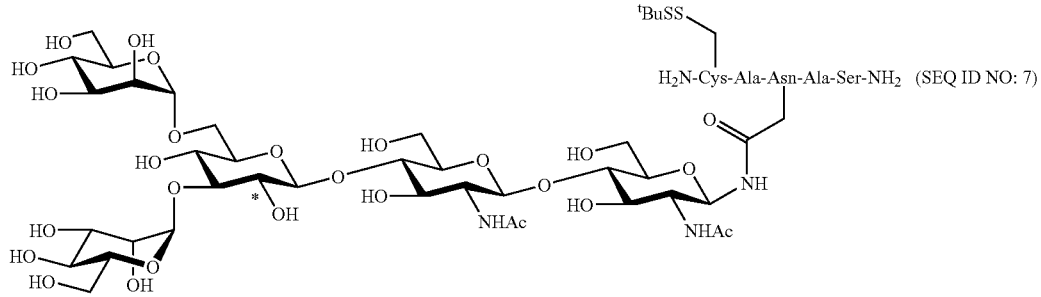

27

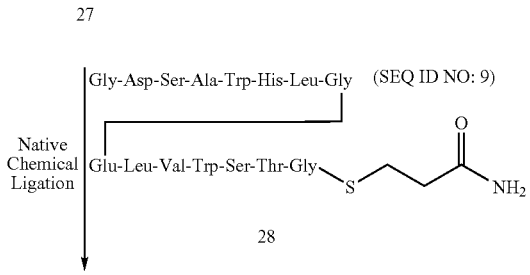

28

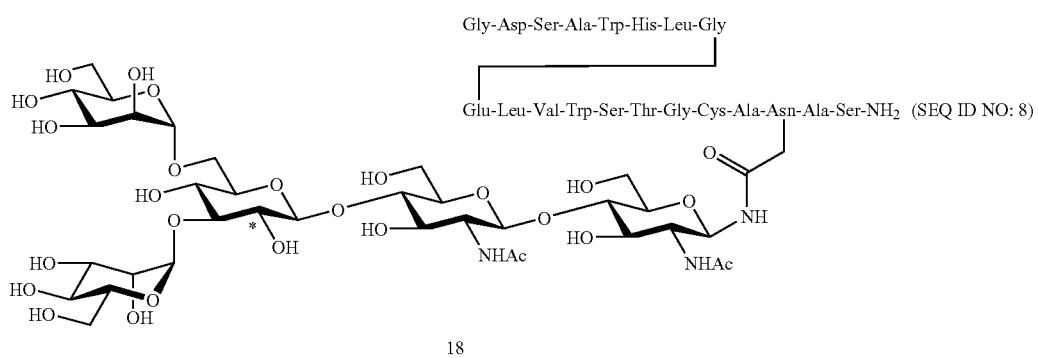

18

$^1$H and/or $^{13}$C NMR data for 23, 24, 25, and 27 are available and are consistent with the expected products.

2) Experimentals

Reagents. All commercial materials were used as received unless otherwise noted. The following solvents were obtained from a dry solvent system and used without further drying: THF, diethyl ether, and DCM. Reagents were obtained from Aldrich or as noted, with the following exceptions: amino acids and resins for solid phase peptide synthesis were purchased from NovaBiochem; Biosynthesis grade DMF from EM Science; and other solvents from Fisher Scientific (HPLC grade).

HPLC. All separations involved a mobile phase of 0.05% TFA (v/v) in water (solvent A)/0.0425% TFA in acetonitrile (solvent B). Preparative, semipreparative, and analytical HPLC separations were performed using a Rainin HXPL solvent delivery system equipped with a Rainin UV-1 detector and one of the following Dynamax-60 Å C18 axial compression columns 250 mm in length equipped with a similarly packed guard column: 41.4 mm diameter (prep), 21.4 mm diameter (semiprep), or 4.6 mm diameter (analytical). Separations were performed at flow rates of 48 mL/min (prep), 16 mL/min (semiprep), or 1 mL/min (analytical), and were monitored at a wavelength between 214 and 230 nm, depending on column loading. LCMS chromatographic separations were performed using a Waters 2695 Separations Module and a Waters 996 Photodiode Array Detector equipped with a Varian Microsorb C18 2×150 mm column at a flow rate of 0.2 mL/min.

ESMS and LCMS. Electrospray mass spectroscopy and LCMS analyses were obtained on a Waters Micromass ZQ mass spectrometer in conjunction with the Waters HPLC apparatus described above.

NMR. $^1$H and $^{13}$C NMR spectra were recorded on Bruker instruments in D$_2$O at 400 or 500 MHz for $^1$H and 100 or 125 MHz for $^{13}$C.

Representative Experimental Details for the Preparation of Glycosylamines:

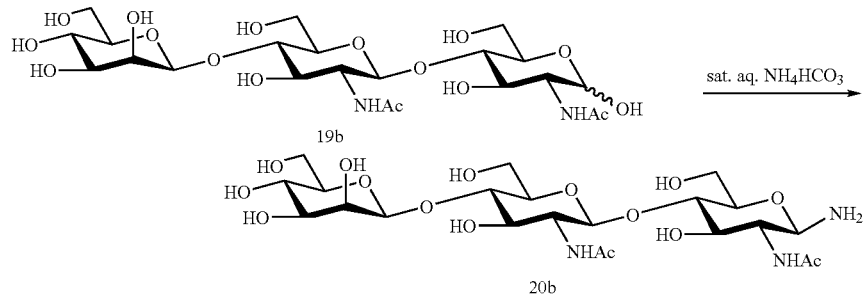

Manβ1→4GlcNAc⊕1→4GlcNAc⊕1-NH$_2$ (20b): To a room-temperature stirred solution of the reducing saccharide 19b (12.4 mg, 21.1 μmol) in 8 mL HPLC grade water in a 100 mL pear flask was added solid ammonium hydrogencarbonate (5.6 g, 70.8 mmol). Additional ammonium hydrogencarbonate was added after the reaction had proceeded for a total of 1 day (2 g), 3 days (3.7 g), and 5 days (1.2 g). The solution had become clear prior to the addition at 3 days. After six days the contents of the flask were shell frozen, lyophilized, dissolved in water (~20 mL) and stirred for 2 minutes, then lyophilized again; this was repeated until the white solid reached a constant crude mass of 15.8 mg, which was used directly in the next step. ESMS calcd for $C_{22}H_{40}N_3O_{15}$ [M+H$^+$] m/z 586.25, found 586.2.

GlcNAcβ1→4GlcNAcβ1-NH$_2$ (20a): ESMS calcd for $C_{16}H_{29}N_3O_{10}Na$ [M+Na$^+$] m/z 446.18, found 446.0.

(Manα1)$_2$→3,6Glcβ1→4GlcNAcβ1→4GlcNAcβ1-NH$_2$ (Scheme 9, unnumbered in text): ESMS calcd for $C_{34}H_{58}N_3O_{25}$ [M–H$^+$] m/z 908.34, found 908.3.

Representative Experimental Details for Manual Fmoc/$^t$Bu Solid Phase Peptide Synthesis:

FmocNH-Cys(S$^t$Bu)-Ala-Asp-Val-Ser-NH$_2$ (SEQ ID NO: 12) (21b): To a tared peptide synthesis vessel was added Fmoc-2,4-dimethoxy-4'-(carboxymethyloxy)-benzhydrylamine linked to aminomethyl resin (Bachem, 200-400 mesh, 0.55 mmol/g, 0.5583 g, 0.3071 mmol). The resin was swelled in DMF for ~45 min with agitation from argon bubbling. A stock solution of HATU was prepared by adding DMF (21 mL) to HATU (2.63 g, 6.91 mmol) in a glass vial, followed by stirring until the solid dissolved completely. Deblock solution consisted of a 80:18:12 (v:v:v) mixture of DMF:piperidine: DBU. Deblock was accomplished in two successive 5 mill reactions separated by a 20-sec. DMF flow rinse. The resin was prepared for coupling by 3×20 sec. DMF flow rinses. Meanwhile, to slightly more than 4 equiv (based on resin loading) of amino acid were added 3.4 mL of the HATU stock solution and DIEA (0.8 mL); the yellow solution was swirled occasionally for ~7 min, then poured into the deblocked, rinsed, drained resin. After coupling for ~45 min with agitation by bubbling argon, the resin was drained and washed with 3×20 sec. DMF flow rinses. After the final coupling, the Fmoc-peptide-resin was washed 3× with DCM, then once with diethyl ether, then dried under vacuum overnight. Cleavage of the peptide from the resin was accomplished using a cocktail of 5% phenol, 5% water, 2.5% triethylsilane, and 87.5% TFA (w/v/v/v) for 1-2 hours under argon, followed by dropwise addition to ether over a dry ice-acetone bath to precipitate the peptide. After allowing the ether suspension to warm to room temperature the solution was centrifuged, and the ether filtered off. The residue was dissolved in water-acetonitrile-methanol-DMF and lyophilized. Semipreparative HPLC (50-62% B/12 min, RT~11-12 min) gave good separation. The combined fractions showing pure material were lyophilized, affording 21b as a white powder. Anal. HPLC 50-60% B/10 min, RT 8.3 min; ESMS calcd for $C_{37}H_{51}N_6O_{10}S_2$ [M+H$^+$] m/z=803.31, found 803.2.

FmocNH-Cys(S$^t$Bu)-Ala-Asp-Ala-Ser-NH$_2$ (SEQ ID NO: 6) (21a): Anal. HPLC 30-60% B/30 min, RT 23.9 min; ESMS calcd for $C_{35}H_{47}N_6O_{10}S_2$ [M+H$^+$] m/z 775.28, found 775.2.

Representative experimental details for glycosylamine aspartate acylation:

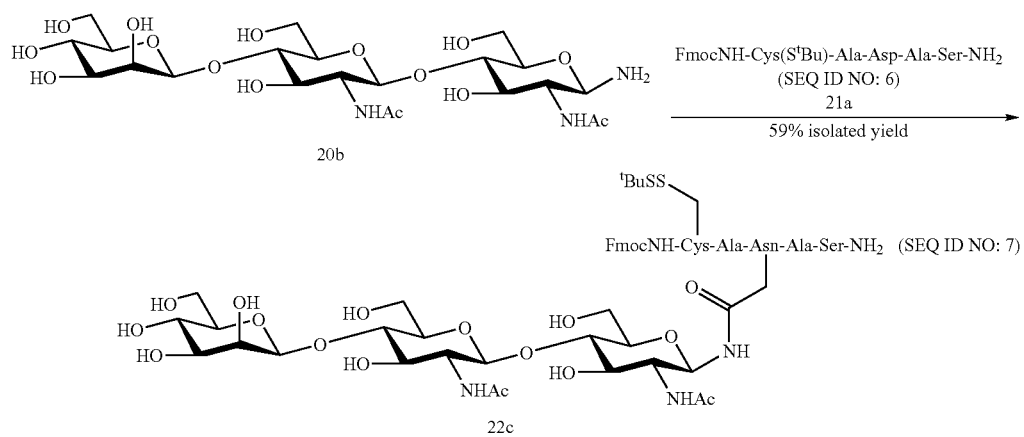

FmocNH-Cys(S'Bu)-Ala-Asn(Manβ1→4GlcNAcβ1→4GlcNAcβ1)-Ala-Ser-NH$_2$ (SEQ ID NO: 7) (22c): To a 20 mL glass vial charged with a stirbar and peptide 21a (34.9 mg, 45.0 µmol) was added DMSO (250 µL) and triethylamine (11 µL, 79 µmol). After stirring the mixture for ~1 min, solid HATU (44.3 mg, 117 µmol) was added, at which point the stirred solution became orange- FmocNH-Cys(S'Bu)-Ala-Asn [(Man+1)$_2$→3, 6Glcβ1→4GlcNAcβ1→4GlcNAcβ1]-Ala-Ser-NH$_2$ (SEQ ID NO: 7) (Scheme 9, unnumbered in text): Anal. HPLC 30-60% B/30 min, RT 16.3 min; ESMS calcd for C$_{69}$H$_{103}$N9O$_{34}$S$_2$Na [M+Na$^+$] m/z 1688.60, found 1688.3.

Representative experimental details for solution phase Fmoc-glycopeptide deprotection:

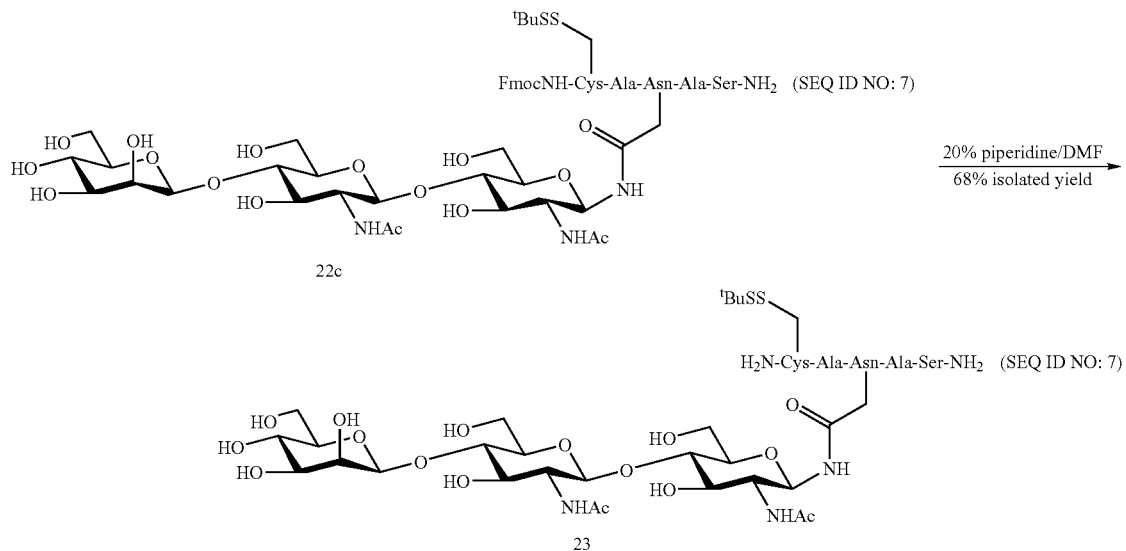

yellow. Immediately upon complete dissolution of the HATU the solution was transferred via 1.0 mE glass syringe to the 100 mL pear flask in which glycosylamine 20b was lyophilized. The glass vial was rinsed with DMSO (250 µL), which was also transferred to the 100 mL pear flask using the same syringe. After stirring for ~2 min the contents of the pear flask were transferred to a 2 mL LCMS vial using the same syringe; the pear flask was washed with DMSO (2×250 µL) that was then collected and transferred to the LCMS vial using the same syringe. Some solid particles remained in the stirred solution, even after 30 min. Monitoring by LCMS showed no additional product formation after ~2 hr., but also showed evidence of starting glycosylamine. Additional triethylamine (11 µL, 79 µmol) and HATU (15.3 mg, 40.2 µmol) were added; the solution turned orange. At 3.5 hr. from the initial dissolution of the glycosylamine the entire reaction mixture was purified by semiprep HPLC (30-60% B/30 min). The combined fractions from 16.2 to 17.8 min were concentrated at reduced pressure until precipitate formed, then shell frozen and lyophilized, affording 22c as a white powder (16.7 mg, 12.4 µmol, 59% yield). LCMS 37-47% B/10 min, RT 9.6 min; ESMS calcd for C$_{57}$H$_{84}$N$_9$O$_{24}$S$_2$ [M+H$^+$] m/z 1342.51, found 1342.6.

FmocNH-Cys(S'Bu)-Ala-Asn(GlcNAcβ1→4GlcNAcβ1)-Ala-Ser-NH$_2$ (SEQ ID NO: 7) (22a): Anal. HPLC 30-60% B/30 min, RT 18.4 min; ESMS calcd for C$_{51}$H$_{73}$N$_9$O$_{19}$S$_2$Na [M+Na$^+$] m/z 1202.44, found 1202.25.

FmocNH-Cys(S'Bu)-Ala-Asn(GlcNAcβ1→4GlcNAcβ1)-Val-Ser-NH$_2$ (SEQ ID NO: 13) (22b): Anal. HPLC 40-60% B/20 min, RT 10.1 min; ESMS calcd for C$_{53}$H$_{78}$N$_9$O$_{19}$S$_2$ [M+H$^+$] m/z 1208.49, found 1208.3.

H$_2$N-Cys(S'Bu)-Ala-Asn(Manβ1→4GlcNAcβ1→4GlcNAcβ1)-Ala-Ser-NH$_2$ (SEQ ID NO: 7) (23): To Fmoc-protected 22c (16.7 mg, 12.4 µmol) in a 100 mL pear flask (in which 22c was lyophilized) was added a 4:1 mixture of DMF:piperidine (220 µL). The mixture was swirled constantly until the solid dissolved completely, then occasionally for a total of 35 min. The contents of the flask combined with a single wash of the flask (100 µL 4:1 DMF:piperidine) were injected directly onto a semiprep HPLC column (5-25% B/20 min). All fractions showing desired material by ESMS were combined and concentrated to dryness at reduced pressure. The residue was dissolved in a total of 2.6 mL water and repurified by HPLC (5-25% B/20 min). The combined fractions from 14 to 16 min showing clean material by LCMS were combined, analyzed by LCMS, and lyophilized, affording 23 as a white powder (9.4 mg, 8.4 µmol, 68% yield). LCMS10-20% B/10 min, R$_T$ 6.2 min; ESMS calcd for C$_{42}$H$_{74}$N$_9$O$_{22}$S$_2$ [M+H$^+$] m/z 1120.44, found 1120.5. $^1$NMR and $^{13}$C NMR spectra for 23 are consistent with the expected product.

Automated Fmoc/Bu Solid Phase Peptide Thioester Synthesis, Cleavage, and Deprotection:

H$_2$N-Ser-Leu-Orn-Ala-Asn-Lys-Glu-Thr-Thr-Glu-Arg-Ile-Asn-Gly-SEt (SEQ ID NO: 16) (24): Thioester 24 was synthesized on NovaSyn TGA resin using standard automated Fmoc/'Bu protocols with the noted exceptions. The resin was loaded as follows. DCC (~10-fold excess relative to resin) was dissolved in a minimal amount of THF and added to Fmoc-Gly-OH (~10-fold excess relative to resin) dissolved in THF in a peptide synthesis vessel, at which time immediate precipitation was observed. After 15 min DMF was added to make a 1:1 mixture of THF and DMF; the resulting suspension was stirred for an additional 15 min, then filtered under argon directly into another synthesis vessel containing unfunctionalized resin suspended in DMF. Following the addition of a large excess of pyridine, the reaction mixture was stirred for ~1 hr., then filtered and rinsed 3× with THF. The resin was then suspended in THF; acetic anhydride and pyridine (both ~50 equiv relative to resin) were added simultaneously. The reaction was stirred for 90 min, drained, washed 3× with THF and 3× with diethyl ether, and dried overnight under vacuum. Automated peptide synthesis was performed on an Applied Biosystems Pioneer continuous flow peptide synthesizer. The standard protocols were modified to allow a 1.2-fold increase in flow rate and a 2-fold increase in time for the deblocking step. The deblock mixture was a mixture 80:18:2 of DMF:piperidine:DBU. The following side chain protection schemes for Fmoc amino acids from NovaBiochem were employed: Ser($^t$Bu), Orn(Boc), Asn (Trt), Lys(Boc), Glu(O$^t$Bu)-Thr($\Psi^{Me,Me}$pro),[1] Glu(O$^t$Bu), and Arg(Pbf). Upon completion of the automated synthesis on a 0.02 mmol scale the peptide-resin was washed into a peptide synthesis vessel with DCM. Under argon the resin was washed with 4×20 mL DCM flow rinse, then suspended in DCM (1 mL) under argon. A 10 mL pear flask equipped with a stirbar was evacuated and dried by heating for ~2 min, then placed under argon and over an ice bath. Trimethylaluminum (2.0 M in toluene, 0.2 mL, 0.4 mmol, 20 equiv) was added via syringe and diluted with DCM (0.4 mL). Ethanethiol (80 µL, 1.1 mmol, 54 equiv) was added dropwise, with the evolution of gas through about half of the addition. After stirring over an ice bath for 10 min, the contents of the pear flask were added to the stirred resin in the synthesis vessel in 1 mL portions. The resulting suspension was stirred under argon for 4 h. Meanwhile a protecting group cleavage cocktail was prepared consisting of phenol (0.3386 g), water (350 µL), and TFA (~13.5 mL). The contents of the synthesis vessel were filtered slowly into 2 mL of the TFA cleavage cocktail stirred over an ice bath in a 25 mL roundbottom flask; significant foaming was observed, and the reaction mixture turned yellow. The resin was washed 3×3.5 mL with the TFA cleavage cocktail and filtered into the roundbottom flask; foaming was observed during the first wash. After all of the foam had dissolved, the flask was removed from the ice bath and concentrated at reduced pressure (after removing the stirbar). To the brown, oily residue was added the remainder of the TFA cocktail (3.5 mL). The orange solution was stirred 75 min, then concentrated at reduced pressure after removing the stirbar. The dark, oily residue was triturated with ether, giving a thick, white suspension, which was transferred to a polypropylene conical tube. The tube was centrifuged and the ether decanted; this was repeated 2× more, and the solid dissolved in 50% B (HPLC buffer), analyzed by LCMS, and lyophilized. Semiprep HPLC purification (15-25% B/10 min, RT ~10.5 min) followed by concentration at reduced pressure and lyophilization afforded 24 as a white powder (10.3 mg, 6.47 µmol, 32% yield from unfunctionalized hydroxymethyl resin). LCMS 15-25% B/10 min, RT 13.6 min; ESMS calcd for $C_{65}H_{115}N_{21}O_{23}S$ [M+2H$^+$] m/z 795.92, found 796.1. The $^1$H NMR spectrum of 24 is consistent with the expected product.

Representative experimental details for native chemical ligation:

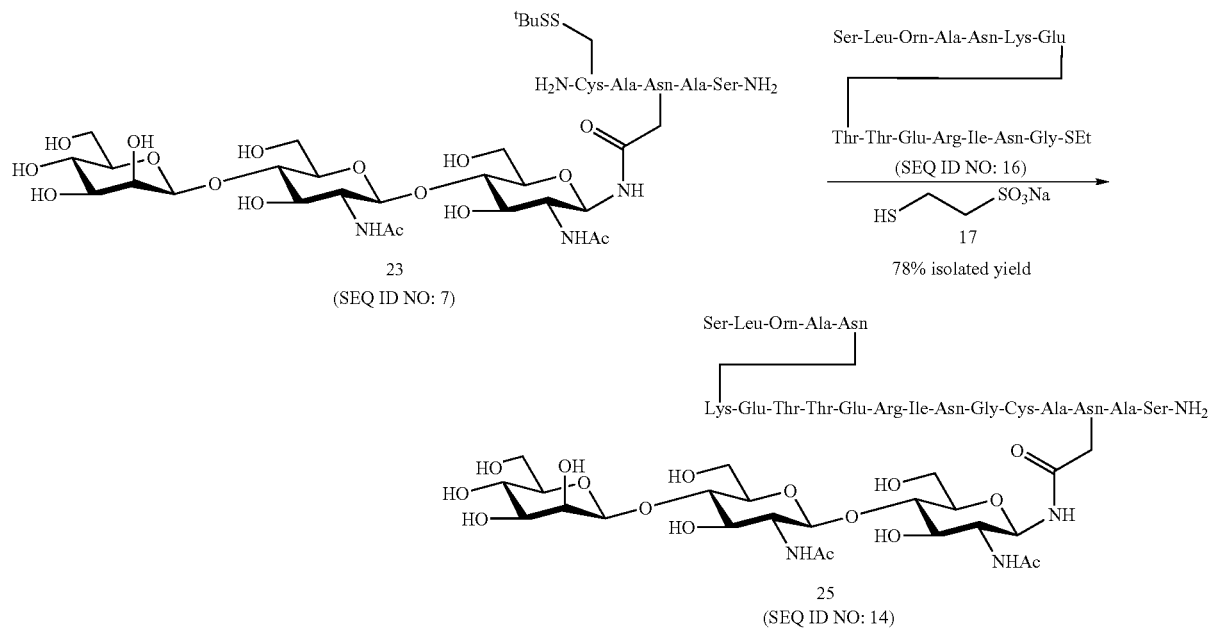

H$_2$N-Ser-Leu-Orn-Ala-Asn-Lys-Glu-Thr-Thr-Glu-Arg-Ile-Asn-Gly-Cys-Ala-Asn (Manβ1→4GlcNAcβ1→4GlcNAcβ1)-Ala-Ser-NH$_2$ (SEQ ID NO: 31) (25): Solid thioester 24 (16.1 mg, 10.1 µmol, 1.3 equiv) was weighed into a 50 mL pear flask containing lyophilized 23 (8.6 mg, 7.7 µmol). A solution was prepared consisting of mercaptoethane-2-sulfonate 17 (17.5 mg, 107 µmol, 13.8 equiv) dissolved in 1.0 mL phosphate buffer, 0.2 M in sodium chloride and phosphate, pH ~7.4; this solution was added to the 50 mL pear flask and the mixture stirred vigorously for 5 min until the solids dissolved. After stirring for 1 h, the reaction seemed sluggish (by LCMS), so additional mercaptoethane-2-sulfonate 17 (17.1 mg, 104 µmol, 13.5 equiv) was added. The reaction was essentially complete after 4 h; at 5.5 h the excess thioester was quenched with a small amount of 2-aminoethanethiol hydrochloride.[2] After an additional 4 h, the reaction was acidified with TFA (40 µL) and purified by semiprep HPLC (5-25% B/20 min); all fractions showing evidence of desired material by ESMS were combined, concentrated, and lyophilized. The resulting white powder was dissolved in water; to this solution was added tris(carboxyethyl)phosphine (~25 mg, 87 µmol, 10 equiv).[3] After stirring for 2 h the reaction mixture was purified by semiprep HPLC (9-20% B/22 min); the fractions from 13.33-15.5 min were combined and concentrated. The fractions from 13.0-13.33 min were combined, concentrated, and repurified using the same gradient; the pure fractions were combined with the pure material from the initial purification and lyophilized, affording 25 as a white solid (15.3 mg, 5.97 µmol, 78% yield). LCMS 10-25% B/15 min, RT 11.5 min; ESMS calcd for $C_{101}H_{177}N_{30}O_{45}S$ [M+3H$^+$] m/z 854.07, found 854.4. $^1$H NMR and $^{13}$C NMR spectra for 25 are consistent with the expected product.

H$_2$N-Cys(S$^t$Bu)-Ala-Asn[(Manα1)$_2$→3, 6Glcβ1→4GlcNAcβ1→4GlcNAcβ1]-Ala-Ser-NH$_2$ (SEQ ID NO: 7) (27): See the preparation of 22c for a procedure similar to that required for 27. Anal. HPLC 10-22% B/12 min, RT 9.9 min; ESMS calcd for $C_{54}H_{93}N_9O_{32}S_2Na$ [M+Na$^+$] m/z 1466.53, found 1466.4. The $^1$H NMR spectrum for 27 is consistent with the expected product.

Manual Boc Solid Phase Peptide Synthesis and Cleavage:
H$_2$N-Gly-Asp-Ser-Ala-Trp-His-Leu-Gly-Glu-Leu-Val-Trp-Ser-Thr-Gly-S(CH$_2$)$_2$C(O)NH$_2$ (SEQ ID NO: 9) (28): Peptide 28 was synthesized manually on tert-butoxycarbonyl-amino acyl-3-mercapto-propionamide-4-methylbenzhydrylamine-copoly(styrene-1% DVB) (Boc-AA-[COS]-MBHA) according to the in situ neutralization O-benzotriazol-1-yl-N,N,N',N',-tetramethyluronium hexafluorophosphate (HBTU) activation protocol for Boc solid-phase peptide synthesis.[4] After chain assembly, peptides were treated with HF for 1 hr at 0° C. to give the corresponding fully unprotected peptide. The 3-thiopropionic acid linker on MBHA resin is labile to HF-cleavage conditions, thereby releasing linear thioester peptides upon global deprotection. Following removal of HF, the crude peptide product was precipitated using cold ether, washed thoroughly with ether, dissolved in 50% CH$_3$CN/50% water/0.1% TFA, and purified by preparative HPLC. Thioester 28 was characterized by analytical HPLC, ESMS and amino acid analysis, and was determined to be >95% pure. ESMS calcd for $C_{76}H110N_{20}O_{23}S$ [M+2H$^+$] m/z 851.39, found 851.9.

H$_2$N-Gly-Asp-Ser-Ala-Trp-His-Leu-Gly-Glu-Leu-Val-Trp-Ser-Thr-Gly-Cys-Ala-Asn[(Manα1)$_2$→3, 6Glcβ1→4GlcNAcβ1 →4GlcNAcβ1]-Ala-Ser-NH$_2$ (SEQ ID NO: 8) (18): See the preparation of 25 for a procedure similar to that required for 18. Anal. HPLC 5-45% B/20 min, RT 18.0 min; ESMS calcd for $C_{123}H_{188}N_{28}O_{54}S$ [M+2H$^+$] m/z 1476.63, found 1476.7.

1. The Glu-Thr pseudoproline derivative was deemed necessary for efficient couplings based on Fmoc monitoring profiles and LCMS of crude cleavage mixtures of unsuccessful attempts at synthesizing the peptide.

2. Unfortunately the carboxylic acid derivative of the thioester happened to nearly coelute with the desired, ligated material, hence the desire to quench the thioester with something other than water.

3. LCMS evidence at this point indicated the presence of a mixed disulfide derivative of the desired product with mercaptoethane-2-sulfonate.

4. Schnölzer, M.; Alewood, P.; Jones, A.; Alewood, D.; Kent, S. B. H. *Int. J. Pept. Protein Res.* 1992, 40, 180-193.

Example 2

N-Linked Normal and Transformed PSA Glycopeptides

Localized cancer of the prostate gland can often be arrested, whereas progression to the metastatic state dramatically decreases quality of life and survival rates. The feasibility of early diagnosis of prostate tumors was enhanced with the identification of prostate specific antigen (PSA) as a cancer screening marker.[1-3] PSA, which is a glycoprotein secreted by the prostatic epithelium, manifests high tissue specificity.[4] It consists of 237 amino acid residues and possesses a single N-glycosylation site that typically carries an N-acetyllactosamine type glycan.[4] Despite the microheterogeneity of normal PSA, its carbohydrates appear to be of the dibranched type (e.g., 1, FIG. 1).[4,5] By contrast, glycans isolated from LnCaP prostatic cancer cells include tri- and even tetrabranched structures (e.g., 2 and 3, FIG. 1).[6] Since the distinctions between normal and "transformed" PSA are limited to glycan composition, they are invisible to current assays which employ antibodies that recognize the glycoprotein's conserved polypeptide domain.[7] Unfortunately, even state-of-the-art diagnostic methods based on PSA levels may fail to distinguish between pre-metastatic prostate cancer and benign prostatic hyperplasia.[8,9] Clinical measurements of PSA levels do not necessarily identify isoforms specific to malignant tissue.[10] This issue is often resolved through invasive biopsy procedures.

We envisioned that differentiated antibodies, sensitive to particular PSA glycoforms, could well form the basis of a new and potentially highly efficient diagnostic strategy to monitor not only the levels of PSA, but also the likely aggressiveness of the disease. Furthermore, sensitive screening might enable the pinpointing of malignant transformations at an early stage of the disease, when serum PSA levels are particularly uninformative.

For such antibodies to be elicited, a source of defined and homogeneous PSA fragments bearing N-glycans with various degrees of branching is crucial. Challenging as it surely would be, it seemed to us that chemical synthesis might provide the best and most versatile solution to this need. To deal with the complexity of the targets, we hoped to chart new strategies for oligosaccharide assembly, stressing utmost convergency and stereochemical control. We report herein the first chemical synthesis of multibranched N-acetyllactosamine-type glycans and their incorporation into PSA glycopeptide fragments 1-3.

In this introductory study, we selected the most common of the multibranched, N-acetyllactosamine type PSA glycans as our targets.[4] Also, we chose not to prepare sialylated forms of the glycans, since these add significantly to the heterogeneity of serum PSA.[11] Indeed, in the setting of diagnostic assays, samples are first subjected to sialidase digestion.

Earlier, we had found, in simple models, that a sequence consisting of Kochetkov amination[12] of an oligosaccharide bearing a free reducing end, followed by Lansbury aspartylation[13] and thence by native chemical ligation[14,15] (NCL), provides a way of building complex N-linked polypeptides.[16,17] As will be shown, these protocols served us well in a highly complex setting.

Scheme 10.

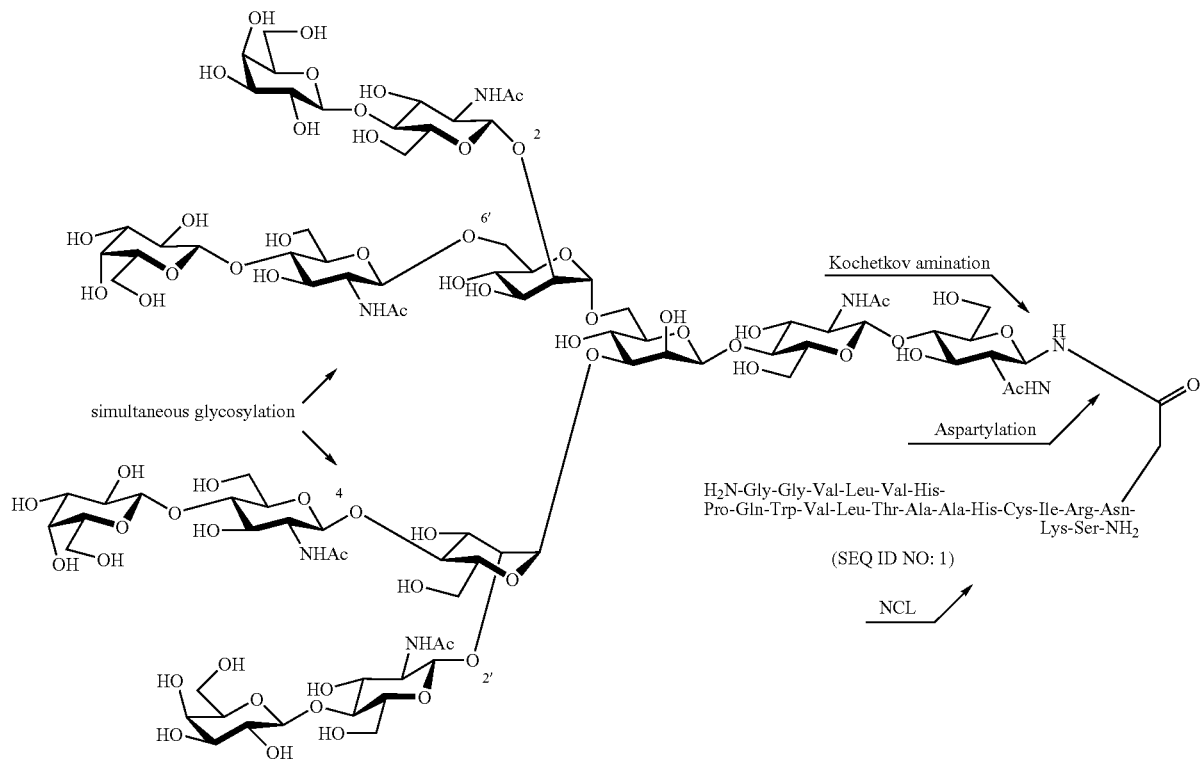

1, 2, 3

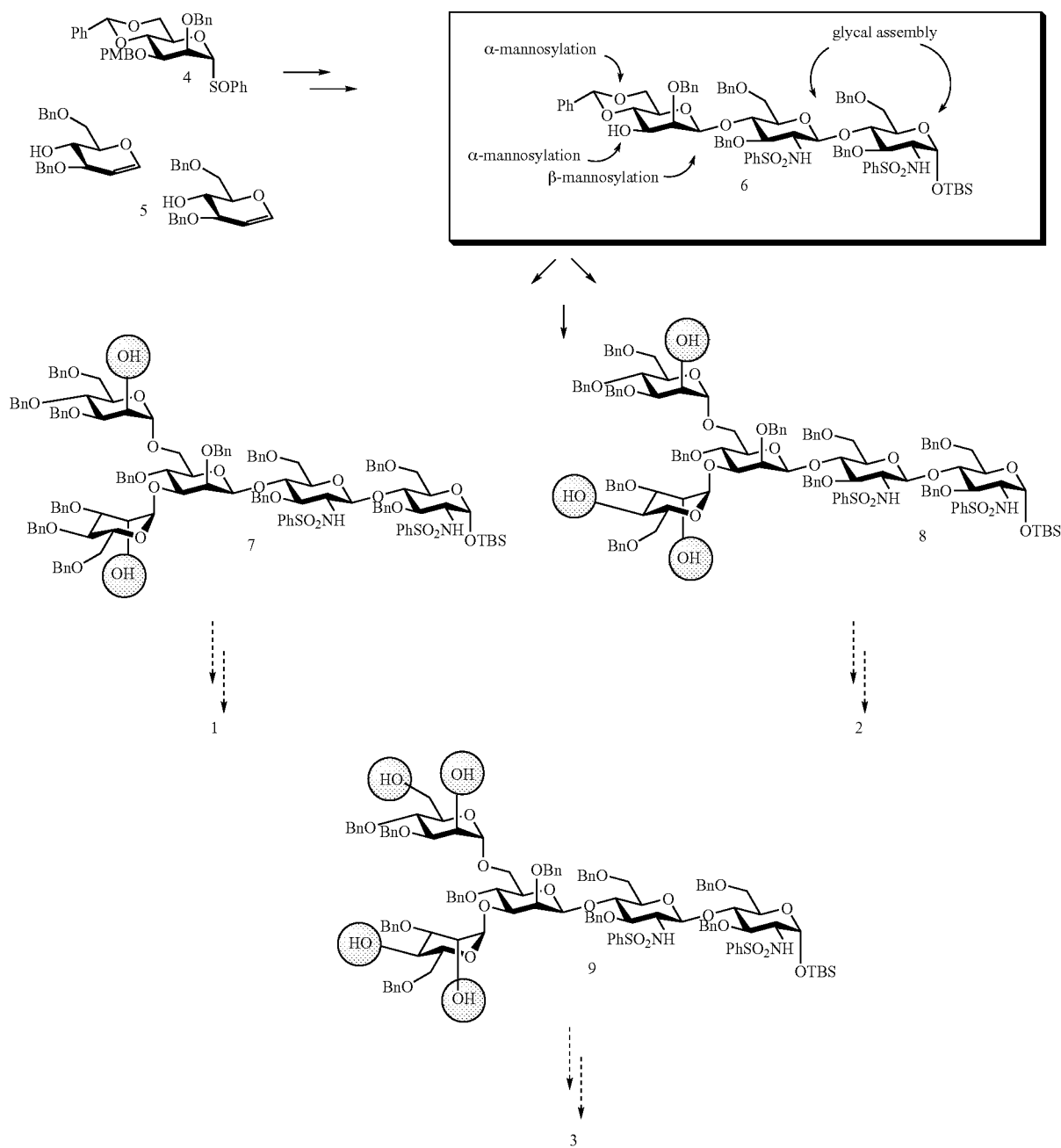

(a) Structures of PSA[27-47] glycopeptides 1-3
(b) and exemplary retrosynthetic analyses thereof. 1, "Normal" dibranched PSA fragment with N-acetyllactosamines at 2,2'; 2, tribranched at 2, 4, 2' positions; 3, tetrabranched at 2, 4, 2', 6'.

In one aspect, the invention addresses the complexity of the carbohydrate domains featuring interwoven high mannose and lactosamine blocks. To solve the transformed PSA glycan construction problem, it would be necessary to go well beyond the preparation of symmetrically dibranched glycans (projecting from the 2 and 2' positions of wing mannoses of the pentasaccacharide core system). While tribranched glycans isolated from natural sources have been used in glycopeptide preparation,[18] symmetrical dibranched structures represented the limit of previous chemical syntheses.[19-23] In certain embodiments, the invention encompasses a synthetic strategy which would pave the way for reaching larger, more branched and less symmetric constructs from a common intermediate (cf. 4) with high stereoselection and maximum convergency.[24]

In certain embodiments, it was proposed that introduction of several N-acetyllactosamines can be accomplished in a single glycosylation event. This transformation has been demonstrated in a similar setting in simpler models.[25,26] The PSA glycan synthesis problem could then be translated into that of producing pentasaccharides 30, 31 and 32 with differentiated "free OH" acceptor sites. This retrosynthesis took us back to trisaccharide 4 as a common intermediate.[27] This key building block contains virtual (see benzylidene acetal) and identified acceptor loci.[28] By α-mannosylation with suitably differentiated α-mannosyl donors, permuted core pentasaccharides 30, 31 and 32 quickly became accessible. The central intermediate trisaccharide 4 is smoothly assembled by a combination of glycal assembly in the context of sulfonamidoglycosylation and sulfonamidohydroxylation[29] (see 8→AB rings of 4) and Crich's β-mannosylation chemistry[30,31] (see 29→ring C of 4).[27] Building blocks 4 and 5 are prepared from D-glucal and mannose, respectively.

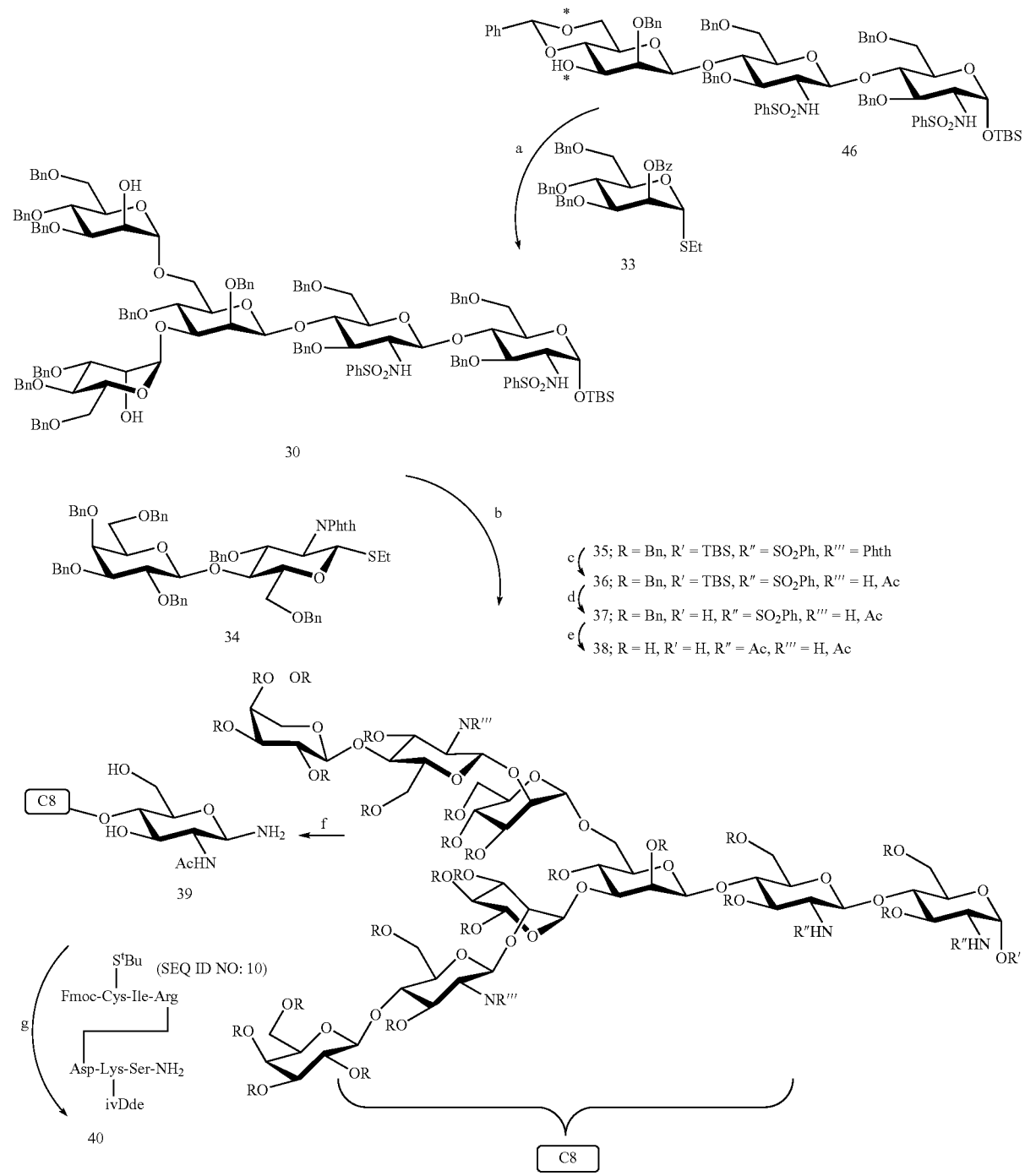

-continued

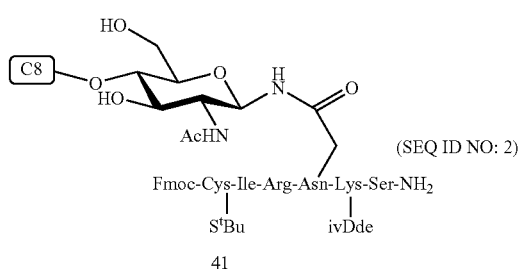

(SEQ ID NO: 2)

41

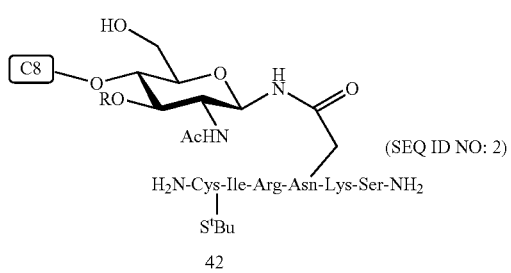

(SEQ ID NO: 2)

42

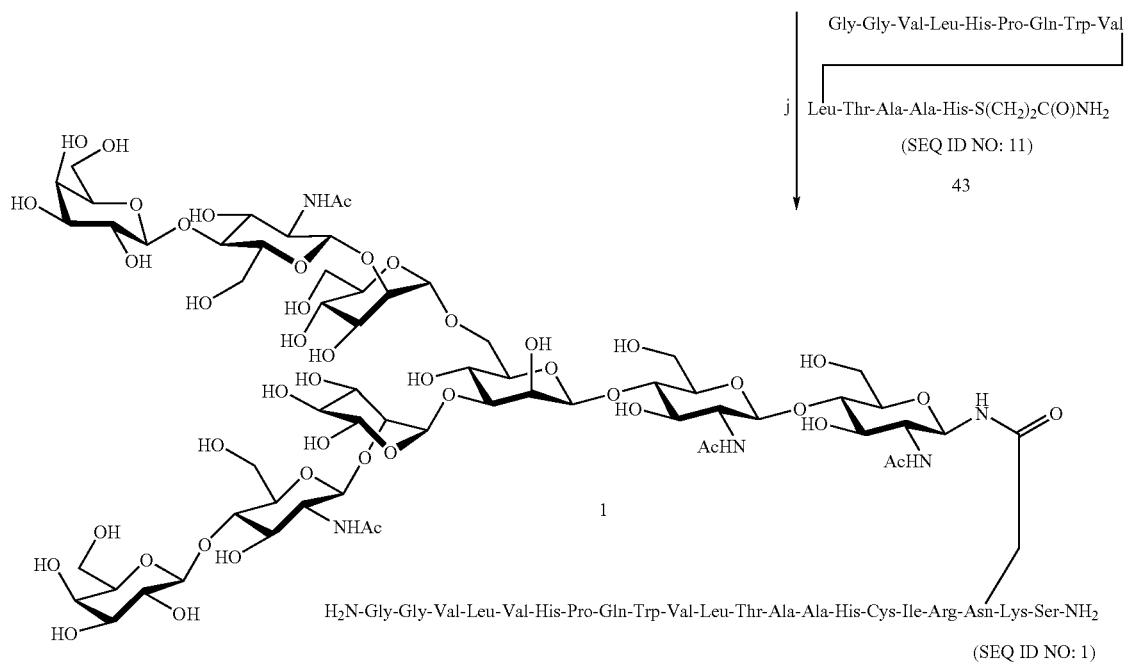

Reagents and conditions: (a) i. BH$_3$.THF, Bu$_2$BOTf, THF, 72%; ii. 33, (BrC$_6$H$_4$)$_3$NSbCl$_6$, MeCN, 74%; iii. NaGMe/MeGH, 89%; (b) MeOTf, DTBP, CH$_2$Cl$_2$, 60%; (c) i. ethylenediamine, n-BuOH/toluene, 90° C., ii. A$_2$O/py, iii. NaOMe/MeOH, 72%; (c) TBAF/AcOH, THF, 76%; (e) i. Na/NH$_3$, −78° C., ii. Ac$_2$O, iii. NaOMe/MeOH, 65%; (f) NH$_4$HCO$_3$/H$_2$O; (g) 40, HATU, Hünig's base, DMSO, 61% from 38; (h) (NH$_2$)$_2$, piperidine, DMF, 62%; (j) 43, MES-Na, pH=7.4, 17%.

The validity of the concept was first field tested in the context of a synthesis of the non-transformed type glycan 1 (Scheme 1). Thus, trisaccharide 4 was prepared following the logic described above.[27] Reductive cleavage of the benzylidene acetal generated a diol that coupled at two points (see asterisks in 6) with monoester-containing α-mannosyl donor 33 to assemble a pentasaccharide containing two esters. Cleavage of the two benzoates led to bis acceptor 30. Indeed, two-fold glycosylation using donor 34 proceeded smoothly to establish the protected core system (35) corresponding to 1. The two phthalimides were then converted into acetamides, the anomeric hydroxyl group was liberated by desilylation, and the product subjected to global deprotection (sodium in liquid ammonia). Here, we exploited our remarkable finding that the integrity of the reducing end hemiacetal is maintainable during global Birch debenzylation.[32] Amine-specific diacetylation afforded free glycan 38 as a mixture of anomers.[33] Free β-glycosylamine 39 was obtained from nonasaccharide 38 by a Kochetkov amination protocol. Coupling with excess hexapeptide 40 gave glycoconjugate 41. The Fmoc and ivDde protecting groups in 41 were shed, and the resulting amine was subjected to NCL with pentadecapeptide thioester 43. This sequence afforded the fully characterized normal PSA[27-47] glycopeptide fragment, presented as a homogeneous nonasaccharide uneicosapeptide 1.

Having tested our strategy in the control synthesis of 1, we sought to apply these notions to the syntheses of 2 and 3, as described in Schemes 12 and 13.

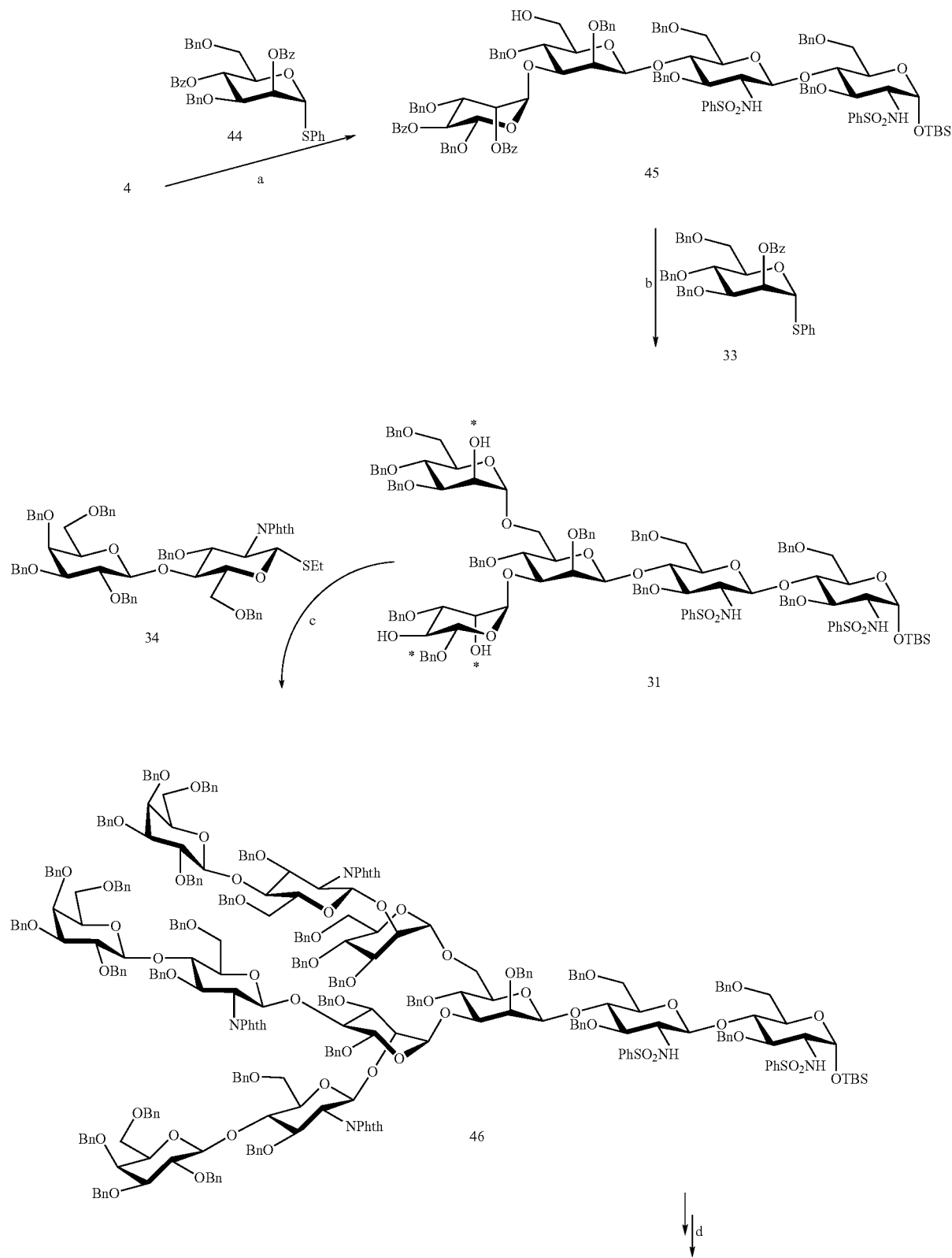
Scheme 12.
Exemplary synthesis of tribranched transformed PSA glycopeptide 2.

-continued

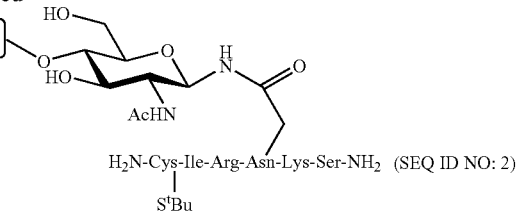

47

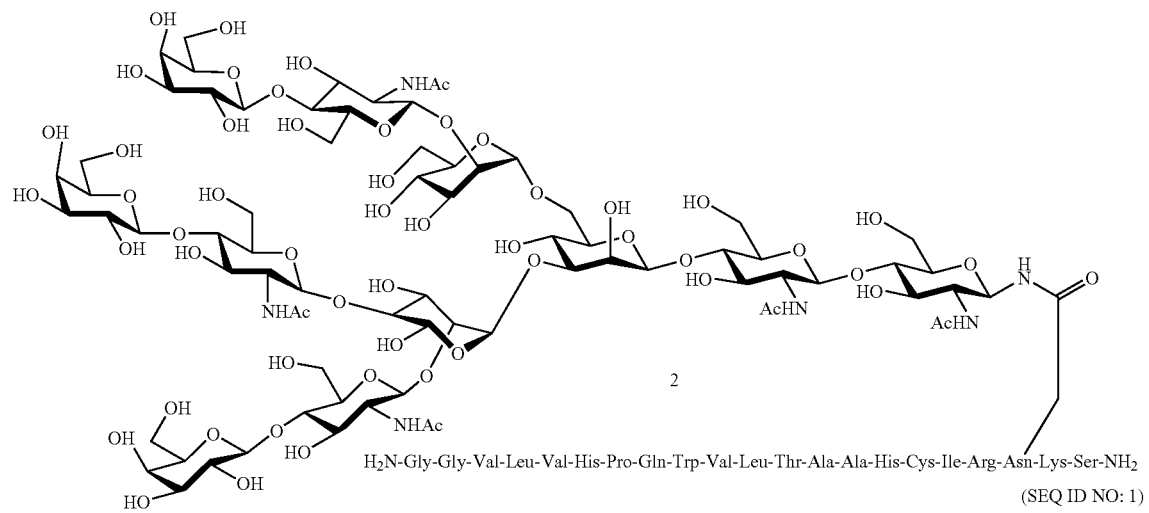

(SEQ ID NO: 1)

One important point to be appreciated is that simple permutations in the processing and advancement of key trisaccharide 4, and selection of the resident protection patterns in the α-mannosylation donors used in ring extension reactions of the strategic trisaccharide, build high diversity and high complexity at a stage where the systems are still of relatively modest size.

In certain embodiments, a synthesis of the non-symmetrically branched PSA glycan 2 is provided. In certain embodiments, the hydroxyls at C3 and C6 of the ring C system were sequentially functionalized. Thus, we first accomplished a-mannosylation at C3,[34] using donor 44 bearing two ester linkages, leading to 4,6-benzylidene protected tetrasaccharide. Controlled reductive cleavage of the benzylidene acetal[35] exposes the C6 hydroxyl of the C ring in 45, which was α-mannosylated with the previously employed monoester α-mannosyl donor 33. At this stage, the three esters were readily cleaved, thereby exposing trivalent acceptor system 31. Three-fold β-lactosylation was accomplished using β-lactosamine donor 34 with stereodirecting phthalimide groups at C2'. Indeed, three such donors were incorporated, leading to the protected core system (46) corresponding to 2. The steps for progressing from 46 to 2 were much as those worked out in advancing from 35 to 1 (vide supra).

In certain other embodiments, a synthesis of the highly branched system 3 is provided. Toward this end, we revisited tetrasaccharide 45. Reductive cleavage of the benzylidene acetal, as before, was now followed by mannosylation with 48, bearing esters at C2' and C6'. This reaction provided the required pentasaccharide, containing four acceptor sites momentarily masked as benzoate esters. The hydroxy centers to be functionalized were smoothly unveiled (see 32). At this stage, four-fold glycosylation was accomplished with lactosamine donor 11, but this time in more modest yield. The tridecasaccharide core system (cf. 48) was obtained, but this time in 19% yield.

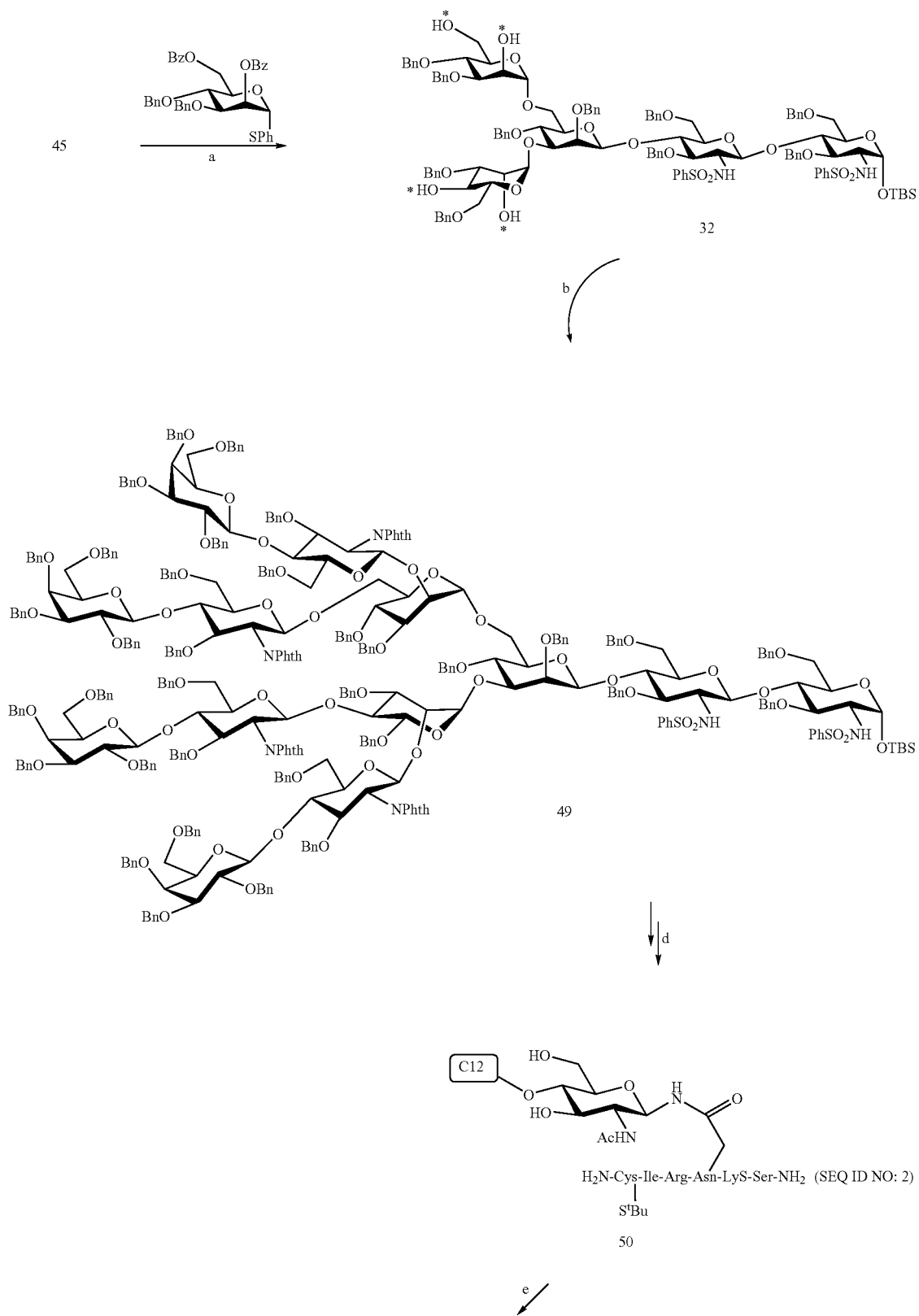

-continued

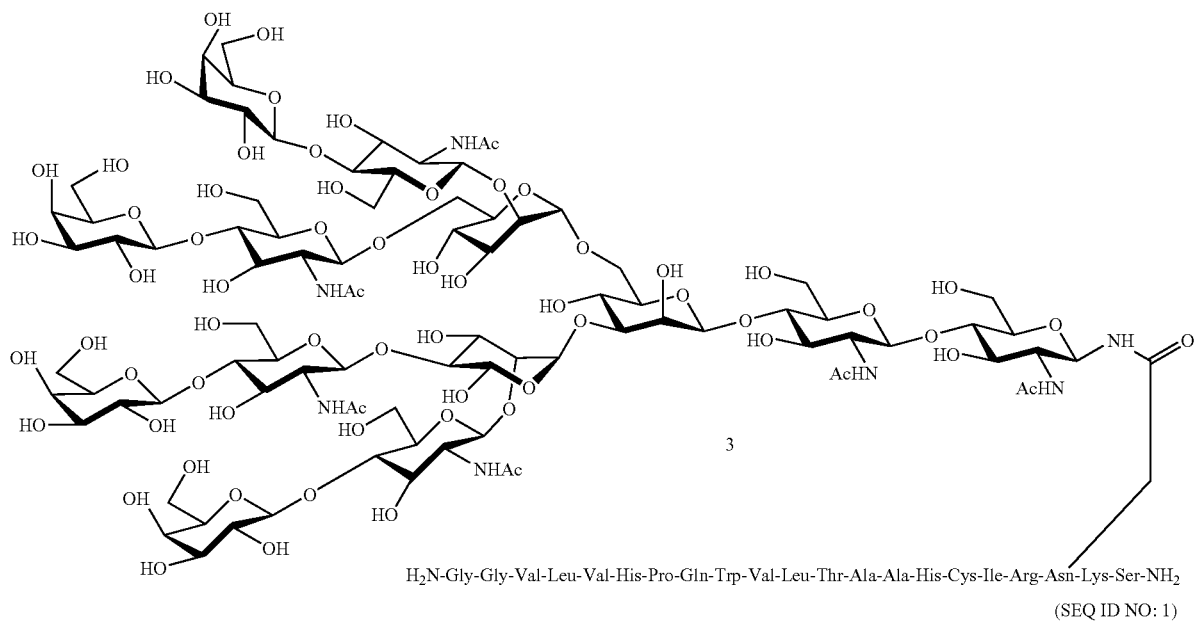

H$_2$N-Gly-Gly-Val-Leu-Val-His-Pro-Gln-Trp-Val-Leu-Thr-Ala-Ala-His-Cys-Ile-Arg-Asn-Lys-Ser-NH$_2$ (SEQ ID NO: 1)

Fortunately, the sequence from protected oligosaccharide to deprotected Kotchetkov amination product worked well, as did the introduction of 40 via aspartylation and deprotection (cf. 50). Upon NCL with 43, the tridecassacharide-uneicosapeptide glycoconjugate 3 was delivered in homogeneous form.

In summary, a universal strategy for the preparation of complex N-linked glycopeptides from a common precursor has been developed. This new methodology has proven its mettle in the preparation of normal and transformed PSA fragments.

Materials and Methods

Reagents. All commercial materials were used as received unless otherwise noted. The following solvents were obtained from a dry solvent system and used without further purification: THF, diethyl ether, toluene, and DCM. Reagents were obtained from Aldrich or as noted, with the following exceptions: amino acids and resins for solid phase peptide synthesis were purchased from NovaBiochem; Biosynthesis grade DMF from EM Science; and other solvents from Fisher Scientific (HPLC grade).

HPLC. All separations involved a mobile phase of 0.05% TFA (v/v) in water (solvent A)/0.0425% TFA in acetonitrile (solvent B). Preparative, semipreparative, and analytical HPLC separations were performed using a Rainin HXPL solvent delivery system equipped with a Rainin UV-1 detector and one of the following Dynamax-60 Å C18 axial compression columns 250 mm in length equipped with a similarly packed guard column: 41.4 mm diameter (prep), 21.4 mm diameter (semiprep), or 4.6 mm diameter (analytical). Separations were performed at flow rates of 48 mL/min (prep), 16 mL/min (semiprep), or 1 mL/min (analytical), and were monitored at a wavelength between 214 and 230 nm, depending on column loading. LCMS chromatographic separations were performed using a Waters 2695 Separations Module and a Waters 996 Photodiode Array Detector equipped with a Varian Microsorb C18 2×150 mm column at a flow rate of 0.2 mL/min.

ESMS and LCMS. Electrospray mass spectroscopy and LCMS analyses were obtained on a Waters Micromass ZQ mass spectrometer in conjunction with the Waters HPLC apparatus described above.

NMR. $^1$H and $^{13}$C NMR spectra were recorded on Bruker instruments in CDCl$_3$, C$_6$D$_5$CD$_3$, or D$_2$O at 400 or 500 MHz for $^1$H and 100 or 125 MHz for $^{13}$C.

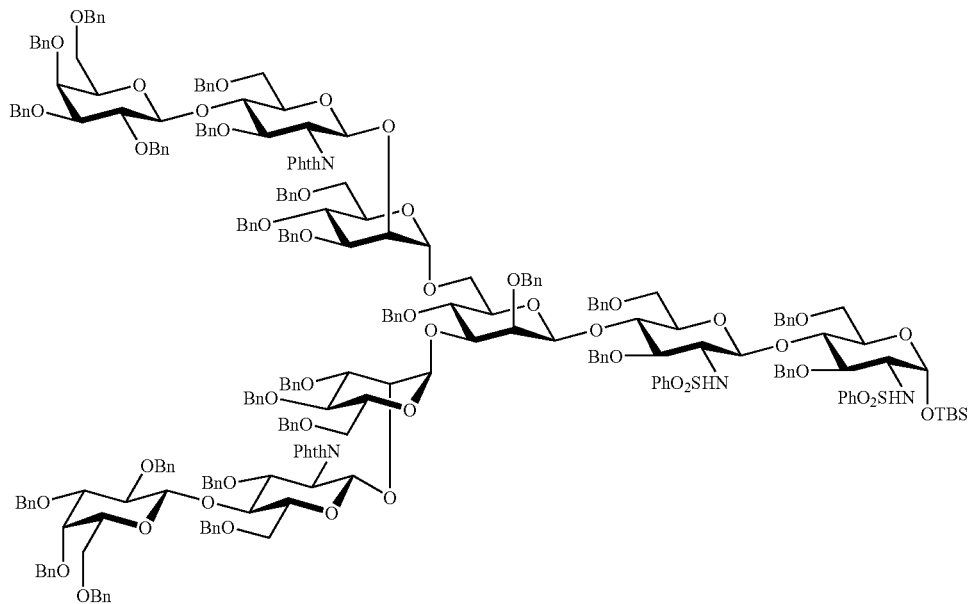

Nonasaccharide 35. Saccharides 30 (120.6 mg, 52.3 µmol) and 33 (388.7 mg, 368.0 µmol, 7.03 equiv) were combined in an oven-dried 10 mL roundbottom flask and concentrated from dry toluene, then placed under high vacuum for 3 hr. The flask was then fitted with a stirbar and a rubber septum with an argon inlet. The material was dissolved in 2 mL dry dichloromethane; to the stirred solution were added di-tert-butylpyridine (DTBP, 300 µL, 1.34 mmol, 25.5 equiv) and flame-dried 4 Å molecular sieves (0.5 g). The suspension was stirred for 30 min under argon, then cooled to 0° C. over an ice bath; methyl triflate (120 µL, 1.06 mmol, 20.2 equiv) was added via plastic syringe. The reaction was allowed to warm slowly to room temperature. After 41.5 hr, the mixture was diluted with ethyl acetate, filtered through a plug of silica gel, and eluted with ethyl acetate. Some toluene was added and the solution concentrated almost to dryness; ethyl acetate was added, and the organics in a 60 mL separatory funnel were washed with saturated sodium bicarbonate, dried over magnesium sulfate, and concentrated to give 800 mg of an oily solid, yellow residue. The material was purified by column chromatography on silica gel, loaded with methylene chloride and eluted with 10%→20%→30%→40% ethyl acetate in hexanes. The fractions containing desired material were combined and concentrated, affording nonasaccharide 35 as an amorphous white solid (135.6 mg, 31.6 µmol, 60% yield). $R_f$=0.32 (40% ethyl acetate in hexanes); $R_f$=0.71 (20% ethyl acetate in toluene). $[\alpha]_D$=+0.5° (c 1.9, $CHCl_3$); $^1$H-NMR (400 MHz, $CDCl_3$, selected signals), δ: 0.04 (s, 3H), 0.08 (s, 3H), 0.92 (s, 9H), 2.75 (br. d, J=9.3 Hz, 1H), 2.87 (dd, J=6.4, 10.7 Hz, 1H), 2.97 (d, J=10.6 Hz, 1H), 5.06 (d, J=2.2 Hz, 1H), 5.19 (d, J=7.1 Hz, 1H), 7.70 (d, J=7.6 Hz, 2H), 7.74 (d, J=7.5 Hz, 2H); $^{13}$C-NMR (100 MHz, $CDCl_3$), δ: −5.7, −4.5, 17.9, 25.7, 29.6, 55.5, 57.8, 58.3, 66.2, 67.7, 68.0, 68.1, 69.0, 69.4, 69.7, 69.9, 70.3, 70.5, 71.7, 72.2, 72.3, 72.5, 72.8, 72.85, 72.9, 73.0, 73.6, 73.9, 74.0, 74.1, 74.3, 74.4, 74.5, 74.6, 74.8, 74.9, 75.0, 76.0, 76.4, 77.5, 77.6, 78.9, 79.4, 79.8, 80.8, 82.2, 82.3, 92.6, 95.9, 96.7, 97.9, 98.8, 100.6, 101.4, 102.7, 102.9, 123.0, 123.2, 126.1, 126.7, 127.0, 127.1-128.4, 128.7, 131.8, 132.1, 132.3, 133.4, 133.8, 137.4, 137.9, 138.0, 138.2, 138.3, 138.4, 138.42, 138.46, 138.5, 13836, 138.7, 138.8, 138.85, 138.9, 138.95, 139.0, 140.6, 141.1, 167.4, 168.2, 168.4.

ESI-MS calcd for $C_{256}H_{268}N_4O_{50}S_2Si$ $[M+2H]^{2+}$ m/z=2144.89, found: 2145.3.

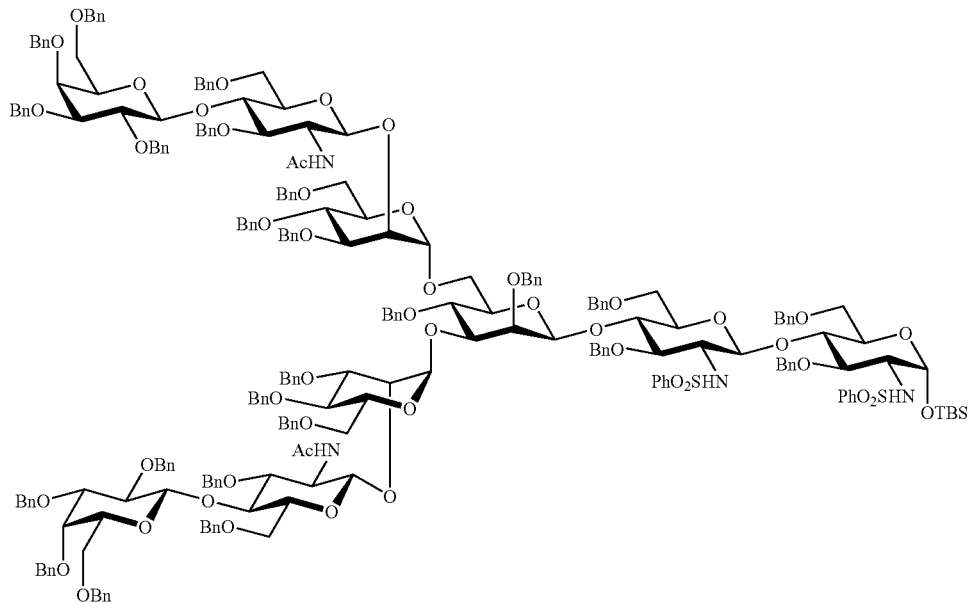

Di-N-acetyl nonasaccharide 36. To nonasaccharide 35 (178.1 mg, 41.5 μmol) in a 50 mL roundbottom flask with a stirbar were added freshly dried toluene (1 mL) and n-butanol (8 mL), and the contents were washed in with additional toluene (1 mL). The flask was briefly evacuated, then placed under argon using a septum with an argon needle inlet. Ethylenediamine (2.0 mL, 29.9 mmol) was added, and the reaction was heated to 90° C. and stirred for 40 hr. After cooling to room temperature, the stirbar was rinsed with toluene and removed, and the reaction mixture concentrated at low pressure, then concentrated twice more from toluene, affording 204 mg of the crude diamine ($R_f$=0.29 in 5% ethanol in toluene with 2% triethylamine) as a pale yellow oil with some solid. Under argon, pyridine (3.0 mL, 37 mmol) and acetic anhydride (2.5 mL, 26.5 mmol) were added. After 17 hr of stirring at room temperature, the reaction mixture was concentrated, as before, 3 times from dry toluene, yielding. 213 mg of a foam with some solid. Under argon, the material was dissolved in dry THF (2 mL) and dry methanol (5 mL). Sodium methoxide, 25% by weight in methanol (100 μL, 437 μmol, 10.5 equiv) was added via micropipette. After stirring 45.5 hr, the reaction was quenched by the addition of solid ammonium chloride (82.7 mg, 1.55 mmol) all at once. The suspension was concentrated, then transferred to a 60 mL separatory funnel using ethyl acetate and water. The aqueous layer was removed and the organics were washed once with saturated brine, dried with magnesium sulfate, filtered, and concentrated to give 172.0 mg of a crude oil. Purification by preparative TLC on 4 20×20 cm×1 mm thickness PK6F plates developed with 15% ethanol in toluene afforded desired nonasaccharide 36 as a foam (122.8 mg, 29.8 μmol, 72% yield). $R_f$=0.35 (5% ethanol in toluene). $[\alpha]_D$=+10.6° (c 3.5, CHCl$_3$); $^1$H-NMR (500 MHz, CDCl$_3$, selected signals), δ: 0.07 (s, 3H), 0.10 (s, 3H), 0.94 (s, 9H), 1.71 (s, 3H), 1.74 (s, 3H), 5.05 (s, 1H), 5.11 (s, 1H), 5.23 (d, J=6.8 Hz, 1H), 5.59 (d, J=6.9 Hz, 1H), 7.69 (d, J=7.5 Hz, 2H), 7.77 (d, J=7.5 Hz, 2H); $^{13}$C-NMR (125 MHz, CDCl$_3$), δ: −5.7, −4.5, 18.0, 26.4, 25.8, 29.7, 56.8, 57.4, 58.0, 58.2, 66.6, 67.6, 68.2, 68.5, 69.1, 69.2, 69.4, 69.9, 70.0, 70.9, 71.8, 72.6, 72.9, 73.2, 73.3, 73.4, 73.7, 73.9, 74.0, 74.3, 74.6, 74.9, 75.0, 75.1, 76.1, 76.2, 76.3, 76.9, 77.2, 77.6, 77.7, 77.8, 78.2, 78.6, 79.8, 79.8, 79.9, 81.2, 82.4, 92.7, 98.1, 98.2, 98.4, 99.6, 100.6, 101.9, 102.7, 102.9, 126.2, 126.9-128.8, 132.2, 132.3, 137.6, 138.0, 138.05, 138.1, 138.3, 138.4, 138.45, 138.5, 138.7, 138.8, 139.0, 139.1, 139.4, 139.5, 140.6, 141.2, 170.6, 170.8.

ESI-MS calcd for $C_{244}H_{266}N_4O_{48}S_2SiNa_2$ $[M+2Na]^{2+}$ m/z=2078.88, found: 2079.3.

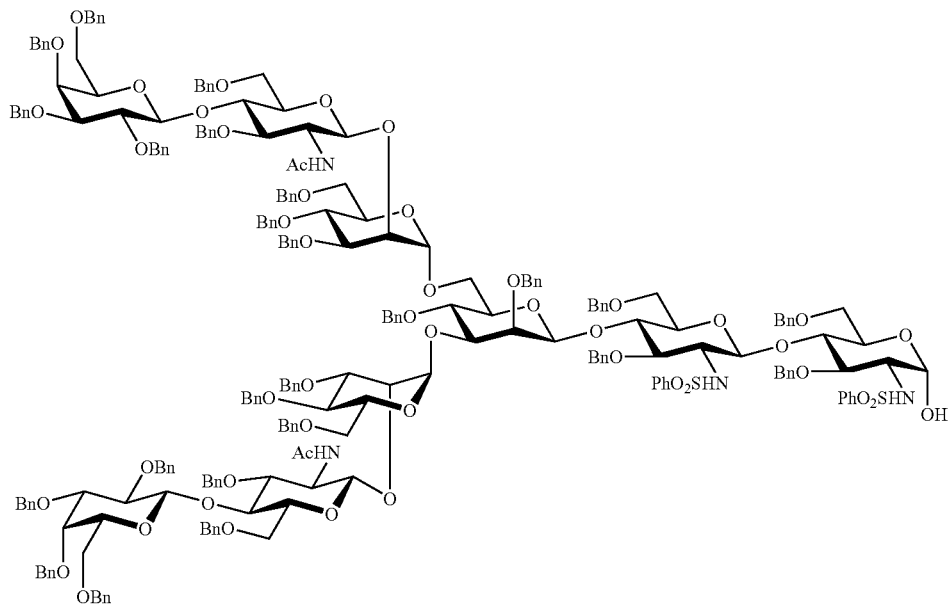

Reducing nonasaccharide 37. To nonasaccharide 36 (122.8 mg, 29.8 μmmol) under argon in a 50 mL roundbottom flask fitted with a stirbar and a septum with an argon inlet was added acetic acid, 1.0 M in THF (2.0 mL, 2.0 mmol). Over an ice-water bath, TBAF, 1.0 M in THF (0.8 mL, 0.8 mmol, 27 equiv) was added, then the ice-bath was removed. After stirring for 21 hr at ambient temperature, the stirbar was rinsed and removed and the reaction mixture was concentrated at low pressure. The residue was transferred to a 60 mL separatory funnel with 30 mL ethyl acetate, washed with 2×10 mL saturated sodium bicarbonate and 1×10 mL saturated brine, dried over magnesium sulfate, filtered, and concentrated, yielding 138.1 mg crude product. Purification by preparative TLC on 4 20×20 cm×1 mm thickness PK6F plates developed with 10% ethanol in toluene afforded the desired nonasaccharide 37 as a foam (90.7 mg, 22.7 μmol, 76% yield). $R_f$=0.32 (5% ethanol in toluene). $[\alpha]_D$=+4.0° (c 3.5, CHCl$_3$);

$^1$H-NMR (400 MHz, CDCl$_3$, selected signals), δ: 1.70 (s, 3H), 1.73 (s, 3H), 5.05 (s, 1H), 5.09 (s, 1H), 5.23 (d, J=7.0 Hz, 1H), 5.58 (d, J=6.7 Hz, 1H), 7.68 (d, J=7.4 Hz, 2H), 7.76 (d, J=7.6 Hz, 2H); $^{13}$C-NMR (100 MHz, CDCl$_3$), δ: 22.7, 22.9, 23.4, 23.7, 28.9, 29.3, 29.7, 30.3, 31.9, 38.7, 56.8, 57.0, 57.3, 58.4, 67.0, 67.8, 68.1, 68.2, 68.5, 68.8, 69.2, 69.5, 70.0, 70.8, 71.8, 72.6, 72.9, 73.2, 73.4, 73.7, 73.9, 74.0, 74.4, 74.6, -74.7, 75.0, 75.4, 76.0, 76.1, 77.2, 77.7, 78.1, 78.5, 79.5, 79.9, 81.3, 82.3, 82.4, 91.3, 98.2, 98.3, 99.6, 100.3, 101.8, 102.8, 102.9, 126.2, 127.0-128.8, 129.7, 130.8, 132.4, 132.5, 137.4, 138.0, 138.1, 138.2, 138.3, 138.4, 138.5, 138.7, 138.8, 138.9, 139.0, 139.4, 139.5, 140.2, 141.4, 170.6, 171.0.

ESI-MS calcd for $C_{238}H_{252}N_4O_{48}S_2Na_2$ [M+2Na]$^{2+}$ m/z 2021.83. found 2021.7.

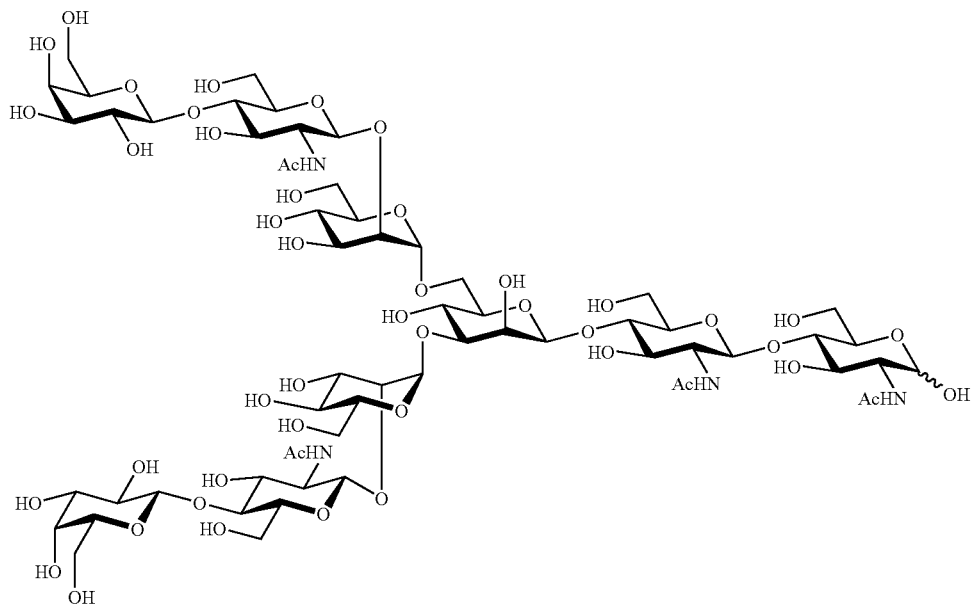

Deprotected nonasaccharide 38. (for preparation, see undecamer 46c). From 90.7 mg (0.0227 mmol) of 37, obtained 24 mg (0.015 mmol, 64% yield) of 38 as a white powder. $^1$H-NMR (400 MHz, D$_2$O, selected signals), δ: 2.02 (s, 3H), 2.03 (s, 3H), 2.04 (s, 3H), 2.11 (s, 3H), 4.10 (br. s, 1H), 4.18 (br. s, 1H), 4.24 (br. s, 1H), 4.46 (dd, J=2.3, 7.7 Hz, 1H), 4.58 (m, 3H), 4.91 (s, 1H), 5.10 (s, 1H), 5.17 (d, J=2.1 Hz, 1H). ESI-MS calcd for C$_{62}$H$_{104}$N$_4$O$_{46}$Na [M+Na]$^+$ m/z=1663.58, for C$_{62}$H$_{104}$N$_4$O$_{46}$Na$_2$ [M+2Na]$^{2+}$ m/z=843.29, found: 1663.4, 843.3.

Glycosylamine 39. The starting material reducing saccharide 38 (20 mg, 12.2 μmol) in a 50 mL pear flask was dissolved in water (10 mL). To this clear, colorless solution was added solid ammonium hydrogencarbonate (6.28 g, 79.7 mmol); the suspension was stirred vigorously and heated immediately to 40° C. over a warm water bath. As the solution became almost clear, additional ammonium hydrogencarbonate was added at almost 2 hr., (2.99 g, 37.8 mmol) and at 8.5 hr. (5.00 g, 63.2 mmol). At 30 hr., the cloudy reaction mixture was allowed to cool, with stirring. The slurry was then trans-

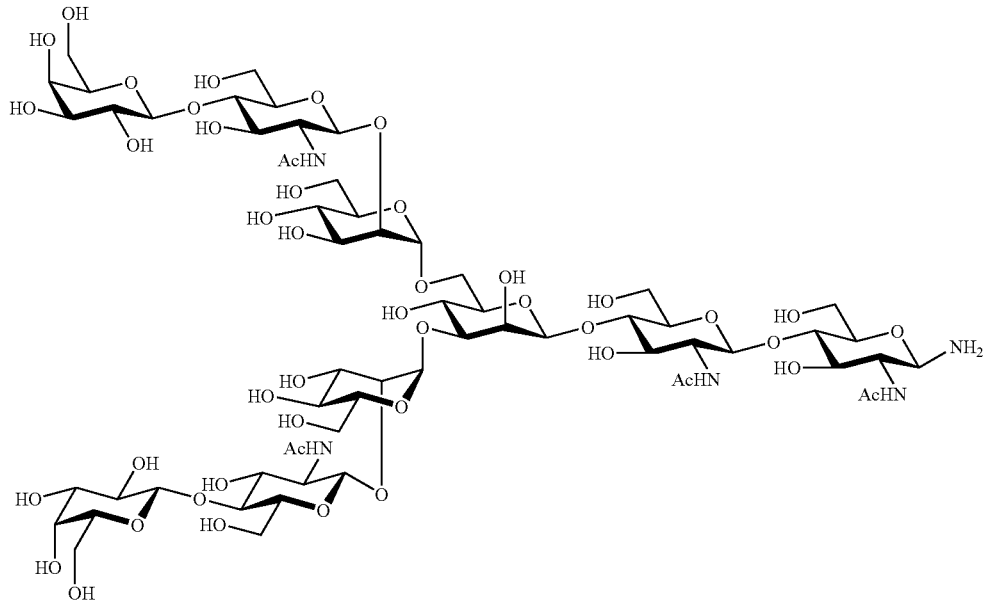

ferred to a tared, 50 mL polypropylene conical tube, washed in with water to a total volume of 35 mL, immediately shell frozen, and lyophilized to give 650 mg white powder. This white powder was dissolved in 15 mL water, then immediately shell frozen and lyophilized again, affording 33.8 mg white powder. Similar lyophilization thrice more from 10 mL water (used to transfer the material to a 15 mL polypropylene conical tube) gave 28.0, 25.2, and 24.4 mg white or off-white solid. The ammonium bicarbonate seemed to be gone and the dry mass fairly constant when the lyophilized solid became relatively dense and granular. The crude solid was taken directly into the next reaction.

ESI-MS calcd for $C_{62}H_{105}N_5O_{45}Na$ [M+Na]$^+$ m/z=1662.60, for $C_{62}H_{105}N_5O_{45}Na_2$ [M+2Na]$^{2+}$ m/z=842.79, found: 1662.5, 842.8.

Fmoc-NH-Cys(S$^t$Bu)-Ile-Arg-Asp-Lys(ivDde)-Ser-NH$_2$ (Peptide 40): Automated peptide synthesis was performed on an Applied Biosystems Pioneer continuous flow peptide synthesizer. Peptide 40 was synthesized using Applied Biosystems Fmoc-PAL-PEG-PS resin under standard automated Fmoc/$^t$Bu protocols. The deblock mixture was a mixture 80:18:2 of DMF:piperidine:DBU. The following side chain protection schemes for Fmoc amino acids from NovaBiochem were employed: Cys(S$^t$Bu), Arg(Pbf), Asp($^t$Bu), Lys (ivDde), Ser($^t$Bu). Upon completion of the automated synthesis on a 0.25 mmol scale the peptide-resin was washed into a peptide synthesis vessel with methanol, rinsed with dichloromethane and diethyl ether, and dried under vacuum. A fraction (83%) of the dry resin was subjected to a cleavage cocktail of 5% phenol, 5% water, 2.5% triethylsilane, and 87.5% TFA (w/v/v/v) for 1-2 hours under argon. The resin was removed by filtration, and the resulting solution concentrated at reduced pressure. The dark, oily residue was triturated with diethyl ether to give a thick, white suspension, which was transferred to a polypropylene conical tube. The tube was centrifuged and the ether decanted; this was repeated 2× more. The resulting solid was dissolved in a mixture of 8 mL of 50% B (HPLC buffer) and 2 mL DMF. Semiprep HPLC purification (52-68% B/16 min, RT ~10.5 min) followed by concentration at reduced pressure until foaming began and lyophilization afforded 17 as a white powder (157.5 mg, 0.127 mmol, 61% yield from unfunctionalized resin).

LCMS 50-70% B over 10 min, RT 11.6 min.

ESI-MS calcd for $C_{60}H_{90}N_{11}O_{13}S_2$ [M+H]$^+$ m/z=1236.62, found: 1236.8.

(SEQ ID NO: 2)

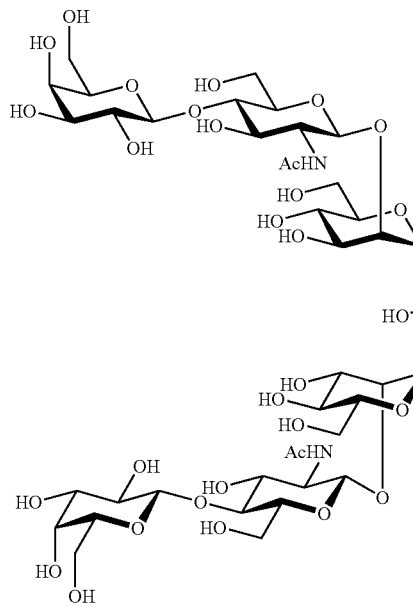
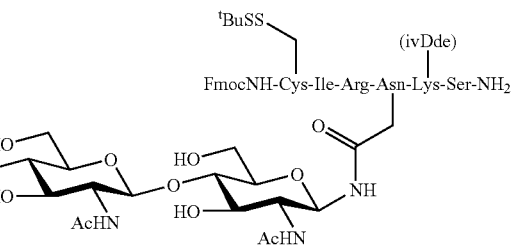

Nonasaccharide—hexapeptide 41. To a 4 mL glass vial charged with a small stirbar, peptide 40 (44.4 mg, 35.9 µmol, 3.0 equiv) and HATU (27 mg, 71 µmol, 5.9 equiv) were added DMSO (100 µL), then diisopropylethylamine (9.0 µL, 52 µmol, 4.3 equiv), then DMSO (300 µL). With stirring, the solid dissolved in ~30 sec to give an orange-brown solution. After 4 min, the solution was transferred via 500 µL syringe to a 15 mL polypropylene conical tube containing glycosylamine 39 (24.4 mg crude, 12 µmol). After swirling, the reaction mixture was centrifuged briefly, then stirred to dissolve all remaining solid over 5 min. To follow the reaction by LCMS, 1 µL samples were diluted with 20 µL DMSO and analyzed. The reaction had ceased, incomplete, by 3 hr, but was rejuvenated at 7 hr by addition of HATU (9.0 mg, 24 µmol, 2.0 equiv) and DIEA (1.0 µL, 5.7 µmol, 0.48 equiv), then addition of DIEA at 9 hr (3.7 µL, 21 µmol, 1.8 equiv) and at 10.5 hr (3.2 µL, 18 µmol, 1.5 equiv). Almost no glycosylamine remained by 11 hr. The entire reaction mixture was purified by semiprep HPLC (30-70% B over 20 min). The combined fractions from 13.95 to 15.35 min were shell frozen and lyophilized in a 50 mL polypropylene conical tube, affording the desired 41 as a white solid (21 mg, 7.3 µmol, 61% yield). NMR spectra were not recorded due to a lack of solubility in any appropriate solvent besides DMSO, which would require repurification and associated loss of material.

LCMS 30-70% B over 20 min, RT 15.7 min.

ESI-MS calcd for $C_{122}H_{194}N_{16}O_{57}S_2$ [M+2H]$^{2+}$ m/z=1429.61, found: 1429.6

(SEQ ID NO: 2)

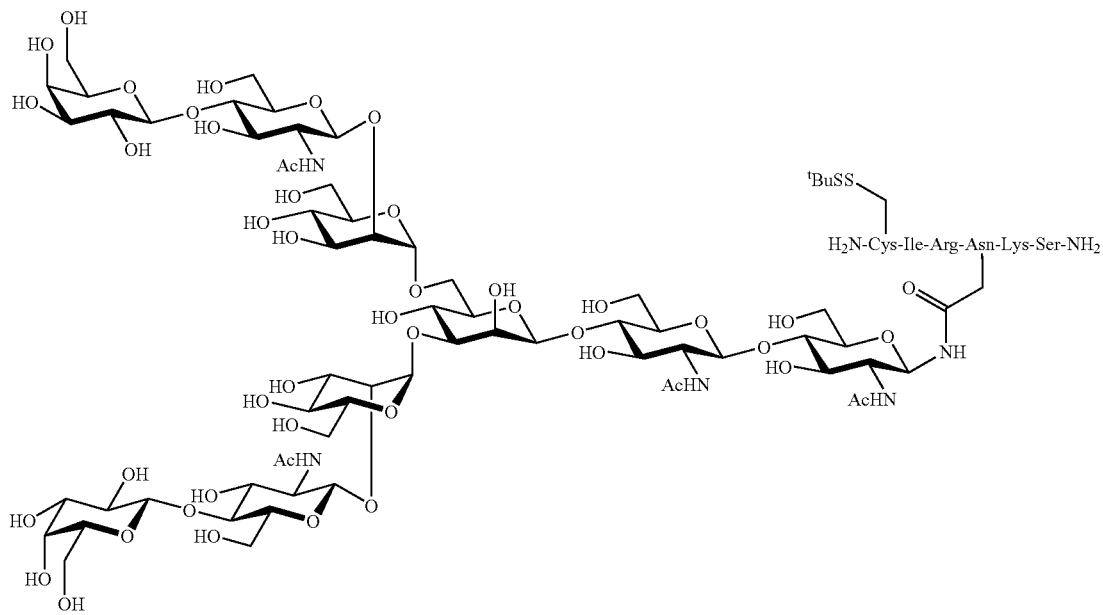

Deprotected glycopeptide 42. To protected glycopeptide 41 (21 mg, 7.3 μmol) in a 50 mL polypropylene conical tube was added a cocktail (1 mL) consisting of hydrazine, piperidine, and DMF in a volume ratio of 5:15:80, respectively. After 30 min with occasional stirring, the reaction mixture was cooled over an ice bath and acidified to pH~3 with an ice-cold solution of TFA:water (1:10). The entire reaction mixture was purified by semiprep HPLC (5-15% B over 20 min). The fractions from 16.9 to 17.8 min were combined and concentrated. The fractions eluting directly before and after the major fraction were repurified by HPLC as before. The fractions containing the desired 42 were combined and concentrated, then lyophilized, affording the desired 42 as a white solid (10.9 mg, 4.5 μmol, 62% yield). $^1$H-NMR (400 MHz, D$_2$O, selected signals), δ: 0.86 (t, J=7.5 Hz, 3H), 0.90 (d, J=6.8 Hz, 3H), 1.17 (m, 1H), 1.32 (s, 9H), 2.00 (s, 3H), 2.03 (br. s, 6H), 2.06 (s, 3H), 2.73 (dd, J=6.8, 16.2 Hz, 1H), 2.86 (dd, J=6.3, 16.2 Hz, 1H), 0.86 (br. t, J=7.6 Hz, 2H), 3.13-3.22 (m, 4H), 3.28 (dd, J=5.6, 14.6 Hz, 1H), 4.09 (d, J=3.1 Hz, 1H), 4.17 (d, J=2.2 Hz, 1H), 4.23-4.34 (m, 5H), 4.40 (t, J=5.4 Hz, 1H), 4.45 (d, J=7.7 Hz, 1H), 4.46 (d, J=7.8 Hz, 1H), 4.56-4.60 (m, 3H), 4.70 (t, J=6.4 Hz, 1H), 4.91 (br, s 1H), 5.01 (d, J=9.6 Hz, 1H), 5.10 (br. s, 1H); $^{13}$C-NMR (125 MHz, D$_2$O, selected signals), δ: 12.8, 17.4, 24.7, 24.9, 25.0, 25.1, 27.2, 27.4, 29.0, 30.9, 31.6, 33.0, 69.2, 39.3, 41.9, 43.3, 46.5, 47.3, 52.6, 55.4, 56.1, 56.4, 56.7, 57.6, 57.7, 58.2, 60.9, 62.7, 63.8, 64.4, 64.5, 68.5, 68.6, 70.0, 70.1, 71.3, 72.1, 72.9, 73.7, 74.7, 74.8, 75.2, 75.6, 76.3, 77.1, 77.4, 78.1, 79.0, 79.2, 81.0, 81.2, 81.4, 82.3, 83.1, 99.8, 102.1, 102.2, 102.3, 103.2, 104.1, 105.7, 107.7.

LCMS 8-18% B over 10 min, RT 9.4 min.

ESI-MS calcd for $C_{94}H_{166}N_{16}O_{53}S_2$ [M+2H]$^{2+}$ m/z=1215.51, found: 1215.6.

H$_2$N-Gly-Gly-Val-Leu-Val-His-Pro-Gln-Trp-Val-Leu-Thr-Ala-Ala-His-S(CH$_2$)$_2$CONH$_2$ (SEQ ID NO: 11) (Thioester 43): Peptide thioester 43 was synthesized manually on the solid phase using tert-butoxycarbonyl-amino acyl-3-mercapto-propionamide-4-methylbenzhydrylamine-co-poly(styrene-1% DYB) (Boc-AA-[COS]-MBHA) according to the in situ neutralization O-benzotriazol-1-yl-N,N,N',N',-tetramethyluronium hexafluorophosphate (HBTU) activation protocol for Boc solid-phase peptide synthesis.[1] After chain assembly, a fraction of the peptide-resin (~300 mg) was treated with HF (~10 mL) and p-cresol (~0.5 g) for 1 hr at 0° C. to give the corresponding fully unprotected peptide. Following removal of HF, the crude peptide product was precipitated using cold ether, washed thoroughly with ether, and dissolved in 50% acetonitrile/50% water/0.1% TFA. Semiprep HPLC purification (27-29% B/10 min, RT ~7.3 min) followed by concentration at reduced pressure and lyophilization afforded 43 as a white powder (28 mg, 0.017 mmol).

LCMS 20-40% B over 10 min, RT 12.4 min.

ESI-MS calcd for $C_{77}H_{119}N_{22}O_{18}S$ [M+H]$^+$ m/z=1671.88, for $C_{77}H_{120}N_{22}O_{18}S$ [M+2H]$^{2+}$ m/z=836.44, found: 1672.0, 836.6.

[1] Schnölzer, M.; Alewood, P.; Jones, A.; Alewood, D.; Kent, S. B. H. *Int. J. Pept. Protein Res.* 1992, 40, 180-193.

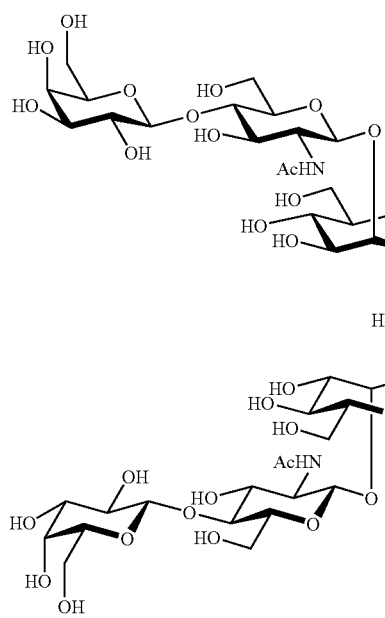

(SEQ ID NO: 1)

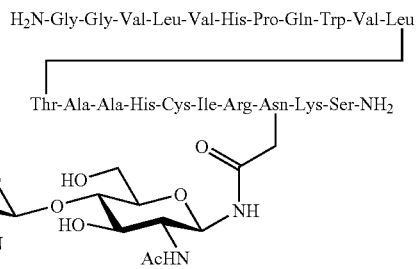

Nonasaccharide-uneicosapeptide glycoconjugate 1. To a 1 mL eppendorf tube charged with MES-Na (14.2 mg, 86.5 µmol, 38 equiv) was added aqueous phosphate buffered saline (1.0 mL, 0.2 M sodium chloride, 0.2 M phosphate, pH 7.4). The buffered solution was then added to a 100 mL roundbottom flask containing thioester 43 (5.8 mg, 3.5 µmol, 1.5 equiv) and glycopeptide 42 (5.5 mg, 2.3 µmol). The cloudy mixture was stirred over 2 hr, during which time acetonitrile (500 µL) was added, then placed under argon and stirred for a week to ensure complete destruction of the thioester, which co-eluted by HPLC with the desired material. The reaction was quenched by the addition of tris(carboxyethyl)phosphine (TCEP) (37.0 mg, 129 µmol, 56 equiv), giving a clear solution, which was stirred for 2.5 hr, acidified to pH~2 with TFA, and purified by semiprep HPLC (20-40% B over 20 min). The combined fractions from 11.2 to 12.0 min were shell frozen and lyophilized, affording the desired PSA fragment 1 as a white solid (1.5 mg, 0.38 µmol, 17% yield). $^1$H-NMR (400 MHz, D$_2$O, selected signals), δ: 1.19 (d, J=6.3 Hz, 3H), 1.32 (d, J=7.2 Hz, 3H), 1.35 (d, J=7.2 Hz, 3H), 2.88 (d, J=6.8 Hz, 2H), 2.97-3.07 (m, 4H), 4.26-4.35 (m, 5H), 4.37-4.41 (m, 2H), 4.45 (d, J=7.8 Hz, 2H), 4.50 (t, J=6.7 Hz, 1H), 4.56-4.60 (m, 3H), 4.91 (s, 1H), 4.94 (dd, J=5.5, 8.4 Hz, 1H), 5.01 (d, J=9.5 Hz, 1H), 5.10 (s, 1H), 7.10 (t, J=7.2 Hz, 1H), 7.18 (m, 2H), 7.23 (s, 1H), 7.28 (s, 1H), 7.42 (d, J=8.0 Hz, 1H), 7.58 (d, J=8.2 Hz, 1H), 8.53 (d, J=1.2 Hz, 1H), 8.60 (d, J=1.2 Hz, 1H).

LCMS 25-35% B over 10 min, RT 8.6 min.

ESI-MS calcd for C$_{164}$H$_{270}$N$_{37}$O$_{70}$S [M+3H]$^{3+}$ m/z=1303.28, for C$_{164}$H$_{271}$N$_{37}$O$_{70}$S [M+4H]$^{4+}$ m/z=977.71, found: 1303.3, 977.8.

Figure 6:
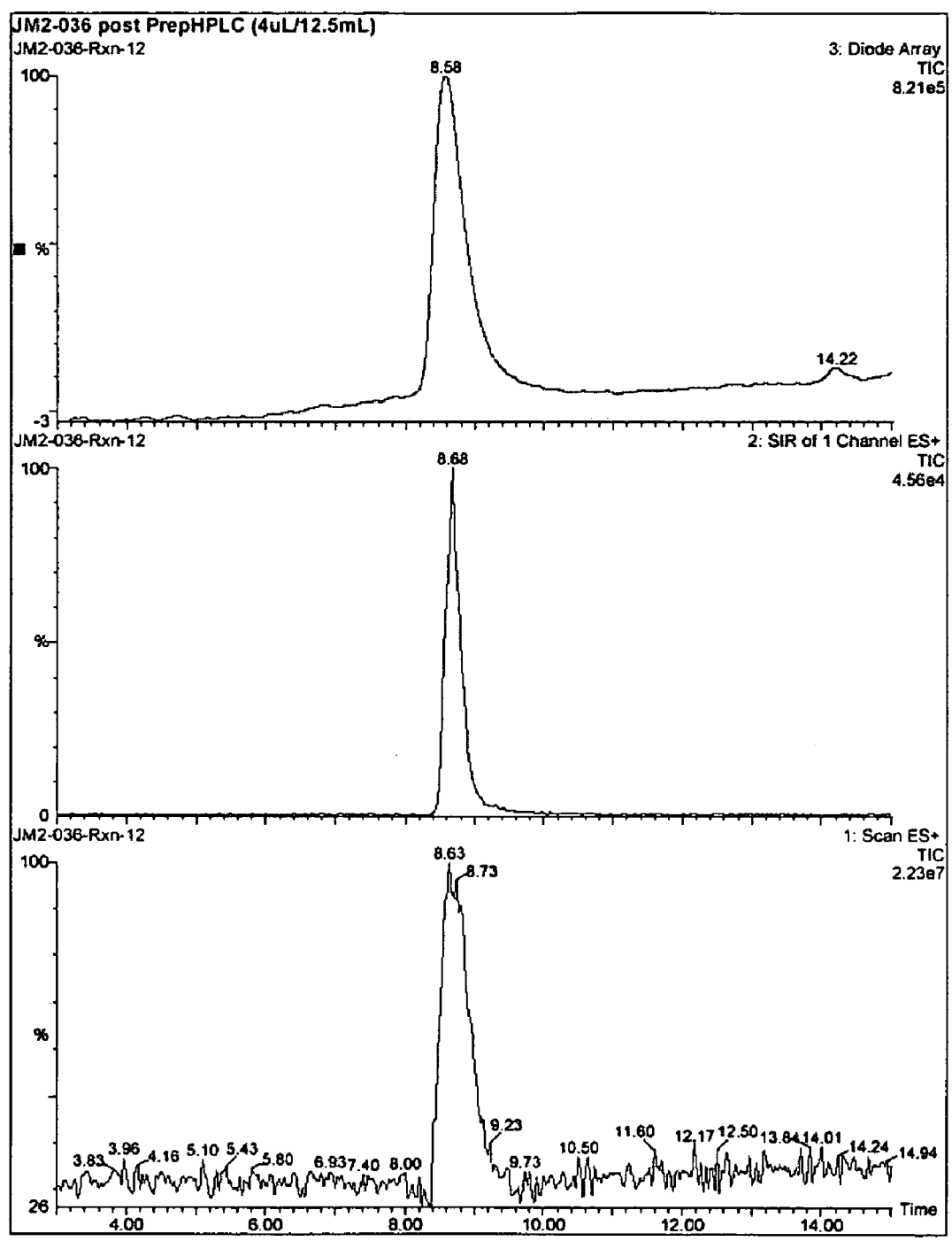
FIG. 6 depicts LCMS traces for construct 1.

LCMS traces for compound 1 are shown in FIG. 6.

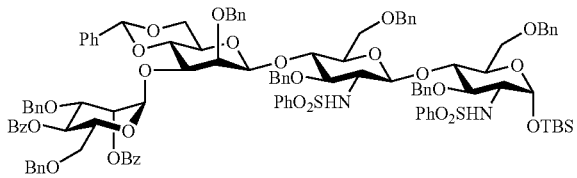

4,6-O-benzyldene protected tetrasaccharide 4a. A solution of thiomannoside donor 44 (180.0 mg, 0.27 mmol) in dry acetonitrile (1.75 ml) was stirred with 3 Å molecular sieves for 1 h and then cooled to 15° C. The solution was then treated with solid promoter (BrC$_6$H$_4$)NSbCl$_6$ (210 mg, 0.34 mmol) followed by the trisaccharide acceptor 4 (129 mg, 0.09 mmol) in dry acetonitrile (0.75 ml). The reaction mixture was protected from light and stirred at 15° C. for 40 min before the addition of another portion of (BrC$_6$H$_4$)NSbCl$_6$ (48 mg, 0.08 mmol). Stirring was continued for another 12 h at room temperature at which point the reaction was quenched by addition of triethylamine, filtered through a Celite pad, and concentrated. The residue was purified by flash chromatography on silica gel (eluent: ethyl acetate/hexanes 1/2) and then by preparative TLC (eluent: ethyl acetate/toluene 1/5) to afford starting trisaccharide acceptor 4 (18 mg) and desired tetrasaccharide 4a (127 mg, 71%, 83% b.r.s.m.) as a colorless oil. [α]$_D$=−31.0° (c 2.2, CHCl$_3$); $^1$H-NMR (CDCl$_3$, 400 MHz), δ: 0.05 (s, 3H), 0.11 (s, 3H), 0.93 (s, 3H), 3.00 (dt, J=4.6, 9.8 Hz, 1H), 3.18 (dt, J=7.8, 3.6 Hz, 1H), 3.26-3.41 (m, 6H), 3.45 (dd, J=3.1, 11.0 Hz, 1H), 3.51 (dt, J=11.0, 2.1 Hz, 1H), 3.59-3.68 (m, 3H), 3.76-3.87 (m, 4H), 3.92-3.99 (m, 2H), 4.02-4.16 (m, 4H), 4.21 (d, J=12.0 Hz, 1H), 4.28 (d, J=12.0 Hz, 1H), 4.29-4.35 (m, 2H), 4.38 (d, J=12.8 Hz, 1H), 4.39 (d, J=10.8 Hz, 1H), 4.43-4.54 (m, 4H), 4.61 (d, J=12.5

Hz, 1H), 4.74 (d, J=11.5 Hz, 1H), 4.76 (d, J=12.0 Hz, 1H), 4.83-4.93 (m, 2H), 5.12 (d, J=1.5 Hz, 1H), 5.45 (d, J=1.3 Hz, 1H), 5.53 (s, 1H), 5.69 (t, J=10.0 Hz, 1H), 5.80 (dd, J=2.0, 3.0 Hz, 1H), 6.93-6.99 (m, 2H), 7.02-7.09 (m, 3H), 7.12-7.17 (m, 4H), 7.18-7.49 (m, 4H), 7.54-7.63 (m, 2H), 7.74-7.79 (m, 4H), 7.90-7.99 (m, 2H), 8.05-8.09 (m, 2H); $^{13}$C-NMR (100 MHz, CDCl$_3$), δ: −5.7, −4.4, 18.0, 25.8, 58.0, 58.7, 67.1, 67.6, 68.1, 68.2, 68.6, 69.5, 69.7, 70.7, 71.1, 73.4, 73.5, 73.6, 73.7, 74.0, 74.6, 75.2, 75.3, 76.0, 76.3, 77.2, 78.2, 78.3, 80.0, 92.8, 98.9, 100.9, 101.0, 101.1, 125.8, 127.0, 127.1, 127.3, 127.4, 127.5, 127.6, 127.65, 127.7, 127.8, 127.9, 128.0, 128.03, 128.1, 128.14, 128.2, 128.25, 128.3, 128.33, 128.4, 128.45, 128.5, 128.7, 128.8, 128.9, 129.3, 129.5, 129.7, 129.8, 129.9, 132.2, 132.3, 133.1, 133.2, 137.1, 137.4, 137.6, 137.8, 137.9, 138.4, 138.5, 140.7, 141.5, 165.39, 165.42.

HRMS: Calcd. for $C_{112}H_{120}N_2O_{25}S_2SiNa$ [M+Na]$^+$ 2007.7289, Found: 2007.7309

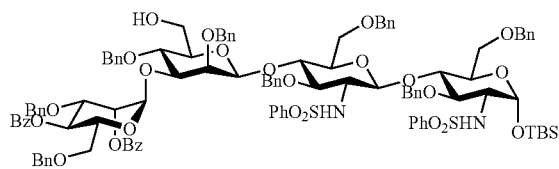

Tetrasaccharide acceptor 45. 4,6-O-Benzylidene protected tetrasaccharide 4a (100.0 mg, 0.05 mmol) was taken up in a 1 M solution of BH$_3$ in tetrahydrofuran (1.00 mL, 1.00 mmol), and the resulting mixture was stirred at 0° C. for 5 min before the addition of 1 M Bu$_2$BOTf in dichloromethane (0.15 mL, 0.15 mmol). Stirring was continued at this temperature for 2 h and then the reaction was quenched by sequential addition of triethylamine and methanol (caution!). The solution was concentrated and coevaporated with methanol 5 times. The residue was dried and subjected to preparative TLC (eluent: ethyl acetate/hexanes 1/2) to afford starting material 4a (12 mg) and desired alcohol 45 (85 mg, 85%, 96% b.r.s.m.). [α]$_D$=−34.0° (c 1.0, CHCl$_3$); $^1$H-NMR (CDCl$_3$, 400 MHz), δ: 0.06 (s, 3H), 0.11 (s, 3H), 0.94 (s,9H), 2.10 (br.s, 1H), 3.01 (dq, J=9.0, 3.0 Hz, 1H), 3.22 (dd, J=11.2, 3.0 Hz, 1H), 3.27-3.34 (m, 4H), 3.37 (dd, J=7.8, 15.7 Hz, 2H), 3.41-3.50 (m, 4H), 3.56-3.62 (m, 3H), 3.64 (dd, J=3.0, 9.6 Hz, 1H), 3.72-3.79 (m, 2H), 3.90 (d, J=3.0 Hz, 1H), 3.96 (t, J=9.5 Hz, 1H), 4.02-4.10 (m, 2H), 4.20 (d, J=7.5 Hz, 1H), 4.22-4.29 (m, 3H), 4.31-4.35 (m, 2H), 4.35-4.52 (m, 7H), 4.57 (d, J=12.7 Hz, 1H), 4.62 (d, J=10.8 Hz, 1H), 4.64 (d, J=12.1 Hz, 1H), 4.74 (d, J=11.4 Hz, 1H), 4.76-4.84 (m, 3H), 4.99 (d, J=12.5 Hz, 1H), 5.13 (d, J=1.7 Hz, 1H), 5.34 (d, J=1.5 Hz, 1H), 5.67 (t, J=10.7 Hz, 1H), 5.70-5.73 (m, 1H), 6.95-7.46 (m, 52H), 7.55-7.64 (m, 2H), 7.72-7.80 (m, 4H), 7.82-7.85 (m, 2H), 8.06-8.10 (m, 2H); $^{13}$C-NMR (CDCl$_3$, 100 MHz), δ: −5.7, −4.4, 18.0, 25.8, 57.9, 58.4, 61.3, 67.7, 68.4, 68.7, 68.8, 69.4, 69.9, 71.0, 71.1, 73.1, 73.4, 73.5, 73.6, 74.0, 74.1, 74.3, 74.6, 75.2, 76.0, 76.1, 76.9, 77.2, 77.5, 78.6, 79.7, 81.4, 92.8, 99.9, 100.8, 101.2, 126.6, 127.0, 127.06, 127.1, 127.2, 127.3, 127.34, 127.4, 127.44, 127.5, 127.6, 127.7, 127.75, 127.8, 127.87, 127.9, 128.0, 128.07, 128.1, 128.15, 128.2, 128.23, 128.26, 128.3, 128.4, 128.45, 128.5, 128.52, 128.62, 128.8, 129.0, 129.5, 129.6, 129.8, 130.0, 132.3, 132.4, 133.1, 133.2, 137.3, 137.7, 137.8, 137.9, 138.3, 138.4, 138.9, 140.7, 141.1, 165.3, 165.5.

HRMS: Calcd. for $C_{112}H_{122}N_2O_{25}S_2SiNa$ [M+Na]$^+$ 2009.7445, Found: 2009.7450

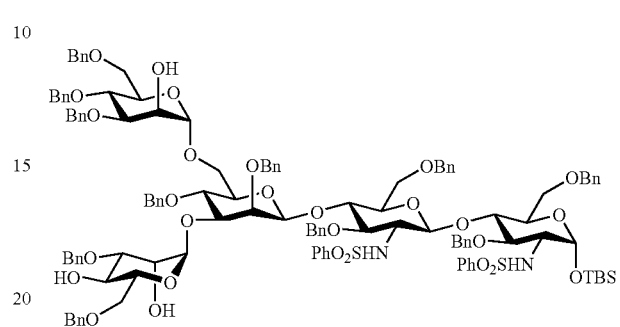

Pentasaccharide 31. Thiomannoside donor 33 (323 mg, 0.16 mmol) was coupled with tetrasaccharide acceptor 45 (323 mg, 0.05 mmol) following the procedure for the preparation of tetrasaccharide 4a. Purification of the reaction mixture using flash chromatography (eluent: ethyl acetate/hexanes 1/3 to 1/2) afforded pentasaccharide 45a (ESI-MS: Calcd. for $C_{146}H_{154}N_2O_{31}S_2SiNa$ [M+Na]$^+$ 2546.0, Found: 2546.0), containing trace amounts of impurities. This material was dissolved in dry methanol (10.0 mL) and treated with sodium methoxide (25 wt.% in methanol, 0.3 mL). The reaction mixture was stirred overnight at room temperature, quenched with ammonium chloride and concentrated. The dry residue was suspended in ethyl acetate, filtered, and concentrated. Purification by preparative TLC (eluent: ethyl acetate/hexanes 1/2) gave the desired triol 31 (255 mg, 72% for 2 steps from acceptor 45). [α]$_D$=+6.60 (c 1.3, CHCl$_3$); $^1$H-NMR (400 MHz, CDCl$_3$) δ: 0.05 (s, 3H), 0.09 (s, 3H), 0.92 (s, 9H), 2.30 (br. s, 3H), 3.10 (dq, J=9.3, 2.2 Hz, 1H), 3.17-3.36 (m, 7H), 3.39-3.72 (m, 12H), 3.73-3.91 (m, 8H), 3.95 (dd, J=2.0, 2.9 Hz, 1H), 4.11 (d, J=7.4 Hz, 1H), 4.20 (d, J=8.1 Hz, 1H), 4.23-4.34 (H, 4H), 4.37-4.60 (m, 13H), 4.65 (d, J=11.9 Hz, 1H), 4.70-4.81 (m, 3H), 4.83 (d, J=11.7 Hz, 1H), 4.88 (d, J=1.4 Hz, 1H), 4.93 (d, J=12.0 Hz, 1H), 5.11 (d, J=2.2 Hz, 1H), 5.12 (d, J=1.1 Hz, 1H), 7.10-7.35 (m, 57H), 7.37-7.44 (m, 4H), 7.71 (br. d, J=8.4 Hz, 1H), 7.76 (br. d, J=8.3 Hz, 1H); $^{13}$C-NMR (100 MHz, CDCl$_3$), δ: 5.65, −4.42, 18.03, 25.82, 58.0, 58.5, 66.3, 67.6, 67.7, 67.8, 67.9, 68.8, 69.0, 69.8, 70.4, 71.1, 71.4, 71.5, 72.0, 73.1, 73.2, 73.4, 73.5, 73.6, 74.2, 74.5, 74.6, 74.7, 74.8, 75.0, 75.7, 76.1, 77.2, 77.4, 78.6, 79.3, 79.5, 79.7, 80.9, 92.8, 100.0, 100.8, 101.2, 101.4, 127.0, 127.3, 127.4, 127.45, 127.5, 127.6, 127.65, 127.7, 127.76, 127.8, 127.86, 127.9, 128.1, 128.15, 128.2, 128.24, 128.3, 128.4, 128.46, 128.5, 128.6, 128.8, 128.9, 132.3, 132.34, 137.6, 137.7, 137.8, 137.86, 137.94, 138.0, 138.2, 138.45, 138.5, 139.0, 140.7, 141.2.

HRMS: Calcd. for $C_{125}H_{142}N_2O_{28}S_2SiNa$ [M+Na]$^+$ 2233.8858, Found: 2233.8859

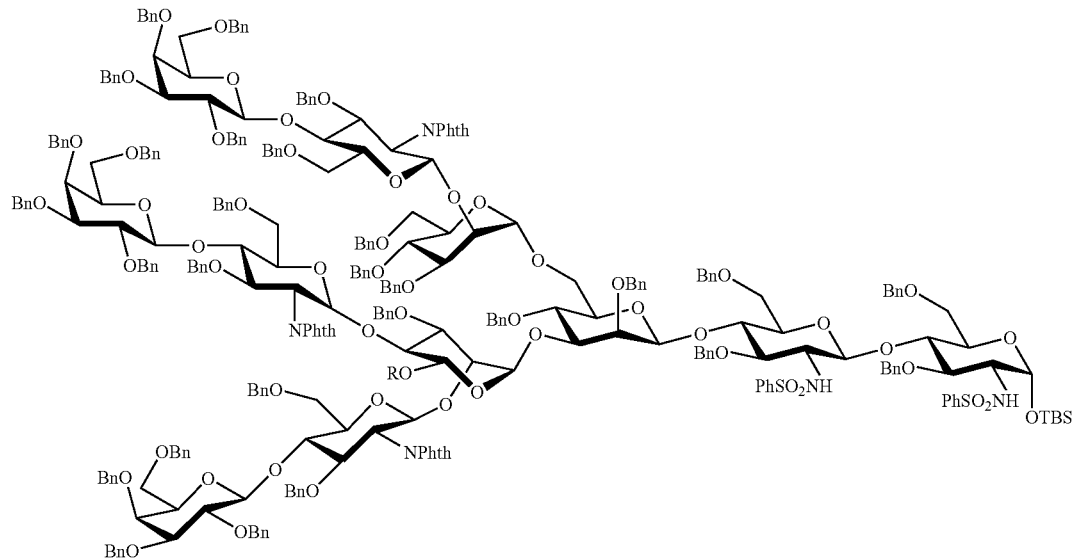

Undecasaccharide 46. Solutions of lactosamine donor 34 (528 mg, 0.500 mmol) and pentasaccharide triol 31 (100 mg, 0.045 mmol) in dry acetonitrile (3.0 mL and 3.0 mL) were stirred with 3 Å molecular sieves for 1 h at room temperature. The solution of donor 34 was cooled to 10° C. and treated with solid promoter (BrC$_6$H$_4$)NSbCl$_6$ (255 mg, 0.41 mmol) followed by dropwise addition of the acceptor solution. The reaction mixture was stirred at this temperature for 40 min and another potion of promoter (84 mg, 0.14 mmol) was added. The reaction mixture was allowed to warm to room temperature and stirred for 20 h (the reaction was monitored by ESI-MS analysis) in absence of light and then quenched by the addition of triethylamine, filtered through a pad of Celite, and concentrated. ESI-MS of the crude reaction mixture showed the presence of the product undecasaccharide and intermediate nonasaccharides; no starting acceptor or monoglycosylated compounds were found. The reaction mixture was subjected to column chromatography on silica gel (eluent: ethyl acetate/hexanes 1/4 to 1/2) and fractions containing glycosylated materials were combined and concentrated. The resulting mixture was further purified by preparative TLC (eluent: ethyl acetate/toluene 1/5) to give the mixture of nonasaccharides (45 mg) and desired undecasaccharide 46 (95 mg, 41%) yield. $[\alpha]_D$=+5.5° (c 1.0, CHCl$_3$); $^1$H-NMR (400 MHz, CDCl$_3$, selected signals), δ: 0.13 (s, 3H), 0.17 (s, 3H), 1.01 (s, 9H), 2.73 (br. d, J=9.6 Hz, 1H), 2.96 (dd, J=5.0, 10.0 Hz, 1H), 3.03 (d, J=11.0 Hz, 1H), 4.02 (d, J=9.0 Hz, 1H), 5.18 (d, J=2.7 Hz, 1H), 5.25 (d, J=7.5 Hz, 1H), 5.45 (d, J=7.8 Hz, 1H), 6.70-6.78 (m, 2H), 7.79 (d, J=8.2 Hz, 1H), 7.85 (d, J=8.0 Hz, 1H); $^{13}$C-NMR (100 MHz, CDCl$_3$), δ: −5.7, −4.5, 18.0, 25.8, 55.6, 57.9, 58.3, 67.8, 68.0, 68.1, 68.2, 69.9, 71.7, 72.2, 72.4, 72.45, 52.5, 72.6, 72.8, 72.85, 73.0, 73.1, 73.3, 73.34, 73.6, 73.7, 73.9, 74.2, 74.3, 74.4, 74.5, 74.7, 74.9, 75.0, 75.7, 76.0, 76.4, 77.2, 77.8, 78.5, 79.3, 79.8, 79.85, 82.2, 82.4, 92.7, 96.1, 96.8, 97.9, 99.3, 100.7, 101.4, 102.5, 102.7, 102.8, 122.6, 122.9, 123.0, 125.3, 126.6, 126.9-128.6, 128.8, 129.0, 131.6, 131.8, 131.9, 132.3, 133.1, 133.2, 133.4, 137.4, 138.0, 138.1, 138.2, 138.3, 138.4-138.6, 138.7, 138.8, 138.9, 138.95, 139.0, 139.1, 140.7, 141.14, 166.9, 167.4, 167.8, 168.0, 168.2, 168.4.

ESI-MS: Calcd. for C$_{311}$H$_{319}$N$_5$O$_{61}$S$_2$SiNa$_2$ [M+2Na]$^{2+}$ 2618.6, Found: 2618.5

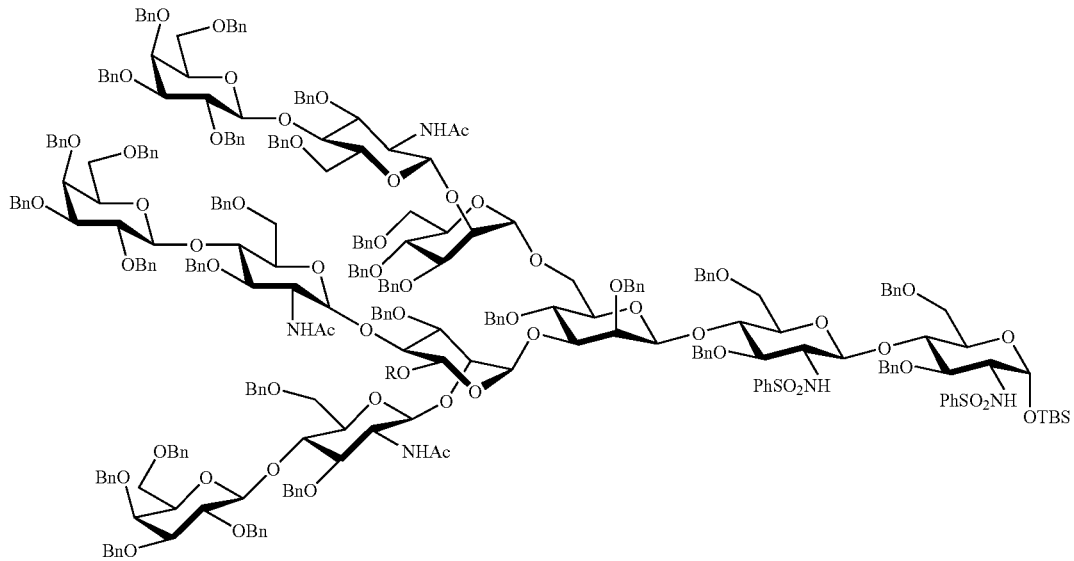

Tri-N-acetyl undecasaccharide 46a was obtained in 77% yield from 46 (34.0 mg, 0.0065 mmol) following phthalimide deprotection and acetylation as described for nonasaccharide 36. $[\alpha]_D$=+10.7° (c 1.3, CHCl$_3$); $^1$H-NMR (400 MHz, C$_6$D$_5$CD$_3$, selected signals), δ: 0.24 (s, 3H), 0.26 (s, 3H), 1.04 (s, 9H), 1.70 (s, 3H), 1.76 (s, 6H), 2.70-2.77 (m, 1H), 2.87-2.96 (m, 1H), 3.15 (q, J=8.1 Hz, 1H), 5.39 (br. s, 1H), 5.45 (d, J=7.0 Hz, 1H), 5.50 (d, J=8.0 Hz, 1H), 5.57 (br. s, 1H), 6.0 (br. d, J=8.9 Hz, 1H), 6.76-6.83 (m, 2H), 6.87-6.93 (m, 2H), 7.74 (br. d, J=7.7 Hz, 3H), 7.78 (d, J=7.8 Hz, 2H), 7.87 (d, J=7.6 Hz, 2H); $^{13}$C-NMR (100 MHz, C$_6$D$_5$CD$_3$), δ: −4.5, −3.7, 19.1, 24.2, 24.3, 26.8, 57.8, 58.9, 59.7, 59.8, 67.5, 67.7, 69.1-69.7, 70.4, 70.6, 71.2, 71.4, 72.3, 72.7, 73.1, 73.5, 73.6, 73.8, 73.9-74.7, 75.1-75.5, 75.6-76.3, 76.5, 76.6, 77.5, 77.8, 78.0, 78.1, 78.3, 78.5, 78.8, 78.9, 79.3, 80.8, 81.0, 81.1, 81.281.3, 81.4, 83.7, 83.8, 94.4, 99.2, 100.1, 100.4, 101.6, 102.2, , 102.4, 103.8, 104.1, 104.15, 125.2, 125.4-126.4, 127.5-130.4, 137.8, 137.9, 138.4, 139.5, 139.55, 139.6, 139.7 139.8, 139.9, 139.93, 140.0, 140.06, 140.1, 140.3, 140.4, 140.5, 141.08, 141.13, 141.5, 142.2, 142.6, 170.8, 171.3.

ESI-MS: Calcd. for C$_{293}$H$_{319}$N$_5$O$_{58}$S$_2$SiNa$_2$ [M+2Na]$^{2+}$ 2686.6, Found: 2686.7

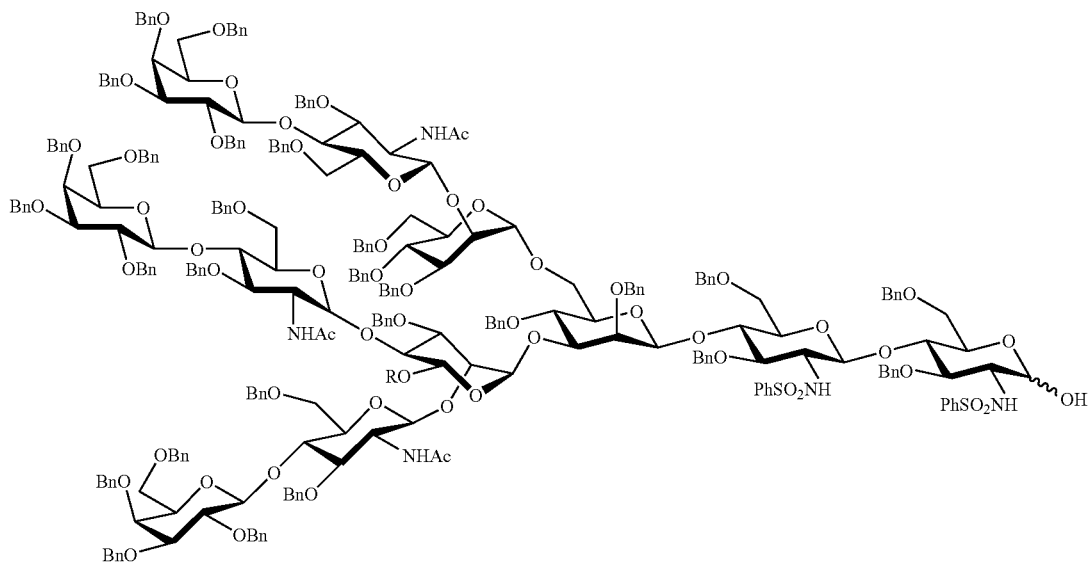

Reducing undecasaccharide 46b was obtained from -TBS protected 46a (27.0 mg, 0.0055 mmol) in 95% yield as described for nonasaccharide 37. $^1$H-NMR (400 MHz, C$_6$D$_5$CD$_3$, selected signals), δ: 1.73 (s, 6H), 1.77 (s, 3H), 2.84-3.06 (m, 2H), 3.13-3.24 (m, 1H), 5.40 (s, 1H), 5.45-5.53 (m, 2H), 6.77-6.83 (m, 2H), 6.87 (d, J=8.1 Hz, 1H), 7.69-7.75 (m, 2H), 7.80 (d, J=7.0 Hz, 2H), 7.86-7.93 (m, 2H). ESI-MS: Calcd. for C$_{287}$H$_{305}$N$_5$O$_{58}$S$_2$Na$_2$ [M+2Na]$^{2+}$ 2429.5, Found: 2429.6

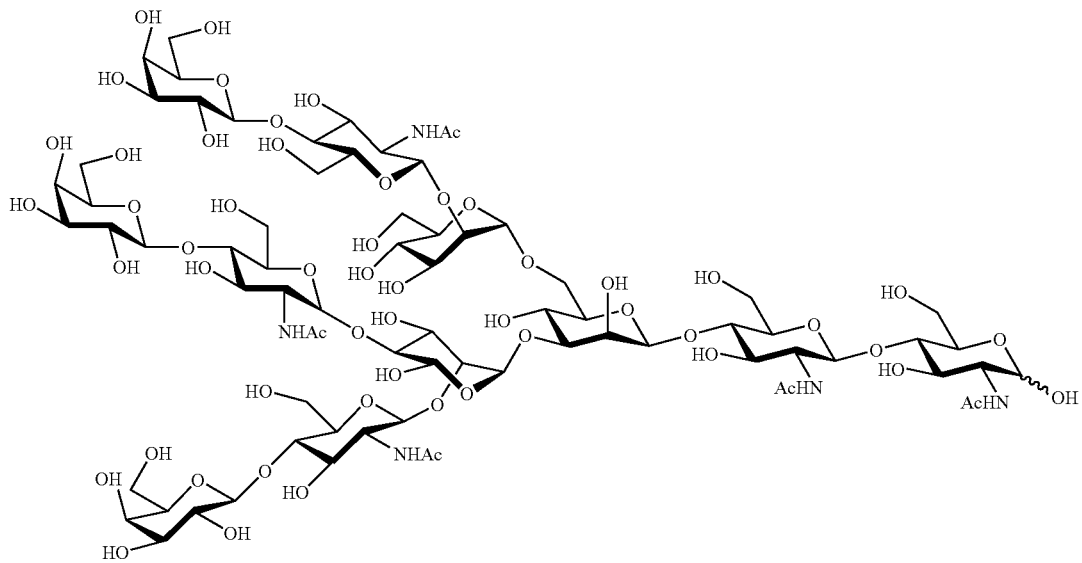

Deprotected undecasaccharide 46c. Liquid NH₃ (15 mL) was condensed at −78° C. into a 2-neck flask (25 mL) equipped with stirbar and Dewar-type condenser. Solid sodium (24 mg, 1.5 mmol) was added, and the resulting deep blue solution was stirred for 10 min. A solution of undecasaccharide 46b (23 mg, 0.0048 mol) in THF (1.0 mL) was added, and the reaction was stirred for an additional 120 min at −78° C. Upon removing the cold finger, solid NH₄Cl (100 mg) was added and the suspension was vigorously stirred until the blue color disappeared. The reaction vessel was subsequently removed from its cooling bath, warmed to 25° C., and the resulting white solid was dried for 3 h. This residue was suspended in sat. aq. NaHCO₃ (4.0 mL), the mixture was cooled in an ice bath and treated with Ac₂O (0.2 ml). The reaction mixture was warmed to room temperature and stirred for 2 h. The whole solution was then purified using a Bio-Rad P-2 gel filtration column to afford the desired deprotected saccharide 46c as a mixture of α/β-anomers (8.9 mg, 94%). ¹H-NMR (400 MHz, D₂O), δ; 1.93-2.03 (m, 15H), 3.38-4.05 (m, 65H), 4.14 (br. s, 2H), 4.39 (br. d, J=7.5 Hz, 3H), 4.45-4.56 (m, 4H), 4.85 (s, 1H), 4.97 and 5.11 (d, J=9.4 Hz and s, 1H), 5.04 (s, 1H).

ESI-MS: Calcd. for $C_{76}H_{127}N_5O_{56}N_2Na$ $[M+2Na]^{2+}$ 1025.9, Found: 1026.0

Calcd. for $C_{76}H_{127}N_5O_{56}N_2Na_2[M+Na]^+$ 2028.7, Found: 2028.8

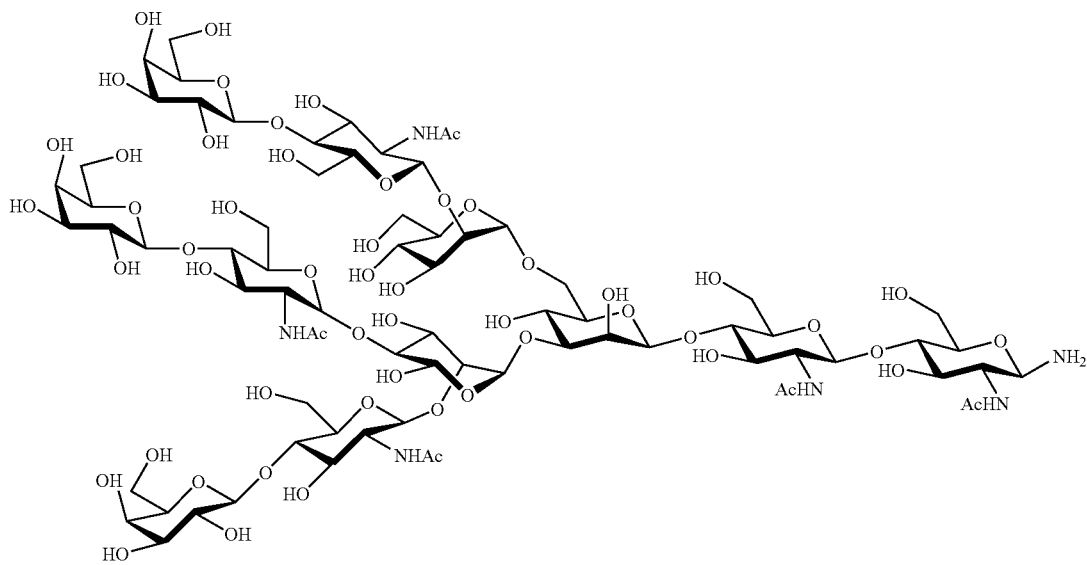

Glycosylamine 46d was prepared from reducing saccharide 46c (8.9 mg, 0.0044 mmol) by Kochetkov amination (see 39) and used in the next step without further purification. ¹H-NMR (400 MHz, D₂O), δ: 1.93-2.05 (m, 15H), 3.34-4.08 (m, 66H), 4.14 (br. s, 2H), 4.39 (br. d, J=7.2 Hz, 3H), 4.45-4.55 (m, 4H), 4.85 (s, 1H), 5.04 (s, 1H).

ESI-MS: Calcd. for $C_{76}H_{128}N_6O_{55}N_2Na$ $[M+2Na]^{2+}$ 1025.4, Found: 1025.5

Calcd. for $C_{76}H_{128}N_6O_{55}N_2Na_2[M+Na]^+$ 2027.7, Found: 2027.8 fication by HPLC and lyophilization. NMR spectra were not recorded due to a lack of solubility in any appropriate solvent besides DMSO, which would require repurification and associated loss of material.

(SEQ ID NO: 2)

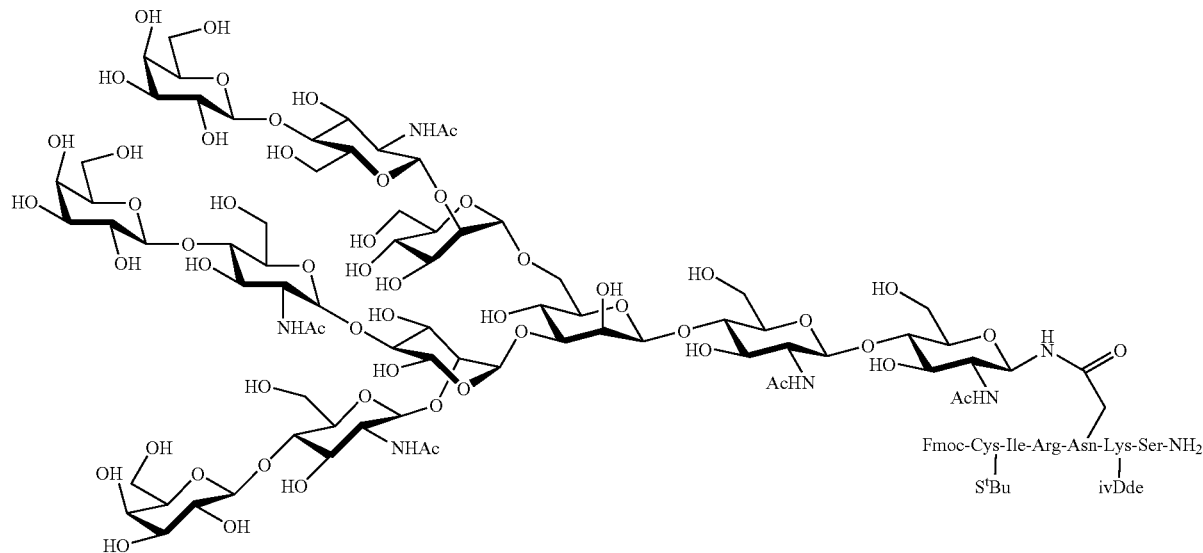

Glycopeptide 46e. Glycosylamine 46d was aspartylated with hexapeptide 40 following the protocol described for the preparation of 41 to provide 46e in 25% yield (from the reducing saccharide 46c (8.9 mg, 0.0044 mmol)) after purification by HPLC and lyophilization.

ESI-MS: Calcd. for $C_{136}H_{217}N_{17}O_{67}S_2$ $[M+2H]^{2+}$ 1312.2, Found: 1312.3

Calcd. for $C_{136}H_{218}N_{17}O_{67}S_2$ $[M+3H]^{3+}$ 1075.1, Found: 1075.1

(SEQ ID NO: 2)

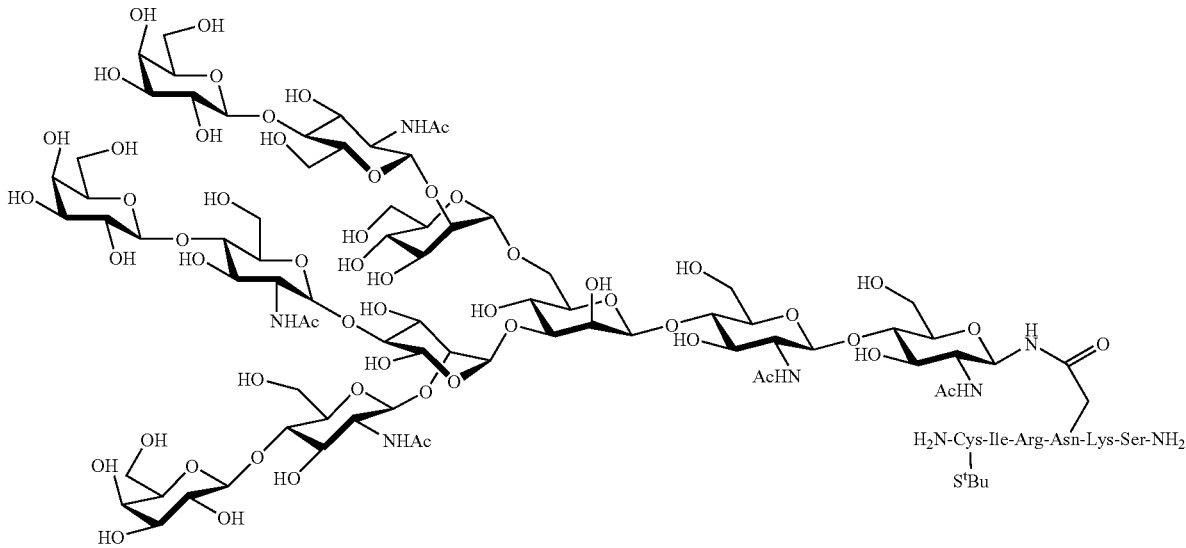

Deprotected glycopeptide 47. Fmoc and ivDde protections were removed from amino groups in 46e (3.5 mg, 0.0011 mmol) by treatment with hydrazine/piperidine in DMF (see 42) to give 47 in 66% yield (2.0 mg, 0.00072 mmol). $^1$H-NMR (400 MHz, D$_2$O, selected signals), δ: 0.76-0.78 (m, 6H), 1.05-1.16 (m, 1H), 1.26 (s, 9H), 1.92-2.03 (m, 15H), 2.68 (dd, J=6.3, 16.1 Hz, 1H), 2.80 (dd, J=6.4, 16.1 Hz, 1H), 2.93 (t, J=7.6 Hz, 2H), 3.06-3.25 (m, 5H), 4.04 (br. s, 1H), 4.12-4.16 (m, 2H), 4.19-4.29 (m, 5H), 4.35 (t, J=6.0 Hz, 1H), 4.40 (br. d, J=7.2 Hz, 3H), 4.45-4.55 (m, 4H), 4.85 (s, 1H), 4.95 (d, J=9.8 Hz, 1H), 5.05 (s, 1H).

HSI-MS: Calcd. for $C_{108}H_{189}N_{17}O_{63}S_2[M+2H]^{2+}$ 1398.1, Found: 1398.3

Tetra-O-benzoate 45b. Tetrasaccharide acceptor 45 (259 mg, 0.13 mmol) was coupled with thiomannoside 48 (264 mg, 0.40 mmol) as described for the preparation of 4a. Preparative TLC of the product mixture (eluent: ethyl acetate/toluene 1/10; in mixtures of ethyl acetate/hexanes the product and starting acceptor have identical R$_f$ values) afforded the desired pentasaccharide 45b (244 mg, 74%). [α]$_D$=−8.6° (c 1.22, CHCl$_3$); $^1$H-NMR (400 MHz, CDCl$_3$), δ: −0.01 (s, 3H), 0.04 (s, 3H), 0.85 (s, 9H), 2.95-3.01 (m, 2H), 3.10 (br. d, J=10.3 Hz, 1H), 3.17-3.33 (m, 6H), 3.35-3.44 (m, 2H), 3.46-3.62 (m, 5H), 3.68-3.83 (m, 5H), 3.88-3.99 (m, 5H), 4.11 (dd, J=3.0, 9.6 Hz, 1H), 4.14-4.25 (m, 5H), 4.28 (d, J=10.0 Hz, 1H), 4.31-4.53 (m, 12H), 4.56 (d, J=12.0 Hz, 1H), 4.59-4.65

(SEQ ID NO: 1)

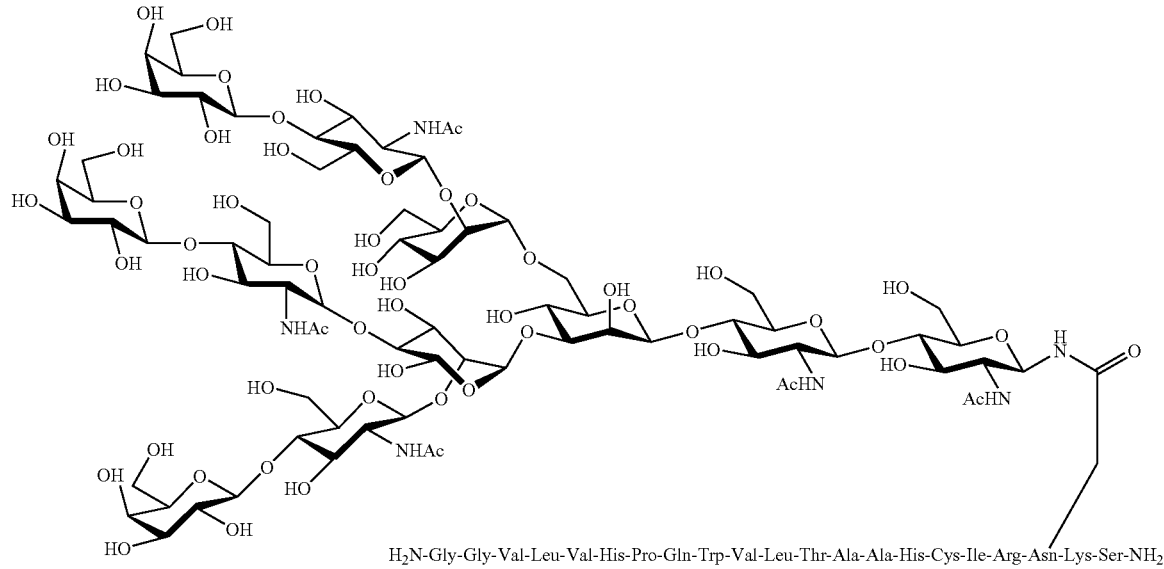

Glycopeptide 2 was produced by ligation of 47 and 43 in 38% yield (3.2 mg isolated) as described for the preparation of 1. $^1$H-NMR (400 MHz, D$_2$O, selected signals), δ: 1.19 (d, J=6.6 Hz, 3H), 1.32 (d, J=7.1 Hz, 3H), 1.35 (d, J=7.1 Hz, 3H), 2.88 (d, J=7.0 Hz, 2H), 4.45 (br. d, J=7.4 Hz, 3H), 4.50 (t, J=6.5 Hz, 1H), 4.53-4.61 (m, 4H), 5.01 (d, J=10.0 Hz, 1H), 5.11 (br. s, 1H), 7.10 (t, J=7.4 Hz, 1H), 7.16-7.22 (m, 2H), 7.23 (s, 1H), 7.28 (s, 1H), 7.42 (d, J=8.2 Hz, 1H), 7.58 (d, J=8.0 Hz, 1H), 8.52 (br. s, 1H), 8.59 (br. s, 1H).

ESI-MS: Calcd. for $C_{178}H_{293}N_{38}O_{80}S$ [M+3H]$^{3+}$ 1425.0, Found: 1424.9

Calcd. for $C_{178}H_{294}N_{38}O_{80}S$ [M+4H]$^{4+}$ 1069.0, Found: 1069.1

Figure 7:
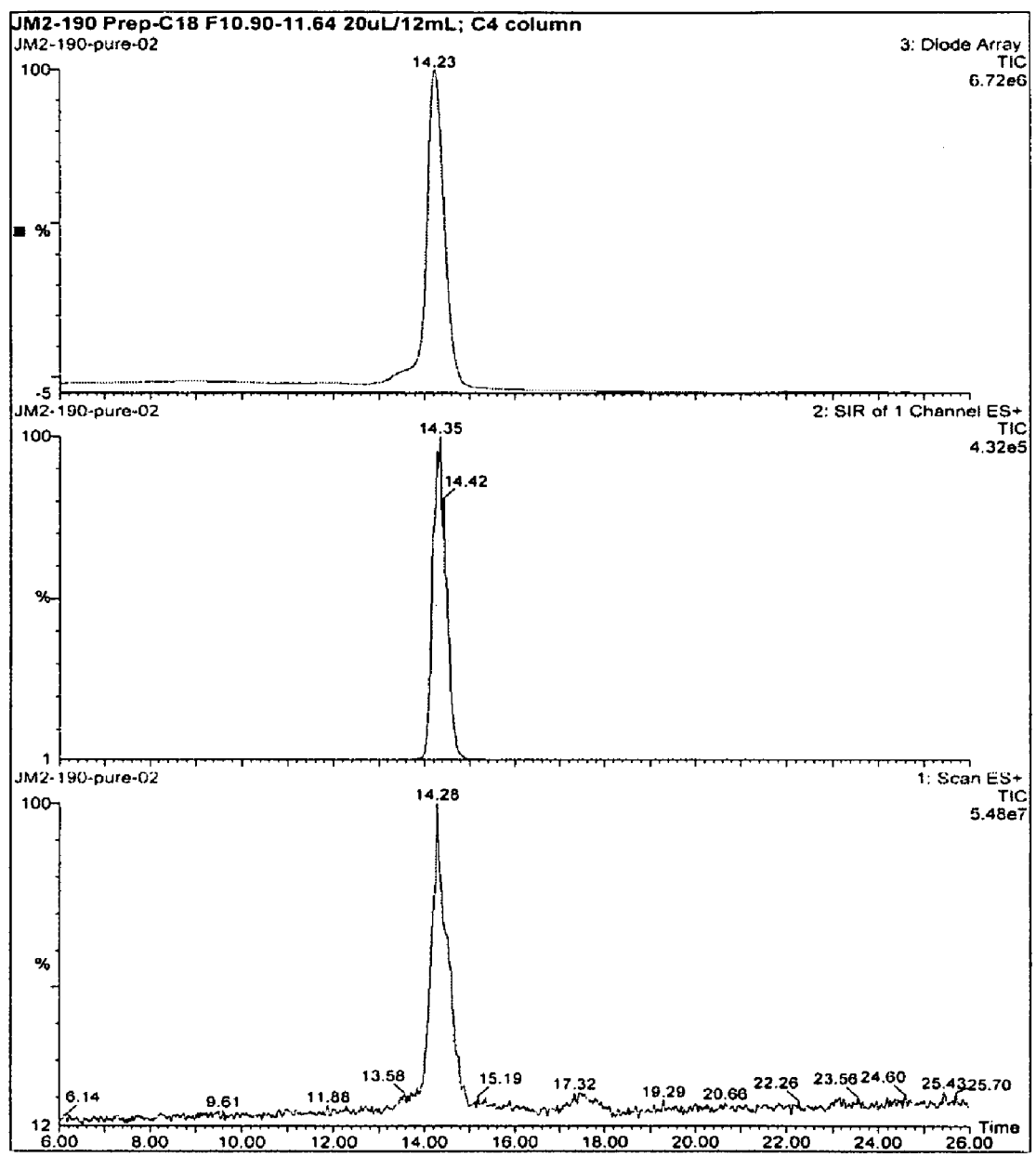
FIG. 7 depicts LCMS traces for construct 2.

LCMS traces for compound 2 are shown in FIG. 7.

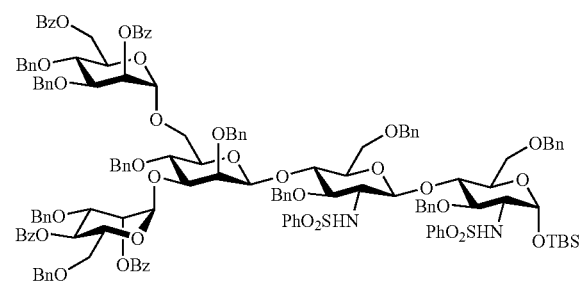

(m, 3H), 4.69 (d, J=11.4 Hz, 1H), 4.73 (d, J=11.2 Hz, 1H), 4.77-4.86 (m, 3H), 5.04-5.09 (m, 2H), 5.20 (d, J=1.2 Hz, 1H), 5.56 (br. t, J=2.2 Hz, 1H), 5.66-5.68 (m, 1H), 5.69 (t, J=10.0 Hz, 1H), 6.86-6.95 (m, 4H), 6.97-7.44 (m, 60H), 7.48-7.56 (m, 5H), 7.61 (br. d, J=8.0 Hz, 2H), 7.70 (br. d, J=8.0 Hz, 2H), 7.83 (br. d, J=8.0 Hz, 2H), 7.91-7.98 (m, 4H), 8.04 (br. d, J=8.3 Hz, 2H). $^{13}$C-NMR (100 MHz, CDCl$_3$), δ: −5.69, −4.51, 17.96, 25.76, 57.9, 58.8, 63.1, 66.3, 67.7, 68.3, 68.5, 68.7, 69.5, 69.7, 70.0, 70.9, 71.1, 71.2, 72.9, 73.2, 73.5, 73.6, 73.9, 74.3, 74.5, 74.7, 75.1, 75.9, 76.9, 77.2, 77.6, 78.4, 78.5, 79.1, 82.8, 92.8, 98.0, 100.0, 100.8, 101.9, 126.6, 126.9, 126.96, 127.0, 127.1, 127.2, 127.3, 127.4, 127.5, 127.6, 127.64, 127.7, 127.85, 127.9, 128.0, 128.1, 128.2, 128.25, 128.3, 128.34, 128.36, 128.4, 128.5, 128.6, 128.7, 129.0, 129.4, 129.55, 129.6, 129.64, 129.76, 129.82, 129.9, 130.0, 130.1, 132.1, 132.3, 132.9, 133.0, 133.1, 133.2, 137.4, 137.5, 137.6, 137.7, 137.74, 137.8, 137.9, 138.0, 138.3, 138.4, 139.1, 140.6, 141.1, 165.1, 165.4, 165.5, 166.0.

ESI-MS: Calcd. for $C_{146}H_{152}N_2O_{32}S_2SiNa$ [M+Na]$^+$ 2559.9, Found: 2559.8

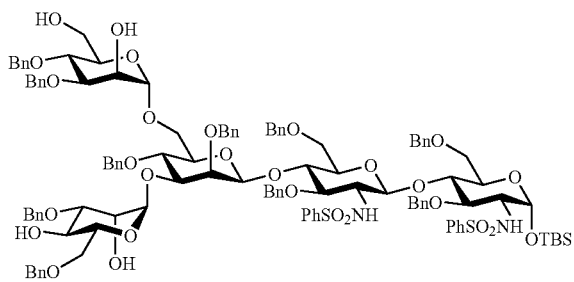

Pentasaccharide tetraol 32. Pentasaccharide 45b (244 mg. 0.096 mmol) was dissolved in dry methanol (20.0 mL) and treated with sodium methoxide (25 wt.% in methanol, 0.5 mL). The reaction mixture was stirred overnight at room temperature, quenched with ammonium chloride and concentrated. The dry residue was suspended in ethyl acetate, filtered, and concentrated. Purification by preparative TLC (eluent: ethyl acetate/hexanes 1/2) gave the desired tetraol 32 (187 mg, 92%). [α]$_D$=+3.7° (c 1.87, CHCl$_3$); $^1$H-NMR (400 MHz, CDCl$_3$), δ: 0.08 (s, 3H), 0.13 (s, 3H), 0.95 (s, 9H), 2.52 (s, 4H), 3.15 (br. d, J=10.4 Hz, 1H), 3.20-3.32 (m, 4H), 3.34-3.42 (m, 3H), 3.46-3.51 (m, 2H), 3.52-3.98 (m, 20H), 4.16 (d, J=7.6 Hz, 1H), 4.25-4.39 (m, 5H), 4.41-4.69 (m, 12H), 4.74 (d, J=12.0 Hz, 1H), 4.79 (d, J=12.0 Hz, 1H), 4.84-4.98 (m, 4H), 5.14 (d, J=2.6 Hz, 1H), 5.18 (br. s, 1H), 7.12-7.49 (m, 56H), 7.74 (br. d, J=8.2 Hz, 2H), 7.79 (br. d, J=8.0 Hz, 2H), 8.07 (d, J=7.8 Hz, 1H); $^{13}$C-NMR (100 MHz, CDCl$_3$), δ: −5.7, −4.5, 18.0, 25.7, 58.0, 58.4, 61.8, 66.1, 67.6, 67.7, 68.0, 68.7, 69.8, 70.3, 71.2, 71.6, 71.9, 72.0, 73.0, 73.3, 73.5, 73.6, 74.0, 74.4, 74.5, 74.7, 74.9, 75.0, 75.6, 76.0, 77.2, 78.5, 79.2, 79.8, 80.8, 92.8, 99.7, 100.7, 101.1, 101.4, 126.9, 127.0, 127.1, 127.2, 127.4, 127.5, 127.6, 127.7, 127.73, 127.8, 127.82, 127.86, 127.9, 128.0, 128.1, 128.2, 128.24, 128.3, 128.36, 128.4, 128.5, 128.7, 128.8, 128.84, 128.9, 129.5, 132.2, 132.3, 132.8, 137.5, 137.6, 137.7, 137.8, 137.9, 138.4, 138.43, 138.9, 140.6, 141.1.

HRMS: Calcd. for C$_{118}$H$_{136}$N$_2$O$_{28}$S$_2$SiNa [M+Na]$^+$ 2143.8388, Found: 2143.8383

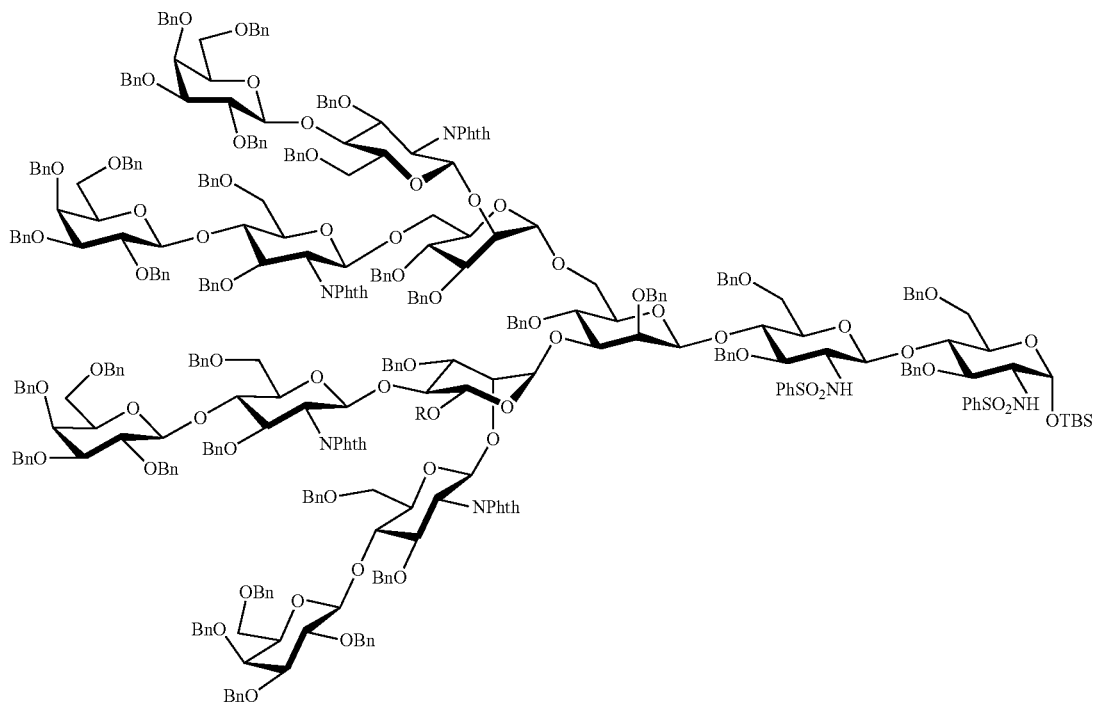

Tridecasaccharide 49. Tetraol acceptor 32 (93 mg, 0.044 mmol) was coupled with lactosamine donor 34 (480 mg, 0.455 mmol) using (BrC$_6$H$_4$)NSbCl$_6$ (308 mg, 0.5 mmol) as described in the preparation of undecamer 46 to give a mixture of intermediate undecamers and the desired tridecasaccharide 49 (51 mg, 19%). $[\alpha]_D$=+0.6° (c 1.01, CHCl$_3$); $^1$H-NMR (400 MHz, CDCl$_3$, selected signals), δ: 0.02 (s, 3H), 0.06 (s, 3H), 0.90 (s, 9H), 2.49-2.64 (m, 1H), 2.67-2.75 (m, 1H), 2.78-2.87 (m, 1H), 5.01-5.04 (m, 1H), 5.08 (br. s, 1H), 5.35 (br. d, J=6.3 Hz, 1H), 6.63-6.71 (m, 2H), 7.68 (d, J=7.8 Hz, 2H), 7.77 (d, J=7.4 Hz, 2H); $^{13}$C-NMR (100, CDCl$_3$), δ: −5.7, −4.5, 18.0, 25.8, 55.6, 58.0, 67.6, 67.7, 68.1-68.3, 70.1, 72.2, 72.3, 72.7-73.0, 73.2-73.4, 73.7, 73.8, 74.0, 74.2, 74.3-74.5, 74.7, 74.9, 75.0, 75.2, 76.0, 76.2, 77.2, 77.7, 78.0, 78.8, 79.8, 79.7, 80.0, 82.2, 82.3, 82.4, 82.5, 92.7, 99.2, 100.8-101.3, 102.4-103.1, 122.5-123.6, 126.4-129.2, 131.4-131.9, 132.4, 132.9-133.7, 137.6, 137.8-139.2, 140.8, 140.85, 166.0-168.4.

ESI-MS: Calcd. for C$_{366}$H$_{372}$N$_6$O$_{72}$S$_2$SiNa$_2$ [M+2Na]$^{2+}$ 3070.2, Found: 3070.3

Calcd. for C$_{366}$H$_{372}$N$_6$O$_{72}$S$_2$SiNa$_3$ [M+3Na]$^{3+}$ 2054.5, Found: 2054.7

Tetra-N-acetyl tridecasaccharide 49a was obtained in 79% yield from 49 (85.0 mg, 0.0139 mmol) following phthalimide deprotection and acetylation as described for nonasaccharide 36. $^1$H-NMR (400 MHz, CDCl$_3$, selected signals), δ: 0.04 (s, 3H), 0.06 (s, 3H), 0.90 (s, 9H), 1.60 (s, 3H), 1.62 (s, 3H), 1.87 (s, 3H), 1.90 (s, 3H), 2.90-3.00 (m, 2H), 3.10 (d, J=8.8 Hz, 2H), 4.07 (d, J=12.0 Hz, 1H), 5.08 (d, J=1.8 Hz, 1H), 5.12-5.17 (m, 1H), 6.87-6.94 (m, 2H), 7.63 (d, J=7.6 Hz, 2H), 7.73 (d, J=7.8 Hz, 2H); $^{13}$C-NMR (100 MHz, CDCl$_3$), δ: −5.6, −4.4, 18.0, 25.8, 26.8, 27.2, 27.3, 67.9-68.3, 72.6, 72.7-73.0, 73.4, 73.5, 73.6, 74.0, 74.5-74.8, 75.0-75.3, 77.7, 77.8, 79.8, 79.9, 82.3, 82.34, 92.8, 100.6-100.8, 101.2-101.6, 102.7-103.0, 126.1, 126.7-129.0, 129.6, 130.5, 130.9, 132.3, 132.4, 137.9-139.3, 139.8, 140.5, 141.3, 141.4, 170.0-171.0.

ESI-MS: Calcd. for C$_{342}$H$_{372}$N$_6$O$_{68}$S$_2$SiNa$_2$ [M+2Na]$^{2+}$ 2894.3, Found: 2894.5

Calcd. for C$_{342}$H$_{372}$N$_6$O$_{68}$S$_2$SiNa$_3$ [M+3Na]$^{3+}$ 1937.2, Found: 1937.1

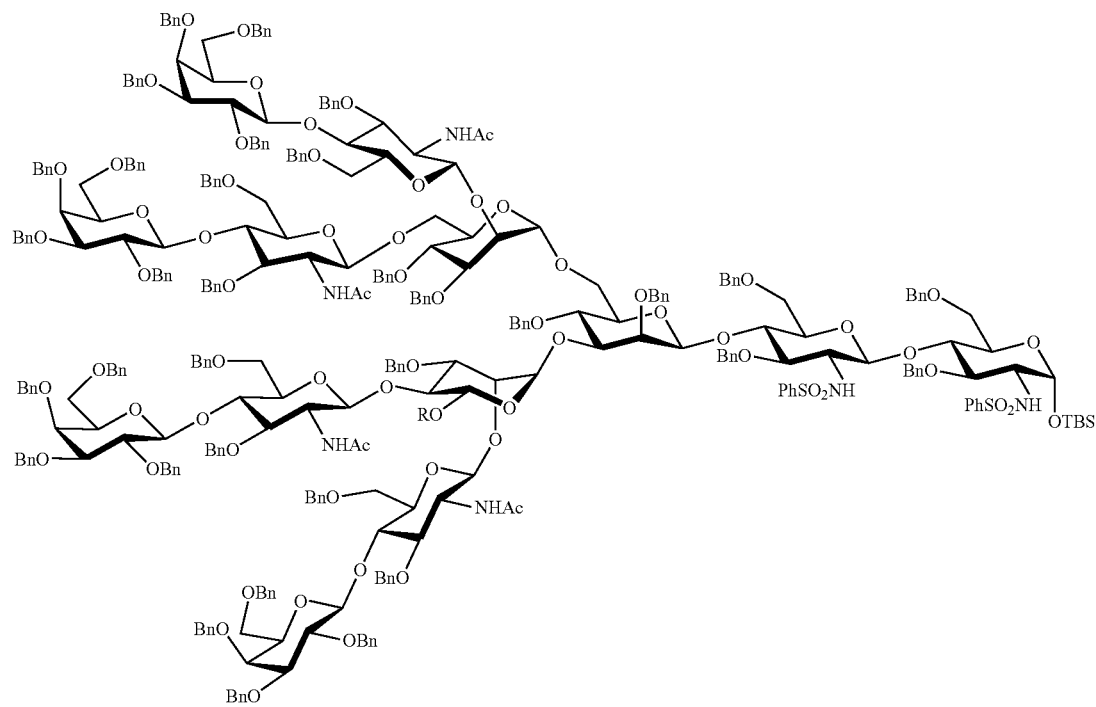

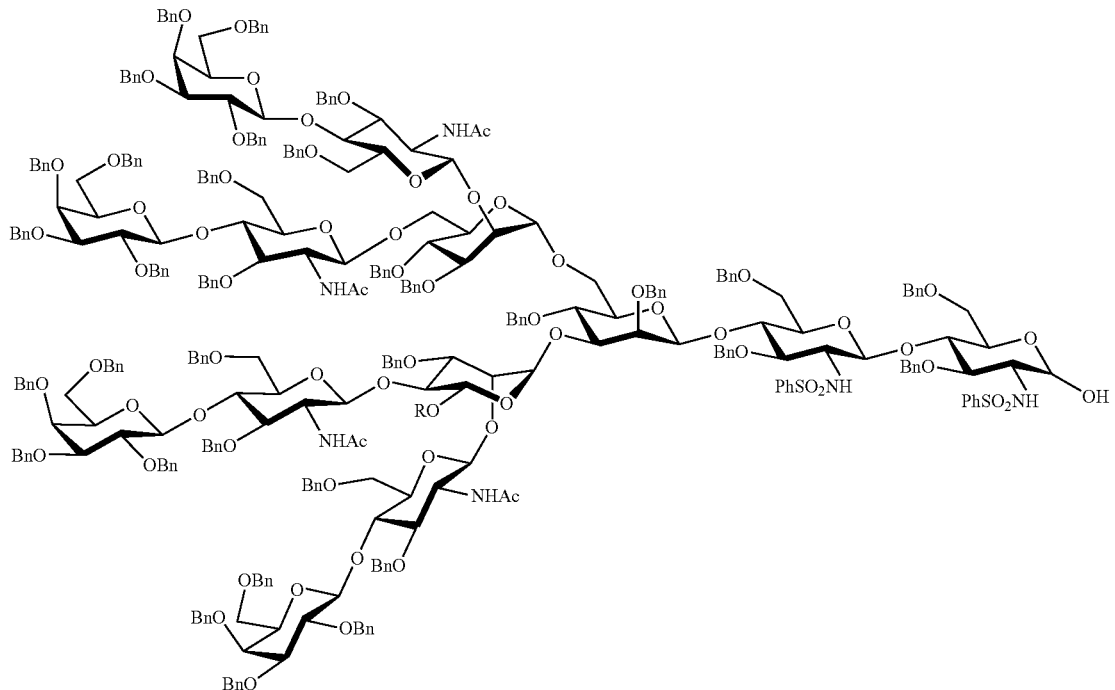
Reducing tridecasaccharide 49b was obtained from -TBS protected 49a (63.0 mg, 0.0109 mmol) in 97% yield as described for nonasaccharide 37. $^1$H-NMR (400 MHz, CDCl$_3$, selected signals), δ: 1.59 (s, 3H), 1.63 (s, 3H), 1.86 (s, 3H), 1.89 (s, 3H), 2.84-2.91 (m, 1H), 2.91-3.02 (m, 3H), 5.01-5.06 (m, 1H), 5.10-5.18 (m, 1H), 6.88-6.95 (m, 2H), 7.66 (d, J=7.7 Hz, 2H), 7.73 (d, J=7.8 Hz, 2H).
ESI-MS: Calcd. for $C_{336}H_{358}N_6O_{68}S_2Na_2$ $[M+2Na]^{2+}$ 2837.2, Found: 2837.4
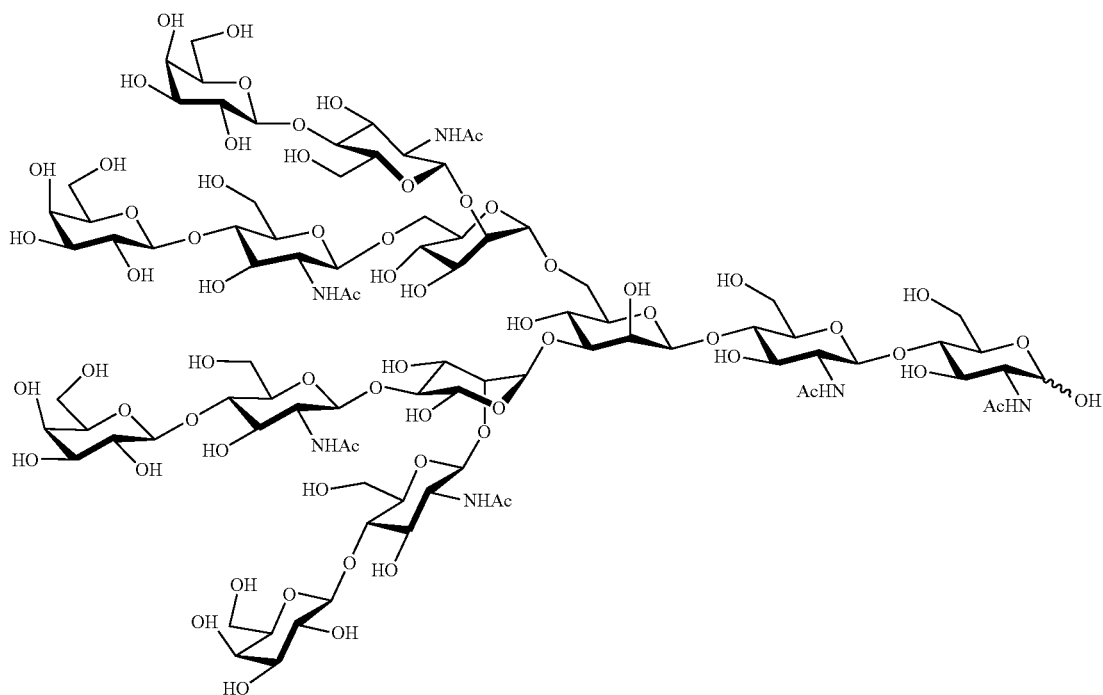

Deprotected tridecasaccharide 49c. Reduction of 49b (32.0 mg, 0.0057 mmol) with sodium in liquid ammonia and acetylation (see 46c) afforded tridecasaccharide 49c in 81% yield (10.9 mg, 0.0046 mmol). $^1$H-NMR (400 MHz, D$_2$O, selected signals), δ: 1.93-2.05 (m, 18H), 3.23 (t, J=9.4 Hz, 1H), 4.02 (br. s, 1H), 4.09-4.16 (s, 3H), 4.36-4.43 (m, 4H), 4.45-4.56 (m, 5H), 4.79 (s, 1H), 5.05 (s, 1H), 5.11 (s, 1H).

ESI-MS: Calcd. for $C_{90}H_{150}N_6O_{66}Na_2$ [M+2Na]$^{2+}$ 1208.5, Found: 1208.5,

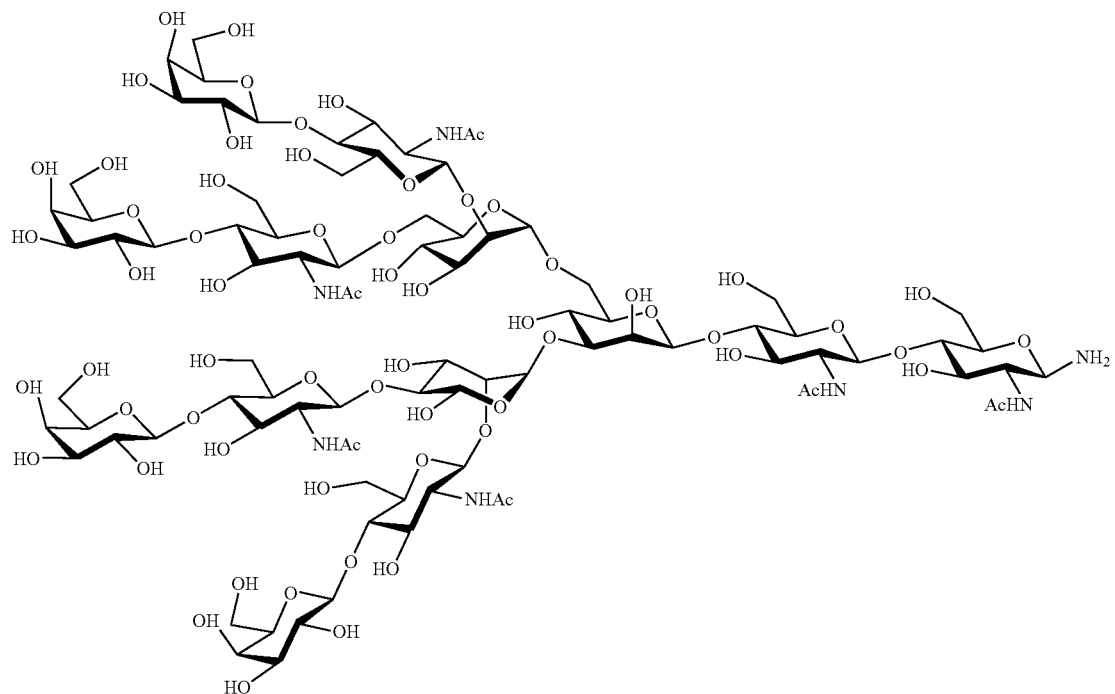

Glycosylamine 49d was prepared from reducing saccharide 49c (5.9 mg, 0.0025 mmol) by Kochetkov amination (see 39) and used in the next step without further purification.

ESI-MS: Calcd. for $C_{90}H_{151}N_7O_{65}Na_2$ [M+2Na$^{2+}$ 1208.0, Found: 1208.1

Calcd. for $C_{90}H_{151}N_7O_{65}Na$ [M+Na]$^+$ 2392.9, Found: 2393.0

(SEQ ID NO: 2)

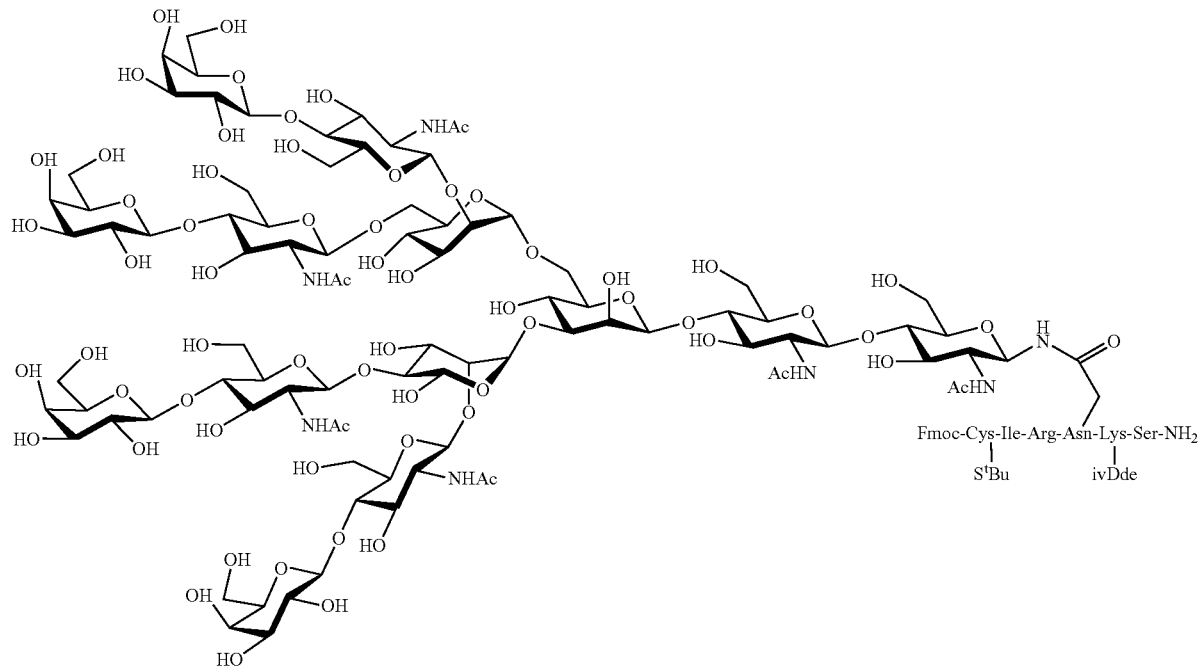

Glycopeptide 49e. Glycosylamine 49d was aspartylated with hexapeptide 40 following the protocol described for the preparation of 41 to provide 49e. This compound was used directly in the deprotection (see 50) after HPLC purification and partial concentration from DMF (DMF was added to avoid foaming of the solution). NMR spectra were not recorded due to a lack of solubility in any appropriate solvent besides DMSO, which would require repurification and associated loss of material.

ESI-MS: Calcd. for $C_{150}H_{241}N_{18}O_{77}S_2$ $[M+3H]^{3+}$ 1196.8, Found: 1196.8

(SEQ ID NO: 2)

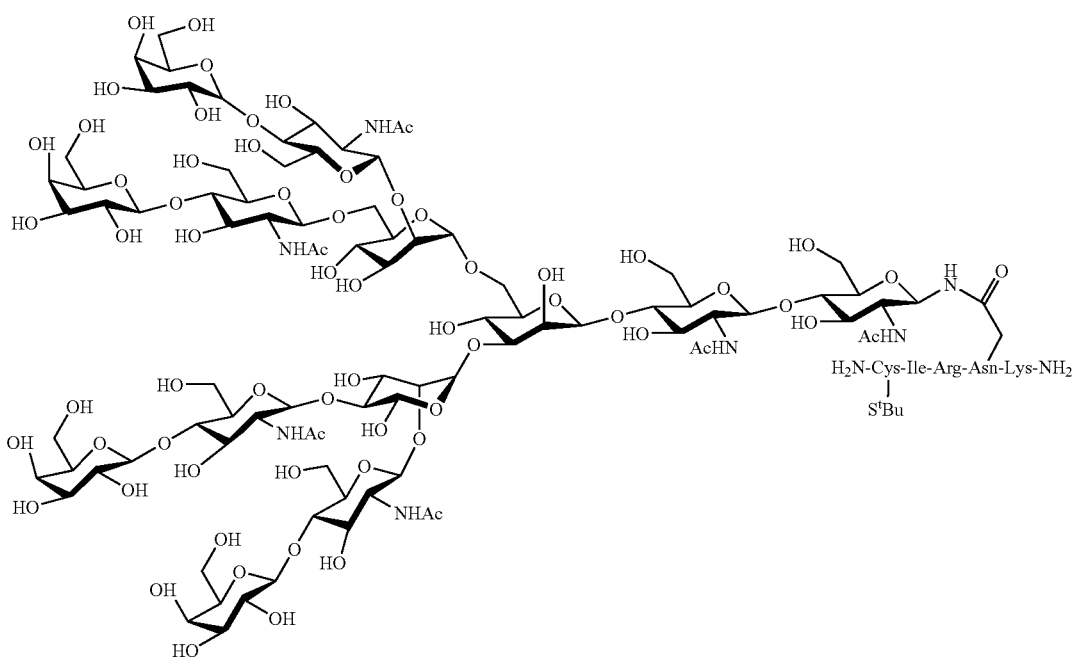

Deprotected glycopeptide 50. Fmoc and ivDde amine protecting groups were removed from 49e by treatment with hydrazine/piperidine in DMF (see 42) to give 50 in 52% yield (4.1 mg, 0.0013 mmol) for the three steps starting with the global deprotection/acetylation product (49c) (5.9 mg, 0.0025 mmol). $^1$H-NMR (400 MHz, D$_2$O, selected signals), δ: 0.78-0.87 (m, 6H), 1.05-1.16 (m, 1H), 1.26 (s, 9H), 1.93-2.03 (m, 18H), 2.91 (t, J=7.2 Hz, 2H), 3.33 (t, J=9.0 Hz, 1H), 4.01 (br. s, 1H), 4.10-4.16 (m, 3H), 4.17-4.29 (m, 5H), 4.34 (t, J=5.8 Hz, 1H), 4.37-4.43 (m, 4H), 4.45-4.55 (m, 5H), 4.64 (t, J=6.5 Hz, 1H), 4.79 (s, 1H), 4.95 (d, J=10.0 Hz, 1H), 5.06 (s, 1H).

ESI-MS: Calcd. for $C_{122}H_{212}N_{18}O_{73}S_2$ [M+2H]$^{2+}$ 1580.7, Found: 1580.8

Calcd. for $C_{122}H_{213}N_{18}O_{73}S_2$ [M+3H]$^{3+}$ 1054.1, Found: 1054.2

Example 3

Biological Studies

Figure 9:
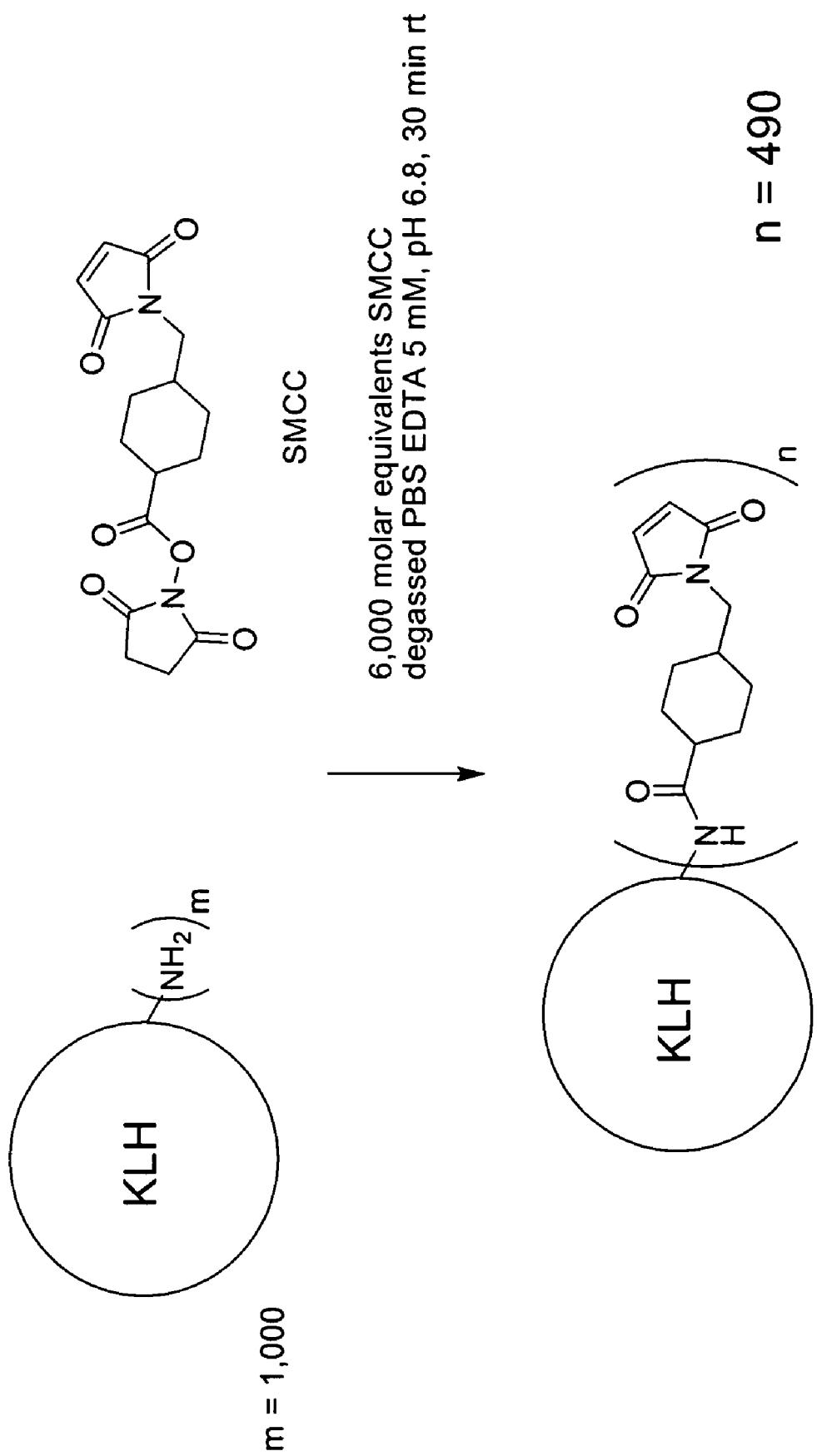
FIG. 9 depicts maleimide functionalization of KLH.
Figure 10:
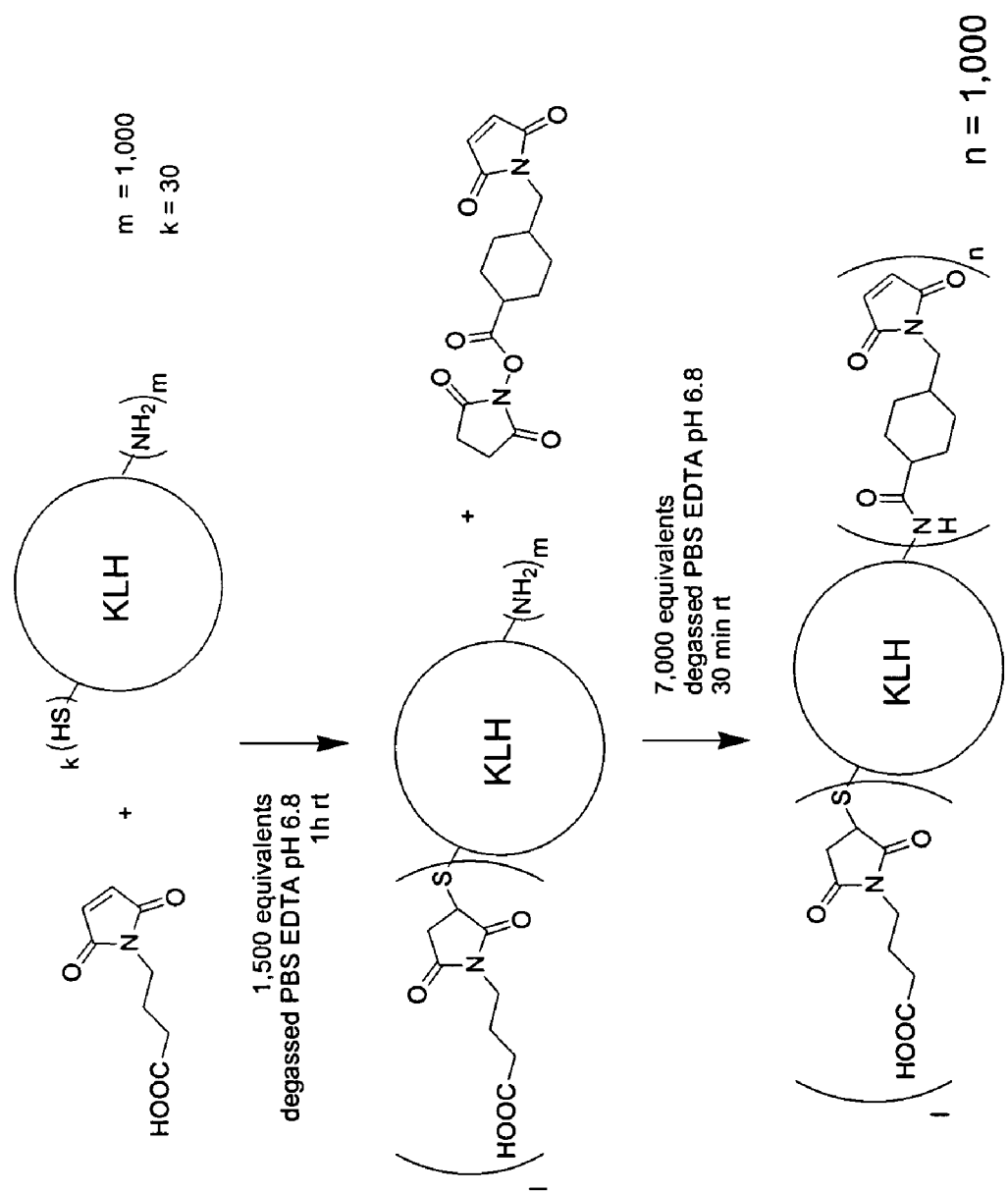
FIG. 10 depicts an exemplary KLH activation protocol.
Figure 11:
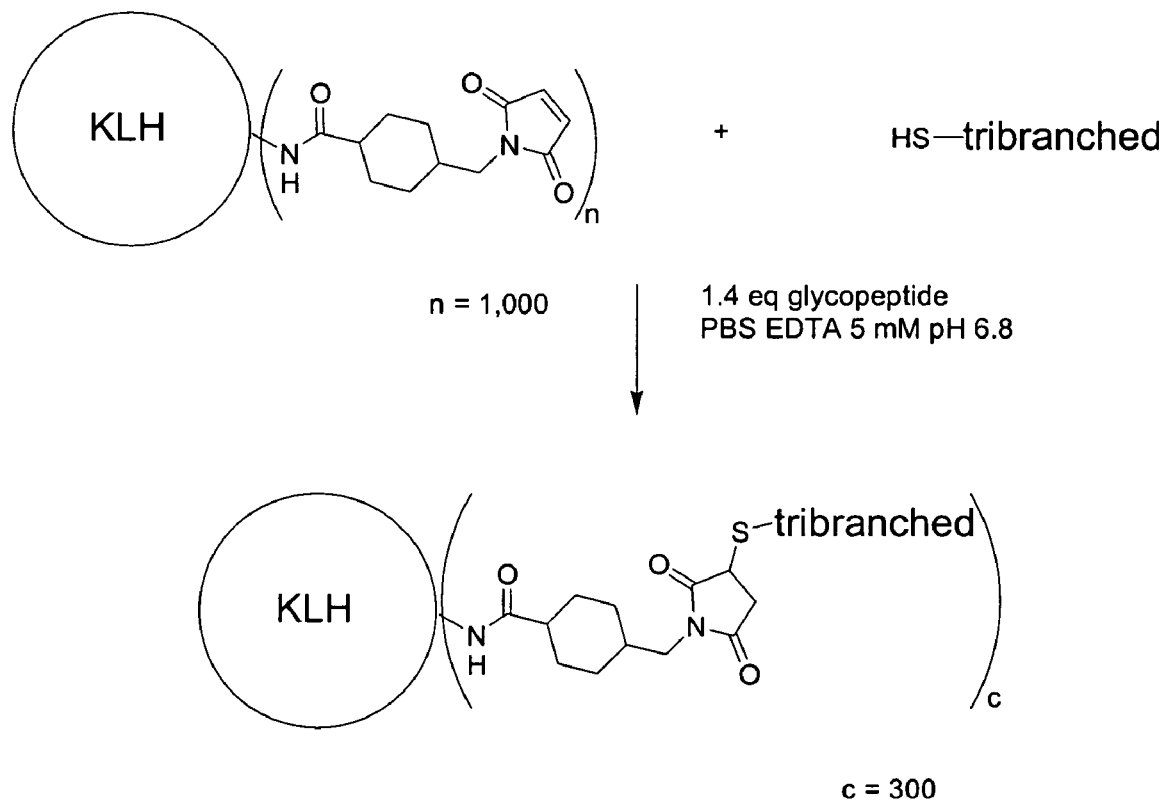
FIG. 11 depicts an exemplary conjugation of a tribranched glycopeptide to KLH.

Formation and identification of antibody against transformed PSA glycopeptide fragments. To evaluate the efficiency of the transformed PSA glycopeptide fragments in generation of specific antibody, glycopeptide 11+21 (2), was conjugated to KLH in 20% yield, and the resulting glycopeptide-KLH construct contained about 250 glycopeptides per KLH. An exemplary attachment scheme is outlined in FIGS. 9-11. Note that "tribranched-SH" denotes glycopeptide 11+21 (2), where the thiol group represents a cysteine thiol group from the peptide portion of the glycopeptide.

(SEQ ID NO: 1)

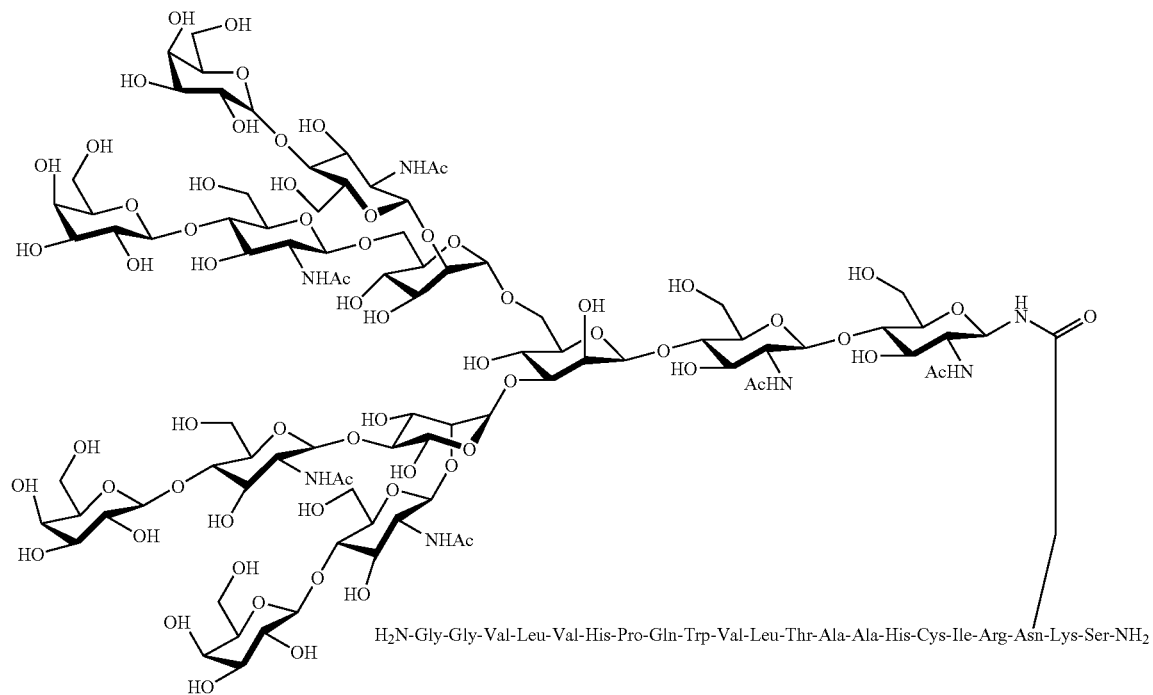

Tridecasaccharide—uneicosapeptide glycoconjugate 3 was produced in 65% yield (2.3 mg isolated) by ligation of 50 and 43 as described for the preparation of 1. $^1$H-NMR (400 MHz, D$_2$O, selected signals), δ: 1.16-1.22 (m, 2H), 1.28-1.42 (m, 6H), 2.96-3.05 (m, 2H), 4.11 (s, 1H), 4.45-4.52 (m, 4H), 4.53-4.64 (m, 5H), 5.02 (d, J=10.2 Hz, 1H), 5.14 (s, 1H), 7.04-7.12 (m, 1H), 7.15-7.33 (m, 4H), 7.38-7.46 (m, 1H), 7.51-7.60 (m, 1H), 8.47-8.65 (m, 2H).

ESI-MS: Calcd. for $C_{192}H_{316}N_{39}O_{90}S$ [M+3H]$^{3+}$ 1546.7, Found: 1546.9

Calcd. for $C_{192}H_{317}N_{39}O_{90}S$ [M+4H]$^{4+}$ 1160.3, Found: 1160.3

Figure 8:
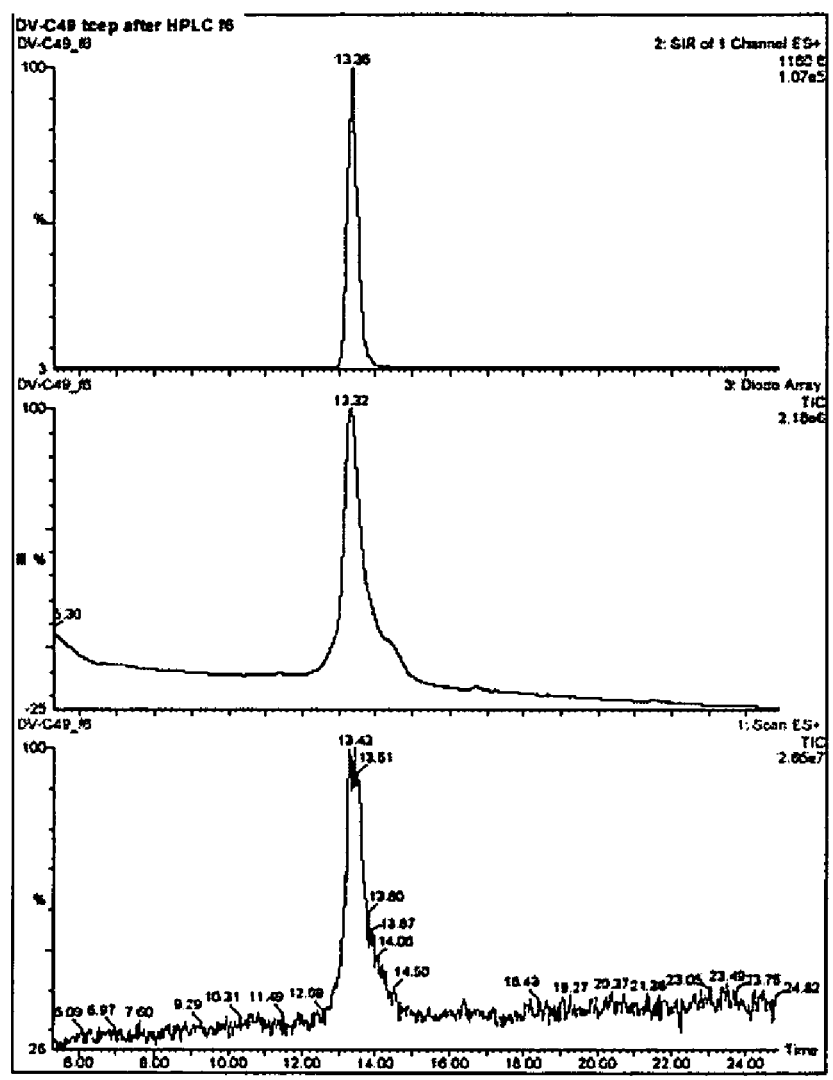
FIG. 8 depicts LCMS traces for construct 3.

LCMS traces for construct 3 are shown in FIG. 8.

Figure 12A:
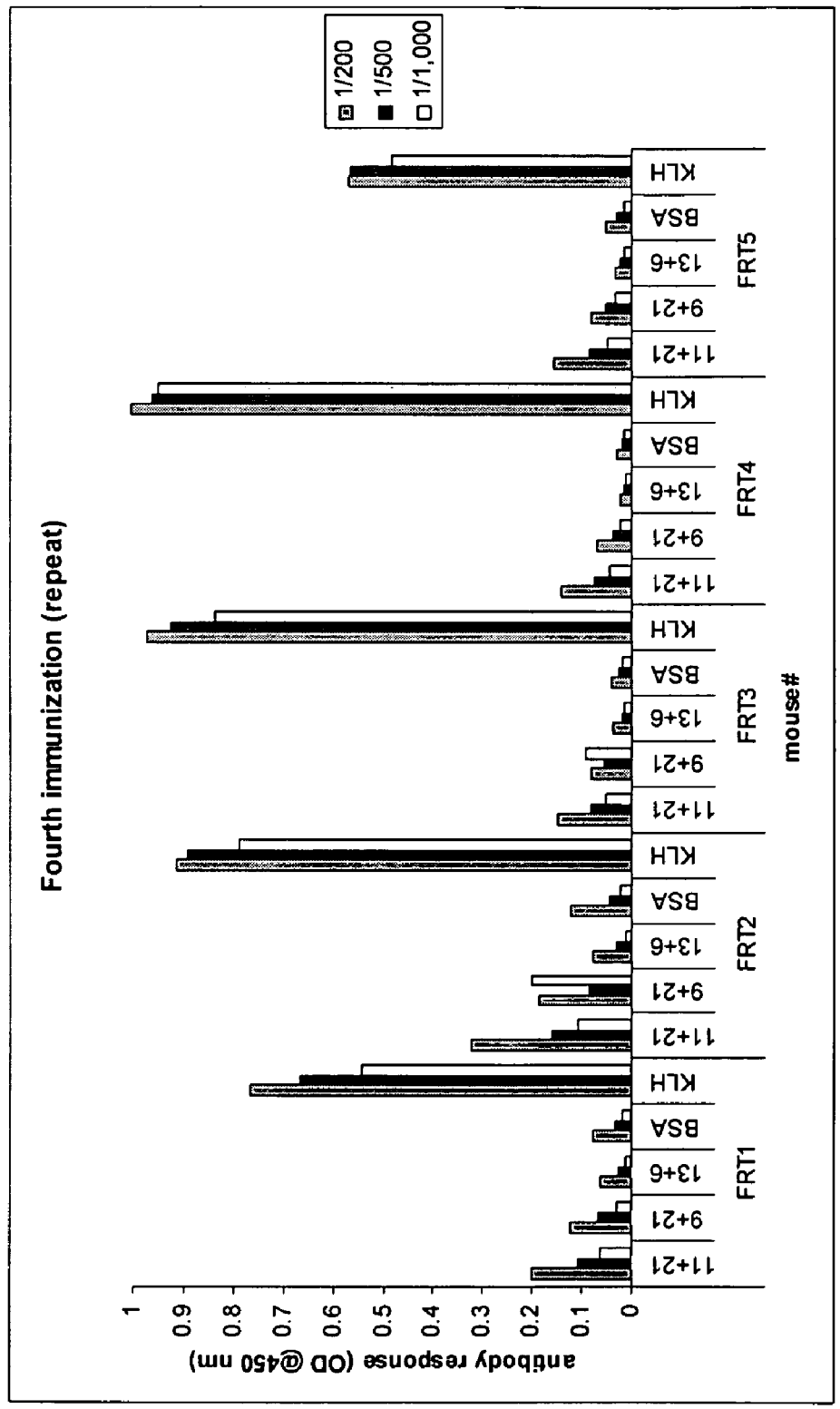
FIG. 12 depicts results of mouse antibody responses to glycopeptides 1, 3 and 50.
Figure 12B:
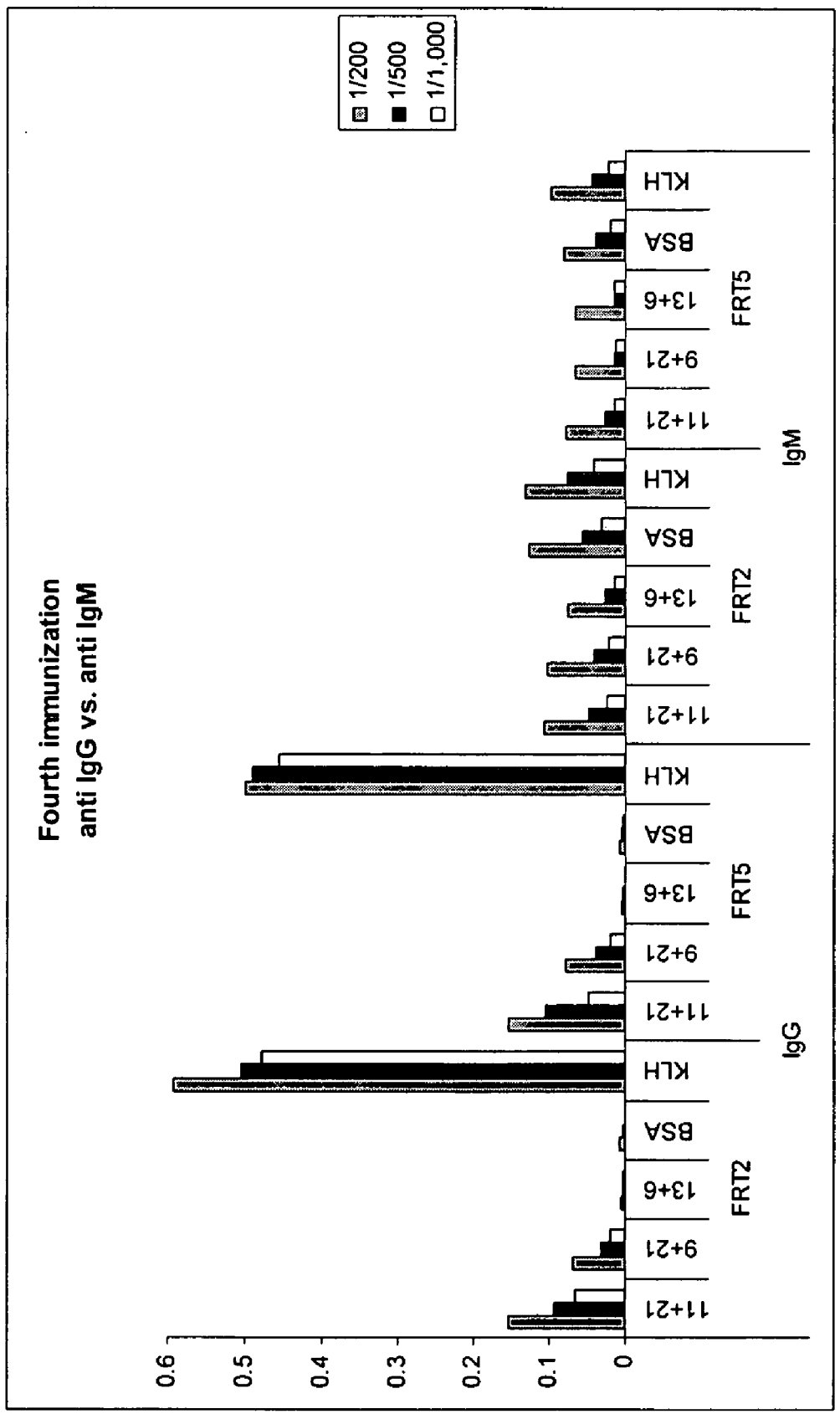

Five mice were repeatedly immunized with this glycopeptide-KLH construct, and the antibody response in the sera of immunized mice was evaluated using ELISA assay. After four immunizations, all five mice had a response against 11+21 (2), and 9+21 (1) (FIG. 12A, note that BSA is negative control and KLH is positive control). Interestingly, the antibody response against 11+21 (2) is consistently stronger than 9+21 (1). The weaker response against 13+6 (50) might be due to its inefficient attachment into the plate. Our further experiments using anti IgGs and anti IgMs suggest that the glycopeptide-KLH construct generates IgGs type antibody (FIG. 12B).

Figure 13:
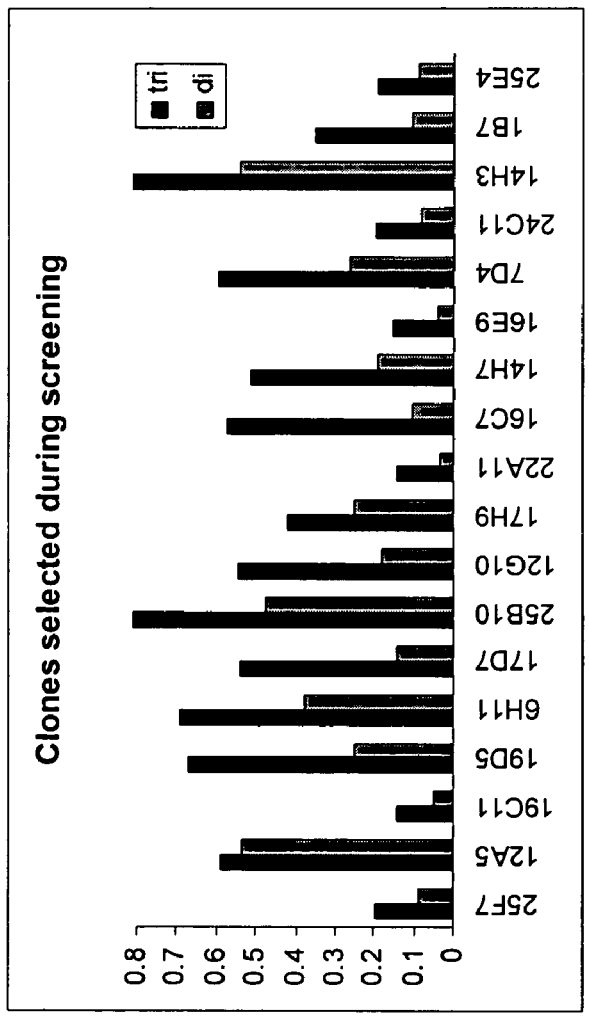
FIG. 13 depicts resultas of hybridoma screening experiments.

Clones of the hybridomas react with the tribranched structure to a far greater extent than the dibranched structure (See FIG. 13).

In summary, our preliminary data showed that the antibody response is more selective for the transformed PSA glycopeptide fragments, 11+21 (2), and could be used in distinguishing the normal versus transformed PSA level for the diagnostic purposes.

Preparation of the protein carrier conjugate for immunization. In order to elicit a sustained immune response against the tribranched glycopeptide, we chose Keyhole Limpet Hemocyanin (KLH) as a protein carrier. KLH has proven to be effective in many vaccine applications, because of its enormous molecular mass and poor solubility.

The unique thiol on the glycopeptide is a convenient handle for conjugation to a maleimide-functionalized KLH. We initially performed test conjugations with a commercially available maleimide-activated KLH, but the extent of the maleimide derivatization was unsatisfactory. Since it is believed that the density of antigen presented at the surface of the protein carrier is an important factor to achieve good immunogenicity, we decided to prepare a more extensively functionalized KLH. The lysines of KLH were derivatized using a large excess of succinimidyl-4-[N-maleimidomethyl]cyclohexane-1-carboxylate (SMCC). The initial constructs were unstable and lost their maleimide moiety rapidly and precipitated. We hypothesized this phenomenon was due to crosslinking with the KLH native thiols. Therefore, to prevent this from occuring, KLH was first reacted with maleimidobutyric acid in order to block free thiols. This preliminary step allowed a higher degree of maleimide functionalization, and also stability of the construct (data not shown). Up to 1,000 maleimide moieties were grafted on KLH using this protocol, as assessed by $^{35}$S-Cysteine labeling.

Coupling of the tribranched glycopeptide 11+21 (2) to this activated KLH yielded a conjugate bearing about 300 residues, as assessed by carbohydrate HPLC analysis after total hydrolysis (data not shown). The coupling efficiency was 20%.

Experimental Section:

General procedure for KLH activation and glycopeptide conjugation. Lyophilized KLH (Pierce Biotechnology, Inc., Rockford, Ill.) (15 mg, 0.001875 µmol) was reconstitued in 1.5 mL degassed water and allowed to react 2 hours at room temperature with maleimidobutyric acid (0.515 mg, 2.81 µmol) in degassed sodium acetate buffer pH 7.0. The heterobifunctional linker LC-SMCC (Succinimidyl 4-[N-maleimidomethyl]cyclohexane-1-carboxy-(6-amidocaproate)) (5.9 mg, 13.1 µmol) was solubilized in 200 µL DMSO and added to the reaction mixture. After 2 hours at room temperature, the activated protein was purified by size exclusion chromatography (10DG column, Biorad Laboratories, Hercules, Calif.) in degassed PBS containing 5 mM EDTA, pH 6.4, and concentrated using Microcon devices of 50 kDa molecular weight cut-off (Millipore Corporation, Bedford, Mass.).

The tribranched glycopeptide 11+21 (2) (1.05 mg, 0.246 µmol) was solublized in degassed water, and added to the activated KLH (1.4 mg, 0.000175 µmol) stored in PBS EDTA 5 mM. Sodium carbonate (200 mM) was added to adjust the pH to 6.8. The reaction was allowed to proceed over 18 hours at room temperature. Purification and concentration of the conjugate was performed as described above for the activated KLH.

REFERENCES ASSOCIATED WITH EXAMPLE 2

1. Ambruster, D. A. *Clin. Chem.* 1993, 39, 181-195.
2. Abrahamsson, P. A.; Lilja, H.; Oesterling, J. E. *Urol. Clin. N. Am.* 1997, 24, 353.
3. Egawa, S. Biomed. *Pharmacother.* 2001, 55, 130-134.
4. Okada, T.; Sato, Y.; Kobayashi, N.; Sumida, K.; Satomura, S.; Matsuura, S.; Takasaki, M.; Endo, T. *Biochim. Biophys. Acta-Gen. Subj.* 2001, 1525, 149-160.
5. Belanger, A.; Vanhalbeek, H.; Graves, H. C. B.; Grandbois, K.; Stamey, T. A.; Huang, L. H.; Poppe, I.; Labrie, F. *Prostate* 1995, 27, 187-197.
6. Prakash, S.; Robbins, P. W. *Glycobiology* 2000, 10, 173-176.
7. Ward, A. M.; Catto, J. W. F.; Hamdy, F. C. *Ann. Clin. Biochem.* 2001, 38, 633-651.
8. Semjonow, A.; Hertle, L. *Urol.-Ausg. A* 1995, 34, 290-296.
9. Semjonow, A.; Brandt, B.; Oberpenning, F.; Roth, S.; Hertle, L. *Prostate* 1996, 3-16.
10. Masters, J. G.; Keegan, P. E.; Hildreth, A. J.; Greene, D. R. J. *Br. J. Urol.* 1998, 81, 419-423.
11. Hilz, H.; Noldus, J.; Hammerer, P.; Buck, F.; Luck, M.; Huland, H. *Eur. Urol.* 1999, 36, 286-292.
12. Likhosherstov, L. M.; Novikova, O. S.; Derevitskaja, V. A.; Kochetkov, N. K. *Carbohydr. Res.* 1986, 146, C1-C5.
13. Cohen-Anisfeld, S. T.; Lansbury, P. T. *J. Am. Chem. Soc.* 1993, 115, 10531-10537.
14. Dawson, P. E.; Muir, T. W.; Clark-Lewis, I.; Kent, S. B. H. *Science* 1994, 266, 776-779.
15. Tolbert, T. J.; Wong, C. H. *J. Am. Chem. Soc.* 2000, 122, 5421-5428.
16. Bertozzi, C. R.; Kiessling, L. L. *Science* 2001, 291, 2357-2364.
17. Miller, J. S.; Dudkin, V. Y.; Lyon, G. J.; Muir, T. W.; Danishefsky, S. J. *Angew. Chem. Int. Ed.* 2003, 42, 431-+.
18. Meinjohanns, E.; Meldal, M.; Paulsen, H.; Dwek, R. A.; Bock, K. J. *Chem. Soc.-Perkin Trans.* 1 1998, 549-560
19. Wang, Z. G.; Zhang, X. F.; Visser, M.; Live, D.; Zatorski, A.; Iserloh, U.; Lloyd, K. O.; Danishefsky, S. J. *Angew. Chem. Int. Ed.* 2001, 40, 1728-1732.
20. Unverzagt, C. *Carbohydr. Res.* 1997, 305, 423-431.
21. Unverzagt, C.; Andre, S.; Seifert, J.; Kojima, S.; Fink, C.; Srikrishna, G.; Freeze, H.; Kayser, K.; Gabius, H. J. *J. Med Chem.* 2002, 45, 478-491.
22. Prahl, I.; Unverzagt, C. *Angew. Chem. Int Ed* 2002, 41, 4259-4262
23. Seifert, J.; Lergenmuller, M.; Ito, Y. *Angew. Chem. Int. Ed.* 2000, 39, 531-534.
24. During the manuscript revision process, a synthesis of complex-type glycans (not linked to peptides) with bisecting GlcNAc was described: Weiss, H.; Unverzagt, C. *Angew. Chem. Int. Ed.* 2003, 42, 4261-4263.
25. Lönn, H.; Lönngren, J. *Carbohydr. Res.* 1983, 120, 17-24.
26. Matsuzaki, Y.; Ito, Y.; Nakahara, Y.; Ogawa, T. *Tetrahedron Lett.* 1993, 34, 1061-1064.
27. Dudkin, V. Y.; Miller, J. S.; Danishefsky, S. J. *Tetrahedron Lett.* 2003, 44, 1791-1793.
28. Dudkin, V. Y.; Crich, D. *Tetrahedron Lett.* 2003, 44, 1787-1789.
29. Griffith, D. A.; Danishefsky, S. J. *J. Am. Chem. Soc.* 1990, 112, 5811-5819.
30. Crich, D.; Sun, S. X. *J. Am. Chem. Soc.* 1998, 120, 435-436.
31. Crich, D.; Sun, S. *Tetrahedron* 1998, 54, 8321-8348.
32. Iserloh, U.; Dudkin, V.; Wang, Z. G.; Danishefsky, S. J. *Tetrahedron Lett.* 2002, 43, 7027-7030.
33. Calarese, D. A.; Scanlan, C. N.; Zwick, M. B.; Deechongkit, S.; Mimura, Y.; Kunert, R.; Zhu, P.; Wormald, M. R.; Stanfield, R. L.; Roux, K. H.; Kelly, J. W.; Rudd, P. M.; Dwek, R. A.; Katinger, H.; Burton, D. R.; Wilson, I. A. *Science* 2003, 300, 2065-2071.
34. Zhang, Y. M.; Mallet, J. M.; Sinay, P. *Carbohydr. Res.* 1992, 236, 73-88.

35. Jiang, L.; Chan, T. H. *Tetrahedron Lett.* 1998, 39, 355-358.

ABBREVIATIONS AND GLOSSARY

A: alanine
Ac: acetyl
ACT: α1-antichymotrypsin
Ala: alanine
Arg: arginine
Asn: asparagine
Asp: aspartic acid
Bn: benzyl
Boc: tert-butyloxycarbonyl
BPH: benign prostatic hyperplasia
BSP: benzenesulfinyl piperidine
Bu: butyl
Bz: benzoyl
CAN: ceric ammonium nitrate
coll: sym-collidine
C-terminus: peptide carbonyl terminus
Cys: cysteine
D: aspartic acid
DIEA: N,N-diisopropylethylamine
DMF: dimethyl formamide
DMSO: dimethyl sulfoxide
DTBMP: di-tert-butylmethylpyridine
DTBP: di-tert-butylpyridine
Et: ethyl
Fmoc: 9-fluorenylmethyloxycarbonyl
G: glycine
Gal: galactose
Glc: glucose
Gln: glutamine
Glu: glutamic acid
Gly: glycine
H: histidine
HATU: 7-azahydroxybenzotriazolyl tetramethyluronium hexafluorophosphate
His: histidine
Ile: isoleucine
K: lysine
kDa: kilodaltons
KLH: keyhole limpet hemocyanin
L: leucine
Leu: leucine
LnCaP: a metastatic prostate cancer cell line
Lys: lysine
Man: mannose
MES-Na: 2-mercaptoethanesulfonic acid, sodium salt
MHC: major histocompatibility complex
N: asparagine
NAc: N-acetyl
NCL: native chemical ligation
N-terminus: peptide amine terminus
O-linked: linked through an ethereal oxygen
Pam3Cys: tripalmitoyl-S-glycerylcysteinylserine
PBS: phosphate-buffered saline
PCa: prostate cancer
Ph: phenyl
Phth: phthalimido-
PMB: p-methoxybenzyl
Pro: proline
PSA: prostate specific antigen
Py: pyridine
QS21: a glycosteroidal immunoaduvant
R: arginine
S: serine
sat. aq.: saturated aqueous
Ser: serine
T: threonine
TBAF: tetra-n-butylammonium fluoride
TBS: tert-butyldimethylsilyl
tBu: tert-butyl
Tf: trifluoromethanesulfonate
THF: tetrahydrofuran
Thr: threonine
t-PSA: total prostate specific antigen
Trp: tryptophan
V: valine
Val: valine
W: tryptophan

OTHER REFERENCES CITED IN THE DOCUMENT

1. Armbruster, D. A. "Prostate-Specific Antigen—Biochemistry, Analytical Methods, and Clinical Application." *Clin. Chem.* 1993, 39, 181-195.
2. Hilz, H.; Noldus, J.; Hammerer, P.; Buck, F.; Luck, M.; Huland, H. "Molecular heterogeneity of free PSA in sera of patients with benign and malignant prostate tumors." *Eur. Urol.* 1999, 36, 286-292.
3. Mikolajczyk, S. D.; Grauer, L. S.; Millar, L. S.; Hill, T. M.; Kumar, A.; Rittenhouse, H. G.; Wolfert, R. L.; Saedi, M. S. "A precursor form of PSA (PPSA) is a component of the free PSA in prostate cancer serum." *Urology* 1997, 50, 710-714.
4. Abrahamsson, P. A.; Lilja, H.; Oesterling, J. E. "Molecular forms of serum prostate-specific antigen—The clinical value of percent free prostate-specific antigen." *Urol. Clin. N. Am.* 1997, 24, 353.
5. Beduschi, M.; Oesterling, J. E. "Percent free prostate-specific antigen: The next frontier in prostatespecific antigen testing." *Urology* 1998, 51, 98-109.
6. Egawa, S.; Soh, S.; Ohori, M.; Uchida, T.; Gohji, K.; Fujii, A.; Kuwao, S.; Koshiba, K. "The ratio of free to total serum prostate specific antigen and its use in differential diagnosis of prostate carcinoma in Japan." *Cancer* 1997, 79, 90-98.
7. Huber, P. R.; Schmid, H. P.; Mattarelli, G.; Strittmatter, B.; Vansteenbrugge, G. J.; Maurer, A. "Serum-Free Prostate-Specific Antigen—Isoenzymes in Benign Hyperplasia and Cancer of the Prostate." *Prostate* 1995, 27, 212-219.
8. Junker, R.; Brandt, B.; Zechel, C.; Assmann, G. "Comparison of prostate-specific antigen (PSA) measured by four combinations of free PSA and total PSA assays." *Clin. Chem.* 1997, 43, 1588-1594.
9. Kochanska-Dziurowicz, A. A.; Mielniczuk, M. R.; Stojko, A.; Kaletka, J. "The clinical utility of measuring free-to-total prostate-specific antigen (PSA) ratio and PSA density in differentiating between benign prostatic hyperplasia and prostate cancer." *Br. J. Urol.* 1998, 81, 834-838.
10. Leinonen, J.; Stenman, U. H. "Significance of free and bound prostate-specific antigen." *Endocr.-Relat. Cancer* 1996, 3, 191-197.
11. Nurmikko, P.; Pettersson, K.; Piironen, T.; Hugosson, J.; Lilja, H. "Discrimination of prostate cancer from benign disease by plasma measurement of intact, free prostate-specific antigen lacking an internal cleavage site at Lys (145)-Lys(146)." *Clin. Chem.* 2001, 47, 1415-1423.
12. Reiter, W.; Stieber, P.; Schmeller, N.; Nagel, D.; Jansen, H. M.; Schambeck, C.; Fabricius, P. G.; Pahl, H.; Mattes, M.; Constabel, H.; FatehMoghadam, A. "The ratio of free to total prostate specific antigen: An advantageous addition in the differential diagnosis of benign hyperplasia and cancer of the prostate?" *Anticancer Res.* 1997, 17, 2987-2991.

13. Zhang, W. M.; Finne, P.; Leinonen, J.; Salo, J.; Stenman, U. H. "Determination of prostate-specific antigen complexed to alpha(2)-macroglobulin in serum increases the specificity of free to total PSA for prostate cancer." *Urology* 2000, 56, 267-272.

14. Stamey, T. A.; Yang, N.; Hay, A. R.; McNeal, J. E.; Freiha, F. S.; Redwine, E. "Prostate-Specific Antigen as a Serum Marker for Adenocarcinoma of the Prostate." *N. Engl. J. Med.* 1987, 317, 909-916.

15. Hudson, M. A.; Bahnson, R. R.; Catalona, W. J. "Clinical Use of Prostate Specific Antigen in Patients with Prostate Cancer." *J. Urol.* 1989, 142, 1011-1017.

16. Ward, A. M.; Catto, J. W. F.; Hamdy, F. C. "Prostate specific antigen: biology, biochemistry and available commercial assays." *Ann. Clin. Biochem.* 2001, 38, 633-651.

17. Semjonow, A.; Brandt, B.; Oberpenning, F.; Roth, S.; Hertle, L. "Discordance of assay methods creates pitfalls for the interpretation of prostate-specific antigen values." *Prostate* 1996, 3-16.

18. Ravery, V.; Boccon-Gibod, L. "Free/total prostate-specific antigen ratio—hope and controversies." *Eur. Urol.* 1997, 31, 385-388.

19. Masters, J. G.; Keegan, P. E.; Hildreth, A. J.; Greene, D. R. J. "Free/total serum prostate-specific antigen ratio: How helpful is it in detecting prostate cancer?" *Br. J. Urol.* 1998, 81, 419-423.

20. Carter, H. B.; Morrell, C. H.; Pearson, J. D.; Brant, L. J.; Plato, C. C.; Metter, E. J.; Chan, D. W.; Fozard, J. L.; Walsh, P. C. "Estimation of Prostatic Growth Using Serial Prostate-Specific Antigen Measurements in Men with and without Prostate Disease." *Cancer Res.* 1992, 52, 3323-3328.

21. Carter, H. B.; Pearson, J. D. "PSA Velocity for the Diagnosis of Early Prostate Cancer—a New Concept." *Urol. Clin. N. Am.* 1993, 20, 665-670.

22. Dennis, J. W.; Laferte, S.; Waghome, C.; Breitman, M. L.; Kerbel, R. S. "Beta-1-6 Branching of Asn-Linked Oligosaccharides Is Directly Associated with Metastasis." *Science* 1987, 236, 582-585.

23. Fernandes, B.; Sagman, U.; Auger, M.; Demetrio, M.; Dennis, J. W. "Beta-1-6 Branched Oligosaccharides as a Marker of Tumor Progression in Human Breast and Colon Neoplasia." *Cancer Res.* 1991, 51, 718-723.

24. Dennis, J. W.; Laferte, S. "Oncodevelopmental Expression of GlcNAc-Beta-1-6Man-Alpha-1-6Man-Beta-1-Branched Asparagine-Linked Oligosaccharides in Murine Tissues and Human-Breast Carcinomas." *Cancer Res.* 1989, 49, 945-950.

25. Matsumoto, H.; Muramatsu, H.; Muramatsu, T.; Shimazu, H. "Carbohydrate Profiles Shown by a Lectin and a Monoclonal Antibody Correlate with Metastatic Potential and Prognosis of Human Lung Carcinomas." *Cancer* 1992, 69, 2084-2090.

26. Belanger, A.; Vanhalbeek, H.; Graves, H. C. B.; Grandbois, K.; Stamey, T. A.; Huang, L. H.; Poppe, I.; Labrie, F. "Molecular Mass and Carbohydrate Structure of Prostate Specific Antigen—Studies for Establishment of an International PSA Standard." *Prostate* 1995, 27, 187-197.

27. Okada, T.; Sato, Y.; Kobayashi, N.; Sumida, K.; Satomura, S.; Matsuura, S.; Takasaki, M.; Endo, T. "Structural characteristics of the N-glycans of two isoforms of prostate-specific antigens purified from human seminal fluid." *Biochim. Biophys. Acta-Gen. Subj.* 2001, 1525, 149-160.

28. Prakash, S.; Robbins, P. W. "Glycotyping of prostate specific antigen." *Glycobiology* 2000, 10, 173-176.

29. Wang, T. J.; Linton, H. J.; Sokoloff, R. L.; Grauer, L. S.; Rittenhouse, H. G.; Wolfert, R. L. "Western blotting analysis of antibodies to prostate-specific antigen: Specificities for prostate-specific antigen and prostate-specific antigen fragments." *Tumor Biol.* 1999, 20, 79-85.

30. O'Connor, S. E.; Imperiali, B. "A molecular basis for glycosylation-induced conformational switching." *Chem. Biol.* 1998, 5, 427-437.

31. Kent, S. B. H. "Chemical Synthesis of Peptides and Proteins." *Annu. Rev. Biochem.* 1988, 57, 957-989.

32. Tam, J. P.; Lu, Y. A. "Coupling Difficulty Associated with Interchain Clustering and Phase-Transition in Solid-Phase Peptide-Synthesis." *J. Am. Chem. Soc.* 1995, 117, 12058-12063.

33. Thaler, A.; Seebach, D.; Cardinaux, F. "Lithium Salt Effects in Peptide Synthesis. 2. Improvement of Degree of Resin Swelling and of Efficiency of Coupling in Solid-Phase Synthesis." *Helv. Chim. Acta* 1991, 74, 628-643.

34. Ragupathi, G. "Carbohydrate antigens as targets for active specific immunotherapy." *Cancer Immunol. Immun.* 1996, 43, 152-157.

35. Helling, F.; Shang, A.; Calves, M.; Zhang, S. L.; Ren, S. L.; Yu, R. K.; Oettgen, H. F.; Livingston, P. O. "G(D3) Vaccines for Melanoma—Superior Immunogenicity of Keyhole Limpet Hemocyanin Conjugate Vaccines." *Cancer Res.* 1994, 54, 197-203.

36. Harris, J. R.; Markl, J. "Keyhole limpet hemocyanin (KLH): A biomedical review." *Micron* 1999, 30, 597-623.

37. Kellner, J.; Erhard, M.; Schranner, I.; Losch, U. "The Influence of Various Adjuvants on Antibody Synthesis Following Immunization with an Hapten." *Biol. Chem. Hoppe-Seyler* 1992, 373, 51-55.

38. Metzger, J.; Wiesmuller, K. H.; Schaude, R.; Bessler, W. G.; Jung, G. "Synthesis of Novel Immunologically Active Tripalmitoyl-S-Glycerylcysteinyl Lipopeptides as Useful Intermediates for Immunogen Preparations." *Int. J. Pept. Protein Res.* 1991, 37, 46-57.

39. Kensil, C. R.; Patel, U.; Lennick, M.; Marciani, D. "Separation and Characterization of Saponins with Adjuvant Activity from Quillaja-Saponaria Molina Cortex." *J. Immunol.* 1991, 146, 431-437.

40. Livingston, P. O.; Adluri, S.; Helling, F.; Yao, T. J.; Kensil, C. R.; Newman, M. J.; Marciani, D. "Phase-1 Trial of Immunological Adjuvant QS-21 with a GM2 Ganglioside-Keyhole Limpet Hemocyanin Conjugate Vaccine in Patients with Malignant-Melanoma." *Vaccine* 1994, 12, 1275-1280.

41. Zhang, S. L.; Graeber, L. A.; Helling, F.; Ragupathi, G.; Adluri, S.; Lloyd, K. O.; Livingston, P. O. "Augmenting the immunogenicity of synthetic MUCI peptide vaccines in mice." *Cancer Res.* 1996, 56, 3315-3319.

42. Musselli, C.; Livingston, P. O.; Ragupathi, G. "Keyhole limpet hemocyanin conjugate vaccines against cancer: the Memorial Sloan Kettering experience." *J. Cancer Res. Clin. Oncol.* 2001, 127, R20-R26.

43. Adluri, S.; Helling, F.; Ogata, S.; Zhang, S. L.; Itzkowitz, S. H.; Lloyd, K. O.; Livingston, P. O. "Immunogenicity of Synthetic TF-KLH (Keyhole Limpet Hemocyanin) and STn-KLH Conjugates in Colorectal Carcinoma Patients." *Cancer Immunol. Immun.* 1995, 41, 185-192.

44. Kudryashov, V.; Glunz, P. W.; Williams, L. J.; Hintermann, S.; Danishefsky, S. J.; Lloyd, K. O. "Toward optimized carbohydrate-based anticancer vaccines: Epitope clustering, carrier structure, and adjuvant all influence antibody responses to Lewis(y) conjugates in mice." *Proc. Natl. Acad Sci. U.S.A.* 2001, 98, 3264-3269.
45. Ragupathi, G.; Howard, L.; Cappello, S.; Koganty, R. R.; Qiu, D. X.; Longenecker, B. M.; Reddish, M. A.; Lloyd, K. O.; Livingston, P. O. "Vaccines prepared with sialyl-Tn and sialyl-Tn trimers using the 4-(4-maleimidomethyl)cyclohexane-1-carboxyl hydrazide linker group result in optimal antibody titers against ovine submaxillary mucin and sialyl-Tn-positive tumor cells." *Cancer Immunol. Immun.* 1999, 48, 1-8.
46. Glunz, P. W.; Hintermann, S.; Williams, L. J.; Schwarz, J. B.; Kuduk, S. D.; Kudryashov, V.; Lloyd, K. O.; Danishefsky, S. J. "Design and synthesis of Le(y)-bearing glycopeptides that mimic cell surface Le(y) mucin glycoprotein architecture." *J. Am. Chem. Soc.* 2000, 122, 7273-7279.

What is claimed is:

1. An isolated compound having the structure:

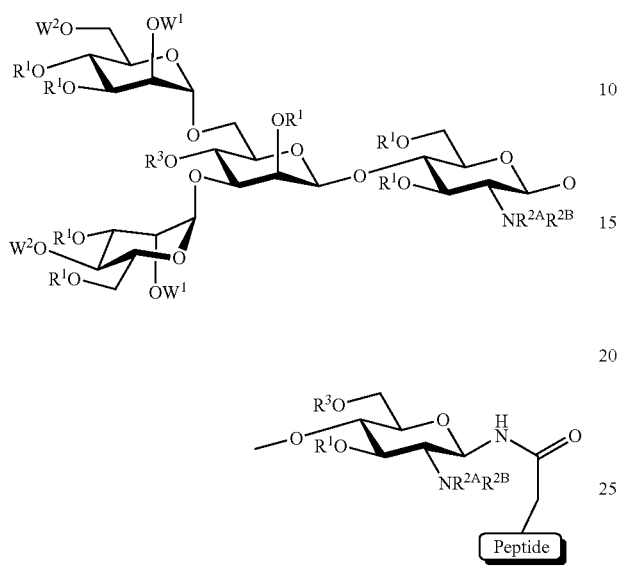

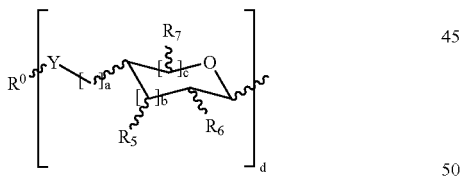

wherein each occurrence of $R^1$ is independently hydrogen or an oxygen protecting group;
each occurrence of $R^{2A}$ and $R^{2B}$ is independently hydrogen or a nitrogen protecting group;
each occurrence of $R^3$ is independently hydrogen, a protecting group or a carbohydrate domain comprising a saccharide moiety having the structure:

wherein Y is NH or O; wherein a, b and c are each independently 0, 1 or 2; d is an integer from 1-3; with the proviso that the d bracketed structure represents a furanose or pyranose moiety and the sum of b and c is 1 or 2; wherein $R^0$ is hydrogen, a linear or branched chain alkyl, acyl, arylalkyl or aryl group; wherein each occurrence of $R^5$, $R^6$ and $R^7$ is independently hydrogen, OH, $OR^i$, $NR^{ii}R^{iii}$, $NHCOR^i$, F, $CH_2OH$, $CH_2OR^i$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$, $R^{ii}$ and $R^{iii}$ is independently hydrogen, a protecting group, a sialic acid moiety, CHO, $COOR^{iv}$, or a substituted or unsubstituted linear or branched chain alkyl, acyl, arylalkyl or aryl group, or $R^{ii}$ and $R^{iii}$, taken together with the nitrogen atom to which they are attached, form a substituted or unsubstituted heterocyclic or heteroaryl moiety; and wherein each occurrence of $R^{iv}$ is independently H, or a substituted or unsubstituted linear or branched chain alkyl, arylalkyl or aryl group;

each occurrence of $W^1$ and $W^2$ is independently $R^1$, $R^3$ or a moiety having the structure:

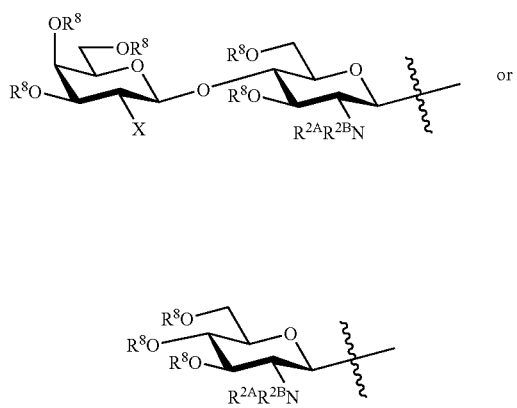

wherein X is $-OR^1$ or $-NR^{2A}R^{2B}$; and each occurrence of $R^8$ is independently $R^1$ or a sialic acid moiety;
with the proviso that at least one occurrence of $W^1$ or $W^2$ does not comprise mannose;
wherein the peptide comprises not more than 60 amino acid residues and comprises the N-glycosylation site of naturally occurring PSA;
wherein the peptide has the following structure:

(SEQ ID NO: 2)

Cys-Ile-Arg-Asn-Lys-Ser;

or an elongated version thereof;
wherein any one or more of the amino acid residues of said peptide may bear one or more protecting groups;
with the proviso that the compound is not a naturally occurring PSA glycoprotein.

2. The compound of claim 1 having the structure:

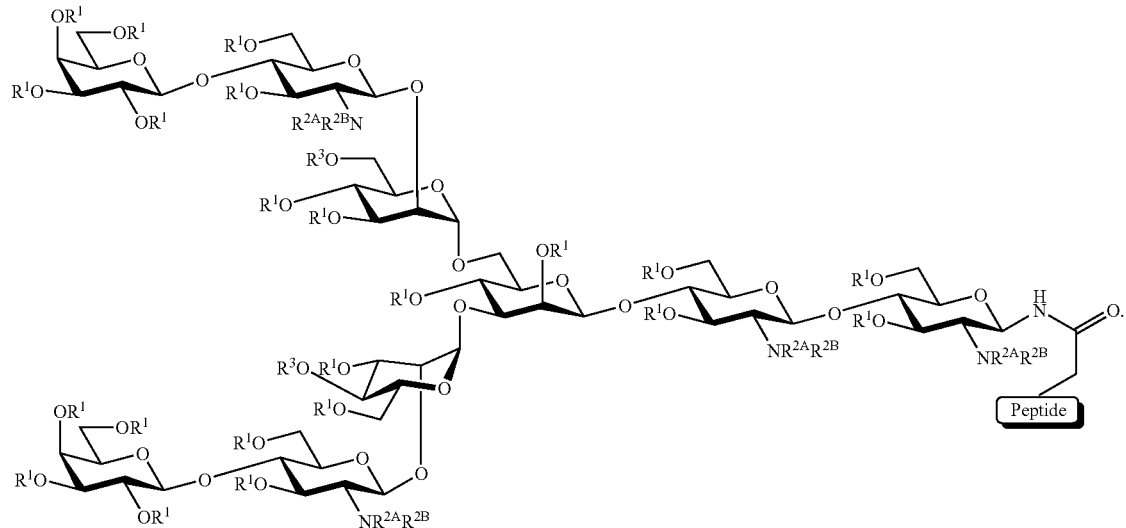

3. The compound of claim 1 or 2, wherein each occurrence of $R^1$ is independently hydrogen, alkyl, alkenyl, alkynyl, heteroalkyl, heteroalkenyl, heteroalkynyl, aryl, heteroaryl, alkylaryl, alkylheteroaryl, —Si($R^{1A}$)$_3$, —C(=O)$R^{1A}$, —C(=S)$R^{1A}$, —C(=N$R^{1A}$)$R^{1B}$, —SO$_2R^{1A}$, wherein $R^{1A}$ and $R^{1B}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{1C}$ or —Z$R^{1C}$, wherein Z is —O—, —S—, —NR$^{1D}$, wherein each occurrence of $R^{1C}$ and $R^{1D}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety.

4. The compound of claim 3, wherein each occurrence of $R^1$ is independently hydrogen, alkylaryl, —Si($R^{1A}$) or —C(=O)$R^{1A}$.

5. The compound of claim 4, wherein each occurrence of $R^1$ is independently hydrogen, Bn or Bz.

6. The compound of claim 1 or 2, wherein for each occurrence of —NR$^{2A}R^{2B}$, at least one occurrence of $R^{2A}$ or $R^{2B}$ is independently a nitrogen protecting group.

7. The compound of claim 1 or 2, wherein each occurrence of $R^{2A}$ and $R^{2B}$ is independently hydrogen, alkyl, alkenyl, —C(=O)$R^{2C}$, —C(=O)O$R^{2C}$, —S$R^{2C}$, SO$_2R^{2C}$, or $R^{2A}$ and $R^{2B}$, taken together with the nitrogen atom to which they are attached, form a substituted or unsubstituted heterocyclic or heteroaryl moiety; wherein each occurrence of $R^{2C}$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{2D}$ or —Z$R^{2D}$, wherein Z is —O—, —S—, —NR$^{2E}$, wherein each occurrence of $R^{2D}$ and $R^{2E}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety.

8. The compound of claim 1 or 2, wherein for each occurrence of —NR$^{2A}R^{2B}$, at least one occurrence of $R^{2A}$ or $R^{2B}$ is independently —C(=O)$R^{2A}$ or SO$_2R^{2A}$; or $R^{2A}$ and $R^{2B}$, taken together with the nitrogen atom to which they are attached, form a substituted or unsubstituted heterocyclic or heteroaryl moiety.

9. The compound of claim 8, wherein for each occurrence of —NR$^{2A}R^{2B}$, at least one occurrence of $R^{2A}$ or $R^{2B}$ is independently acyl, —SO$_2$Ph or $R^{2A}$ and $R^{2B}$, taken together with the nitrogen atom to which they are attached, form an azide or a substituted or unsubstituted phthalimide moiety.

10. The compound of claim 2, wherein at least one occurrence of $R^3$ comprises a saccharide moiety having the structure:

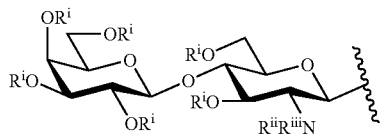

wherein each occurrence of $R^i$ is independently hydrogen, alkyl, alkenyl, alkynyl, heteroalkyl, heteroalkenyl, heteroalkynyl, aryl, heteroaryl, alkylaryl, alkylheteroaryl, —Si($R^{iA}$)$_3$, —C(=O)$R^{iA}$, —C(=S)$R^{iA}$, —C(=N$R^{iA}$)$R^{iB}$, —SO$_2R^{iA}$, wherein $R_{iA}$ and $R^{iB}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{iC}$ or —Z$R^{iC}$, wherein Z is —O—, —S—, —N$R^{iD}$, wherein each occurrence of $R^{iC}$ and $R^{iD}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety; and each occurrence of $R^{ii}$ and $R^{iii}$ is independently hydrogen, alkyl, alkenyl, —C(=O)$R^{iiA}$, —C(=O)O$R^{iiA}$, —S$R^{iiA}$, SO$_2R^{iiA}$, or $R^{ii}$ and $R^{iii}$, taken together with the nitrogen atom to which they are attached, form a substituted or unsubstituted heterocyclic or heteroaryl moiety; wherein each occurrence of $R^{iiA}$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{iiB}$ or —Z$R^{iiB}$, wherein Z is —O—, —S—, —N$R^{iiC}$, wherein each occurrence of $R^{iiB}$ and $R_{iiC}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety.

11. The compound of claim 10, wherein each occurrence of $R^i$ is independently hydrogen, alkylaryl, —Si($R^{iA}$) or —C(=O)$R^{iA}$.

12. The compound of claim 11, wherein each occurrence of $R^i$ is independently hydrogen, Bn or Bz.

13. The compound of claim 10, wherein at least one occurrence of $R^{ii}$ or $R^{iii}$ is independently —C(=O)$R^{iiA}$ or SO$_2R^{iiA}$; or $R^{ii}$ and $R^{iii}$, taken together with the nitrogen atom to which they are attached, form a substituted or unsubstituted heterocyclic or heteroaryl moiety.

14. The compound of claim 13, wherein at least one occurrence of $R^{ii}$ or $R^{iii}$ is independently acyl, —SO$_2$Ph or $R^{ii}$ and $R^{iii}$, taken together with the nitrogen atom to which they are attached, form an azide or a substituted or unsubstituted phthalimide moiety.

15. The compound of claim 2, wherein each occurrence of $R^3$ is independently a saccharide moiety having the structure:

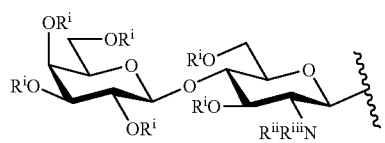

wherein each occurrence of $R^i$ is independently hydrogen, alkyl, alkenyl, alkynyl, heteroalkyl, heteroalkenyl, heteroalkynyl, aryl, heteroaryl, alkylaryl, alkylheteroaryl, —Si($R^{iA}$)$_3$, —C(=O)$R^{iA}$, —C(=S)$R^{iA}$, —C(=N$R^{iA}$)$R^{iB}$, SO$_2R^{iA}$, wherein $R^{iA}$ and $R^{iB}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{iC}$ or —Z$R^{iC}$, wherein Z is —O—, —S—, —N$R^{iD}$, wherein each occurrence of $R^{iC}$ and $R^{iD}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety; and each occurrence of $R^{ii}$ and $R^{iii}$ is independently hydrogen, alkyl, alkenyl, —C(=O)$R^{iiA}$, —C(=O)O$R^{iiA}$, —S$R^{iiA}$, SO$_2R^{iiA}$, or $R^{ii}$ and $R^{iii}$, taken together with the nitrogen atom to which they are attached, form a substituted or unsubstituted heterocyclic or heteroaryl moiety; wherein each occurrence of $R^{iiA}$ is independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{iiB}$ or —Z$R^{iiB}$, wherein Z is —O—, —S—, —N$R^{iiC}$, wherein each occurrence of $R^{iiB}$ and $R^{iiC}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety.

16. The compound of claim 2 having the structure:

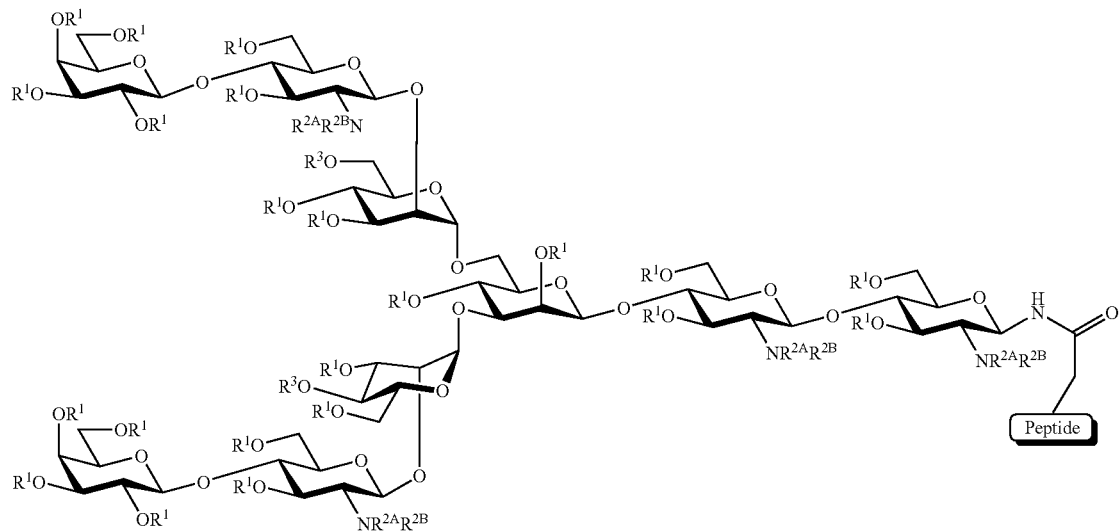

wherein each occurrence of $R^3$ is independently hydrogen, alkyl, alkenyl, alkynyl, heteroalkyl, heteroalkenyl, heteroalkynyl, aryl, heteroaryl, alkylaryl, alkylheteroaryl, —Si$(R^{3A})_3$, —C(=O)$R^{3A}$, —C(=S)$R^{3A}$, —C(=NR$^{3A}$)$R^{3B}$, SO$_2$$R^{3A}$, wherein $R^{3A}$ and $R^{3B}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{3C}$ or —Z$R^{3C}$, wherein Z is —O—, —S—, —NR$^{3D}$, wherein each occurrence of $R^{3C}$ and $R^{3D}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety.

17. The compound of claim 2 having the structure:

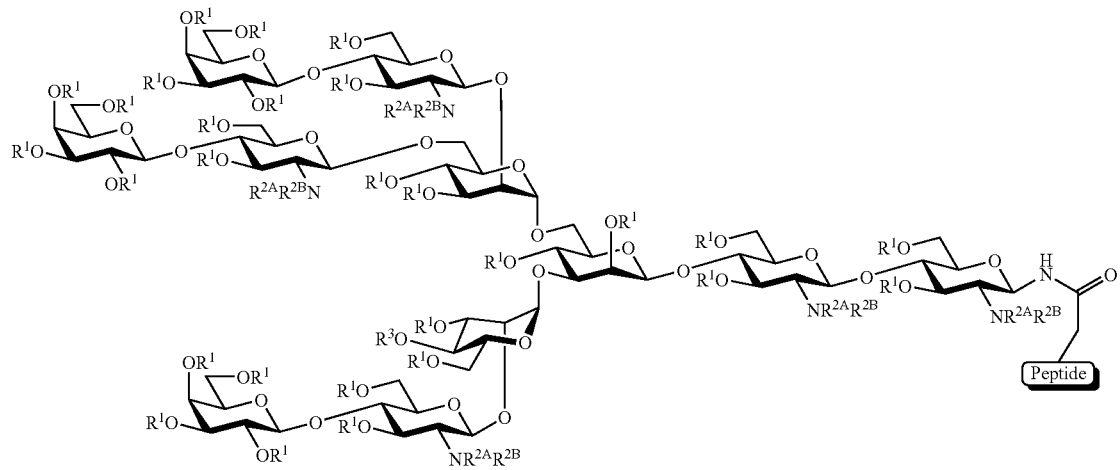

wherein $R^3$ is independently hydrogen, alkyl, alkenyl, alkynyl, heteroalkyl, heteroalkenyl, heteroalkynyl, aryl, heteroaryl, alkylaryl, alkylheteroaryl, —Si$(R^{3A})_3$, —C(=O)$R^{3A}$, —C(=s)$R^{3A}$, —C(=NR$^{3A}$)$R^{3B}$, —SO$_2$$R^{3A}$, wherein $R^{3A}$ and $R^{3B}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{3C}$ or —Z$R^{3C}$, wherein Z is —O—, —S—, —NR$^{3D}$, wherein each occurrence of $R^{3C}$ and $R^{3D}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety.

18. The compound of claim 2 having the structure:

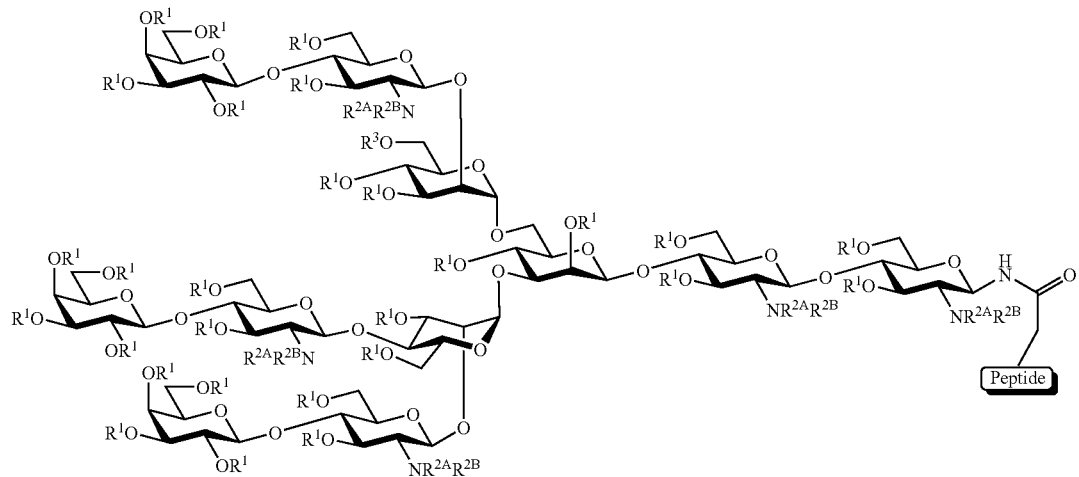

wherein $R^3$ is independently hydrogen, alkyl, alkenyl, alkynyl, heteroalkyl, heteroalkenyl, heteroalkynyl, aryl, heteroaryl, alkylaryl, alkylheteroaryl, —Si$(R^{3A})_3$, —C(=O)$R^{3A}$, —C(=S)$R^{3A}$, —C(=N$R^{3A}$)$R^{3B}$, —SO$_2$$R^{3A}$, wherein $R^{3A}$ and $R^{3B}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^{3C}$ or —Z$R^{3C}$, wherein Z is —O—, —S—, —NR$^{3D}$, wherein each occurrence of $R^{3C}$ and $R^{3D}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety.

19. The compound of claim 2 having the structure:

20. The compound of any one of claims 1, 2, 16, 17, 18, or 19, wherein the peptide has the following structure:

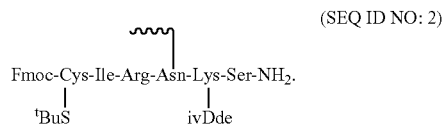

21. The compound of any one of claims 1, 2, 16, 17, 18, or 19, wherein the peptide has the following structure:

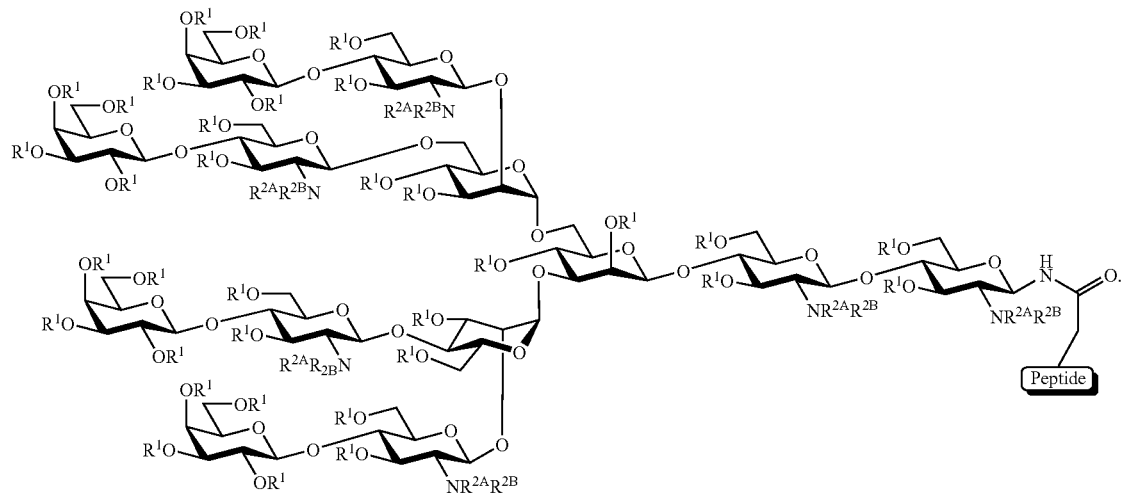

(SEQ ID NO: 2)
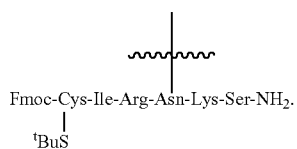
Fmoc-Cys-Ile-Arg-Asn-Lys-Ser-NH$_2$.
|
$^t$BuS
22. The compound of any one of claims 1, 2, 16, 17, 18, or 19, wherein the peptide has the following structure:
(SEQ ID NO: 1)
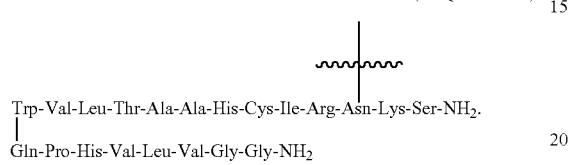
Trp-Val-Leu-Thr-Ala-Ala-His-Cys-Ile-Arg-Asn-Lys-Ser-NH$_2$.
|
Gln-Pro-His-Val-Leu-Val-Gly-Gly-NH$_2$
23. The compound of any one of claims 1, 2, 16, 17, 18, or 19, wherein the peptide ha consists of the following structure:
Cys-Ile-Arg-Asn-Lys-Ser.
(SEQ ID NO: 2)
\* \* \* \* \*

UNITED STATES PATENT AND TRADEMARK OFFICE
CERTIFICATE OF CORRECTION

PATENT NO. : 7,645,454 B2
APPLICATION NO. : 11/145002
DATED : January 12, 2010
INVENTOR(S) : Danishefsky et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 496 days.

Signed and Sealed this

Sixteenth Day of November, 2010

David J. Kappos
*Director of the United States Patent and Trademark Office*

SEQUENCE LISTING

```
<160> NUMBER OF SEQ ID NOS: 16

<210> SEQ ID NO 1
<211> LENGTH: 21
<212> TYPE: PRT
<213> ORGANISM: Homo sapiens

<400> SEQUENCE: 1

Gly Gly Val Leu Val His Pro Gln Trp Val Leu Thr Ala Ala His Cys
1               5                   10                  15

Ile Arg Asn Lys Ser
            20

<210> SEQ ID NO 2
<211> LENGTH: 6
<212> TYPE: PRT
<213> ORGANISM: Homo sapiens

<400> SEQUENCE: 2

Cys Ile Arg Asn Lys Ser
1               5

<210> SEQ ID NO 3
<211> LENGTH: 5
<212> TYPE: PRT
<213> ORGANISM: Homo sapiens

<400> SEQUENCE: 3

Leu Ala Asn Val Thr
1               5

<210> SEQ ID NO 4
<211> LENGTH: 10
<212> TYPE: PRT
<213> ORGANISM: Homo sapiens

<400> SEQUENCE: 4

Val Ile Thr Ala Phe Asn Glu Gly Leu Lys
1               5                   10

<210> SEQ ID NO 5
<211> LENGTH: 9
<212> TYPE: PRT
<213> ORGANISM: Homo sapiens

<400> SEQUENCE: 5

Val Ile Ala Phe Asn Glu Gly Leu Lys
1               5

<210> SEQ ID NO 6
<211> LENGTH: 5
```

```
<212> TYPE: PRT
<213> ORGANISM: Artificial Sequence
<220> FEATURE:
<223> OTHER INFORMATION: Precursor to peptide portion of glycopeptide

<400> SEQUENCE: 6

Cys Ala Asp Ala Ser
1               5

<210> SEQ ID NO 7
<211> LENGTH: 5
<212> TYPE: PRT
<213> ORGANISM: Artificial Sequence
<220> FEATURE:
<223> OTHER INFORMATION: Peptide portion of glycopeptide

<400> SEQUENCE: 7

Cys Ala Asn Ala Ser
1               5

<210> SEQ ID NO 8
<211> LENGTH: 20
<212> TYPE: PRT
<213> ORGANISM: Homo sapiens

<400> SEQUENCE: 8

Gly Asp Ser Ala Trp His Leu Gly Glu Leu Val Trp Ser Thr Gly Cys
1               5                   10                  15

Ala Asn Ala Ser
            20

<210> SEQ ID NO 9
<211> LENGTH: 15
<212> TYPE: PRT
<213> ORGANISM: Homo sapiens

<400> SEQUENCE: 9

Gly Asp Ser Ala Trp His Leu Gly Glu Leu Val Trp Ser Thr Gly
1               5                   10                  15

<210> SEQ ID NO 10
<211> LENGTH: 6
<212> TYPE: PRT
<213> ORGANISM: Homo sapiens

<400> SEQUENCE: 10

Cys Ile Arg Asp Lys Ser
1               5

<210> SEQ ID NO 11
<211> LENGTH: 15
<212> TYPE: PRT
<213> ORGANISM: Homo sapiens

<400> SEQUENCE: 11

Gly Gly Val Leu Val His Pro Gln Trp Val Leu Thr Ala Ala His
1               5                   10                  15

<210> SEQ ID NO 12
<211> LENGTH: 5
<212> TYPE: PRT
<213> ORGANISM: Artificial Sequence
<220> FEATURE:
<223> OTHER INFORMATION: Precursor to peptide portion of glycopeptide

<400> SEQUENCE: 12
```

Cys Ala Asp Val Ser
1               5

<210> SEQ ID NO 13
<211> LENGTH: 5
<212> TYPE: PRT
<213> ORGANISM: Artificial Sequence
<220> FEATURE:
<223> OTHER INFORMATION: Peptide portion of glycopeptide

<400> SEQUENCE: 13

Cys Ala Asn Val Ser
1               5

<210> SEQ ID NO 14
<211> LENGTH: 19
<212> TYPE: PRT
<213> ORGANISM: Artificial Sequence
<220> FEATURE:
<223> OTHER INFORMATION: Peptide portion of glycopeptide
<220> FEATURE:
<221> NAME/KEY: misc_feature
<222> LOCATION: (3)..(3)
<223> OTHER INFORMATION: Xaa is Orn

<400> SEQUENCE: 14

Ser Leu Xaa Ala Asn Lys Glu Thr Thr Glu Arg Ile Asn Gly Cys Ala
1               5                   10                  15

Asn Ala Ser

<210> SEQ ID NO 15
<211> LENGTH: 15
<212> TYPE: PRT
<213> ORGANISM: Homo sapiens

<400> SEQUENCE: 15

His Val Leu Val Gly Gly Pro Gln Trp Val Leu Thr Ala Ala His
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Peptide portion of glycopeptide
<220> FEATURE:
<221> NAME/KEY: misc_feature
<222> LOCATION: (3)..(3)
<223> OTHER INFORMATION: Xaa is Orn

<400> SEQUENCE: 16

Ser Leu Xaa Ala Asn Lys Glu Thr Thr Glu Arg Ile Asn Gly
1               5                   10